United States Patent
Maderna et al.

(10) Patent No.: US 7,759,518 B2
(45) Date of Patent: *Jul. 20, 2010

(54) DERIVATIVES OF N-(ARYLAMINO) SULFONAMIDES AS INHIBITORS OF MEK

(75) Inventors: Andreas Maderna, Stony Point, NY (US); Jean-Michel Vernier, San Diego, CA (US); Dinesh Barawkar, Foothill Ranch, CA (US); Varaprasad Chamakura, Bangalore (IN); Hassan el Abdellaoui, Jamestown, NC (US); Zhi Hong, Irvine, CA (US)

(73) Assignee: Ardea Biosciences, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/323,279

(22) Filed: Nov. 25, 2008

(65) Prior Publication Data

US 2009/0082457 A1    Mar. 26, 2009

Related U.S. Application Data

(63) Continuation of application No. 11/830,733, filed on Jul. 30, 2007, which is a continuation-in-part of application No. PCT/US2006/028326, filed on Jul. 21, 2006.

(60) Provisional application No. 60/701,814, filed on Jul. 21, 2005, provisional application No. 60/706,719, filed on Aug. 8, 2005, provisional application No. 60/731,633, filed on Oct. 28, 2005, provisional application No. 60/833,886, filed on Jul. 7, 2006.

(51) Int. Cl.
C07C 307/06 (2006.01)
A61K 31/63 (2006.01)

(52) U.S. Cl. .............. 564/84; 564/86; 514/601
(58) Field of Classification Search .......... 564/80, 564/84, 86; 514/601
See application file for complete search history.

(56) References Cited

U.S. PATENT DOCUMENTS

| | | | |
|---|---|---|---|
| 5,861,510 A | 1/1999 | Piscopio et al. |
| 5,863,949 A | 1/1999 | Robinson et al. |
| 6,316,462 B1 | 11/2001 | Bishop et al. |
| 6,440,966 B1 | 8/2002 | Barrett et al. |
| 6,469,004 B1 | 10/2002 | Barrett et al. |
| 6,545,030 B1 | 4/2003 | Barrett et al. |
| 6,750,217 B2 | 6/2004 | Barrett et al. |
| 6,770,778 B2 | 8/2004 | Barrett et al. |
| 6,780,870 B2 | 8/2004 | Carter et al. |
| 6,891,066 B2 | 5/2005 | Rewcastle et al. |
| 7,115,632 B1 | 10/2006 | Bedell et al. |
| 2003/0092748 A1 | 5/2003 | Barrett et al. |
| 2003/0149015 A1 | 8/2003 | Barrett et al. |
| 2004/0029898 A1 | 2/2004 | Boyle et al. |
| 2004/0054172 A1 | 3/2004 | Barrett et al. |
| 2004/0171632 A1 | 9/2004 | Gowan et al. |
| 2004/0176418 A1 | 9/2004 | Thiruvengadam et al. |
| 2005/0004186 A1 | 1/2005 | Barrett et al. |
| 2005/0026970 A1 | 2/2005 | Barrett et al. |
| 2005/0054701 A1 | 3/2005 | Wallace et al. |
| 2006/0030610 A1 | 2/2006 | Koch et al. |
| 2006/0140872 A1 | 6/2006 | Furue et al. |
| 2008/0058340 A1 | 3/2008 | Maderna et al. |

FOREIGN PATENT DOCUMENTS

| | | |
|---|---|---|
| EP | 239362 A2 | 9/1987 |
| EP | 606046 | 7/1994 |
| EP | 780386 | 6/1997 |
| EP | 0818442 A2 | 1/1998 |
| EP | 931788 A2 | 7/1999 |
| EP | 0945864 A2 | 9/1999 |
| EP | 1004578 A2 | 5/2000 |
| WO | WO-90-05719 A1 | 5/1990 |
| WO | WO-96-27583 A1 | 3/1996 |
| WO | WO-96-33182 A1 | 10/1996 |
| WO | WO-98-07697 A1 | 2/1998 |
| WO | WO-98-30566 A1 | 7/1998 |
| WO | WO-98-03516 A1 | 8/1998 |
| WO | WO-98-33768 A1 | 8/1998 |
| WO | WO-98-34915 A1 | 8/1998 |
| WO | WO-98-34918 A1 | 8/1998 |
| WO | WO-99-07675 A1 | 2/1999 |
| WO | WO-99-29667 A1 | 6/1999 |
| WO | WO-99-52889 A1 | 10/1999 |
| WO | WO-99-52910 A1 | 10/1999 |
| WO | WO-00-42003 A1 | 7/2000 |
| WO | WO-00-42022 A1 | 7/2000 |
| WO | WO-00-42029 A1 | 7/2000 |

(Continued)

OTHER PUBLICATIONS

U.S. Appl. No. 60/148,464, filed Aug. 12, 1999, Noe et al.

(Continued)

*Primary Examiner*—Shailendra Kumar
*Assistant Examiner*—Yate' K Cutliff
(74) *Attorney, Agent, or Firm*—Millen, White, Zelano & Branigan, P.C.

(57) ABSTRACT

This invention concerns N-(2-arylamino)aryl sulfonamides, which are inhibitors of MEK and are useful in treatment of cancer and other hyperproliferative diseases.

4 Claims, No Drawings

FOREIGN PATENT DOCUMENTS

| | | |
|---|---|---|
| WO | WO-02-06213 A2 | 1/2002 |
| WO | WO-02-06213 A3 | 1/2002 |
| WO | WO-03-077855 A2 | 9/2003 |
| WO | WO-03-077855 A3 | 9/2003 |
| WO | WO-03-077914 A1 | 9/2003 |
| WO | WO-2004-083167 A1 | 9/2004 |
| WO | WO-2005-028426 A1 | 3/2005 |

OTHER PUBLICATIONS

Berge et al., "Pharmaceutical salts," J. Pharm. Sci. 66(1): 1-19, 1977.

Buchwald et al., "Long-term, continuous intravenous heparin administration by an implantable infusion pump in ambulatory patients with recurrent venous thrombosis," Surgery 88(4): 507-16, 1980.

Bundgaard, H. Chapter 5: Design and application of prodrugs. A Textbook of Drug Design and Development. Krosgaard-Larsen, et al., eds., pp. 113-191, 1991.

Bundgaard, H., "Means to enhance penetration: Prodrugs as a means to improve the delivery of peptide drugs," Advanced Drug Delivery Reviews 8: 1-38, 1992.

Cobb et al., "How MAP Kinaes are Regulated," J. Biol. Chem. 270(25):14843-14846 (1995).

Fedorak et al., "A novel colon-specific steroid prodrug enhances sodium chloride absorption in rat colitis," Am J Physiol 269(2 Pt 1): G210-8, 1995.

Fleisher et al., "Improved oral drug delivery: solubility limitations overcome by the use of prodrugs," Advanced Drug Delivery Reviews 19(2): 115-30, 1996.

Furniss et al., ed., Vogel's Textbook of Practical Organic Chemistry, 5th Ed. Suppl. (Longman Scientific and Technical Ltd, Essex, UK) pp. 809-16, 1991.

Heller, A., "Electrical wiring of redox enzymes," Acc Chem Res 23(5): 128-34, 1990.

Hochhaus et al. A selective HPLC/RIA for dexamethasone and its prodrug dexamethasone-21-sulphobenzoate sodium in biological fluids. Biomed Chromatogr. 1992; 6(6):283-286.

Goodson, J. Dental applications. Medical Applications of Controlled Release, vol. 2, Applications and Evaluations. Langer, et al., eds. (CRC Press, Boca Raton, FL) pp. 115-138, 1984.

Langer, R., "New methods of drug delivery," Science 249(4976): 1527-33, 1990.

Larsen, et al., "Prodrug forms for the sulfonamide group. I. Evaluation of N-acyl derivative, N-sulfonylamidines, N-sulfonylsulfilimines and sulfonylureas as possible prodrug derivatives," Int J Pharmaceutics 37(1-2): 87-95, 1987.

Larsen et al., "Prodrug forms for the sulfonamide group. II. Water-soluble amino acid derivatives of N-methylsulfonamides as possible prodrugs," Int J Pharmaceutics 47(1-3): 103-10, 1988.

Lee et al., "The Raf/MEK/ERK Signal Transduction Cascade as a Target for Chemotherapeutic Intervention in Leukemia," Leukemia 16(4):486-507 (2002).

McLeod et al., "A glucocorticoid prodrug facilitates normal mucosal function in rat colitis without adrenal suppression," Gastroenterology 106(2): 405-13, 1994.

PCT/US06/28326 search report dated Jan. 18, 2008.

PCT/US08/71392 Search Report dated Oct. 16, 2008.

PCT/US08/71397 Search Report dated Oct. 22, 2008.

Robinson et al., "Discovery of the hemifumarate and (alpha-L-alanyloxy)methyl ether as prodrugs of an antirheumatic oxindole: prodrugs for the enolic OH group," J Med Chem 39(1): 10-8, 1996.

Saudek et al., "A preliminary trial of the programmable implantable medication system for insulin delivery," N Engl J Med 321(9): 574-9, 1989.

Sefton, M., "Implantable pumps," Crit Rev Biomed Eng 14(3): 201-40, 1987.

Sinkula et al., "Rationale for design of biologically reversible drug derivatives: prodrugs," J Pharm Sci 64(2): 181-210, 1975.

Treat et al., "Liposome encapsulated doxorubicin: Preliminary results of phase I and phase II trials," Liposomes in the Therapy of Infectious Diseases and Cancer. Lopez-Bernstein, et al., eds. (Alan R. Liss, New York) pp. 353-365, 1989.

Widder, K. et al., Method in Enzymology vol. 42 (1985), pp. 309-396.

DERIVATIVES OF N-(ARYLAMINO) SULFONAMIDES AS INHIBITORS OF MEK

CROSS REFERENCE TO RELATED APPLICATIONS

This application is a continuation application of U.S. application Ser. No. 11/830,733, filed Jul. 30, 2007, incorporated herein by reference in its entirety, and which is a continuation-in-part application of International Application Ser. No PCT/US2006/028326 filed Jul. 21, 2006, which is incorporated herein by reference in its entirety and to which application we claim priority under 35 USC §120, which claims priority to U.S. Provisional Application Ser. No. 60/701,814, filed Jul. 21, 2005; to U.S. Provisional Application Ser. No. 60/706,719, filed Aug. 8, 2005; and to U.S. Provisional Application Ser. No. 60/731,633, filed Oct. 28, 2005 all of which are hereby incorporated by reference herein in their entirety.

U.S. Application Ser. No. 11/830,733 also claims the benefit of U.S. Provisional Application No. 60/833,886 filed Jul. 28, 2006, which application is incorporated herein by reference.

FIELD OF THE INVENTION

This invention concerns N-(2-arylamino)aryl sulfonamides, which are inhibitors of MEK. Such compounds are useful in the treatment of cancer and other hyperproliferative diseases.

BACKGROUND OF THE INVENTION

Oncogenes—genes that contribute to the production of cancers—are generally mutated forms of certain normal cellular genes ("proto-oncogenes"). Oncogenes often encode abnormal versions of signal pathway components, such as receptor tyrosine kinases, serine-threonine kinases, or downstream signaling molecules. The central downstream signaling molecules are the Ras proteins, which are anchored on the inner surfaces of cytoplasmic membranes, and which hydrolyze bound guanosine triphosphate (GTP) to guanosine diphosphate (GDP). When activated by a growth factor, growth factor receptors initiate a chain of reactions that leads to the activation of guanine nucleotide exchange activity on Ras. Ras alternates between an active "on" state with a bound GTP (hereafter "Ras.GTP") and an inactive "off state with a bound GDP. The active "on" state, Ras.GTP, binds to and activates proteins that control the growth and differentiation of cells.

For example, in the "mitogen-activated protein kinase (MAP kinase) cascade," Ras.GTP leads to the activation of a cascade of serine/threonine kinases. One of several groups of kinases known to require a Ras.GTP for their own activation is the Raf family. The Raf proteins activate "MEK1" and "MEK2," abbreviations for mitogen-activated ERK-activating kinases (where ERK is extracellular signal-regulated protein kinase, another designation for MAPK). MEK1 and MEK2 are dual-function serine/threonine and tyrosine protein kinases and are also known as MAP kinase kinases. Thus, Ras.GTP activates Raf, which activates MEK1 and MEK2, which activate MAP kinase (MAPK). Activation of MAP kinase by mitogens appears to be essential for proliferation, and constitutive activation of this kinase is sufficient to induce cellular transformation. Blockade of downstream Ras signaling, as by use of a dominant negative Raf-1 protein, can completely inhibit mitogenesis, whether induced from cell surface receptors or from oncogenic Ras mutants.

The interaction of Raf and Ras is a key regulatory step in the control of cell proliferation. To date, no substrates of MEK other than MAPK have been identified; however, recent reports indicate that MEK may also be activated by other upstream signal proteins such as MEK kinase or MEKK1 and PKC. Activated MAPK translocates and accumulates in the nucleus, where it can phosphorylate and activate transcription factors such as Elk-1 and Sap1a, leading to the enhanced expression of genes such as that for c-fos.

Once activated, Raf and other kinases phosphorylate MEK on two neighboring serine residues, $S^{218}$ and $S^{222}$ in the case of MEK1. These phosphorylations are required for activation of MEK as a kinase. In turn, MEK phosphorylates MAP kinase on two residues separated by a single amino acid: a tyrosine, $Y^{185}$ and a threonine, $T^{183}$. MEK appears to associate strongly with MAP kinase prior to phosphorylating it, suggesting that phosphorylation of MAP kinase by MEK may require a prior strong interaction between the two proteins. Two factors—MEK's unusual specificity and its requirement for a strong interaction with MAP kinase prior to phosphorylation—suggest that MEK's mechanism of action may differ sufficiently from the mechanisms of other protein kinases as to allow for selective inhibitors of MEK. Possibly, such inhibitors would operate through allosteric mechanisms rather than through the more usual mechanism involving blockage of an ATP binding site.

Thus, MEK1 and MEK2 are validated and accepted targets for anti-proliferative therapies, even when the oncogenic mutation does not affect MEK structure or expression. See, e.g., U.S. Patent Publications 2003/0149015 by Barrett et al. and 2004/0029898 by Boyle et al.

Several examples of 1-substituted-2(p-substituted-phenylamino)-aryl inhibitors of MEK have been reported. U.S. Pat. Nos. 6,440,966 and 6,750,217 and corresponding publication WO 00/42003 described carboxylic and hydroxamic acid esters and N-substituted amide derivatives of sulfonamide-substituted-2(4-iodophenylamino)-benzoic acid esters and N-substituted benzamides as functioning as MEK inhibitors. The sulfonamide may also be N-substituted.

U.S. Pat. No. 6,545,030 and corresponding publication WO 00/42029 describe MEK inhibitors that are 1-heterocyclyl-2(4-iodophenylamino)-benzene, where the heterocycle is a five-membered nitrogen-containing ring such as pyrazole, triazole, oxazole, isoxazole, and isoxazolinone. The more recent U.S. Patent Publication 2005/004186 describes related compounds in which the 4-iodo substituent of the '030 patent is replaced by a very broad genus of moieties including alkyl, alkoxy, acyloxy, alkenyl, carbamoyl, carbamoylalkyl, carboxyl, carboxylalkyl, N-acylsulfonamido, and others.

U.S. Pat. No. 6,469,004 and corresponding publication WO 00/42022 describe carboxylic and hydroxamic acid esters of a group of heterocyclo-condensed phenylene compounds, i.e., benzimidazoles, benzooxazoles, benzothiazoles, benzothiadiazoles, quinazolines, etc. The heterocycles are 7-F-6-(4-iodo-phenylamino)-5-carboxylic acid esters, carboxylic acid amides or hydroxamic acid esters. More recent publication U.S. 2005/0026970 described similar compounds in which the 4-iodo substituent was replaced by a very broad genus of structures. Related compounds are described in patent publications WO 03/077855, WO 03/77914 and US 2005/0554701. Further examples of 2-(4-iodophenylamino)-phenylhydroxamic acid esters which are reported to be useful as MEK inhibitors can be found in WO 2005/028426. Patent Publication WO 02/06213 and corresponding U.S. application Ser. No. 10/333,399 (U.S. 2004/0054172) describe hydroxy-substituted acid esters of 1-oxamic acid-2(4-halophenylamino)-3,4-difluorobenzene. U.S.

Pat. No. 6,891,066 and corresponding publication WO 03/62191 describe similar compounds wherein the 4-halo substituent is replaced by a very broad genus of structures. Among the substituents in the 4-position were methyl, ethyl, ethynyl, and 2-hydroxyethyl. Specific related compounds are described in U.S. Pat. No. 6,770,778.

Patent Publication WO 04/083167, published Sep. 30, 2004, (in Japanese) discloses more than two thousand—but provides NMR data for only 400—1-(N-substituted sulfonyl urea)-2(2,4-dihalophenylamino)-3,4-difluorobenzenes and asserts that they useful as MEK inhibitors. Data indicating inhibition of MEK were presented for a subgroup of just twelve. In addition to a secondary or tertiary amine, these twelve compounds all contained one of the following groups: an N,N-disubstituted sulfonyl urea, N-piperazinesulfonamide, N-piperidinesulfonamide or N-pyrrolidinesulfonamide.

The MEK cascade has also been implicated in inflammatory diseases and disorders. U.S. Application Publication No. 2006/0030610 to Koch et al., U.S. Application Publication No. 2006/0140872 to Furue et al. This includes both acute and chronic inflammation disorders. Examples of such disorders are allergic contact dermatitis, rheumatoid arthritis, osteoarthritis, inflammatory bowel diseases, chronic obstructive pulmonary disorder, psoriasis, multiple sclerosis, asthma, diseases and disorders related to diabetic complications, and inflammatory complications of the cardiovascular system such as acute coronary syndrome. Among inflammatory bowel diseases are Crohn's disease and ulcerative colitis.

All cited references are incorporated herein by reference.

SUMMARY OF THE INVENTION

This invention provides compounds of formula I, or pharmaceutically acceptable salts, solvates, polymorphs, esters, tautomers or prodrugs thereof:

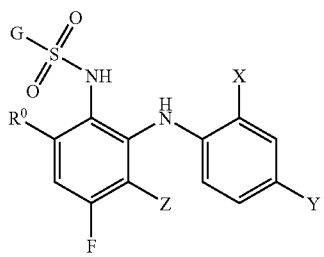

formula I wherein

Z is H or F;

X is F, Cl, $CH_3$, $CH_2OH$, $CH_2F$, $CHF_2$, or $CF_3$;

Y is I, Br, Cl, $CF_3$, $C_1$-$C_3$ alkyl, $C_2$-$C_3$ alkenyl, $C_2$-$C_3$ alkynyl, cyclopropyl, OMe, OEt, SMe, phenyl or Het, where Het is a 5- to 10-membered mono- or bicyclic heterocyclic group, which group is saturated, olefinic, or aromatic, containing 1-5 ring heteroatoms selected independently from N, O, and S; where all said phenyl or Het groups are optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O—(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$ alkyl-S(=O)$_2$NH— or trifluoromethyl;

all said methyl, ethyl, $C_1$-$C_3$ alkyl, and cyclopropyl groups are optionally substituted with OH;

all said methyl groups are optionally substituted with one, two, or three F atoms;

$R^0$ is H, F, Cl, Br, I, $CH_3NH$—, $(CH_3)_2N$—, $C_1$-$C_6$ alkyl, $C_1$-$C_4$ alkoxy, $C_3$-$C_6$ cycloalkyl, $C_2$-$C_6$ alkenyl, $C_2$-$C_6$ alkynyl, phenyl, monosubstituted phenyl, $O(C_1$-$C_4$ alkyl), O—C(=O)($C_1$-$C_4$ alkyl) or C(=O)O($C_1$-$C_4$ alkyl); where said alkyl, alkoxy, cycloalkyl, alkenyl, alkynyl and phenyl groups are optionally substituted with 1-3 substituents selected independently from F, Cl, Br, I, OH, CN, cyanomethyl, nitro, phenyl and trifluoromethyl;

said $C_1$-$C_6$ alkyl and $C_1$-$C_4$ alkoxy groups also optionally substituted with $OCH_3$ or $OCH_2CH_3$; G is $G_1$, $G_2$, $R_{1a}$, $R_{1b}$, $R_{1c}$, $R_{1d}$, $R_{1e}$, $Ar_1$, $Ar_2$ or $Ar_3$; where $G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or $G_1$ is a $C_3$-$C_8$ diamino alkyl group;

$G_2$ is a 5- or 6-membered ring, which is saturated, unsaturated, or aromatic, containing 1-3 ring heteroatoms selected independently from N, O, and S, optionally substituted with 1-3 substituents selected independently from F, Cl, OH, O($C_1$-$C_3$ alkyl), $OCH_3$, $OCH_2CH_3$, $CH_3C$(=O)NH, $CH_3C$(=O)O, CN, $CF_3$, and a 5-membered aromatic heterocyclic group containing 1-4 ring heteroatoms selected independently from N, O, and S;

$R_{1a}$ is methyl, optionally substituted with 1-3 fluorine atoms or 1-3 chlorine atoms, or with OH, cyclopropoxy, or $C_1$-$C_3$ alkoxy, where said cyclopropoxy group or the $C_1$-$C_3$ alkyl moieties of said $C_1$-$C_3$ alkoxy groups are optionally substituted with one hydroxy or methoxy group, and where all $C_3$— alkyl groups within said $C_1$-$C_4$ alkoxy are optionally further substituted with a second OH group;

$R_{1b}$ is $CH(CH_3)$—$C_{1-3}$ alkyl or $C_3$-$C_6$ cycloalkyl, said alkyl and cycloalkyl groups optionally substituted with 1-3 substituents selected independently from F, Cl, Br, I, OH, $OCH_3$, and CN;

$R_{1c}$ is $(CH_2)_nO_mR'$; where m is 0 or 1; and where when m is 0, n is 1 or 2;

when m is 1, n is 2 or 3;

R' is $C_1$-$C_6$ alkyl, optionally substituted with 1-3 substituents selected independently from F, Cl, OH, $OCH_3$, $OCH_2CH_3$, and $C_3$-$C_6$ cycloalkyl;

$R_{1d}$ is C(A)(A')(B)—; where

B is H or $C_{1-4}$ alkyl, optionally substituted with one or two OH groups;

A and A' are independently H or $C_{1-4}$ alkyl, optionally substituted with one or two OH groups; or A and A', together with the carbon atom to which they are attached, form a 3- to 6-member saturated ring;

$R_{1e}$ is

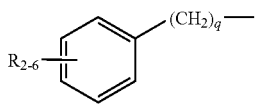

where
  q is 1 or 2;
  $R_2$ and $R_3$ are each independently, H, F, Cl, Br, $CH_3$, $CH_2F$, $CHF_2$, $CF_3$ $OCH_3$, $OCH_2F$, $OCHF_2$, $OCF_3$, ethyl, n-propyl, isopropyl, cyclopropyl, isobutyl, sec-butyl, tert-butyl or methylsulfonyl;
  $R_4$ is H, F, Cl, Br, $CH_3$, $CH_2F$, $CHF_2$, $CF_3$ $OCH_3$, $OCH_2F$, $OCHF_2$, $OCF_3$, ethyl, n-propyl, isopropyl, cyclopropyl, isobutyl, sec-butyl, tert-butyl, methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholyl carbonyl amino, N-morpholylsulfonyl and N-pyrrolidinylcarbonylamino;
  $R_5$ is H, F, Cl or methyl;
  $R_6$ is H, F, Cl or methyl;
$Ar_1$ is

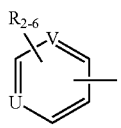

where
  U and V are, independently, N, $CR_2$ or $CR_3$;
  $R_2$, $R_3$ and $R_4$ are, independently, H, F, Cl, Br, $CH_3$, $CH_2F$, $CHF_2$, $CF_3$ $OCH_3$, $OCH_2F$, $OCHF_2$, $OCF_3$, ethyl, n-propyl, isopropyl, cyclopropyl, isobutyl, sec-butyl, tert-butyl, acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl;
  $R_5$ and $R_6$ are, independently, H, F, Cl or methyl;
$Ar_2$ is

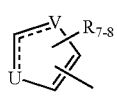

where
  the dashed line represents alternative formal locations for the second ring double bond;
  U is —S—, —O— or —N═, and where
    when U is —O— or —S—, V is —CH═, —CCl═ or —N═;
    when U is —N═, V is —CH═, —CCl═, or —N═;
  $R_7$ is H or methyl;
  $R_8$ is H, acetamido, methyl, F or Cl;
$Ar_3$ is

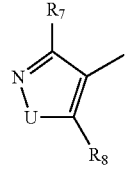

where
  U is —NH—, —$NCH_3$— or —O—;
  $R_7$ and $R_8$ are, independently, H, F, Cl, or methyl.

In some embodiments, the invention provides a compound of formula I, where G is $G_1$ or $G_2$. In other embodiments, G is $G_1$. In further or additional embodiments, G is $G_2$.

In some embodiments, the invention provides a compound of formula I, where G is $R_{1a}$, $R_{1b}$, $R_{1c}$, $R_{1d}$, $R_{1e}$, $Ar_1$, $Ar_2$ or $Ar_3$. In further or additional embodiments, G is $R_{1a}$, $R_{1b}$, $R_{1c}$, $R_{1d}$ or $R_{1e}$. In further or additional embodiments, G is $R_{1a}$. In further or additional embodiments, G is $R_{1b}$. In further or additional embodiments, G is $R_{1c}$. In further or additional embodiments, G is $R_{1d}$. In further or additional embodiments, G is $R_{1e}$. In further or additional embodiments, G is $Ar_1$, $Ar_2$ or $Ar_3$. In further or additional embodiments, G is $Ar_1$. In further or additional embodiments, G is $Ar_2$. In further or additional embodiments, G is $Ar_3$ In some embodiments, the invention provides compounds of formula I, or their pharmaceutically acceptable salts. In further or additional embodiments, the invention provides compounds of formula I, or their solvates. In further or additional embodiments, the invention provides compounds of formula I, or their polymorphs. In further or additional embodiments, the invention provides compounds of formula I, or their tautomers. In further or additional embodiments, the invention provides compounds of formula I, or their prodrugs.

In some embodiments, Z is H. In some embodiments, Z is F. In some embodiments, X is F. In some embodiments, X is Cl. In some embodiments, X is $CH_3$. In some embodiments, X is $CH_2OH$. In some embodiments, X is $CH_2F$. In some embodiments, X is $CHF_2$. In some embodiments, X is $CF_3$. In some embodiments, X is F, Cl, or $CH_3$.

In some embodiments, G is $G_1$ or $G_2$, X is F, Cl, or $CH_3$; Y is I, Br, Cl, $CF_3$, $C_1$-$C_3$ alkyl, phenyl, pyridyl, pyrrolyl, pyrazolyl, said phenyl, pyridyl, pyrrolyl, and pyrazolyl groups optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(═O)—, $C_1$-$C_3$ alkyl-C(═S)—, $C_1$-$C_3$ alkoxy-C(═S)—, $C_1$-$C_3$ alkyl-C(═O)O—, $C_1$-$C_3$ alkyl-O—(C═O)—, $C_1$-$C_3$ alkyl-C(═O)NH—, $C_1$-$C_3$ alkyl-C(═NH)NH—, $C_1$-$C_3$ alkyl-NH—(C═O)—, di-$C_1$-$C_3$ alkyl-N—(C═O)—, $C_1$-$C_3$ alkyl-C(═O)N($C_1$-$C_3$ alkyl)-, $C_1$-$C_3$ alkyl-S(═O)$_2$NH— or trifluoromethyl; and Z is H or F. In further or additional embodiments, G is $G_1$ or $G_2$, and $R^0$ is F, Cl, $C_1$-$C_4$ alkyl or $C_1$-$C_4$ alkoxy, said $C_1$-$C_4$ alkyl group and the $C_1$-$C_4$ alkyl moiety of said $C_1$-$C_4$ alkoxy group optionally substituted with F, Cl, $OCH_3$, or $OCH_2CH_3$. In further or additional embodiments, G is $G_1$ or $G_2$, and $R^0$ is H, F, Cl, $C_1$-$C_4$ alkyl, methoxy, ethoxy, or 2-methoxy-ethoxy.

In some embodiments, $G_1$ is N-methyl-2-aminoethyl. In further or additional embodiments, $G_1$ is $(CH_3)_2N$—$CH_2CH_2$—NH—$(CH_2)_n$—, where n is 1, 2, or 3. In further or additional embodiments, $G_1$ is $(CH_3)_2N$—$CH_2CH_2$—NH—

$(CH_2)_n$—, where n is 1, 2, or 3, and X is F. In further or additional embodiments, $G_1$ is $(CH_3)_2N$—$CH_2CH_2$—NH—$(CH_2)_n$—, where n is 1, 2, or 3, X is F and Z is F.

In some embodiments, $G_2$ is 1-piperidyl, 2-piperidyl, 3-piperidyl, or 4-piperidyl. In further or additional embodiments, $G_2$ is morpholyl, 1-piperazyl, or 2-piperazyl.

In some embodiments, G is $R_{1a}$, $R_{1b}$, $R_{1c}$, $R_{1d}$, $R_{1e}$, $Ar_1$, $Ar_2$ or $Ar_3$ and X is F, Cl, or $CH_3$. In further or additional embodiments, 6 is $R_{1a}$, $R_{1b}$, $R_{1c}$, $R_{1d}$, $R_{1e}$, $Ar_1$, $Ar_2$ or $Ar_3$, X is F, Cl, or $CH_3$ and Y is I, Br, Cl, $CF_3$, or $C_1$-$C_3$ alkyl In further or additional embodiments, G is $R_{1a}$, $R_{1b}$, $R_{1c}$, $R_{1d}$, $R_{1e}$, $Ar_1$, $Ar_2$ or $Ar_3$, X is F, Cl, or $CH_3$, Y is I, Br, Cl, $CF_3$, or $C_1$-$C_3$ alkyl and Z is H or F In further or additional embodiments, G is $R_{1a}$, $R_{1b}$, $R_{1c}$, $R_{1d}$, $R_{1e}$, $Ar_1$, $Ar_2$ or $Ar_3$ and $R^0$ is F, Cl, $C_1$-$C_4$ alkyl or $C_1$-$C_4$ alkoxy, said $C_1$-$C_4$ alkyl group and the $C_1$-$C_4$ alkyl moiety of said $C_1$-$C_4$ alkoxy group optionally substituted with F, Cl, $OCH_3$, or $OCH_2CH_3$. In further or additional embodiments, G is $R_{1a}$, $R_{1b}$, $R_{1c}$, $R_{1d}$, $R_{1e}$, $Ar_1$, $Ar_2$ or $Ar_3$ and $R^0$ is H, F, Cl, $C_1$-$C_4$ alkyl, methoxy, ethoxy, or 2-methoxy-ethoxy.

In some embodiments, G is $R_{1a}$; and Z is F. In further or additional embodiments, G is $R_{1a}$ where $R_{1a}$ is $CH_3$, $R^0$ is H; and Y is Br, I, $CF_3$, or $CH_3$. In some embodiments, G is $R_{1b}$ and Z is F. In further or additional embodiments, G is $R_{1b}$, Z is F, and $R^0$ is H, F, or $OCH_3$. In further or additional embodiments, G is $R_{1b}$, Z is F, $R^0$ is H, F, or $OCH_3$, and X is F or $CH_3$. In further or additional embodiments, G is $R_{1b}$, Z is F, $R^0$ is H, F, or $OCH_3$, X is F or $CH_3$ and Y is Br, I or $CH_3$. In further or additional embodiments, G is $R_{1b}$ where $R_{1b}$ is $C_3$-$C_6$ cycloalkyl. In further or additional embodiments, G is $R_{1b}$ where $R_{1b}$ is substituted $C_3$-$C_6$ cycloalkyl. In further or additional embodiments, G is $R_{1b}$ where $R_{1b}$ is unsubstituted $C_3$-$C_6$ cycloalkyl. In further or additional embodiments, G is $R_{1b}$ where $R_{1b}$ is unsubstituted $C_3$-$C_6$ cycloalkyl and $R^0$ is H. In further or additional embodiments, G is $R_{1b}$ where $R_{1b}$ is isopropyl or cyclopropyl.

In some embodiments, G is $R_{1c}$, and Y is I, Br, $CH_3$, or $CF_3$. In further or additional embodiments, G is $R_{1c}$, Y is I, Br, $CH_3$, or $CF_3$, and Z is F. In further or additional embodiments, G is $R_{1c}$, Y is I, Br, $CH_3$, or $CF_3$, Z is F and m is zero.

In some embodiments, G is $R_{1d}$ and $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$, $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino and X is F, Cl, $CH_3$, or mono-, di- or tri-fluoromethyl. In further or additional embodiments, G is $R_{1d}$, $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino, X is F, Cl, $CH_3$, or mono-, di- or tri-fluoromethyl and Y is I, Br, Cl, or mono-, di- or tri-fluoromethyl. In further or additional embodiments, G is $R_{1d}$, $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino, X is F, Cl, $CH_3$, or mono-, di- or tri-fluoromethyl, Y is I, Br, Cl, or mono-, di- or tri-fluoromethyl and Z is H or F. In further or additional embodiments, G is $R_{1d}$ and $R^0$ is F, Cl, methyl, ethyl, methoxy, ethoxy, or 2-methoxy-ethoxy.

In further or additional embodiments, G is $R_{1d}$, $R^0$ is F, Cl, methyl, ethyl, methoxy, ethoxy, or 2-methoxy-ethoxy and X is F, Cl, or $CH_3$. In further or additional embodiments, G is $R_{1d}$, $R^0$ is F, Cl, methyl, ethyl, methoxy, ethoxy, or 2-methoxy-ethoxy, X is F, Cl, or $CH_3$ and Y is I, Br, Cl, or mono-, di- or tri-fluoromethyl. In further or additional embodiments, G is $R_{1d}$, $R^0$ is F, Cl, methyl, ethyl, methoxy, ethoxy, or 2-methoxy-ethoxy, X is F, Cl, or $CH_3$, Y is I, Br, Cl, or mono-, di- or tri-fluoromethyl and Z is H or F. In further or additional embodiments, G is $R_{1d}$ and $R^0$ is H; X is F, Cl, $CH_3$, or mono-, di- or tri-fluoromethyl. In further or additional embodiments, G is $R_{1d}$, $R^0$ is H; X is F, Cl, $CH_3$, or mono-, di- or tri-fluoromethyl and Y is I, Br, Cl, or mono-, di- or tri-fluoromethyl. In further or additional embodiments, G is $R_{1d}$, $R^0$ is H; X is F, Cl, $CH_3$, or mono-, di- or tri-fluoromethyl, Y is I, Br, Cl, or mono-, di- or tri-fluoromethyl and Z is H or F.

In further or additional embodiments, G is $R_{1d}$ where $R_{1d}$ is C(A)(A') is $C_1$-$C_6$ cycloalkyl. In further or additional embodiments, G is $R_{1d}$ where $R_{1d}$ is C(A)(A') is $C_1$-$C_6$ cycloalkyl and B is H. In further or additional embodiments, G is $R_{1d}$ where $R_{1d}$ is C(A)(A') is $C_1$-$C_6$ cycloalkyl and B is methyl, ethyl, 2-hydroxyethyl, n-propyl, 3-hydroxypropyl, 2,3-dihydroxypropyl, 3,4-dihydroxybutyl, isopropyl, 1-methyl-2-hydroxy ethyl, n-butyl, sec-butyl, isobutyl, or 2-hydroxymethyl-3-hydroxy propyl.

In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl. In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the R configuration. In further or additional embodiments, G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the S configuration. In further or additional embodiments, G is $R_{1d}$ where $R_{1d}$ is C(A)(A') is $C_1$-$C_6$ cycloalkyl and B is methyl, optionally substituted with one OH group, or $C_2$-$C_4$ alkyl, optionally substituted with one or two OH groups. In further or additional embodiments, G is $R_{1d}$ where $R_{1d}$ is C(A)(A') is $C_1$-$C_6$ cycloalkyl and $R^0$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$ where $R_{1d}$ is C(A)(A') is $C_1$-$C_6$ cycloalkyl and $R^0$ is F, Cl, methyl, ethyl, methoxy, ethoxy, or 2-methoxyethoxy. In further or additional embodiments, G is $R_{1d}$ where $R_{1d}$ is C(A)(A') is $C_1$-$C_6$ cycloalkyl and $R^0$ is H; X is F, Cl, $CH_3$, or mono-, di- or tri-fluoromethyl.

In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3-dihydroxypropyl or 3,4-dihydroxybutyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is $C_1$-$C_6$ cycloalkyl and B is 2,3- dihydroxypropyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is $C_1$-$C_6$ cycloalkyl and B is 3,4-dihydroxybutyl, in which the chiral carbon in B is in the S configuration, which is substantially free of the R isomer.

In further or additional embodiments, G is $R_{1d}$ where $R_{1d}$ is C(A)(A') is cyclopropyl. In further or additional embodiments, G is $R_{1d}$ where $R_{1d}$ is C(A)(A') is cyclopropyl and B is H. In further or additional embodiments, G is $R_{1d}$ where $R_{1d}$ is C(A)(A') is cyclopropyl and B is methyl, ethyl, 2-hydroxyethyl, n-propyl, 3-hydroxypropyl, 2,3-dihydroxypropyl, 3,4-dihydroxybutyl, isopropyl, 1-methyl-2-hydroxy ethyl, n-butyl, sec-butyl, isobutyl, or 2-hydroxymethyl-3-hydroxy propyl. In further or additional embodiments, G is $R_{1d}$ where $R_{1d}$ is C(A)(A') is cyclopropyl and B is 2,3-dihydroxypropyl or 3,4-dihydroxybutyl. In further or additional embodiments, G is $R_{1d}$ where $R_{1d}$ is C(A)(A') is cyclopropyl and B is 2,3-dihydroxypropyl or 3,4-dihydroxybutyl, in which the chiral carbon in B is in the R configuration. In further or additional embodiments, G is $R_{1d}$ where $R_{1d}$ is C(A)(A') is cyclopropyl and B is 2,3-dihydroxypropyl or 3,4-dihydroxybutyl, in which the chiral carbon in B is in the S configuration. In further or additional embodiments, G is $R_{1d}$ where $R_{1d}$ is C(A)(A') is cyclopropyl and B is methyl, optionally substituted with one OH group, or $C_2$-$C_4$ alkyl, optionally substituted with one or two OH groups. In further or additional embodiments, G is $R_{1d}$ where $R_{1d}$ is C(A)(A') is cyclopropyl and $R_1$ is fluoro, chloro, methyl, ethyl, propyl, isopropyl, sec-butyl, iso-butyl, tert-butyl, cyclopropyl, cyclobutyl, fluoromethyl, methoxy, fluoromethoxy, methylamino or dimethylamino. In further or additional embodiments, G is $R_{1d}$ where $R_{1d}$ is C(A)(A') is cyclopropyl and $R^0$ is F, Cl, methyl, ethyl, methoxy, ethoxy, or 2-methoxy-ethoxy. In further or additional embodiments, G is $R_{1d}$ where $R_{1d}$ is C(A)(A') is cyclopropyl and $R^0$ is H; X is F, Cl, $CH_3$, or mono-, di- or tri-fluoromethyl.

In further or additional embodiments, the invention provides a composition comprising a compound of formula I, where G is $R_{1d}$ where $R_{1d}$ is C(A)(A') is cyclopropyl and B is 2,3-dihydroxypropyl or 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 2,3-dihydroxypropyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 3,4-dihydroxybutyl, in which the chiral carbon in B is in the R configuration, which is substantially free of the S isomer. In further or additional embodiments, the invention provides a composition comprising a compound of formula I, where G is $R_{1d}$ where $R_{1d}$ is C(A)(A') is cyclopropyl and B is 2,3-dihydroxypropyl or 3,4-dihydroxybutyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is cyclopropyl and B is 2,3-dihydroxypropyl, in which the chiral carbon in B is in the S configuration, which is substantially free of the R isomer. In further or additional embodiments, the invention provides a composition comprising a compound of formula I, where G is $R_{1d}$ where $R_{1d}$ is C(A)(A') is cyclopropyl and B is 3,4-dihydroxybutyl, in which the chiral carbon in B is in the S configuration, which is substantially free of the R isomer.

In some embodiments, G is $R_{1e}$ and n is 1. In further or additional embodiments, G is $R_{1e}$, $R^0$ is H, $R_{4-6}$ are H, $R_2$ and $R_3$ are, independently, H, F, Cl, Br, $CH_3$, $CH_2F$, $CHF_2$, $CF_3$, $OCH_3$, $OCH_2F$, $OCHF_2$, $OCF_3$, ethyl, n-propyl, isopropyl, cyclopropyl, isobutyl, sec-butyl, tert-butyl, and methylsulfonyl, X is F and Y is I.

In some embodiments, G is $Ar_1$ where $Ar_1$ is phenyl optionally substituted with one group selected from acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl, optionally substituted with 1-3 substituents selected independently from F, Cl, and $CH_3$. In further or additional embodiments, G is $Ar_1$ where $Ar_1$ is phenyl optionally substituted with one group selected from acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl, optionally substituted with 1-3 substituents selected independently from F, Cl, and $CH_3$, $R^0$ is H, X is F, Cl, or methyl and Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$. In some embodiments, G is $Ar_1$ where $Ar_1$ is

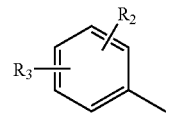

and where $R_2$ and $R_3$ are, independently, H, F, Cl, $CH_3$, $CF_3$, $OCH_3$. In further or additional embodiments, G is $Ar_1$ where $Ar_1$ is

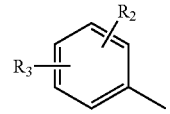

and where $R_2$ and $R_3$ are, independently, H, F, Cl, $CH_3$, $CF_3$, $OCH_3$, X is F or $CH_3$, Y is I, Br, or Cl; and Z is F. In further or additional embodiments, G is $Ar_1$ where $Ar_1$ is phenyl or mono-substituted phenyl. In further or additional embodiments, G is $Ar_1$ where $Ar_1$ is phenyl or mono-substituted phenyl, X is F or $CH_3$, Y is I, Br, or Cl, Z is F; and $R^0$ is F, methyl, ethyl, methoxy, or 2-methoxy-ethoxy. In further or additional embodiments, G is $Ar_1$ where U is N or $CR_2$ and V is N. In further or additional embodiments, G is $Ar_1$ where U is N or $CR_2$ and V is CR. In further or additional embodiments, G is $Ar_1$ where U is N or $CR_2$, V is $CR_2$, $R^0$ is H, X is F, Cl, or methyl and Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$.

In some embodiments, G is $Ar_2$ where $Ar_2$ is

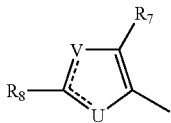

where $R_7$ is H or methyl and $R_8$ is H, acetamido, methyl, F or Cl. In further or additional embodiments, G is $Ar_2$ where $Ar_2$ is

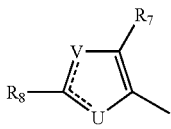

where $R_7$ is H or methyl, $R_8$ is H, acetamido, methyl, F or Cl, $R_1$ is H, X is F, Cl, or methyl, Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$, and Z is F. In further or additional embodiments, G is $Ar_2$ where $Ar_2$ is

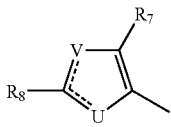

where U is S or O, V is CH=, and $R_8$ is H or $CH_3$, $R_7$ is H or methyl, $R_8$ is H, acetamido, methyl, F or Cl, $R^0$ is H, X is F, Cl, or methyl, Y is Br, I, $CF_3$, $C_1$-$C_3$ alkyl, $C_2$-$C_3$ alkenyl, $C_2$-$C_3$ alkynyl, cyclopropyl, $OCH_3$, $OCH_2CH_3$ or $SCH_3$ and Z is F. In further or additional embodiments, $R^0$ is H. In further or additional embodiments, $R^0$ is H, X is F or Cl and Y is Br, I, $CH_2CH_3$ or $SCH_3$ In some embodiments, G is $Ar_3$ where U is —O—.

In further or additional embodiments, G is $R_{1a}$, where $R_{1a}$ is defined as above. In further or additional embodiments, G is $R_{1a}$, and $R^0$ is H, where $R_{1a}$ is defined as above. In further or additional embodiments, G is $R_{1a}$ and $R^0$ is as defined above, other than H, and $R_{1a}$ is defined as above. In further or additional embodiments, G is $R_{1a}$, where $R_{1a}$ is methyl, monohalomethyl, $C_1$-$C_3$ alkoxymethyl, or cyclopropoxymethyl. In further or additional embodiments, G is $R_{1a}$, where $R_{1a}$ is methyl, monohalomethyl, $C_1$-$C_3$ alkoxymethyl, or cyclopropoxy methyl and where $R^0$ is F, Cl, $C_1$-$C_3$ alkyl, monochloro $C_1$-$C_3$ alkyl, $C_1$-$C_3$ alkoxy, trifluoro methoxy, or 2-methoxy-ethoxy.

In further or additional embodiments, G is $R_{1b}$, where $R_{1b}$ is defined as above. In further or additional embodiments, G is $R_{1b}$, and $R^0$ is H, where $R_{1b}$ is defined as above. In further or additional embodiments, G is $R_{1b}$, $R^0$ is H and Z is F, where $R_{1b}$ is defined as above. In further or additional embodiments, G is $R_{1b}$ and $R^0$ is as defined above, other than H, and $R_{1b}$ is defined as above. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with 1 or 2 substituents selected independently from F, Cl, OH, and $OCH_3$; Y is Br, I, methyl, or trifluoromethyl. In further or additional embodiments, G is $R_{1b}$, where $R_{1b}$ is isopropyl, 2-butyl, 2-pentyl, cyclopropyl, cyclobutyl, cyclopentyl, or cyclohexyl, optionally substituted with 1 or 2 substituents selected independently from F, Cl, OH, and $OCH_3$; Y is Br, I, methyl, or trifluoromethyl; and $R^0$ is F, Cl, $C_1$-$C_3$ alkyl, monochloro $C_1$-$C_3$ alkyl, $C_1$-$C_3$ alkoxy, trifluoromethoxy, or 2-methoxy-ethoxy. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with one Cl or with 1 or 2 OH groups; and Y is Br, I, methyl, or trifluoromethyl. In further or additional embodiments, G is $R_{1b}$, where $R_{1b}$ is isopropyl, 2-butyl, 2-pentyl, cyclopropyl, cyclobutyl, cyclopentyl, or cyclohexyl, all optionally substituted with one Cl or with 1 or 2 OH groups; Y is Br, I, methyl, or trifluoromethyl; and $R^0$ is F, Cl, $C_1$-$C_3$ alkyl, monochloro $C_1$-$C_3$ alkyl, $C_1$-$C_3$ alkoxy, trifluoromethoxy, or 2-methoxy-ethoxy.

In further or additional embodiments, G is $R_{1c}$, where $R_{1c}$ is defined as above. In further or additional embodiments, G is $R_{1c}$, and $R^0$ is H, where $R_{1c}$ is defined as above. In further or additional embodiments, G is $R_{1c}$, and $R^0$ is as defined above, other than H, and $R_{1c}$ is defined as above. In further or additional embodiments, G is $R_{1c}$, and $R^0$ is H, where $R_{1c}$ is $(CH_2)_nO_mR'$, where m is 0 or 1, n is 2 or 3 when m is 1, and n is 1 or 2 when m is 0, and R' is $C_1$-$C_6$ alkyl, optionally substituted with 1-3 substituents selected independently from F, Cl, OH, $OCH_3$, $OCH_2CH_3$, and $C_3$-$C_6$ cycloalkyl. In another more specific subgeneric embodiment, m is zero, n is 1 or 2, and R' is $C_1$-$C_4$ alkyl, optionally substituted as described above. In another more specific subgeneric embodiment, m is 1, n is 2 or 3, and R' is $C_1$-$C_4$ alkyl, optionally substituted as described above. In a still more specific subgeneric embodiment, m is zero, n is 1 or 2, and R' is $C_1$-$C_4$ alkyl, optionally substituted with 1-3 groups selected from OH, $OCH_3$, Cl, and cyclopropyl.

In further or additional embodiments, G is $R_{1d}$, where $R_{1d}$ is defined as above. In further or additional embodiments, G is $R_{1d}$, and $R^0$ is H, where $R_{1d}$ is defined as above. In further or additional embodiments, G is $R_{1d}$ and $R^0$ is as defined above, other than H, and $R_{1d}$ is defined as above. In further or additional embodiments, G is $R_{1d}$, and $R^0$ is H, where $R_{1d}$ is C(A)(A')(B)— where B, A, and A' are, independently, H or $C_{1-4}$ alkyl, optionally substituted with one or two OH groups or halogen atoms, or A and A', together with the carbon atom to which they are attached, form a 3- to 6-member saturated ring, said ring optionally containing one or two heteroatoms selected, independently, from O, N, and S and optionally substituted with one or two groups selected independently from methyl, ethyl, fluoro, chloro, bromo and iodo.

In further or additional embodiments, G is $R_{1e}$, where $R_{1e}$ is defined as above. In further or additional embodiments, G is $R_{1e}$, and $R^0$ is H, where $R_{1e}$ is defined as above. In further or additional embodiments, G is $R_{1e}$ and $R^0$ is as defined above, other than H, and $R_{1e}$ is defined as above.

In further or additional embodiments, G is $Ar_1$, where $Ar_1$ is defined as above. In further or additional embodiments, G is $Ar_1$, and $R^0$ is H, where $Ar_1$ is defined as above. In further or additional embodiments, G is $Ar_1$ and $R^0$ is as defined above, other than H, and $Ar_1$ is defined as above.

In further or additional embodiments, G is $Ar_2$, where $Ar_2$ is defined as above. In further or additional embodiments, G is $Ar_2$, and $R^0$ is H, where $Ar_2$ defined as above. In further or additional embodiments, G is $Ar_2$ and $R^0$ is as defined above, other than H, and $Ar_2$ is defined as above.

In further or additional embodiments, X is F, Cl, or $CH_3$; Y is I, Br, Cl, $CF_3$ or $C_1$-$C_3$ alkyl, and Z is H or F. In further or additional embodiments, X is F, Cl, or $CH_3$; Y is I, Br, Cl, $CF_3$, or $C_1$-$C_3$ alkyl, Z is H or F, and $R^0$ is halogen, $C_1$-$C_6$ alkyl, monohalo $C_1$-$C_6$ alkyl, $C_3$-$C_6$ cycloalkyl, $C_2$-$C_6$ alkenyl, $C_2$-$C_6$ alkynyl, phenyl, monosubstituted phenyl, $OR_3$, O—C(=O)$R_4$, or C(=O)$OR_5$. In further or additional embodiments, X is F, Cl, or $CH_3$; Y is I, Br, Cl, $CF_3$, or $C_1$-$C_3$ alkyl, Z is H or F, and $R^0$ is furyl, thienyl, thiazolyl, isothiazolyl, oxazolyl, isoxazolyl, pyrrolyl, or pyrazolyl. In further or additional embodiments, X is F, Cl, or $CH_3$; Y is I, Br, Cl, $CF_3$, or $C_1$-$C_3$ alkyl, Z is H or F, and $R^0$ is F, Cl, $C_1$-$C_4$ alkyl, $C_1$-$C_3$ alkoxy, trifluoromethoxy, or 2-methoxy-ethoxy.

In another more specific subgeneric embodiment, $R_{1d}$ is cycloalkyl or 1-alkyl-cycloalkyl, in which the 1-alkyl group is optionally substituted with one or two OH groups or with one or two halogen atoms.

In another more specific subgeneric embodiment, $R^0$ is halogen, $C_1$-$C_6$ alkyl, monohalo $C_1$-$C_6$ alkyl, $C_3$-$C_6$ cycloalkyl, $C_2$-$C_6$ alkenyl, $C_2$-$C_6$ alkynyl, phenyl, monosubstituted phenyl, $OR_3$, O—C(=O)$R_4$, or C(=O)$OR_5$; and $R_{1d}$ is cycloalkyl or 1-alkyl-cycloalkyl, in which the 1-alkyl group is optionally substituted with one or two OH groups or with one or two halogen atoms.

In another more specific subgeneric embodiment, $R^0$ is furyl, thienyl, thiazolyl, isothiazolyl, oxazolyl, isoxazolyl, pyrrolyl, or pyrazolyl; and $R_{1d}$ is cycloalkyl or 1-alkyl-cycloalkyl, in which the 1-alkyl group is optionally substituted with one or two OH groups or one or two halogen atoms.

In another more specific subgeneric embodiment, $R_{1d}$ is cycloalkyl or 1-alkyl-cycloalkyl, in which the 1-alkyl group is optionally substituted with one or two OH groups, and where Y is Br, I, methyl, or trifluoromethyl. In another more specific subgeneric embodiment, $R_{1d}$ is cycloalkyl or 1-alkyl-cycloalkyl, in which the 1-alkyl group is optionally substituted with one or two fluorine or chlorine atoms, and where Y is Br, I, methyl, or trifluoromethyl. In another more specific subgeneric embodiment, $R_{1d}$ is cycloalkyl or (1-alley 1)-cycloalkyl, in which the 1-alkyl group is optionally substituted with one or two OH groups, and where $R^0$ is F, Cl, $C_1$-$C_3$ alkyl, monochloro $C_1$-$C_3$ alkyl, $C_1$-$C_3$ alkoxy, trifluoromethoxy, or 2-methoxy-ethoxy. In another more specific subgeneric embodiment, $R_{1d}$ is tetrahydrofuryl, tetrahydrothienyl, pyrrolidyl, piperidyl, piperazinyl, or morpholyl, each optionally substituted as described above, and where Y is Br, I, methyl, or trifluoromethyl. In another more specific subgeneric embodiment, $R_{1d}$ is oxazolidinyl, thiazolidinyl, isoxazolidinyl, isothiazolidinyl, tetrahydrofuryl, tetrahydrothienyl, pyrrolidyl, piperidyl, piperazinyl, or morpholyl, each optionally substituted as described above, and where Y is Br, I, methyl, or trifluoromethyl. In another more specific subgeneric embodiment, $R_{1d}$ is cyclopropyl or 1-alkyl-cyclopropyl, in which the 1-alkyl group is optionally substituted with one or two OH groups, and where $R^{0'}$ is F, Cl, methyl, ethyl, chloromethyl, $C_1$-$C_2$ alkoxy, trifluoromethoxy, or 2-methoxy-ethoxy. In an even more specific embodiment, $R_{1d}$ is 1-(monohydroxyalkyl)cycloalkyl. In another more specific embodiment, $R_{1d}$ is 1-(monohydroxyalkyl)cycloalkyl, where $R^0$ is F, Cl, methyl, ethyl, chloromethyl, $C_1$-$C_2$ alkoxy, trifluoromethoxy, or 2-methoxy-ethoxy. In an even more specific embodiment, $R_{1d}$ is 1-(dihydroxyalkyl)cycloalkyl. In another more specific embodiment, $R_{1d}$ is 1-(dihydroxyalkyl)cycloalkyl, where $R^0$ is F, Cl, methyl, ethyl, chloromethyl, $C_1$-$C_2$ alkoxy, trifluoromethoxy, or 2-methoxy-ethoxy.

In a more specific subgeneric embodiment U is $CR_2$ and V is N. In another more specific, subgeneric embodiment, U and V are both N. In a more specific, subgeneric embodiment, U is $CR_2$ and V is $CR_3$.

In a still more specific subgeneric embodiment, this invention provides a compound of formula I, where G is $Ar_1$ and $Ar_1$ is phenyl or monosubstituted phenyl, $R^0$ is F, methyl, ethyl, $C_1$-$C_3$ alkoxy, trifluoromethoxy, or 2-methoxy-ethoxy; X is F, Cl, or $CH_3$; Y is I; and Z is F. In another subgeneric embodiment, this invention provides a compound of formula I, where G is $Ar_1$, where $Ar_1$ is phenyl or monosubstituted phenyl, $R^0$ is halogen, $C_1$-$C_6$ alkyl, $C_3$-$C_6$ cycloalkyl, $C_2$-$C_6$ alkenyl, $C_2$-$C_6$ alkynyl, all such alkyl, cycloalkyl, alkenyl, and alkynyl groups optionally substituted with 1-3 substituents selected independently from halogen, OH, CN, cyanomethyl, nitro, phenyl, and trifluoromethyl; or $R^0$ is phenyl, $OR_3$, furyl, thienyl, thiazolyl, isothiazolyl, oxazolyl, isoxazolyl, pyrrolyl, or pyrazolyl. In a more specific subgeneric embodiment, this invention provides a compound of formula I, where A is $Ar_1$, where $Ar_1$ is phenyl or monosubstituted phenyl, $R^0$ is F, Cl, $C_1$-$C_3$ alkyl, $C_1$-$C_3$ alkoxy, 2-methoxyethoxy, $C_2$-$C_3$ alkenyl, $C_2$-$C_3$ alkynyl, trifluoromethyl, phenyl, furyl, or thienyl, thiazolyl, isothiazolyl, oxazolyl, isoxazolyl, pyrrolyl, or pyrazolyl; X is F, Cl, or methyl; Y is I, Br, Cl, $CF_3$, or $C_1$-$C_3$ alkyl; and Z is F.

In another still more specific subgeneric embodiment, this invention provides a compound of formula I, where G is $Ar_1$, where $Ar_1$ is phenyl or monosubstituted phenyl, $R^0$ is H; X is F, Cl, or $CH_3$; Y is Br or I; and Z is F.

In another subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen. In a more specific subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is other than H; X is F, Cl, or $CH_3$; Y is I, Br, Cl, $CF_3$, or $C_1$-$C_3$ alkyl, and Z is H or F. In another subgeneric embodiment this invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is F, Cl, $C_1$-$C_3$ alkyl, monochloro $C_1$-$C_3$ alkyl, $C_1$-$C_3$ alkoxy, trifluoromethoxy, methyloxy-methoxy, or 2-methoxy-ethoxy; X is F, Cl, or $CH_3$; Y is I, Br, Cl, $CF_3$, or $C_1$-$C_3$ alkyl, and Z is H or F. In another subgeneric embodiment his invention provides a compound of formula I, where G is $Ar_2$, where $Ar_2$ is 2-thienyl, 2-furyl, 3-thienyl, 3-furyl, 2-pyrrolyl, or 3-pyrrolyl, all optionally substituted with methoxycarbonyl, methylcarbamoyl, acetamido, acetyl, methyl, ethyl, trifluoromethyl, or halogen; $R^0$ is H; X is F, Cl, or $CH_3$; Y is I, Br, Cl, $CF_3$, or $C_1$-$C_3$ alkyl, and Z is H or F. In another subgeneric embodiment his invention provides a compound of formula I, where G is $Ar_2$, where $Ar_2$ is thiazolyl, isothiazolyl, oxazolyl, isoxazolyl, pyrrolyl, or pyrazolyl, all optionally substituted with methoxycarbonyl, methylcarbamoyl, acetamido, acetyl, methyl, ethyl, trifluoromethyl, or halogen; $R^0$ is H or methoxy; X is F, Cl, or $CH_3$; Y is I, Br, Cl, $CF_3$, or $C_1$-$C_3$ alkyl, and Z is H or F.

In some embodiments, the invention provides a compound of formula I, selected from the compounds below:

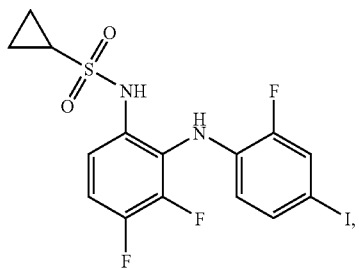
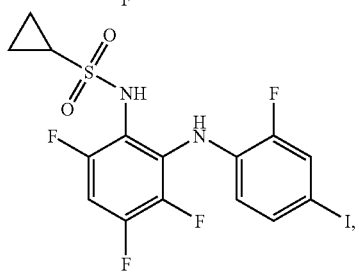
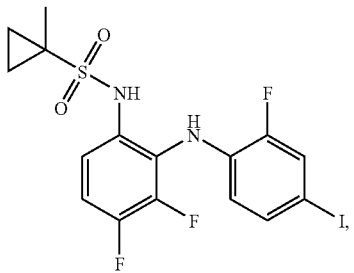
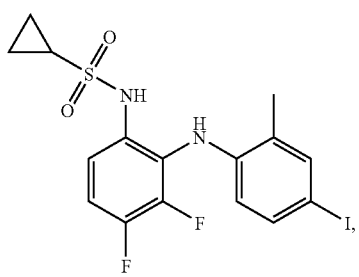
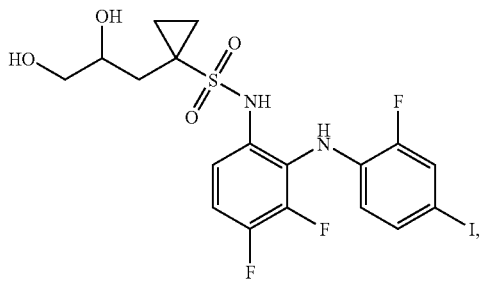
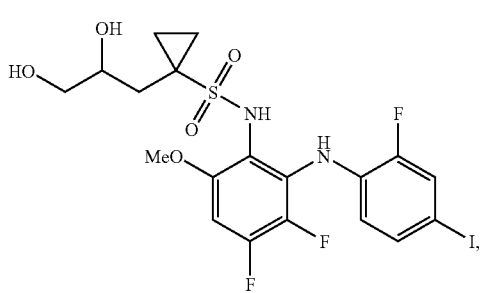
-continued
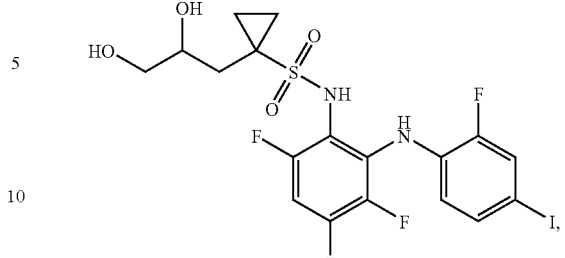
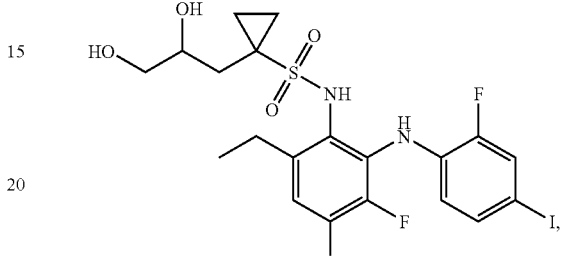
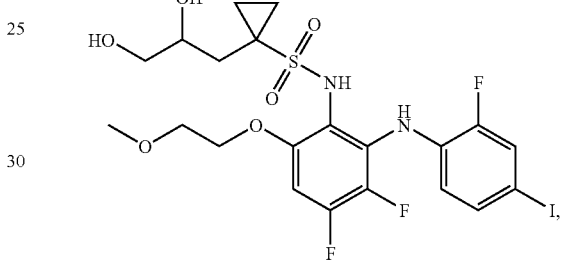
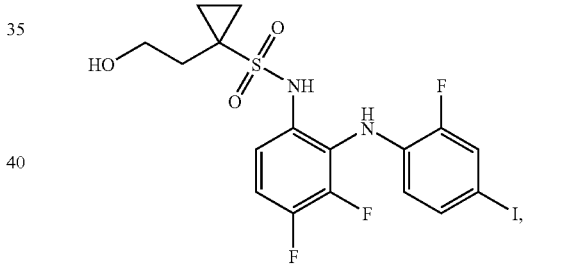
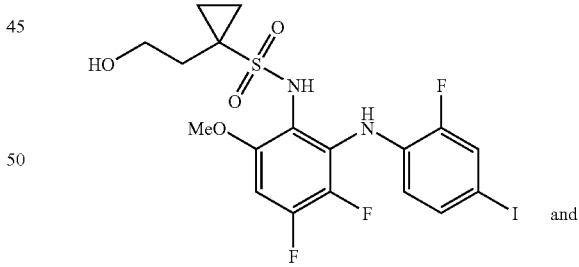
and
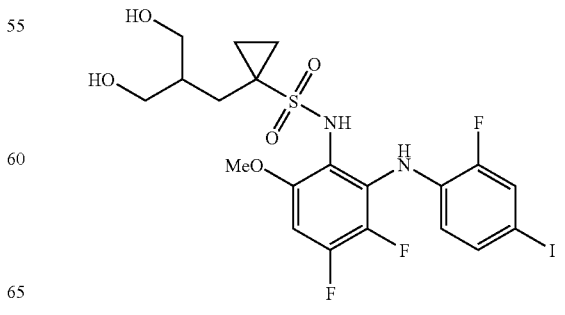

In some embodiments, the invention provides a compound of formula I, selected from:

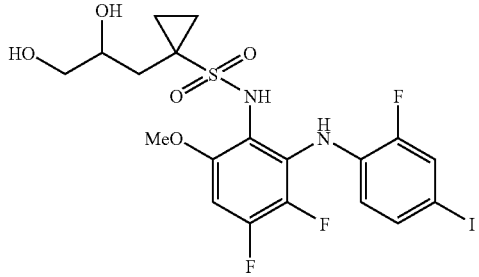

and

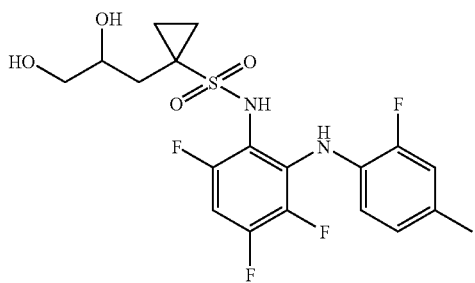

where the 2-OH carbon is in the R configuration.

In some embodiments, the invention provides a compound of formula I, selected from:

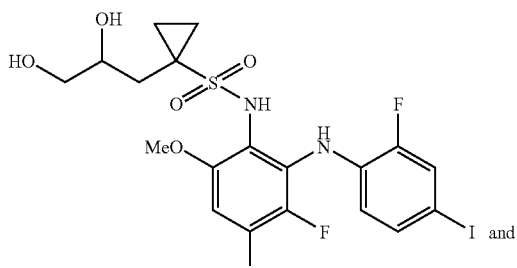

and

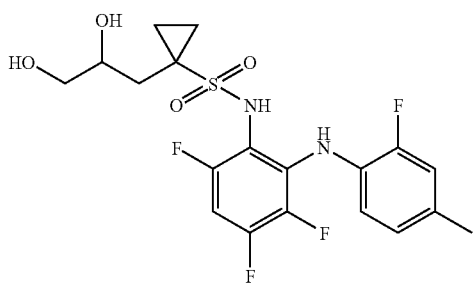

where the 2-OH carbon is in the S configuration.

In some embodiments, the invention provides a composition comprising a compound of formula I, selected from those shown below, where the 2-OH carbon is in the R configuration, substantially free of the S— isomer.

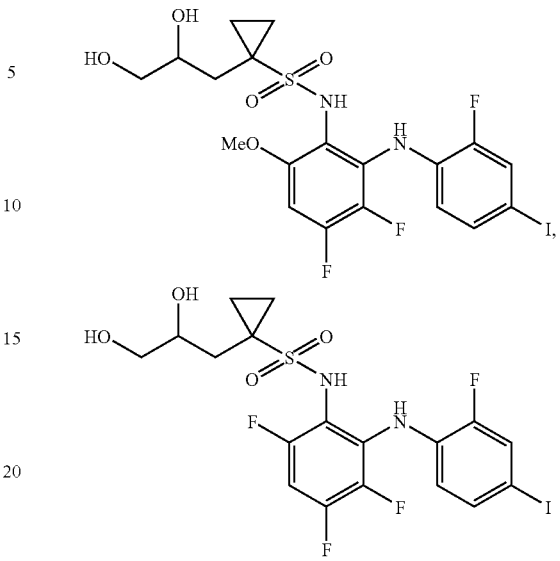

In some embodiments, the invention provides a composition comprising a compound of formula I, selected from those shown below, where the 2-OH carbon is in the S configuration, substantially free of the R— isomer.

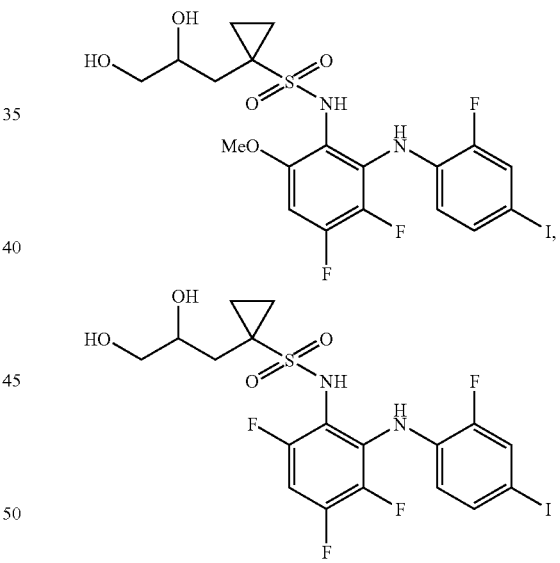

In some embodiments, this invention provides a compound of formula I, where Y is phenyl, pyridyl, or pyrazolyl. In another subgeneric embodiment, this invention provides a compound of formula I, where Y is substituted phenyl, pyridyl, or pyrazolyl. In yet another subgeneric embodiment, this invention provides a compound of formula I, where Y is Br or I. In one subgeneric embodiment, this invention provides a compound of formula I, where G is 1-piperidyl, 2-piperidyl, 3-piperidyl, or 4-piperidyl. In another subgeneric embodiment, this invention provides a compound of formula I, where C is 1-piperazyl or 2-piperazyl. In another subgeneric embodiment, this invention provides a compound of formula I, where G is morpholyl. In another subgeneric embodiment, this invention provides a compound of formula I, where G is N-methyl-2-aminoethyl. In one subgeneric embodiment, this invention provides a compound of formula I, where G is N-methyl-3-amino-n-propyl. In another subgeneric embodiment, this invention provides a compound of formula I, where G is $(CH_3)_2N$—$CH_2CH_2$—$NH$—$(CH_2)_n$—, where n is 1, 2, or 3. In another subgeneric embodiment, this invention provides a compound of formula I, where G is $(CH_3CH_2)_2N$—$CH_2CH_2$—$NH$—$(CH_2)_n$—, where n is 1 or 2. In a more specific subgeneric embodiment, this invention provides a compound of formula I, where G is 1-piperidyl, 2-piperidyl, 3-piperidyl, or 4-piperidyl; $R^0$ is H, halo, or methoxy; X is F; and Y is I. In another more specific subgeneric embodiment, this invention provides a compound of formula I, where G is 1-piperazyl or 2-piperazyl; $R^0$ is H, halo, or methoxy; X is F; and Y is I In another more specific subgeneric embodiment, this invention provides a compound of formula I, where G is morpholyl; $R^0$ is H, halo, or methoxy; X is F; and Y is I. In another more specific subgeneric embodiment, this invention provides a compound of formula I, where G is N-methyl-2-aminoethyl; $R^0$ is H, halo, or methoxy; X is F; and Y is I In another more specific subgeneric embodiment, this invention provides a compound of formula I, where G is N-methyl-3-amino-n-propyl; $R^0$ is H, halo, or methoxy; X is F; and Y is I. In another more specific subgeneric embodiment, this invention provides a compound of formula I, where G is $(CH_3)_2N$—$CH_2CH_2$—$NH$—$(CH_2)_n$—, where n is 1, 2, or 3; $R^0$ is H, halo, or methoxy; X is F; and Y is I. In another more specific subgeneric embodiment, this invention provides a compound of formula I, where G is $(CH_3CH_2)_2N$—$CH_2CH_2$—$NH$—$(CH_2)_n$—, where n is 1 or 2; $R^0$ is H, halo, or methoxy; X is F; and Y is I.

In some embodiments, the invention provides a pharmaceutical composition comprising a compound of formula I or a pharmaceutically acceptable salt, solvate, polymorph, ester, tautomer or prodrug thereof. In some embodiments the pharmaceutical composition further comprises at least one pharmaceutically acceptable carrier.

In some embodiments, the invention provides a pharmaceutical composition comprising a compound of a compound selected from:

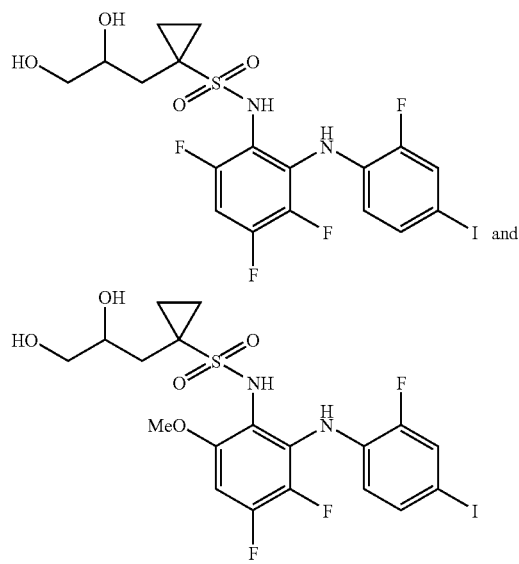

or a pharmaceutically acceptable salt, solvate, polymorph, ester, tautomer or prodrug thereof. In some embodiments, the pharmaceutical composition further comprises at least one pharmaceutically acceptable carrier. In some embodiments, the compound is in the R configuration. In some embodiments, the compound is in the R configuration, substantially free of the S— isomer. In some embodiments, the compound is in the S configuration. In some embodiments, the compound is in the S configuration, substantially free of the R— isomer. In some embodiments, the compound is:

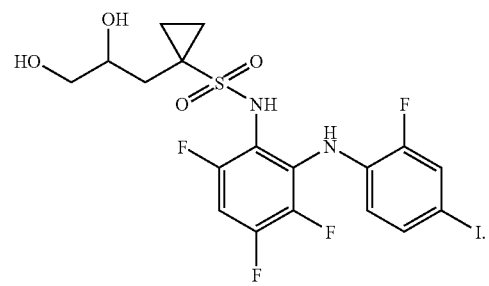

In some embodiments, the compound is:

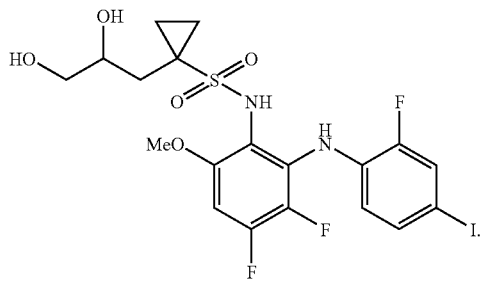

In other aspects, the present invention is directed to pharmaceutical compositions comprising effective amounts of a compound of formula I or a pharmaceutically acceptable salt, solvate, polymorph, ester, tautomer or prodrug thereof. In some embodiments, the pharmaceutical compositions further comprise a pharmaceutically acceptable carrier. Such compositions may contain adjuvants, excipients, and preservatives, agents for delaying absorption, fillers, binders, adsorbents, buffers, disintegrating agents, solubilizing agents, other carriers, and other inert ingredients. Methods of formulation of such compositions are well-known in the art.

In some aspects, the present invention is directed to a method of treating a disease in an individual suffering from said disease comprising administering to said individual an effective amount of a composition comprising a compound of formula I or a pharmaceutically acceptable salt, solvate, polymorph, ester, tautomer or prodrug thereof.

In other aspects, the present invention is directed to a method of treating a disorder in a mammal, comprising administering to said mammal a therapeutically effective amount of the compound of formula I or a pharmaceutically acceptable salt, solvate, polymorph, ester, tautomer or prodrug thereof In other aspects, the present invention is directed to a method of treating a disorder in a human, comprising administering to said mammal a therapeutically effective amount of the compound of formula I or a pharmaceutically acceptable salt, solvate, polymorph, ester, tautomer or prodrug thereof In other aspects, the present invention is directed to a method of treating a hyperproliferative disorder in a mammal, including a human, comprising administering to said mammal a therapeutically effective amount of the compound of formula I or a pharmaceutically acceptable salt, solvate, polymorph, ester, tautomer or prodrug thereof.

In other aspects, the present invention is directed to a method of treating an inflammatory disease, condition, or disorder in a mammal, including a human, comprising administering to said mammal a therapeutically effective amount of the compound of formula I, or a pharmaceutically acceptable salt, ester, prodrug, solvate, hydrate or derivative thereof.

In other aspects, the present invention is directed to a method of treating a disorder or condition which is modulated by the MEK cascade in a mammal, including a human, comprising administering to said mammal an amount of the compound of formula I, or a pharmaceutically acceptable salt, ester, prodrug, solvate, hydrate or derivative thereof, effective to modulate said cascade. The appropriate dosage for a particular patient can be determined, according to known methods, by those skilled in the art.

In other aspects, the present invention is directed to a pharmaceutical composition comprising a compound of formula I or a pharmaceutically acceptable salt, solvate, polymorph, ester, tautomer or prodrug thereof. In some embodiments, the pharmaceutical composition is in a form suitable for oral administration. In further or additional embodiments, the pharmaceutical composition is in the form of a tablet, capsule, pill, powder, sustained release formulation, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.002 to about 6 g/day. In further or additional embodiments the amount of compound of formula I is about 0.005 to about 5 g/day. In further or additional embodiments the amount of compound of formula I is about 0.01 to about 5 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the pharmaceutical composition is for administration to a mammal. In further or additional embodiments, the mammal is human. In further or additional embodiments, the pharmaceutical composition further comprises a pharmaceutical carrier, excipient and/or adjuvant. In further or additional embodiments, the pharmaceutical composition further comprises at least one therapeutic agent In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is taxol, bortezomib or both. In further or additional embodiments, the pharmaceutical composition is administered in combination with an additional therapy. In further or additional embodiments, the additional therapy is radiation therapy, chemotherapy or a combination of both. In further or additional embodiments, the pharmaceutical composition comprises a pharmaceutically acceptable salt of a compound of formula I.

In other aspects, the present invention is directed to a method for inhibiting a MEK enzyme. In some embodiments, the method comprises contacting said MEK enzyme with an amount of a composition comprising a compound of formula I or a pharmaceutically acceptable salt, solvate, polymorph, ester, tautomer or prodrug thereof, sufficient to inhibit said enzyme, wherein said enzyme is inhibited. In further or additional embodiments the enzyme is at least about 1% inhibited. In further or additional embodiments the enzyme is at least about 2% inhibited. In further or additional embodiments the enzyme is at least about 3% inhibited. In further or additional embodiments the enzyme is at least about 4% inhibited. In further or additional embodiments the enzyme is at least about 5% inhibited. In further or additional embodiments the enzyme is at least about 10% inhibited. In further or additional embodiments the enzyme is at least about 20% inhibited. In further or additional embodiments the enzyme is at least about 25% inhibited. In further or additional embodiments the enzyme is at least about 30% inhibited. In further or additional embodiments the enzyme is at least about 40% inhibited. In further or additional embodiments the enzyme is at least about 50% inhibited. In further or additional embodiments the enzyme is at least about 60% inhibited. In further or additional embodiments the enzyme is at least about 70% inhibited. In further or additional embodiments the enzyme is at least about 75% inhibited. In further or additional embodiments the enzyme is at least about 80% inhibited. In further or additional embodiments the enzyme is at least about 90% inhibited. In further or additional embodiments the enzyme is essentially completely inhibited. In further or additional embodiments the MEK enzyme is MEK kinase. In further or additional embodiments the MEK enzyme is MEK1. In further or additional embodiments the MEK enzyme is MEK2. In further or additional embodiments the contacting occurs within a cell. In further or additional embodiments the cell is a mammalian cell. In further or additional embodiments the mammalian cell is a human cell. In further or additional embodiments, the MEK enzyme is inhibited with a composition comprising a pharmaceutically acceptable salt of a compound of formula I.

In other aspects, the present invention is directed to a method of treatment of a MEK mediated disorder in an individual suffering from said disorder comprising administering to said individual an effective amount of a composition comprising a compound of formula I or a pharmaceutically acceptable salt, solvate, polymorph, ester, tautomer or prodrug thereof. In some embodiments, the composition comprising a compound of formula I is administered orally, intraduodenally, parenterally (including intravenous, subcutaneous, intramuscular, intravascular or by infusion), topically or rectally. In some embodiments, the pharmaceutical composition is in a form suitable for oral administration. In further or additional embodiments, the pharmaceutical composition is in the form of a tablet, capsule, pill, powder, sustained release formulations, solution, suspension, for parenteral injection as a sterile solution, suspension or emulsion, for topical administration as an ointment or cream or for rectal administration as a suppository. In further or additional embodiments, the pharmaceutical composition is in unit dosage forms suitable for single administration of precise dosages. In further or additional embodiments, the pharmaceutical composition further comprises a pharmaceutical carrier, excipient and/or adjuvant. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the MEK mediated disorder is a mammal. In further or additional embodiments, the individual is a human. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the MEK mediated disorder is selected from the group consisting of inflammatory diseases, infections, autoimmune disorders, stroke, ischemia, cardiac disorder, neurological disorders, fibrogenetic disorders, proliferative disorders, hyperproliferative disorders, non-cancer hyperproliferative disorders, tumors, leukemias, neoplasms, cancers, carcinomas, metabolic diseases, malignant disease, vascular restenosis, psoriasis, atherosclerosis, rheumatoid arthritis, osteoarthritis, heart failure, chronic pain, neuropathic pain, dry eye, closed angle glaucoma and wide angle glaucoma. In further or additional embodiments, the MEK mediated disorder is an inflammatory disease. In further or additional embodiments, the MEK mediated disorder is a hyperproliferative disease. In further or additional embodiments, the MEK mediated disorder is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, an effective amount of a composition comprising a pharmaceutically acceptable salt of a compound of formula I is administered.

In other aspects, the present invention is directed to a method for degrading, inhibiting the growth of or killing a cancer cell comprising contacting said cell with an amount of a composition effective to degrade, inhibit the growth of or to kill said cell, the composition comprising a compound of formula I or a pharmaceutically acceptable salt, solvate, polymorph, ester, tautomer or prodrug thereof. In some embodiments, the cancer cells comprise brain, breast, lung, ovarian, pancreatic, prostate, renal, or colorectal cancer cells. In further or additional embodiments, the composition is administered with at least one therapeutic agent. In further or additional embodiments, the therapeutic agent is taxol, bortezomib or both. In further or additional embodiments, the therapeutic agent is selected from the group consisting of cytotoxic agents, anti-angiogenesis agents and anti-neoplastic agents. In further or additional embodiments, the anti-neoplastic agents selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In some embodiments, the cancer cells are degraded. In further or additional embodiments, 1% of the cancer cells are degraded. In further or additional embodiments, 2% of the cancer cells are degraded. In further or additional embodiments, 3% of the cancer cells are degraded. In further or additional embodiments, 4% of the cancer cells are degraded. In further or additional embodiments, 5% of the cancer cells are degraded. In further or additional embodiments, 10% of the cancer cells are degraded. In further or additional embodiments, 20% of the cancer cells are degraded. In further or additional embodiments, 25% of the cancer cells are degraded. In further or additional embodiments, 30% of the cancer cells are degraded. In further or additional embodiments, 40% of the cancer cells are degraded. In further or additional embodiments, 50% of the cancer cells are degraded. In further or additional embodiments, 60% of the cancer cells are degraded. In further or additional embodiments, 70% of the cancer cells are degraded. In further or additional embodiments, 75% of the cancer cells are degraded. In further or additional embodiments, 80% of the cancer cells are degraded. In further or additional embodiments, 90% of the cancer cells are degraded. In further or additional embodiments, 100% of the cancer cells are degraded. In further or additional embodiments, essentially all of the cancer cells are degraded. In some embodiments, the cancer cells are killed. In further or additional embodiments, 1% of the cancer cells are killed. In further or additional embodiments, 2% of the cancer cells are killed. In further or additional embodiments, 3% of the cancer cells are killed. In further or additional embodiments, 4% of the cancer cells are killed. In further or additional embodiments, 5% of the cancer cells are killed. In further or additional embodiments, 10% of the cancer cells are killed. In further or additional embodiments, 20% of the cancer cells are killed. In further or additional embodiments, 25% of the cancer cells are killed. In further or additional embodiments, 30% of the cancer cells are killed. In further or additional embodiments, 40% of the cancer cells are killed. In further or additional embodiments, 50% of the cancer cells are killed. In further or additional embodiments, 60% of the cancer cells are killed. In further or additional embodiments, 70% of the cancer cells are killed. In further or additional embodiments, 75% of the cancer cells are killed. In further or additional embodiments, 80% of the cancer cells are killed. In further or additional embodiments, 90% of the cancer cells are killed. In further or additional embodiments, 100% of the cancer cells are killed. In further or additional embodiments, essentially all of the cancer cells are killed. In further or additional embodiments, the growth of the cancer cells is inhibited. In further or additional embodiments, the growth of the cancer cells is about 1% inhibited. In further or additional embodiments, the growth of the cancer cells is about 2% inhibited. In further or additional embodiments, the growth of the cancer cells is about 3% inhibited. In further or additional embodiments, the growth of the cancer cells is about 4% inhibited. In further or additional embodiments, the growth of the cancer cells is about 5% inhibited. In further or additional embodiments, the growth of the cancer cells is about 10% inhibited. In further or additional embodiments, the growth of the cancer cells is about 20% inhibited. In Thither or additional embodiments, the growth of the cancer cells is about 25% inhibited. In further or additional embodiments, the growth of the cancer cells is about 30% inhibited. In further or additional embodiments, the growth of the cancer cells is about 40% inhibited. In further or additional embodiments, the growth of the cancer cells is about 50% inhibited. In further or additional embodiments, the growth of the cancer cells is about 60% inhibited. In further or additional embodiments, the growth of the cancer cells is about 70% inhibited. In further or additional embodiments, the growth of the cancer cells is about 75% inhibited. In further or additional embodiments, the growth of the cancer cells is about 80% inhibited. In further or additional embodiments, the growth of the cancer cells is about 90% inhibited. In further or additional embodiments, the growth of the cancer cells is about 100% inhibited. In further or additional embodiments, a composition comprising a pharmaceutically acceptable salt of a compound of formula I is used.

In other aspects, the present invention is directed to a method for the treatment or prophylaxis of a proliferative disease in an individual comprising administering to said individual an effective amount of a composition comprising a compound of formula I or a pharmaceutically acceptable salt, solvate, polymorph, ester, tautomer or prodrug thereof. In some embodiments, the proliferative disease is cancer, psoriasis, restenosis, autoimmune disease, or atherosclerosis. In further or additional embodiments, the proliferative disease is a hyperproliferative disease. In further or additional embodiments, the proliferative disease is selected from the group consisting of tumors, leukemias, neoplasms, cancers, carcinomas and malignant disease. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the antineoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the proliferative disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of an inflammatory disease in an individual comprising administering to said individual an effective amount of a composition comprising a compound of formula I or a pharmaceutically acceptable salt, solvate, polymorph, ester, tautomer or prodrug thereof. In further or additional embodiments, the inflammatory disease is selected from chronic inflammatory diseases, rheumatoid arthritis, rheumatoid arthritis, spondyloarthropathies, gouty arthritis, osteoarthritis, juvenile arthritis, acute rheumatic arthritis, enteropathic arthritis, neuropathic arthritis, psoriatic arthritis, pyogenic arthritis, atherosclerosis, systemic lupus erythematosus, inflammatory bowel disease, irritable bowel syndrome, ulcerative colitis, reflux esophagitis, Crohn's disease, gastritis, asthma, allergies, respiratory distress syndrome, pancreatitis, chronic obstructive pulmonary disease, pulmonary fibrosis, psoriasis, eczema or scleroderma. In some embodiments, the composition comprising a compound of formula I is administered in combination with an additional therapy. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from the inflammatory disease is a mammal. In further or additional embodiments, the individual is a human. In further or additional embodiments, an effective amount of a composition comprising a pharmaceutically acceptable salt of a compound of formula I is administered.

In other aspects, the present invention is directed to a method for the treatment or prophylaxis of cancer in an individual comprising administering to said individual an effective amount of a composition comprising a compound of formula I or a pharmaceutically acceptable salt, solvate, polymorph, ester, tautomer or prodrug thereof. In further or additional embodiments, the cancer is brain cancer, breast cancer, lung cancer, ovarian cancer, pancreatic cancer, prostate cancer, renal cancer, colorectal cancer or leukemia. In further or additional embodiments, the fibrogenetic disorder is scleroderma, polymyositis, systemic lupus, rheumatoid arthritis, liver cirrhosis, keloid formation, interstitial nephritis or pulmonary fibrosis. In further or additional embodiments, the cancer is brain cancer, breast cancer, lung cancer, ovarian cancer, pancreatic cancer, prostate cancer, renal cancer, colorectal cancer or leukemia. In further or additional embodiments, the cancer is brain cancer or adrenocortical carcinoma. In further or additional embodiments, the cancer is breast cancer. In further or additional embodiments, the cancer is ovarian cancer. In further or additional embodiments, the cancer is pancreatic cancer. In further or additional embodiments, the cancer is prostate cancer. In further or additional embodiments, the cancer is renal cancer. In further or additional embodiments, the cancer is colorectal cancer. In further or additional embodiments, the cancer is myeloid leukemia. In further or additional embodiments, the cancer is glioblastoma. In further or additional embodiments, the cancer is follicular lymphoma. In further or additional embodiments, the cancer is pre-B acute leukemia. In further or additional embodiments, the cancer is chronic lymphocytic B-leukemia. In further or additional embodiments, the cancer is mesothelioma. In further or additional embodiments, the cancer is small cell line cancer. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; anti-neoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method of reducing the size of a tumor, inhibiting tumor size increase, reducing tumor proliferation or preventing tumor proliferation in an individual, comprising administering to said individual an effective amount of a composition comprising a compound of formula I or a pharmaceutically acceptable salt, solvate, polymorph, ester, tautomer or prodrug thereof. In some embodiments, the size of a tumor is reduced. In further or additional embodiments, the size of a tumor is reduced by at least 1%. In further or additional embodiments, the size of a tumor is reduced by at least 2%. In further or additional embodiments, the size of a tumor is reduced by at least 3%. In further or additional embodiments, the size of a tumor is reduced by at least 4%. In further or additional embodiments, the size of a tumor is reduced by at least 5%. In further or additional embodiments, the size of a tumor is reduced by at least 10%. In further or additional embodiments, the size of a tumor is reduced by at least 20%. In further or additional embodiments, the size of a tumor is reduced by at least 25%. In further or additional embodiments, the size of a tumor is reduced by at least 30%. In further or additional embodiments, the size of a tumor is reduced by at least 40%. In further or additional embodiments, the size of a tumor is reduced by at least 50%. In further or additional embodiments, the size of a tumor is reduced by at least 60%. In further or additional embodiments, the size of a tumor is reduced by at least 70%. In further or additional embodiments, the size of a tumor is reduced by at least 75%. In further or additional embodiments, the size of a tumor is reduced by at least 80%. In further or additional embodiments, the size of a tumor is reduced by at least 85%. In further or additional embodiments, the size of a tumor is reduced by at least 90%. In further or additional embodiments, the size of a tumor is reduced by at least 95%. In further or additional embodiments, the tumor is eradicated. In some embodiments, the size of a tumor does not increase. In some embodiments, tumor proliferation is reduced. In some embodiments, tumor proliferation is reduced by at least 1%. In some embodiments, tumor proliferation is reduced by at least 2%. In some embodiments, tumor proliferation is reduced by at least 3%. In some embodiments, tumor proliferation is reduced by at least 4%. In some embodiments, tumor proliferation is reduced by at least 5%. In some embodiments, tumor proliferation is reduced by at least 10%. In some embodiments, tumor proliferation is reduced by at least 20%. In some embodiments, tumor proliferation is reduced by at least 25%. In some embodiments, tumor proliferation is reduced by at least 30%. In some embodiments, tumor proliferation is reduced by at least 40%. In some embodiments, tumor proliferation is reduced by at least 50%. In some embodiments, tumor proliferation is reduced by at least 60%. In some embodiments, tumor proliferation is reduced by at least 70%. In some embodiments, tumor proliferation is reduced by at least 75%. In some embodiments, tumor proliferation is reduced by at least 75%. In some embodiments, tumor proliferation is reduced by at least 80%. In some embodiments, tumor proliferation is reduced by at least 90%. In some embodiments, tumor proliferation is reduced by at least 95%. In some embodiments, tumor proliferation is prevented. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In further or additional embodiments, the therapeutic agent is selected from the group of cytotoxic agents, anti-angiogenesis agents and anti-neoplastic agents. In further or additional embodiments, the anti-neoplastic agent is selected from the group of consisting of alkylating agents, anti-metabolites, epidophyllotoxins; antineoplastic enzymes, topoisomerase inhibitors, procarbazines, mitoxantrones, platinum coordination complexes, biological response modifiers and growth inhibitors, hormonal/anti-hormonal therapeutic agents, and haematopoietic growth factors. In further or additional embodiments, the therapeutic agent is selected from taxol, bortezomib or both. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

In other aspects, the present invention is directed to a method for achieving an effect in a patient comprising the administration of an effective amount of a composition comprising a compound of formula I or a pharmaceutically acceptable salt, solvate, polymorph, ester, tautomer or prodrug thereof, to a patient, wherein the effect is selected from the group consisting of inhibition of various cancers, immunological diseases, and inflammatory diseases. In some embodiments, the effect is inhibition of various cancers. In further or additional embodiments, the effect is inhibition of immunological diseases. In further or additional embodiments, the effect is inhibition inflammatory diseases. In some embodiments, the composition comprising a compound of formula I is administered in combination with an additional therapy. In further or additional embodiments, the additional therapy is radiation therapy, chemotherapy or a combination of both. In further or additional embodiments, the composition comprising a compound of formula I is administered in combination with at least one therapeutic agent. In some embodiments, the composition is administered orally, intraduodenally, parenterally (including intravenous, subcutaneous, intramuscular, intravascular or by infusion), topically or rectally. In further or additional embodiments the amount of compound of formula I is in the range of about 0.001 to about 1000 mg/kg body weight/day. In further or additional embodiments the amount of compound of formula I is in the range of about 0.5 to about 50 mg/kg/day. In further or additional embodiments the amount of compound of formula I is about 0.001 to about 7 g/day. In further or additional embodiments the amount of compound of formula I is about 0.01 to about 7 g/day. In further or additional embodiments the amount of compound of formula I is about 0.02 to about 5 g/day. In further or additional embodiments the amount of compound of formula I is about 0.05 to about 2.5 g/day. In further or additional embodiments the amount of compound of formula I is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments the compound of formula I is administered in a single dose, once daily. In further or additional embodiments the compound of formula I is administered in multiple doses, more than once per day. In further or additional embodiments the compound of formula I is administered twice daily. In further or additional embodiments the compound of formula I is administered three times per day. In further or additional embodiments the compound of formula I is administered four times per day. In further or additional embodiments the compound of formula I is administered more than four times per day. In some embodiments, the individual suffering from cancer is a mammal. In further or additional embodiments, the individual is a human. In further or additional embodiments, an effective amount of a composition comprising a pharmaceutically acceptable salt of a compound of formula I is administered.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain Chemical Terminology

Unless defined otherwise, all technical and scientific terms used herein have the same meaning as is commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can come and go, but equivalent information can be found by searching the internet or other appropriate reference source. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

Definition of standard chemistry terms may be found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —CH$_2$O— is equivalent to —OCH$_2$—.

Unless otherwise noted, the use of general chemical terms, such as though not limited to "alkyl," "amine," "aryl," are equivalent to their optionally substituted forms. For example, "alkyl," as used herein, includes optionally substituted alkyl.

The compounds presented herein may possess one or more stereocenters and each center may exist in the R or S configuration, or combinations thereof. Likewise, the compounds presented herein may possess one or more double bonds and each may exist in the E (trans) or Z (cis) configuration, or combinations thereof. Presentation of one particular stereoisomer, regioisomer, diastereomer, enantiomer or epimer should be understood to include all possible stereoisomers, regioisomers, diastereomers, enantiomers or epimers and mixtures thereof. Thus, the compounds presented herein include all separate configurational stereoisomeric, regioisomeric, diastereomeric, enantiomeric, and epimeric forms as well as the corresponding mixtures thereof. Presentation of one particular chemical structure or chemical name for a compound which contains one or more chiral centers, but which does not designate a particular stereochemistry, should be understood to include all possible stereoisomers, including mixtures of all possible stereoisomers, pure forms or substantially pure forms of one particular stereoisomer and pure forms or substantially pure forms of the alternate stereoisomer. Techniques for inverting or leaving unchanged a particular stereocenter, and those for resolving mixtures of stereoisomers are well known in the art and it is well within the ability of one of skill in the art to choose an appropriate method for a particular situation. See, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

The terms "moiety", "chemical moiety", "group" and "chemical group", as used herein refer to a specific segment or functional group of a molecule. Chemical moieties are often recognized chemical entities embedded in or appended to a molecule.

The term "bond" or "single bond" refers to a chemical bond between two atoms, or two moieties when the atoms joined by the bond are considered to be part of larger substructure.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined below. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons (except in those instances where macromolecular substituents are clearly intended, e.g., polypeptides, polysaccharides, polyethylene glycols, DNA, RNA and the like).

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "A and A', together with the carbon atom to which they are attached, form a 3- to 6-member saturated ring", as used herein, refers to the following structures for compounds of formula I:

Compounds of formula I

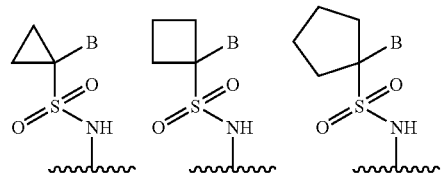

-continued

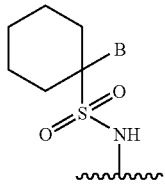

The terms "heteroatom" or "hetero" as used herein, alone or in combination, refer to an atom other than carbon or hydrogen. Heteroatoms are may be independently selected from among oxygen, nitrogen, sulfur, phosphorous, silicon, selenium and tin but are not limited to these atoms. In embodiments in which two or more heteroatoms are present, the two or more heteroatoms can be the same as each another, or some or all of the two or more heteroatoms can each be different from the others.

The term "alkyl" as used herein, alone or in combination, refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated.

The term "alkenyl" as used herein, alone or in combination, refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated.

The term "alkynyl" as used herein, alone or in combination, refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated.

The terms "heteroalkyl", "heteroalkenyl" and "heteroalkynyl" as used herein, alone or in combination, refer to optionally substituted alkyl, alkenyl and alkynyl structures respectively, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, silicon, phosphorous, tin or combinations thereof), or heteroatomic group such as though not limited to —O—O—, —S—S—, —O—S—, —S—O—, =N—N=, —N=N—, —N=N—NH—, —P(O)$_2$—, —O—P(O)$_2$—, —P(O)$_2$—O—, —S(O)—, —S(O)$_2$—, —SnH$_2$— and the like.

The terms "haloalkyl", "haloalkenyl" and "haloalkynyl" as used herein, alone or in combination, refer to optionally substituted alkyl, alkenyl and alkynyl groups respectively, as defined above, in which one or more hydrogen atoms is replaced by fluorine, chlorine, bromine or iodine atoms, or combinations thereof. In some embodiments two or more hydrogen atoms may be replaced with halogen atoms that are the same as each another (e.g. difluoromethyl); in other embodiments two or more hydrogen atoms may be replaced with halogen atoms that are not all the same as each other (e.g. 1-chloro-1-fluoro-1-iodoethyl). Non-limiting examples of haloalkyl groups are fluoromethyl and bromoethyl. A non-limiting example of a haloalkenyl group is bromoethenyl. A non-limiting example of a haloalkynyl group is chloroethynyl.

The term "carbon chain" as used herein, alone or in combination, refers to any alkyl, alkenyl, alkynyl, heteroalkyl, heteroalkenyl or heteroalkynyl group, which is linear, cyclic, or any combination thereof. If the chain is part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining the chain length. If the chain contains heteroatoms as part of the backbone, those atoms are not calculated as part of the carbon chain length.

The terms "cycle", "cyclic", "ring" and "membered ring" as used herein, alone or in combination, refer to any covalently closed structure, including alicyclic, heterocyclic, aromatic, heteroaromatic and polycyclic fused or non-fused ring systems as described herein. Rings can be optionally substituted. Rings can form part of a fused ring system. The term "membered" is meant to denote the number of skeletal atoms that constitute the ring. Thus, by way of example only, cyclohexane, pyridine, pyran and pyrimidine are six-membered rings and cyclopentane, pyrrole, tetrahydrofuran and thiophene are five-membered rings.

The term "fused" as used herein, alone or in combination, refers to cyclic structures in which two or more rings share one or more bonds.

The term "cycloalkyl" as used herein, alone or in combination, refers to an optionally substituted, saturated, hydrocarbon monoradical ring, containing from three to about fifteen ring carbon atoms or from three to about ten ring carbon atoms, though may include additional, non-ring carbon atoms as substituents (e.g. methylcyclopropyl). Whenever it appears herein, a numerical range such as "$C_3$-$C_6$ cycloalkyl" or "$C_{3-6}$ cycloalkyl", means that the cycloalkyl group may consist of 3 carbon atoms, 4 carbon atoms, 5 carbon atoms or 6 carbon atoms, i.e., is cyclopropyl, cyclobutyl, cyclopentyl or cycloheptyl, although the present definition also covers the occurrence of the term "cycloalkyl" where no numerical range is designated. The term includes fused, non-fused, bridged and spiro radicals. A fused cycloalkyl may contain from two to four fused rings where the ring of attachment is a cycloalkyl ring, and the other individual rings may be alicyclic, heterocyclic, aromatic, heteroaromatic or any combination thereof. Examples include, but are not limited to cyclopropyl, cyclopentyl, cyclohexyl, decalinyl, and bicyclo[2.2.1]heptyl and adamantyl ring systems. Illustrative examples include, but are not limited to the following moieties:

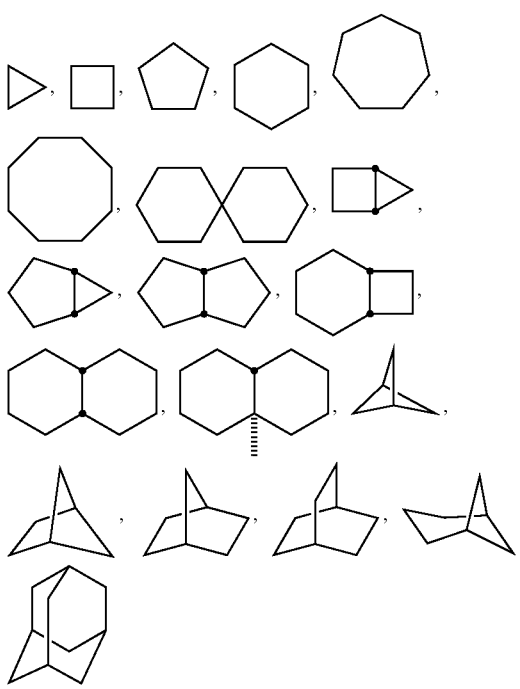

and the like.

The terms "non-aromatic heterocyclyl" and "heteroalicyclyl" as used herein, alone or in combination, refer to optionally substituted, saturated, partially unsaturated, or fully unsaturated nonaromatic ring monoradicals containing from three to about twenty ring atoms, where one or more of the ring atoms are an atom other than carbon, independently selected from among oxygen, nitrogen, sulfur, phosphorous, silicon, selenium and tin but are not limited to these atoms. In embodiments in which two or more heteroatoms are present in the ring, the two or more heteroatoms can be the same as each another, or some or all of the two or more heteroatoms can each be different from the others. The terms include fused, non-fused, bridged and spiro radicals. A fused non-aromatic heterocyclic radical may contain from two to four fused rings where the attaching ring is a non-aromatic heterocycle, and the other individual rings may be alicyclic, heterocyclic, aromatic, heteroaromatic or any combination thereof. Fused ring systems may be fused across a single bond or a double bond, as well as across bonds that are carbon-carbon, carbon-hetero atom or hetero atom-hetero atom. The terms also include radicals having from three to about twelve skeletal ring atoms, as well as those having from three to about ten skeletal ring atoms. Attachment of a non-aromatic heterocyclic subunit to its parent molecule can be via a heteroatom or a carbon atom. Likewise, additional substitution can be via a heteroatom or a carbon atom. As a non-limiting example, an imidazolidine non-aromatic heterocycle may be attached to a parent molecule via either of its N atoms (imidazolidin-1-yl or imidazolidin-3-yl) or any of its carbon atoms (imidazolidin-2-yl, imidazolidin-4-yl or imidazolidin-5-yl). In certain embodiments, non-aromatic heterocycles contain one or more carbonyl or thiocarbonyl groups such as, for example, oxo- and thio-containing groups. Examples include, but are not limited to pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Illustrative examples of heterocycloalkyl groups, also referred to as non-aromatic heterocycles, include:

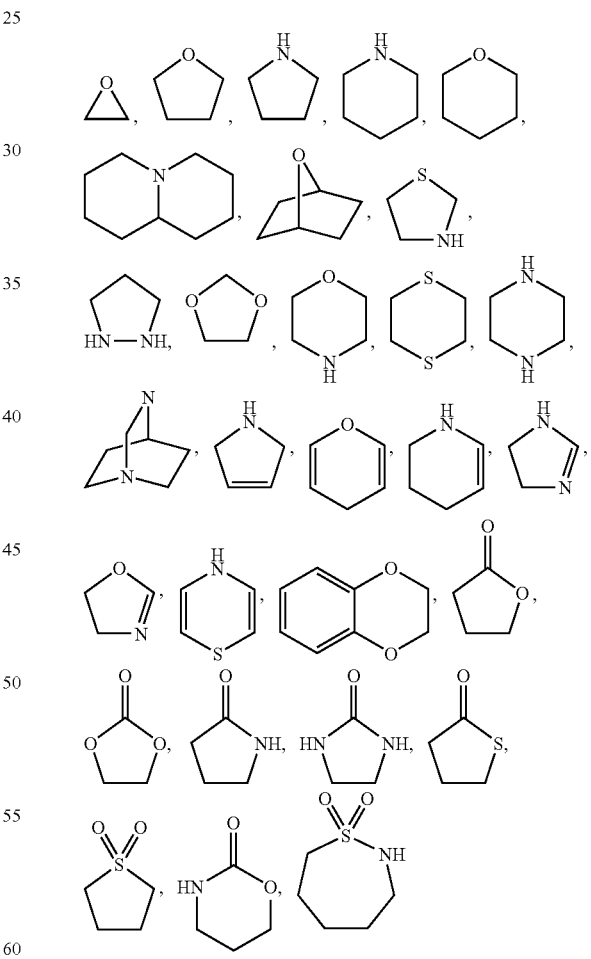

and the like. The terms also include all ring forms of the carbohydrates, including but not limited to the monosaccharides, the disaccharides and the oligosaccharides.

The term "aromatic" as used herein, refers to a planar, cyclic or polycyclic, ring moiety having a delocalized π-electron system containing 4n+2π electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings may be alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, sulfur, phosphorous, silicon, selenium and tin but not limited to these atoms and with the proviso that the ring of said group does not contain two adjacent O or S atoms. In embodiments in which two or more heteroatoms are present in the ring, the two or more heteroatoms can be the same as each another, or some or all of the two or more heteroatoms can each be different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. Bonding to a heteroaryl group can be via a carbon atom or a heteroatom. Thus, as a non-limiting example, an imidazole group may be attached to a parent molecule via any of its carbon atoms (imidazol-2-yl, imidazol-4-yl or imidazol-5-yl), or its nitrogen atoms (imidazol-1-yl or imidazol-3-yl). Likewise, a heteroaryl group may be further substituted via any or all of its carbon atoms, and/or any or all of its heteroatoms. A fused heteroaryl radical may contain from two to four fused rings where the ring of attachment is a heteroaromatic ring and the other individual rings may be alicyclic, heterocyclic, aromatic, heteroaromatic or any combination thereof. A non-limiting example of a single ring heteroaryl group includes pyridyl; fused ring heteroaryl groups include benzimidazolyl, quinolinyl, acridinyl; and a non-fused bi-heteroaryl group includes bipyridinyl. Further examples of heteroaryls include, without limitation, furanyl, thienyl, oxazolyl, acridinyl, phenazinyl, benzimidazolyl, benzofuranyl, benzoxazolyl, benzothiazolyl, benzothiadiazolyl, benzothiophenyl, benzoxadiazolyl, benzotriazolyl, imidazolyl, indolyl, isoxazolyl, isoquinolinyl, indolizinyl, isothiazolyl, isoindolyloxadiazolyl, indazolyl, pyridyl, pyridazyl, pyrimidyl, pyrazinyl, pyrrolyl, pyrazinyl, pyrazolyl, purinyl, phthalazinyl, pteridinyl, quinolinyl, quinazolinyl, quinoxalinyl, triazolyl, tetrazolyl, thiazolyl, triazinyl, thiadiazolyl and the like, and their oxides, such as for example pyridyl-N-oxide. Illustrative examples of heteroaryl groups include the following moieties:

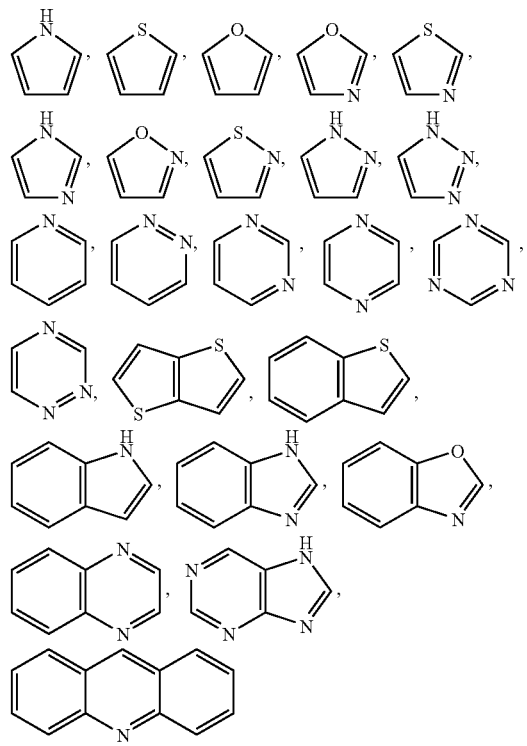

and the like.

The term "heterocyclyl" as used herein, alone or in combination, refers collectively to heteroalicyclyl and heteroaryl groups. Herein, whenever the number of carbon atoms in a heterocycle is indicated (e.g., $C_1$-$C_6$ heterocycle), at least one non-carbon atom (the heteroatom) must be present in the ring. Designations such as "$C_1$-$C_6$ heterocycle" refer only to the number of carbon atoms in the ring and do not refer to the total number of atoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). For heterocycles having two or more heteroatoms, those two or more heteroatoms can be the same or different from one another. Heterocycles can be optionally substituted. Non-aromatic heterocyclic groups include groups having only three atoms in the ring, while aromatic heterocyclic groups must have at least five atoms in the ring. Bonding (i.e. attachment to a parent molecule or further substitution) to a heterocycle can be via a heteroatom or a carbon atom.

The terms "halogen", "halo" or "halide" as used herein, alone or in combination refer to fluoro, chloro, bromo and/or iodo.

The term "amino" as used herein, alone or in combination, refers to the monoradical —$NH_2$.

The term "alkylamino" as used herein, alone or in combination, refers to the monoradical —NH(alkyl) where alkyl is as defined herein.

The term "dialkylamino" as used herein, alone or in combination, refers to the monoradical —N(alkyl)(alkyl) where each alkyl may be identical or non-identical and is as defined herein.

The term "diamino alkyl" as used herein, alone or in combination, refers to an alkyl group containing two amine groups, wherein said amine groups may be substituents on the alkyl group which may be amino, alkylamino, or dialkylamino groups, or wherein one or both of said amine groups may form part of an alkyl chain to form -alkylene-N(H or alkyl)-alkylene-N(H or alkyl or alkylene-)(H or alkyl or alkylene-).

The term "hydroxy" as used herein, alone or in combination, refers to the monoradical —OH.

The term "cyano" as used herein, alone or in combination, refers to the monoradical —CN.

The term "cyanomethyl" as used herein, alone or in combination, refers to the monoradical —CH$_2$CN.

The term "nitro" as used herein, alone or in combination, refers to the monoradical —NO$_2$.

The term "oxy" as used herein, alone or in combination, refers to the diradical —O—.

The term "oxo" as used herein, alone or in combination, refers to the diradical =O.

The term "carbonyl" as used herein, alone or in combination, refers to the diradical —C(=O)—, which may also be written as —C(O)—.

The terms "carboxy" or "carboxyl" as used herein, alone or in combination, refer to the moiety —C(O)OH, which may also be written as —COOH.

The term "alkoxy" as used herein, alone or in combination, refers to an alkyl ether radical, —O-alkyl, including the groups —O-aliphatic and —O-carbocyclyl, wherein the alkyl, aliphatic and carbocyclyl groups may be optionally substituted, and wherein the terms alkyl, aliphatic and carbocyclyl are as defined herein. Non-limiting examples of alkoxy radicals include methoxy, ethoxy, n-propoxy, isopropoxy, n-butoxy, iso-butoxy, sec-butoxy, tert-butoxy and the like.

The term "sulfinyl" as used herein, alone or in combination, refers to the diradical —S(=O)—.

The term "sulfonyl" as used herein, alone or in combination, refers to the diradical —S(=O)$_2$—.

The terms "sulfonamide", "sulfonamido" and "sulfonamidyl" as used herein, alone or in combination, refer to the diradical groups —S(=O)$_2$—NH— and —NH—S(=O)$_2$—.

The terms "sulfamide", "sulfamido" and "sulfamidyl" as used herein, alone or in combination, refer to the diradical group —NH—S(=O)$_2$—NH—.

The term "reactant," as used herein, refers to a nucleophile or electrophile used to create covalent linkages.

It is to be understood that in instances where two or more radicals are used in succession to define a substituent attached to a structure, the first named radical is considered to be terminal and the last named radical is considered to be attached to the structure in question. Thus, for example, the radical arylalkyl is attached to the structure in question by the alkyl group.

Certain Pharmaceutical Terminology

The term "MEK inhibitor" as used herein refers to a compound that exhibits an IC$_{50}$ with respect to MEK activity, of no more than about 100 µM or not more than about 50 µM, as measured in the Mek1 kinase assay described generally herein. "IC$_{50}$" is that concentration of inhibitor which reduces the activity of an enzyme (e.g., MEK) to half-maximal level. Compounds described herein have been discovered to exhibit inhibition against MEK. Compounds of the present invention preferably exhibit an IC$_{50}$ with respect to MEK of no more than about 10 µM, more preferably, no more than about 5 µM, even more preferably not more than about 1 µM, and most preferably, not more than about 200 nM, as measured in the Mek1 kinase assay described herein.

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively non-toxic chemical compounds or agents that facilitate the incorporation of a compound into cells or tissues.

The term "agonist," as used herein, refers to a molecule such as a compound, a drug, an enzyme activator or a hormone modulator which enhances the activity of another molecule or the activity of a receptor site.

The term "antagonist," as used herein, refers to a molecule such as a compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable derivative or prodrug" as used herein, refers to any pharmaceutically acceptable salt, ester, salt of an ester or other derivative of a compound of formula I or formula II, which, upon administration to a recipient, is capable of providing, either directly or indirectly, a compound of this invention or a pharmaceutically active metabolite or residue thereof. Particularly favored derivatives or prodrugs are those that increase the bioavailability of the compounds of this invention when such compounds are administered to a patient (e.g., by allowing orally administered compound to be more readily absorbed into blood) or which enhance delivery of the parent compound to a biological compartment (e.g., the brain or lymphatic system).

The term "pharmaceutically acceptable salt" as used herein, includes salts that retain the biological effectiveness of the free acids and bases of the specified compound and that are not biologically or otherwise undesirable. Compounds described may possess acidic or basic groups and therefore may react with any of a number of inorganic or organic bases, and inorganic and organic acids, to form a pharmaceutically acceptable salt. Examples of pharmaceutically acceptable salts include those salts prepared by reaction of the compounds described herein with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorides, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, oxalates, palmoate, pectinate, persulfate, phenylacetates, phenylpropionates, 3-phenylpropionate, phosphate, picrate, pivalate, propionate, pyrosulfate, pyrophosphate, propiolate, propionates, phthalate, phenylbutyrate, propanesulfonate, pyrophosphates, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds of the invention and their pharmaceutically acceptable acid addition salts. (See for example Berge et al., *J. Pharm. Sci.* 1977, 66, 1-19.) Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N^+(C_{1-4}$ alkyl$)_4$, and the like. Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they may contain. Water or oil-soluble or dispersible products may be obtained by such quaternization. See, for example, Berge et al., supra. These salts can be prepared in situ during the final isolation and purification of the compounds of the invention, or by separately reacting a purified compound in its free base form with a suitable organic or inorganic acid, and isolating the salt thus formed.

As used herein, a "prodrug" is a compound that may be converted under physiological conditions or by solvolysis to the specified compound or to a pharmaceutically acceptable salt of such compound. Prodrugs include compounds wherein an amino acid residue, or a polypeptide chain of two or more amino acid residues, is covalently joined through an amide or ester bond to a free amino, hydroxy, or carboxylic acid group of compounds of Formulas I. The amino acid residues contemplated include but are not limited to the 20 naturally-occurring amino acids. Other suitable amino acids include 4-hydroxyproline, hydroxylysine, demosine, isodemosine, 3-methyl histidine, norvaline, β-alanine, γ-aminobutyric acid, cirtulline, homocysteine, homoserine, ornithine and methionine sulfone. Additional types of prodrugs are well known in the art.

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are well known in the art. See for example *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference. The prodrugs described herein include, but are not limited to, the following groups and combinations of these groups; amine derived prodrugs:

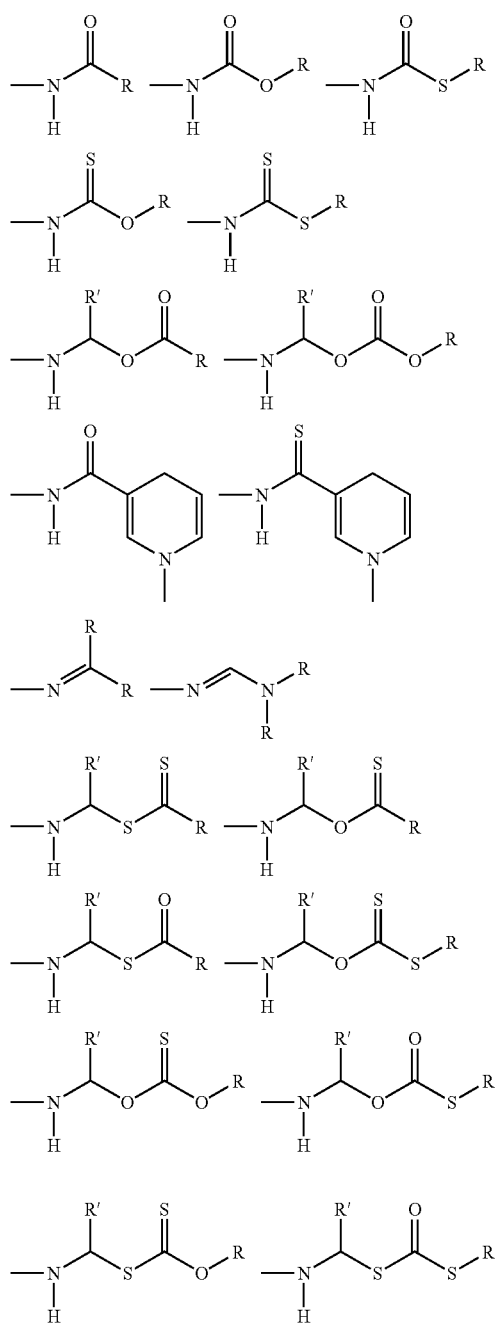

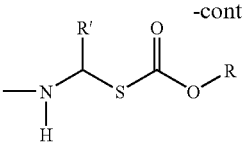

Hydroxy prodrugs include, but are not limited to acyloxyalkyl esters, alkoxycarbonyloxyalkyl esters, alkyl esters, aryl esters and disulfide containing esters.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics*, 9th Edition, McGraw-Hill (1996).

Compounds

Described herein are compounds of formula I, pharmaceutically acceptable salts, solvates, polymorphs, esters, tautomers or prodrugs thereof,

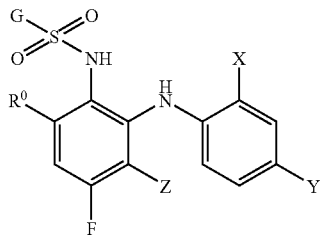

formula I wherein

Z is H or F;

X is F, Cl, $CH_3$, $CH_2OH$, $CH_2F$, $CHF_2$, or $CF_3$;

Y is I, Br, Cl, $CF_3$, $C_1$-$C_3$ alkyl, $C_2$-$C_3$ alkenyl, $C_2$-$C_3$ alkynyl, cyclopropyl, OMe, OEt, SMe, phenyl or Het, where Het is a 5- to 10-membered mono- or bicyclic heterocyclic group, which group is saturated, olefinic, or aromatic, containing 1-5 ring heteroatoms selected independently from N, O, and S; where all said phenyl or Het groups are optionally substituted with F, Cl, Br, I, acetyl, methyl, CN, $NO_2$, $CO_2H$, $C_1$-$C_3$ alkyl, $C_1$-$C_3$ alkoxy, $C_1$-$C_3$ alkyl-C(=O)—, $C_1$-$C_3$ alkyl-C(=S)—, $C_1$-$C_3$ alkoxy-C(=S)—, $C_1$-$C_3$ alkyl-C(=O)O—, $C_1$-$C_3$ alkyl-O-(C=O)—, $C_1$-$C_3$ alkyl-C(=O)NH—, $C_1$-$C_3$ alkyl-C(=NH)NH—, $C_1$-$C_3$ alkyl-NH—(C=O)—, di-$C_1$-$C_3$ alkyl-N—(C=O)—, $C_1$-$C_3$ alkyl-C(=O)N($C_1$-$C_3$ alkyl)-, $C_1$-$C_3$ alkyl-S(=O)$_2$NH— or trifluoromethyl;

all said methyl, ethyl, $C_1$-$C_3$ alkyl, and cyclopropyl groups are optionally substituted with OH;

all said methyl groups are optionally substituted with one, two, or three F atoms;

$R^0$ is H, F, Cl, Br, I, $CH_3NH$—, $(CH_3)_2N$—, $C_1$-$C_6$ alkyl, $C_1$-$C_4$ alkoxy, $C_3$-$C_6$ cycloalkyl, $C_2$-$C_6$ alkenyl, $C_2$-$C_6$ alkynyl, phenyl, monosubstituted phenyl, $O(C_1$-$C_4$ alkyl), O—C(=O)($C_1$-$C_4$ alkyl) or C(=O)O($C_1$-$C_4$ alkyl); where said alkyl, alkoxy, cycloalkyl, alkenyl, alkynyl and phenyl groups are optionally substituted with 1-3 substituents selected independently from F, Cl, Br, I, OH, CN, cyanomethyl, nitro, phenyl and trifluoromethyl;

said $C_1$-$C_6$ alkyl and $C_1$-$C_4$ alkoxy groups also optionally substituted with $OCH_3$ or $OCH_2CH_3$; G is $G_1$, $G_2$, $R_{1a}$, $R_{1b}$, $R_{1c}$, $R_{1d}$, $R_{1e}$, $Ar_1$, $Ar_2$ or $Ar_3$; where $G_1$ is $C_1$-$C_6$ alkyl optionally substituted with one amino, $C_1$-$C_3$ alkylamino, or dialkylamino group, said dialkylamino group comprising two $C_1$-$C_4$ alkyl groups which may be identical or non-identical; or $G_1$ is a $C_3$-$C_8$ diamino alkyl group;

$G_2$ is a 5- or 6-membered ring, which is saturated, unsaturated, or aromatic, containing 1-3 ring heteroatoms selected independently from N, O, and S, optionally substituted with 1-3 substituents selected independently from F, Cl, OH, O($C_1$-$C_3$ alkyl), $OCH_3$, $OCH_2CH_3$, $CH_3C(=O)NH$, $CH_3C(=O)O$, CN, $CF_3$, and a 5-membered aromatic heterocyclic group containing 1-4 ring heteroatoms selected independently from N, O, and S;

$R_{1a}$ is methyl, optionally substituted with 1-3 fluorine atoms or 1-3 chlorine atoms, or with OH, cyclopropoxy, or $C_1$-$C_3$ alkoxy, where said cyclopropoxy group or the $C_1$-$C_3$ alkyl moieties of said $C_1$-$C_3$ alkoxy groups are optionally substituted with one hydroxy or methoxy group, and where all $C_3$— alkyl groups within said $C_1$-$C_4$ alkoxy are optionally further substituted with a second OH group;

$R_{1b}$ is $CH(CH_3)$—$C_{1-3}$ alkyl or $C_3$-$C_6$ cycloalkyl, said alkyl and cycloalkyl groups optionally substituted with 1-3 substituents selected independently from F, Cl, Br, I, OH, $OCH_3$, and CN;

$R_{1c}$ is $(CH_2)_n O_m R'$; where m is 0 or 1; and where when m is 0, n is 1 or 2;

when m is 1, n is 2 or 3;

R' is $C_1$-$C_6$ alkyl, optionally substituted with 1-3 substituents selected independently from F, Cl, OH, $OCH_3$, $OCH_2CH_3$, and $C_3$-$C_6$ cycloalkyl;

$R_{1d}$ is C(A)(A')(B)—; where

B is H or $C_{1-4}$ alkyl, optionally substituted with one or two OH groups;

A and A' are independently H or $C_{1-4}$ alkyl, optionally substituted with one or two OH groups; or A and A', together with the carbon atom to which they are attached, form a 3- to 6-member saturated ring;

$R_{1e}$ is

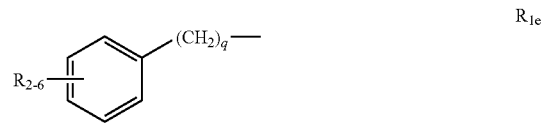

where q is 1 or 2;

$R_2$ and $R_3$ are each independently, H, F, Cl, Br, $CH_3$, $CH_2F$, $CHF_2$, $CF_3$ $OCH_3$, $OCH_2F$, $OCHF_2$, $OCF_3$, ethyl, n-propyl, isopropyl, cyclopropyl, isobutyl, sec-butyl, tert-butyl or methylsulfonyl;

$R_4$ is H, F, Cl, Br, $CH_3$, $CH_2F$, $CHF_2$, $CF_3$ $OCH_3$, $OCH_2F$, $OCHF_2$, $OCF_3$, ethyl, n-propyl, isopropyl, cyclopropyl, isobutyl, sec-butyl, tert-butyl, methylsulfonyl, nitro, acetamido, amidinyl, cyano, carbamoyl, methylcarbamoyl, dimethylcarbamoyl, 1,3,4-oxadiazol-2-yl, 5-methyl-1,3,4-oxadiazol, 1,3,4-thiadiazol, 5-methyl-1,3,4-thiadiazol 1H-tetrazolyl, N-morpholyl carbonyl amino, N-morpholylsulfonyl and N-pyrrolidinylcarbonylamino;

$R_5$ is H, F, Cl or methyl;

$R_6$ is H, F, Cl or methyl;

$Ar_1$ is

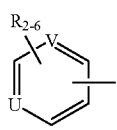

where
U and V are, independently, N, $CR_2$ or $CR_3$;
$R_2$, $R_3$ and $R_4$ are, independently, H, F, Cl, Br, $CH_3$, $CH_2F$, $CHF_2$, $CF_3$ $OCH_3$, $OCH_2F$, $OCHF_2$, $OCF_3$, ethyl, n-propyl, isopropyl, cyclopropyl, isobutyl, sec-butyl, tert-butyl, acetamido, amidinyl, cyano, carbamoyl, methylcarbamoyl, dimethylcarbamoyl, 1,3,4-oxadiazol-2-yl, 5-methyl-1,3,4-oxadiazolyl, 1,3,4-thiadiazolyl, 5-methyl-1,3,4-thiadiazolyl, 1H-tetrazolyl, N-morpholylcarbonylamino, N-morpholylsulfonyl, N-pyrrolidinylcarbonylamino, and methylsulfonyl;
$R_5$ and $R_6$ are, independently, H, F, Cl or methyl;
$Ar_2$ is

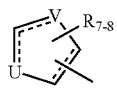

where
the dashed line represents alternative formal locations for the second ring double bond;
U is —S—, —O— or —N═, and where
when U is —O— or —S—, V is —CH═, —CCl═ or —N═;
when U is —N═, V is —CH═, —CCl═, or —N═;
$R_7$ is H or methyl;
$R_8$ is H, acetamido, methyl, F or Cl;
$Ar_3$ is

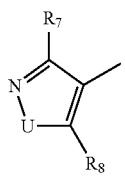

where
U is —NH—, —NCH_3— or —O—;
$R_7$ and $R_8$ are, independently, H, F, Cl, or methyl.

In some embodiments, the invention provides for compounds of formula I and their pharmaceutically acceptable salts. In further or additional embodiments, the invention provides for compounds of formula I and their pharmaceutically acceptable solvates. In further or additional embodiments, the invention provides for compounds of formula I and their pharmaceutically acceptable hydrates. In further or additional embodiments, the invention provides for compounds of formula I and their pharmaceutically acceptable polymorphs. In further or additional embodiments, the invention provides for compounds of formula I and their pharmaceutically acceptable esters. In further or additional embodiments, the invention provides for compounds of formula I and their pharmaceutically acceptable tautomers. In further or additional embodiments, the invention provides for compounds of formula I and their pharmaceutically acceptable prodrugs.

In addition to the definitions given herein for the groups G, $R^0$, X, Y and Z additional substitutions which could be contemplated by those of skill in the chemical and pharmaceutical arts are included.

Compounds of formula I, pharmaceutically acceptable salts, pharmaceutically active metabolites, pharmaceutically acceptable prodrugs, and pharmaceutically acceptable solvates thereof, may modulate the activity of MEK enzymes; and, as such, are useful for treating diseases or conditions in which aberrant MEK enzyme activity contributes to the pathology and/or symptoms of a disease or condition.

The tables below show examples of individual compounds provided or contemplated by this invention. These examples should in no way be construed as limiting.

Table 1 shows embodiments of this invention which are compounds of formula I, wherein G is $R_{1a}$ where $R_{1a}$ is as defined in the table and X, Y and Z are defined in the table.

TABLE 1

| $R_{1a}$ | X | Y | Z |
|---|---|---|---|
| $CH_3$ | F | I | F |
| $CH_3$ | Cl | I | F |
| $CH_3$ | F | Br | F |
| $CH_3$ | Cl | Br | F |
| $CH_3$ | F | $CH_3$ | F |
| $CH_3$ | Cl | $CH_3$ | F |
| $CH_3$ | F | $CF_3$ | F |
| $CH_3$ | Cl | $CF_3$ | F |
| $CH_3$ | F | C≡CH | F |
| $CH_3$ | Cl | C≡CH | F |
| $CH_3$ | F | $SCH_3$ | F |
| $CH_3$ | Cl | $SCH_3$ | F |
| $CH_3$ | F | $(CH_2)_2CH_3$ | F |
| $CH_3$ | Cl | $(CH_2)_2CH_3$ | F |
| $CH_3$ | F | $CH_2CH_3$ | F |
| $CH_3$ | Cl | $CH_2CH_3$ | F |
| $CH_3$ | F | $CH_2OH$ | F |
| $CH_3$ | Cl | $CH_2OH$ | F |
| $CH_3$ | F | ▷ | F |
| $CH_3$ | Cl | ▷ | F |
| $CH_3$ | $CH_3$ | $CH=CH_2$ | F |
| $CH_3$ | $CH_3$ | C≡CH | F |
| $CH_3$ | $CH_3$ | $SCH_3$ | F |
| $CH_2F$ | F | I | F |
| $CH_2F$ | Cl | I | F |
| $CH_2F$ | F | Br | F |
| $CH_2F$ | Cl | Br | F |
| $CH_2F$ | F | $CH_3$ | F |
| $CH_2F$ | Cl | $CH_3$ | F |
| $CH_2F$ | F | $CF_3$ | F |
| $CH_2F$ | Cl | $CF_3$ | F |
| $CF_3$ | F | I | F |
| $CF_3$ | Cl | I | F |
| $CF_3$ | F | Br | F |
| $CF_3$ | Cl | Br | F |
| $CF_3$ | F | $CH_3$ | F |
| $CF_3$ | Cl | $CH_3$ | F |
| $CF_3$ | F | $CF_3$ | F |
| $CF_3$ | Cl | $CF_3$ | F |
| $CH_2Cl$ | F | I | F |
| $CH_2Cl$ | Cl | I | F |
| $CH_2Cl$ | F | Br | F |

TABLE 1-continued

| R$_{1a}$ | X | Y | Z |
|---|---|---|---|
| CH$_2$Cl | Cl | Br | F |
| CH$_2$Cl | F | CH$_3$ | F |
| CH$_2$Cl | Cl | CH$_3$ | F |
| CH$_2$Cl | F | CF$_3$ | F |
| CH$_2$Cl | Cl | CF$_3$ | F |
| CHCl$_2$ | F | I | F |
| CHCl$_2$ | Cl | I | F |
| CHCl$_2$ | F | Br | F |
| CHCl$_2$ | Cl | Br | F |
| CHCl$_2$ | F | CH$_3$ | F |
| CHCl$_2$ | Cl | CH$_3$ | F |
| CHCl$_2$ | F | CF$_3$ | F |
| CHCl$_2$ | Cl | CF$_3$ | F |
| CCl$_3$ | F | I | F |
| CCl$_3$ | Cl | I | F |
| CCl$_3$ | F | Br | F |
| CCl$_3$ | Cl | Br | F |
| CCl$_3$ | F | CH$_3$ | F |
| CCl$_3$ | Cl | CH$_3$ | F |
| CCl$_3$ | F | CF$_3$ | F |
| CCl$_3$ | Cl | CF$_3$ | F |
| CH$_2$OH | F | I | F |
| CH$_2$OH | Cl | I | F |
| CH$_2$OH | F | Br | F |
| CH$_2$OH | Cl | Br | F |
| CH$_2$OH | F | CH$_3$ | F |
| CH$_2$OH | Cl | CH$_3$ | F |
| CH$_2$OH | F | CF$_3$ | F |
| CH$_2$OH | Cl | CF$_3$ | F |
| CH$_2$OMe | F | I | F |
| CH$_2$OMe | Cl | I | F |
| CH$_2$OMe | F | Br | F |
| CH$_2$OMe | Cl | Br | F |
| CH$_2$OMe | F | CH$_3$ | F |
| CH$_2$OMe | Cl | CH$_3$ | F |
| CH$_2$OMe | F | CF$_3$ | F |
| CH$_2$OMe | Cl | CF$_3$ | F |
| CH$_2$OMe | F | C≡CH | F |
| CH$_2$OMe | Cl | SCH$_3$ | F |
| CH$_2$OMe | CH$_3$ | CF$_3$ | F |
| CH$_2$OMe | CH$_3$ | C≡CH | F |
| CH$_2$OEt | F | I | F |
| CH$_2$OEt | Cl | I | F |
| CH$_2$OEt | F | Br | F |
| CH$_2$OEt | Cl | Br | F |
| CH$_2$OEt | F | CH$_3$ | F |
| CH$_2$OEt | Cl | CH$_3$ | F |
| CH$_2$OEt | F | CF$_3$ | F |
| CH$_2$OEt | Cl | CF$_3$ | F |
| 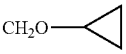 | F | I | F |
| 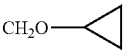 | Cl | I | F |
| 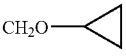 | F | Br | F |
| 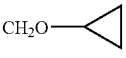 | Cl | Br | F |
| 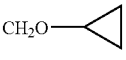 | F | CH$_3$ | F |
| 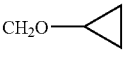 | Cl | CH$_3$ | F |
| 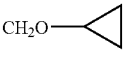 | F | CF$_3$ | F |
| 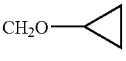 | Cl | CF$_3$ | F |
| 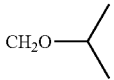 | F | I | F |
| 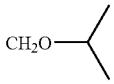 | Cl | I | F |
| 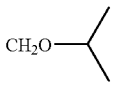 | F | Br | F |
| 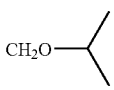 | Cl | Br | F |
| 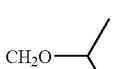 | F | CH$_3$ | F |
| 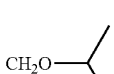 | Cl | CH$_3$ | F |
| 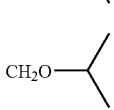 | F | CF$_3$ | F |
|  | Cl | CF$_3$ | F |
| 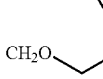 | F | I | F |
| 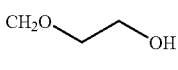 | Cl | I | F |
| 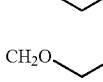 | F | Br | F |
| 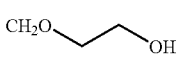 | Cl | Br | F |
| 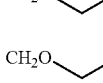 | F | CH$_3$ | F |
| 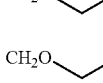 | Cl | CH$_3$ | F |
| 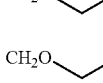 | F | CF$_3$ | F |
| 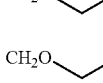 | Cl | CF$_3$ | F |
| 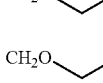 | F | I | F |
| 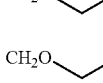 | Cl | I | F |
| 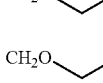 | F | Br | F |
| 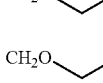 | Cl | Br | F |

TABLE 1-continued

| $R_{1a}$ | X | Y | Z |
|---|---|---|---|
|  | F | $CH_3$ | F |
|  | Cl | $CH_3$ | F |
|  | F | $CF_3$ | F |
|  | Cl | $CF_3$ | F |
|  | F | I | F |
|  | Cl | I | F |
|  | F | Br | F |
|  | Cl | Br | F |
|  | F | $CH_3$ | F |
|  | Cl | $CH_3$ | F |
|  | F | $CF_3$ | F |
|  | Cl | $CF_3$ | F |
| $CH_3$ | F | phenyl | F |
| $CH_3$ | Cl | phenyl | F |
| $CH_3$ | $CH_3$ | phenyl | |
| $CH_3$ | F | 3-pyridyl | F |
| $CH_3$ | Cl | 3-pyridyl | F |
| $CH_3$ | $CH_3$ | 4-pyridyl | |
| $CH_3$ | F | pyrazolyl | F |
| $CH_3$ | Cl | pyrazolyl | F |
| $CH_3$ | F | 4-pyridyl | F |
| $CH_3$ | Cl | 4-pyridyl | F |
| $CH_3$ | $CH_3$ | 2-($CH_3$—$SO_2$—NH)-phenyl | F |
| $CH_3$ | $CH_3$ | 3-($CH_3$—$SO_2$—NH)-phenyl | F |
| $CH_3$ | Cl | 3-($CH_3$—$SO_2$—NH)-phenyl | F |
| $CH_3$ | F | 3-($CH_3$—$SO_2$—NH)-phenyl | F |

Table 2 shows embodiments of this invention which are compounds of formula I, wherein G is $R_{1b}$, where $R_{1b}$ is as defined in the table and X, Y and Z are defined in the table.

TABLE 2

| $R_{1b}$ | X | Y | Z |
|---|---|---|---|
|  | F | I | F |
|  | Cl | I | F |
|  | F | Br | F |
|  | Cl | Br | F |
|  | F | $CH_3$ | F |
|  | Cl | $CH_3$ | F |
|  | F | $CF_3$ | F |
|  | Cl | $CF_3$ | F |
|  | F | C≡CH | F |
|  | Cl | C≡CH | F |
|  | F | $SCH_3$ | F |
|  | Cl | $SCH_3$ | F |
|  | F | $CH_2OH$ | F |
|  | Cl | $CH_2OH$ | F |
|  | F | $(CH_2)_3OH$ | F |
|  | Cl | $(CH_2)_3OH$ | F |
|  | F | $(CH_2)_2CH_3$ | F |
|  | Cl | $(CH_2)_2CH_3$ | F |
|  | F | $CH_2CH_3$ | F |
|  | Cl | $CH_2CH_3$ | F |
|  | F | $(CH_2)_2CH_3$ | F |

TABLE 2-continued

| R$_{1b}$ | X | Y | Z |
|---|---|---|---|
| △ | Cl | (CH$_2$)$_2$CH$_3$ | F |
| △ | CH$_3$ | I | F |
| △ | CH$_3$ | Br | F |
| △ | CH$_3$ | CH$_3$ | F |
| △ | CH$_3$ | CF$_3$ | F |
| △ | CH$_3$ | CH$_2$CH$_3$ | F |
| △ | CH$_3$ | (CH$_2$)$_2$CH$_3$ | F |
| △ | CH$_3$ | C≡CH | F |
| △ | CH$_3$ | SCH$_3$ | F |
| Cl-△ | CH$_3$ | (CH$_2$)$_2$CH$_3$ | F |
| NC-△ | CH$_3$ | I | F |
| △ | F | CH=CH$_2$ | F |
| △ | Cl | CH=CH$_2$ | F |
| △ | CH$_3$ | CH=CH$_2$ | F |
| △ | F | △ | F |
| △ | F | OCH$_3$ | F |
| △ | Cl | (CH$_2$)$_2$CH$_2$OH | F |
| ◇ | F | I | F |
| ◇ | Cl | I | F |
| ◇ | F | Br | F |

TABLE 2-continued

| R$_{1b}$ | X | Y | Z |
|---|---|---|---|
| ◇ | Cl | Br | F |
| ◇ | F | CH$_3$ | F |
| ◇ | Cl | CH$_3$ | F |
| ◇ | F | CF$_3$ | F |
| ◇ | Cl | CF$_3$ | F |
| ⬠ | F | I | F |
| ⬠ | Cl | I | F |
| ⬠ | F | Br | F |
| ⬠ | Cl | Br | F |
| ⬠ | F | CH$_3$ | F |
| ⬠ | Cl | CH$_3$ | F |
| ⬠ | F | CF$_3$ | F |
| ⬠ | Cl | CF$_3$ | F |
| ⬠ | Cl | △ | F |
| OCH$_3$-⬠ | F | (CH$_2$)$_2$CH$_3$ | F |

TABLE 2-continued

| R$_{1b}$ | X | Y | Z |
|---|---|---|---|
| (1,3)-hydroxy-methyl-cyclopentyl | Cl | C≡CH | F |
| (1,3)-chloro-methyl-cyclopentyl | CH$_3$ | SCH$_3$ | F |
| (1,2)-methoxy-methyl-cyclopentyl | Cl | CF$_3$ | F |
| (1,3)-hydroxy-methyl-cyclopentyl | CH$_3$ | CH$_3$ | F |
| (1,2)-methoxy-methyl-cyclopentyl | F | CH$_2$OH | F |
| (1,3)-hydroxy-methyl-cyclopentyl | Cl | (CH$_2$)$_3$OH | F |
| (1,2)-methoxy-methyl-cyclopentyl | F | OCH$_2$CH$_3$ | F |
| cyclohexyl | F | I | F |
| cyclohexyl | Cl | I | F |
| cyclohexyl | F | Br | F |
| cyclohexyl | Cl | Br | F |

TABLE 2-continued

| R$_{1b}$ | X | Y | Z |
|---|---|---|---|
| cyclohexyl | F | CH$_3$ | F |
| cyclohexyl | Cl | CH$_3$ | F |
| cyclohexyl | F | CF$_3$ | F |
| cyclohexyl | Cl | CF$_3$ | F |
| cyclopropyl | F | phenyl | F |
| cyclopropyl | Cl | phenyl | F |
| cyclopropyl | F | 3-pyridyl | F |
| cyclopropyl | Cl | 3-pyridyl | F |
| cyclopropyl | F | pyrazol-4-yl | F |
| cyclopropyl | Cl | pyrazol-4-yl | F |
| cyclopropyl | F | 4-pyridyl | F |
| cyclopropyl | Cl | 4-pyridyl | F |
| cyclopropyl | F | 1-methyl-pyrazol-4-yl | F |
| cyclopropyl | Cl | 1-methyl-pyrazol-4-yl | F |
| cyclopropyl | F | pyrazol-3-yl | F |
| cyclopropyl | Cl | pyrazol-3-yl | F |
| cyclopropyl | F | 2-(CH$_3$—SO$_2$—NH)-phenyl | F |
| cyclopropyl | Cl | 2-(CH$_3$—SO$_2$—NH)-phenyl | F |
| cyclopropyl | F | 3-(CH$_3$—SO$_2$—NH)-phenyl | F |
| cyclopropyl | Cl | 3-(CH$_3$—SO$_2$—NH)-phenyl | F |

TABLE 2-continued

| $R_{1b}$ | X | Y | Z |
|---|---|---|---|
| cyclopropyl | CH₃ | 2-(CH₃—SO₂—NH)-phenyl | F |
| cyclopropyl | CH₃ | 3-(CH₃—SO₂—NH)-phenyl | F |
| cyclopropyl | F | 4-CF₃O-phenyl | F |
| cyclopropyl | Cl | 4-CF₃O-phenyl | F |
| cyclopropyl | CH₃ | 4-CF₃O-phenyl | F |
| 2-Cl-cyclopropyl | Cl | 2-(CH₃—SO₂—NH)-phenyl | F |
| cyclobutyl | F | phenyl | F |
| cyclobutyl |  | phenyl |  |
| cyclobutyl | Cl | 3-pyridyl | F |
| cyclobutyl | F | 3-pyridyl | F |
| cyclobutyl | Cl | pyrazol-4-yl | F |
| cyclobutyl | F | pyrazol-4-yl | F |
| cyclobutyl | Cl | 4-pyridyl | F |
| cyclobutyl | F | 4-pyridyl | F |
| cyclobutyl | Cl | 1-methyl-pyrazol-4-yl | F |
| cyclobutyl | CH₃ | 1-methyl-pyrazol-4-yl | F |
| cyclopentyl | F | pyrazol-3-yl | F |
| cyclopentyl | Cl | pyrazol-3-yl | F |
| cyclopentyl | F | 2-(CH₃—SO₂—NH)-phenyl | F |
| cyclopentyl | Cl | 2-(CH₃—SO₂—NH)-phenyl | F |
| cyclopentyl | F | phenyl | F |
| cyclopentyl | Cl | phenyl | F |
| cyclopentyl | F | 3-pyridyl | F |
| cyclopentyl | Cl | 3-pyridyl | F |
| cyclopentyl | Cl | pyrazol-3-yl | F |

Table 3 shows embodiments of this invention which are compounds of formula I, wherein G is $R_{1c}$ where $R_{1c}$ is as defined in the table and X, Y and Z are defined in the table.

TABLE 3

| $R_{1c}$ | X | Y | Z |
|---|---|---|---|
| CH₂CH₃ | F | I | F |
| CH₂CH₃ | Cl | I | F |
| CH₂CH₃ | F | Br | F |
| CH₂CH₃ | Cl | Br | F |
| CH₂CH₃ | F | CH₃ | F |
| CH₂CH₃ | Cl | CH₃ | F |
| CH₂CH₃ | F | CF₃ | F |
| CH₂CH₃ | Cl | CF₃ | F |
| CH₂CH₃ | CH₃ | CH₃ | F |
| CH₂CH₃ | CH₃ | CH₃ | F |
| CH₂CH₃ | CH₃ | C≡CH | F |
| CH₂CH₃ | CH₃ | SCH₃ | F |
| CH₂CH₃ | F | C≡CH | F |
| CH₂CH₃ | Cl | SCH₃ | F |
| CH₂CH₃ | F | cyclopropyl | F |
| CH₂CH₃ | Cl | cyclopropyl | F |
| CH₂CH₃ | CH₃ | cyclopropyl | F |
| CH(CH₃)₂ | F | OCH₃ | F |
| CH(CH₃)₂ | Cl | OCH₃ | F |
| CH(CH₃)₂ | F | I | F |
| CH(CH₃)₂ | Cl | I | F |
| CH(CH₃)₂ | F | Br | F |
| CH(CH₃)₂ | Cl | Br | F |
| CH(CH₃)₂ | F | CH₃ | F |
| CH(CH₃)₂ | Cl | CH₃ | F |

TABLE 3-continued

| R$_{1c}$ | X | Y | Z |
|---|---|---|---|
| CH(CH$_3$)$_2$ | F | CH$_2$CH$_3$ | F |
| CH(CH$_3$)$_2$ | Cl | CH$_2$CH$_3$ | F |
| CH(CH$_3$)$_2$ | CH$_3$ | CH$_2$CH$_3$ | F |
| CH(CH$_3$)$_2$ | Cl | CH$_2$CH$_3$ | F |
| CH(CH$_3$)$_2$ | Fl | CH(CH$_3$)$_2$ | F |
| CH(CH$_3$)$_2$ | Cl | CH(CH$_3$)$_2$ | F |
| CH(CH$_3$)$_2$ | F | CF$_3$ | F |
| CH(CH$_3$)$_2$ | Cl | CH$_3$ | F |
| CH(CH$_3$)$_2$ | CH$_3$ | Br | F |
| CH(CH$_3$)$_2$ | CH$_3$ | C≡CH | F |
| CH(CH$_3$)$_2$ | CH$_3$ | SCH$_3$ | F |
| CH(CH$_3$)$_2$ | CH$_3$ |  | F |
| CH(CH$_3$)$_2$ | F | CH$_2$OH | F |
| CH(CH$_3$)$_2$ | Cl |  | F |
| n-butyl | F | I | F |
| n-butyl | Cl | I | F |
| n-butyl | F | Br | F |
| n-butyl | Cl | Br | F |
| n-butyl | F | CH$_3$ | F |
| n-butyl | Cl | CH$_3$ | F |
| n-butyl | F | OCH$_3$ | F |
| n-butyl | Cl | OCH$_3$ | F |
| n-butyl | CH$_3$ | OCH$_3$ | F |
| n-butyl | Cl | OCH$_2$CH$_3$ | F |
| n-butyl | F | OCH$_2$CH$_3$ | F |
| n-butyl | CH$_3$ | OCH$_2$CH$_3$ | F |
| n-butyl | F | OCH$_2$CH$_2$OH | F |
| n-butyl | F | CF$_3$ | F |
| n-butyl | Cl | CF$_3$ | F |
| sec-butyl | F | I | F |
| sec-butyl | Cl | I | F |
| sec-butyl | F | Br | F |
| sec-butyl | Cl | Br | F |
| sec-butyl | F | CH$_3$ | F |
| sec-butyl | Cl | CH$_3$ | F |
| sec-butyl | F | CF$_3$ | F |
| sec-butyl | Cl | CF$_3$ | F |
| CH$_2$CF$_3$ | F | I | F |
| CH$_2$CF$_3$ | Cl | I | F |
| CH$_2$CF$_3$ | F | Br | F |
| CH$_2$CF$_3$ | Cl | Br | F |
| CH$_2$CF$_3$ | F | CH$_3$ | F |
| CH$_2$CF$_3$ | Cl | CH$_3$ | F |
| CH$_2$CF$_3$ | F | CF$_3$ | F |
| CH$_2$CF$_3$ | Cl | CF$_3$ | F |
| CH$_2$CCl$_3$ | F | I | F |
| CH$_2$CCl$_3$ | Cl | I | F |
| CH$_2$CCl$_3$ | F | Br | F |
| CH$_2$CCl$_3$ | Cl | Br | F |
| CH$_2$CCl$_3$ | F | CH$_3$ | F |
| CH$_2$CCl$_3$ | Cl | CH$_3$ | F |
| CH$_2$CCl$_3$ | F | CF$_3$ | F |
| CH$_2$CCl$_3$ | Cl | CF$_3$ | F |
|  | F | I | F |
|  | Cl | I | F |
|  | F | Br | F |
|  | Cl | Br | F |
|  | F | CH$_3$ | F |
|  | Cl | CH$_3$ | F |
|  | F | CF$_3$ | F |
|  | Cl | CF$_3$ | F |
| CH$_2$CH$_2$F | F | I | F |
| CH$_2$CH$_2$F | Cl | I | F |
| CH$_2$CH$_2$F | F | Br | F |
| CH$_2$CH$_2$F | Cl | Br | F |
| CH$_2$CH$_2$F | F | CH$_3$ | F |
| CH$_2$CH$_2$F | Cl | CH$_3$ | F |
| CH$_2$CH$_2$F | F | CF$_3$ | F |
| CH$_2$CH$_2$F | Cl | CF$_3$ | F |
| CH$_2$CH$_2$Cl | F | I | F |
| CH$_2$CH$_2$Cl | Cl | I | F |
| CH$_2$CH$_2$Cl | F | Br | F |
| CH$_2$CH$_2$Cl | Cl | Br | F |
| CH$_2$CH$_2$Cl | F | CH$_3$ | F |
| CH$_2$CH$_2$Cl | Cl | CH$_3$ | F |
| CH$_2$CH$_2$Cl | F | CF$_3$ | F |
| CH$_2$CH$_2$Cl | Cl | CF$_3$ | F |
| CH$_2$CH$_2$CH$_2$Cl | F | I | F |
| CH$_2$CH$_2$CH$_2$Cl | Cl | I | F |
| CH$_2$CH$_2$CH$_2$Cl | F | Br | F |
| CH$_2$CH$_2$CH$_2$Cl | Cl | Br | F |
| CH$_2$CH$_2$CH$_2$Cl | F | CH$_3$ | F |
| CH$_2$CH$_2$CH$_2$Cl | Cl | CH$_3$ | F |
| CH$_2$CH$_2$CH$_2$Cl | F | CF$_3$ | F |
| CH$_2$CH$_2$CH$_2$Cl | Cl | CF$_3$ | F |
| CH$_2$CH$_2$OH | F | I | F |
| CH$_2$CH$_2$OH | Cl | I | F |
| CH$_2$CH$_2$OH | F | Br | F |
| CH$_2$CH$_2$OH | Cl | Br | F |
| CH$_2$CH$_2$OH | F | CH$_3$ | F |
| CH$_2$CH$_2$OH | Cl | CH$_3$ | F |
| CH$_2$CH$_2$OH | F | CF$_3$ | F |
| CH$_2$CH$_2$OH | Cl | CF$_3$ | F |
| CH$_2$CH$_2$CH$_2$OH | F | I | F |
| CH$_2$CH$_2$CH$_2$OH | Cl | I | F |
| CH$_2$CH$_2$CH$_2$OH | F | Br | F |
| CH$_2$CH$_2$CH$_2$OH | Cl | Br | F |
| CH$_2$CH$_2$CH$_2$OH | F | CH$_3$ | F |
| CH$_2$CH$_2$CH$_2$OH | Cl | CH$_3$ | F |
| CH$_2$CH$_2$CH$_2$OH | F | CF$_3$ | F |
| CH$_2$CH$_2$CH$_2$OH | Cl | CF$_3$ | F |
| (CH$_2$)$_4$OH | F | I | F |
| (CH$_2$)$_4$OH | Cl | I | F |
| (CH$_2$)$_4$OH | F | Br | F |
| (CH$_2$)$_4$OH | Cl | Br | F |
| (CH$_2$)$_4$OH | F | CH$_3$ | F |
| (CH$_2$)$_4$OH | Cl | CH$_3$ | F |
| (CH$_2$)$_4$OH | F | CF$_3$ | F |
| (CH$_2$)$_4$OH | Cl | CF$_3$ | F |
| CH$_2$CH$_2$OCH$_3$ | F | I | F |
| CH$_2$CH$_2$OCH$_3$ | Cl | I | F |
| CH$_2$CH$_2$OCH$_3$ | F | Br | F |
| CH$_2$CH$_2$OCH$_3$ | Cl | Br | F |
| CH$_2$CH$_2$OCH$_3$ | F | CH$_3$ | F |
| CH$_2$CH$_2$OCH$_3$ | Cl | CH$_3$ | F |
| CH$_2$CH$_2$OCH$_3$ | F | CF$_3$ | F |
| CH$_2$CH$_2$OCH$_3$ | Cl | CF$_3$ | F |
| (CH$_2$)$_3$OCH$_3$ | F | I | F |
| (CH$_2$)$_3$OCH$_3$ | Cl | I | F |
| (CH$_2$)$_3$OCH$_3$ | F | Br | F |
| (CH$_2$)$_3$OCH$_3$ | Cl | Br | F |
| (CH$_2$)$_3$OCH$_3$ | F | CH$_3$ | F |
| (CH$_2$)$_3$OCH$_3$ | Cl | CH$_3$ | F |

TABLE 3-continued

| $R_{1c}$ | X | Y | Z |
|---|---|---|---|
| (CH₂)₃OCH₃ | F | CF₃ | F |
| (CH₂)₃OCH₃ | Cl | CF₃ | F |
| CH₂CH₂OEt | F | I | F |
| CH₂CH₂OEt | Cl | I | F |
| CH₂CH₂OEt | F | Br | F |
| CH₂CH₂OEt | Cl | Br | F |
| CH₂CH₂OEt | F | CH₃ | F |
| CH₂CH₂OEt | Cl | CH₃ | F |
| CH₂CH₂OEt | F | CF₃ | F |
| CH₂CH₂OEt | Cl | CF₃ | F |
|  | F | I | F |
|  | Cl | I | F |
|  | F | Br | F |
|  | Cl | Br | F |
|  | F | CH₃ | F |
|  | Cl | CH₃ | F |
|  | F | CF₃ | F |
|  | Cl | CF₃ | F |
|  | F | I | F |
|  | Cl | I | F |
|  | F | Br | F |
|  | Cl | Br | F |
|  | F | CH₃ | F |
|  | Cl | CH₃ | F |
|  | F | CF₃ | F |
|  | Cl | CF₃ | F |

TABLE 3-continued

| $R_{1c}$ | X | Y | Z |
|---|---|---|---|
| CH₂CH₂CH₂OEt | F | I | F |
| CH₂CH₂CH₂OEt | Cl | I | F |
| CH₂CH₂CH₂OEt | F | Br | F |
| CH₂CH₂CH₂OEt | Cl | Br | F |
| CH₂CH₂CH₂OEt | F | CH₃ | F |
| CH₂CH₂CH₂OEt | Cl | CH₃ | F |
| CH₂CH₂CH₂OEt | F | CF₃ | F |
| CH₂CH₂CH₂OEt | Cl | CF₃ | F |
|  | F | I | F |
|  | Cl | I | F |
|  | F | Br | F |
|  | Cl | Br | F |
|  | F | CH₃ | F |
|  | Cl | CH₃ | F |
|  | F | CF₃ | F |
|  | Cl | CF₃ | F |
|  | F | I | F |
|  | Cl | I | F |
|  | F | Br | F |
|  | Cl | Br | F |
|  | F | CH₃ | F |
| CH₂CH₂CH₂—O—◁ | Cl | CH₃ | F |
| CH₂CH₂CH₂—O—◁ | F | CF₃ | F |
| CH₂CH₂CH₂—O—◁ | Cl | CF₃ | F |

TABLE 3-continued

| $R_{1c}$ | X | Y | Z |
|---|---|---|---|
| CH₂CH₂—O—CH₂CH(OH)CH₂OH (with OH) | F | I | F |
| CH₂CH₂—O—CH₂CH(OH)CH₂OH | Cl | I | F |
| CH₂CH₂—O—CH₂CH(OH)CH₂OH | F | Br | F |
| CH₂CH₂—O—CH₂CH(OH)CH₂OH | Cl | Br | F |
| CH₂CH₂—O—CH₂CH(OH)CH₂OH | F | CH₃ | F |
| CH₂CH₂—O—CH₂CH(OH)CH₂OH | Cl | CH₃ | F |
| CH₂CH₂—O—CH₂CH(OH)CH₂OH | F | CF₃ | F |
| CH₂CH₂—O—CH₂CH(OH)CH₂OH | Cl | CF₃ | F |
| CH₂CH(OH)CH₂CH₂OH | F | I | F |
| CH₂CH(OH)CH₂CH₂OH | Cl | I | F |
| CH₂CH(OH)CH₂CH₂OH | F | Br | F |
| CH₂CH(OH)CH₂CH₂OH | Cl | Br | F |
| CH₂CH(OH)CH₂CH₂OH | F | CH₃ | F |

TABLE 3-continued

| $R_{1c}$ | X | Y | Z |
|---|---|---|---|
| CH₂CH(OH)CH₂CH₂OH | Cl | CH₃ | F |
| CH₂CH(OH)CH₂CH₂OH | F | CF₃ | F |
| CH₂CH(OH)CH₂CH₂OH | Cl | CF₃ | F |
| CH₂CH(OH)CH(OH)CH₂OH | F | I | F |
| CH₂CH(OH)CH(OH)CH₂OH | Cl | I | F |
| CH₂CH(OH)CH(OH)CH₂OH | CH₃ | I | F |
| CH₂CH(OH)CH(OH)CH₂OH | F | Br | F |
| CH₂CH(OH)CH(OH)CH₂OH | Cl | Br | F |
| CH₂CH(OH)CH(OH)CH₂OH | CH₃ | Br | F |
| CH₂CH(OH)CH(OH)CH₂OH | F | CH₃ | F |
| CH₂CH(OH)CH(OH)CH₂OH | Cl | CH₃ | F |

TABLE 3-continued

| $R_{1c}$ | X | Y | Z |
|---|---|---|---|
|  | CH$_3$ | CH$_3$ | F |
|  | F | C≡CH | F |
|  | F | SCH$_3$ | F |
|  | F | CH$_2$CH$_2$CH$_3$ | F |
|  | Cl | CH$_2$CH(OH)CH$_3$ | F |
| 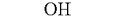 | F | CH(CH$_3$)$_2$ | F |
|  | Cl | CF$_3$ | F |
| CH$_2$CH$_3$ | F | phenyl | F |
| CH$_2$CH$_3$ | Cl | phenyl | F |
| CH$_2$CH$_3$ | F | phenyl | F |
| CH$_2$CH$_3$ | Cl | 3-pyridyl | F |
| CH$_2$CH$_3$ | F | 3-pyridyl | F |
| CH$_2$CH$_3$ | Cl | 4-pyridyl | F |
| CH$_2$CH$_3$ | F | pyrazolyl | F |
| CH$_2$CH$_3$ | Cl | pyrazolyl | F |
| CH$_2$CH$_3$ | CH$_3$ | 4-pyridyl | F |
| CH$_2$CH$_3$ | CH$_3$ | 4-pyridyl | F |
| CH$_2$CH$_3$ | CH$_3$ | 2-(CH$_3$—SO$_2$—NH)-phenyl | F |
| CH$_2$CH$_3$ | CH$_3$ | 3-(CH$_3$—SO$_2$—NH)-phenyl | F |
| CH$_2$CH$_3$ | F | 3-(CH$_3$—SO$_2$—NH)-phenyl | F |
| CH$_2$CH$_3$ | Cl | 3-(CH$_3$—SO$_2$—NH)-phenyl | F |
| CH$_2$CH$_3$ | F | phenyl | F |
| CH$_2$CH$_3$ | Cl | phenyl | F |
| CH$_2$CH$_3$ | CH$_3$ | phenyl 3-pyridyl | F |
| CH(CH$_3$)$_2$ | F | 3-pyridyl | F |
| CH(CH$_3$)$_2$ | Cl | 4-pyridyl | F |
| CH(CH$_3$)$_2$ | F | pyrazolyl | F |
| CH(CH$_3$)$_2$ | Cl | pyrazolyl | F |
| CH(CH$_3$)$_2$ | F | 4-pyridyl | F |
| CH(CH$_3$)$_2$ | Cl | 4-pyridyl | F |
| CH(CH$_3$)$_2$ | F | 2-(CH$_3$—SO$_2$—NH)-phenyl | F |
| CH(CH$_3$)$_2$ | Cl | 3-(CH$_3$—SO$_2$—NH)-phenyl | F |
| CH(CH$_3$)$_2$ | F | 3-(CH$_3$—SO$_2$—NH)-phenyl | F |
| CH(CH$_3$)$_2$ | Cl | 3-(CH$_3$—SO$_2$—NH)-phenyl | F |
| CH(CH$_3$)$_2$ | CH$_3$ | phenyl | F |
| CH(CH$_3$)$_2$ | Cl | phenyl | F |
| CH(CH$_3$)$_2$ | Fl | phenyl | F |
| CH(CH$_3$)$_2$ | Cl | 3-pyridyl 3-pyridyl | F |
| CH(CH$_3$)$_2$ | F | 4-pyridyl | F |
| CH(CH$_3$)$_2$ | Cl | pyrazolyl | F |
| CH(CH$_3$)$_2$ | CH$_3$ | pyrazolyl | F |
| CH(CH$_3$)$_2$ | CH$_3$ | 4-pyridyl | F |
| CH(CH$_3$)$_2$ | CH$_3$ | 4-pyridyl | F |
| CH(CH$_3$)$_2$ | CH$_3$ | 2-(CH$_3$—SO$_2$—NH)-phenyl | F |
| CH(CH$_3$)$_2$ | F | 3-(CH$_3$—SO$_2$—NH)-phenyl | F |
| CH(CH$_3$)$_2$ | Cl | 3-(CH$_3$—SO$_2$—NH)-phenyl 3-(CH$_3$—SO$_2$—NH)-phenyl | F |
| n-butyl | F | phenyl | F |
| n-butyl | Cl | phenyl | F |
| n-butyl | F | phenyl | F |
| n-butyl | Cl | phenyl | F |
| n-butyl | F | 3-pyridyl | F |
| n-butyl | Cl | 4-pyridyl | F |
| n-butyl | F | pyrazolyl | F |
| n-butyl | Cl | pyrazolyl | F |
| n-butyl | CH$_3$ | 4-pyridyl | F |
| n-butyl | Cl | 4-pyridyl | F |
| n-butyl | F | 2-(CH$_3$—SO$_2$—NH)-phenyl | F |
| n-butyl | CH$_3$ | 3-(CH$_3$—SO$_2$—NH)-phenyl | F |
| n-butyl | F | 3-(CH$_3$—SO$_2$—NH)-phenyl 3-(CH$_3$—SO$_2$—NH)-phenyl | F |
| n-butyl | F | phenyl | F |
| n-butyl | Cl | phenyl | F |
| sec-butyl | F | 3-pyridyl | F |
| sec-butyl | Cl | 3-pyridyl | F |
| sec-butyl | F | 4-pyridyl | F |
| sec-butyl | Cl | pyrazolyl | F |
| sec-butyl | F | pyrazolyl | F |
| sec-butyl | Cl | 4-pyridyl | F |
| sec-butyl | F | 4-pyridyl | F |
| sec-butyl | Cl | CF$_3$ | |
| CH$_2$CF$_3$ | F | phenyl | F |
| CH$_2$CF$_3$ | Cl | phenyl | F |
| CH$_2$CF$_3$ | F | phenyl | F |
| CH$_2$CF$_3$ | Cl | 3-pyridyl | F |
| CH$_2$CF$_3$ | F | 3-pyridyl | F |
| CH$_2$CF$_3$ | Cl | 4-pyridyl | F |
| CH$_2$CF$_3$ | F | pyrazolyl | F |
| CH$_2$CF$_3$ | Cl | pyrazolyl 4-pyridyl | F |
| CH$_2$CCl$_3$ | F | 4-pyridyl | F |
| CH$_2$CCl$_3$ | Cl | 2-(CH$_3$—SO$_2$—NH)-phenyl | F |
| CH$_2$CCl$_3$ | F | 3-(CH$_3$—SO$_2$—NH)-phenyl | F |
| CH$_2$CCl$_3$ | Cl | 3-(CH$_3$—SO$_2$—NH)-phenyl | F |
| CH$_2$CCl$_3$ | F | 3-(CH$_3$—SO$_2$—NH)-phenyl | F |
| CH$_2$CCl$_3$ | Cl | phenyl | F |
| CH$_2$CCl$_3$ | F | phenyl | F |

TABLE 3-continued

| $R_{1c}$ | X | Y | Z |
|---|---|---|---|
| $CH_2CCl_3$ | Cl | phenyl<br>3-pyridyl | F |
|  | F | 3-pyridyl | F |
|  | Cl | 4-pyridyl | F |
|  | F | pyrazolyl | F |
|  | Cl | pyrazolyl | F |
|  | F | 4-pyridyl | F |
|  | Cl | 4-pyridyl | F |
|  | F | 2-($CH_3$—$SO_2$—NH)-phenyl | F |
|  | Cl | 3-($CH_3$—$SO_2$—NH)-phenyl<br>3-($CH_3$—$SO_2$—NH)-phenyl | F |
| $CH_2CH_2F$ | F | 3-($CH_3$—$SO_2$—NH)-phenyl | F |
| $CH_2CH_2F$ | Cl | phenyl | F |
| $CH_2CH_2F$ | F | phenyl | F |
| $CH_2CH_2F$ | Cl | phenyl | F |
| $CH_2CH_2F$ | F | 3-pyridyl | F |
| $CH_2CH_2F$ | Cl | 3-pyridyl | F |
| $CH_2CH_2F$ | F | 4-pyridyl | F |
| $CH_2CH_2F$ | Cl | pyrazolyl<br>pyrazolyl | F |
| $CH_2CH_2Cl$ | F | 4-pyridyl | F |
| $CH_2CH_2Cl$ | Cl | 4-pyridyl | F |
| $CH_2CH_2Cl$ | F | 2-($CH_3$—$SO_2$—NH)-phenyl | F |
| $CH_2CH_2Cl$ | Cl | 3-($CH_3$—$SO_2$—NH)-phenyl | F |
| $CH_2CH_2Cl$ | F | 3-($CH_3$—$SO_2$—NH)-phenyl | F |
| $CH_2CH_2Cl$ | Cl | 3-($CH_3$—$SO_2$—NH)-phenyl | F |
| $CH_2CH_2Cl$ | F | phenyl | F |
| $CH_2CH_2Cl$ | Cl | phenyl<br>phenyl | F |
|  | F | 3-pyridyl | F |
| $CH_2CH_2CH_2Cl$ |  |  |  |
| $CH_2CH_2CH_2Cl$ | Cl | 3-pyridyl | F |
| $CH_2CH_2CH_2Cl$ | F | 4-pyridyl | F |
| $CH_2CH_2CH_2Cl$ | Cl | pyrazolyl | F |
| $CH_2CH_2CH_2Cl$ | F | pyrazolyl | F |
| $CH_2CH_2CH_2Cl$ | Cl | 4-pyridyl | F |
| $CH_2CH_2CH_2Cl$ | F | 4-pyridyl | F |
| $CH_2CH_2CH_2Cl$ | Cl | 2-($CH_3$—$SO_2$—NH)-phenyl<br>3-($CH_3$—$SO_2$—NH)-phenyl | F |
| $CH_2CH_2OH$ | F | 3-($CH_3$—$SO_2$—NH)-phenyl | F |
| $CH_2CH_2OH$ | Cl | 3-($CH_3$—$SO_2$—NH)-phenyl | F |
| $CH_2CH_2OH$ | F | phenyl | F |
| $CH_2CH_2OH$ | Cl | phenyl | F |
| $CH_2CH_2OH$ | F | phenyl | F |
| $CH_2CH_2OH$ | Cl | phenyl | F |
| $CH_2CH_2OH$ | F | 3-pyridyl | F |
| $CH_2CH_2OH$ | Cl | 3-pyridyl | F |
| $CH_2CH_2OH$ | F | 3-pyridyl | F |

| $R_{1c}$ | X | Y | Z |
|---|---|---|---|
| $CH_2CH_2OH$ | Cl | 4-pyridyl<br>pyrazolyl | F |
| $CH_2CH_2CH_2OH$ | F | pyrazolyl | F |
| $CH_2CH_2CH_2OH$ | Cl | 4-pyridyl | F |
| $CH_2CH_2CH_2OH$ | F | 4-pyridyl | F |
| $CH_2CH_2CH_2OH$ | Cl | 2-($CH_3$—$SO_2$—NH)-phenyl | F |
| $CH_2CH_2CH_2OH$ | F | 3-($CH_3$—$SO_2$—NH)-phenyl | F |
| $CH_2CH_2CH_2OH$ | Cl | 3-($CH_3$—$SO_2$—NH)-phenyl | F |
| $CH_2CH_2CH_2OH$ | F | 3-($CH_3$—$SO_2$—NH)-phenyl | F |
| $CH_2CH_2CH_2OH$ | Cl | phenyl<br>phenyl | F |
| $(CH_2)_4OH$ | F | phenyl | F |
| $(CH_2)_4OH$ | Cl | 3-pyridyl | F |
| $(CH_2)_4OH$ | F | 3-pyridyl | F |
| $(CH_2)_4OH$ | Cl | 4-pyridyl | F |
| $(CH_2)_4OH$ | F | pyrazolyl | F |
| $(CH_2)_4OH$ | Cl | pyrazolyl | F |
| $(CH_2)_4OH$ | F | 4-pyridyl | F |
| $(CH_2)_4OH$ | Cl | 4-pyridyl<br>2-($CH_3$—$SO_2$—NH)-phenyl | F |
| $CH_2CH_2OCH_3$ | F | 3-($CH_3$—$SO_2$—NH)-phenyl | F |
| $CH_2CH_2OCH_3$ | Cl | 3-($CH_3$—$SO_2$—NH)-phenyl | F |
| $CH_2CH_2OCH_3$ | F | 3-($CH_3$—$SO_2$—NH)-phenyl | F |
| $CH_2CH_2OCH_3$ | Cl | phenyl | F |
| $CH_2CH_2OCH_3$ | F | phenyl | F |
| $CH_2CH_2OCH_3$ | Cl | phenyl | F |
| $CH_2CH_2OCH_3$ | F | 3-pyridyl | F |
| $CH_2CH_2OCH_3$ | Cl | 3-pyridyl<br>4-pyridyl | F |
| $(CH_2)_3OCH_3$ | F | pyrazolyl | F |
| $(CH_2)_3OCH_3$ | Cl | pyrazolyl | F |
| $(CH_2)_3OCH_3$ | F | 4-pyridyl | F |
| $(CH_2)_3OCH_3$ | Cl | 4-pyridyl | F |
| $(CH_2)_3OCH_3$ | F | 2-($CH_3$—$SO_2$—NH)-phenyl | F |
| $(CH_2)_3OCH_3$ | Cl | 3-($CH_3$—$SO_2$—NH)-phenyl | F |
| $(CH_2)_3OCH_3$ | F | 3-($CH_3$—$SO_2$—NH)-phenyl | F |
| $(CH_2)_3OCH_3$ | Cl | 3-($CH_3$—$SO_2$—NH)-phenyl<br>phenyl | F |
| $CH_2CH_2OEt$ | F | phenyl | F |
| $CH_2CH_2OEt$ | Cl | phenyl | F |
| $CH_2CH_2OEt$ | F | 3-pyridyl | F |
| $CH_2CH_2OEt$ | Cl | 3-pyridyl | F |
| $CH_2CH_2OEt$ | F | 4-pyridyl | F |
| $CH_2CH_2OEt$ | Cl | pyrazolyl | F |
| $CH_2CH_2OEt$ | F | pyrazolyl | F |
| $CH_2CH_2OEt$ | Cl | 4-pyridyl | F |

Tables 4a and 4b show embodiments of this invention which are compounds of formula I, where $G=R_{1d}$, Z is F, X is F and $R_{1d}$ and $R^0$ are defined in the table. Each line in the table corresponds to five species which differ only at position Y.

TABLE 4a $Y_a = CH_3$; $Y_b = Br$; $Y_c = I$; $Y_d = Cl$;

| CMPD# | A, A' | B | $R^O$ |
|---|---|---|---|
| 1(a-d) | H, H | H | $OCH_3$ |
| 2(a-d) | H, H | H | $NHCH_3$ |
| 3(a-d) | H, H | H | $CH_2CH_3$ |
| 4(a-d) | H, H | H | $CH_2CH=CH_2$ |
| 5(a-d) | H, H | H | CN |
| 6(a-d) | H, H | H | $CF_3$ |
| 7(a-d) | H, H | H | F |
| 8(a-d) | H, H | H | $C_6H_6$ |
| 9(a-d) | H, H | —$CH_2CH(OH)CH_2OH$ | $OCH_3$ |
| 10(a-d) | H, H | —$CH_2CH(OH)CH_2OH$ | $NHCH_3$ |
| 11(a-d) | H, H | —$CH_2CH(OH)CH_2OH$ | $CH_2CH_3$ |
| 12(a-d) | —$(CH_2)_2$— | —$CH_2(C_3H_5)$ | $OCH_3$ |
| 13(a-d) | —$(CH_2)_2$— | —$CH_2(C_3H_5)$ | $NHCH_3$ |
| 14(a-d) | —$(CH_2)_2$— | —$CH_2(C_3H_5)$ | $CH_2CH_3$ |
| 15(a-d) | —$(CH_2)_2$— | $CH_3$ | F |
| 16(a-d) | —$(CH_2)_2$— | —$CH_2CH_2OH$ | F |
| 17(a-d) | —$(CH_2)_2$— | —$(CH_2)_2CH(OH)CH_2OH$ | F |
| 18(a-d) | $CH_3$, H | —$(CH_2)_2CH(OH)CH_2OH$ | F |
| 19(a-d) | —$(CH_2)_2$— | $CH_3$ | $OCH_3$ |
| 20(a-d) | —$(CH_2)_2$— | —$CH_2CH_2OH$ | $OCH_3$ |
| 21(a-d) | —$(CH_2)_2$— | —$(CH_2)_2CH(OH)CH_2OH$ | $OCH_3$ |
| 22(a-d) | $CH_3$, H | —$(CH_2)_2CH(OH)CH_2OH$ | $OCH_3$ |
| 23(a-d) | —$(CH_2)_2$— | $CH_3$ | H |
| 24(a-d) | —$(CH_2)_2$— | —$CH_2CH_2OH$ | H |
| 25(a-d) | —$(CH_2)_2$— | —$(CH_2)_2CH(OH)CH_2OH$ | H |
| 26(a-d) | $CH_3$, H | —$(CH_2)_2CH(OH)CH_2OH$ | H |
| 27(a-d) | H, H | H | $OCH_3$ |
| 28(a-d) | H, H | H | $NHCH_3$ |
| 29(a-d) | H, H | H | $CH_2CH_3$ |
| 30(a-d) | H, H | H | $CH_2CH=CH_2$ |
| 31(a-d) | H, H | H | CN |
| 32(a-d) | H, H | H | $CF_3$ |
| 33(a-d) | H, H | H | F |
| 34(a-d) | H, H | H | $C_6H_6$ |
| 35(a-d) | H, H | —$CH_2CH(OH)CH_2OH$ | $OCH_3$ |
| 36(a-d) | H, H | —$CH_2CH(OH)CH_2OH$ | $NHCH_3$ |
| 37(a-d) | H, H | —$CH_2CH(OH)CH_2OH$ | $CH_2CH_3$ |
| 38(a-d) | —$(CH_2)_2$— | —$CH_2(C_3H_5)$ | $OCH_3$ |
| 39(a-d) | —$(CH_2)_2$— | —$CH_2(C_3H_5)$ | $NHCH_3$ |
| 40(a-d) | —$(CH_2)_2$— | —$CH_2(C_3H_5)$ | $CH_2CH_3$ |
| 41(a-d) | —$(CH_2)_2$— | $CH_3$ | F |
| 42(a-d) | —$(CH_2)_2$— | —$CH_2CH_2OH$ | F |
| 43(a-d) | —$(CH_2)_2$— | —$(CH_2)_2CH(OH)CH_2OH$ | F |
| 44(a-d) | $CH_3$, H | —$(CH_2)_2CH(OH)CH_2OH$ | F |
| 45(a-d) | —$(CH_2)_2$— | $CH_3$ | $OCH_3$ |
| 46(a-d) | —$(CH_2)_2$— | —$CH_2CH_2OH$ | $OCH_3$ |
| 47(a-d) | —$(CH_2)_2$— | —$(CH_2)_2CH(OH)CH_2OH$ | $OCH_3$ |
| 48(a-d) | $CH_3$, H | —$(CH_2)_2CH(OH)CH_2OH$ | $OCH_3$ |
| 49(a-d) | —$(CH_2)_2$— | $CH_3$ | H |
| 50(a-d) | —$(CH_2)_2$— | —$CH_2CH_2OH$ | H |
| 51(a-d) | —$(CH_2)_2$— | —$(CH_2)_2CH(OH)CH_2OH$ | H |
| 52(a-d) | $CH_3$, H | —$(CH_2)_2CH(OH)CH_2OH$ | H |

TABLE 4b

| CMPD # | A, A' | B | $R^O$ |
|---|---|---|---|
| 1(a-d) | H, H | H | 2-furanyl |
| 2(a-d) | H, H | H | 1,2,3 triazolyl-4-yl |
| 3(a-d) | H, H | H | 4-imidazolyl |
| 4(a-d) | H, H | H | 2-furanyl |
| 5(a-d) | H, H | H | 1,2,3 triazolyl-4-yl |
| 6(a-d) | H, H | H | 4-imidazolyl |
| 7(a-d) | H, H | —$(CH_2)_2CH(OH)CH_2OH$ | 2-furanyl |
| 8(a-d) | H, H | —$(CH_2)_2CH(OH)CH_2OH$ | 1,2,3 triazolyl-4-yl |
| 9(a-d) | H, H | —$(CH_2)_2CH(OH)CH_2OH$ | 4-imidazolyl |
| 10(a-d) | —$(CH_2)_2$— | —$CH_2(C_3H_5)$ | 2-furanyl |
| 11(a-d) | —$(CH_2)_2$— | —$CH_2(C_3H_5)$ | 1,2,3 triazolyl-4-yl |
| 12(a-d) | —$(CH_2)_2$— | —$CH_2(C_3H_5)$ | 4-imidazolyl |
| 13(a-d) | —$(CH_2)_2$— | $CH_3$ | 4-thiazolyl |
| 14(a-d) | —$(CH_2)_2$— | —$CH_2CH_2OH$ | 4-thiazolyl |
| 15(a-d) | —$(CH_2)_2$— | —$(CH_2)_2CH(OH)CH_2OH$ | 4-thiazolyl |
| 16(a-d) | $CH_3$, H | —$(CH_2)_2CH(OH)CH_2OH$ | 4-thiazolyl |
| 17(a-d) | —$(CH_2)_2$— | $CH_3$ | 2-oxazolyl |
| 18(a-d) | —$(CH_2)_2$— | —$CH_2CH_2OH$ | 2-oxazolyl |
| 19(a-d) | —$(CH_2)_2$— | —$(CH_2)_2CH(OH)CH_2OH$ | 2-oxazolyl |
| 20(a-d) | $CH_3$, H | —$(CH_2)_2CH(OH)CH_2OH$ | 2-oxazolyl |
| 21(a-d) | H, H | H | 2-furanyl |
| 22(a-d) | H, H | H | 1,2,3 triazolyl-4-yl |
| 23(a-d) | H, H | H | 4-imidazolyl |
| 24(a-d) | H, H | H | 2-furanyl |
| 25(a-d) | H, H | H | 1,2,3 triazolyl-4-yl |
| 26(a-d) | H, H | H | 4-imidazolyl |
| 27(a-d) | H, H | —$CH_2CH(OH)CH_2OH$ | 2-furanyl |
| 28(a-d) | H, H | —$CH_2CH(OH)CH_2OH$ | 1,2,3 triazolyl-4-yl |
| 29(a-d) | H, H | —$CH_2CH(OH)CH_2OH$ | 4-imidazolyl |
| 30(a-d) | —$(CH_2)_2$— | —$CH_2(C_3H_5)$ | 2-furanyl |
| 31(a-d) | —$(CH_2)_2$— | —$CH_2(C_3H_5)$ | 1,2,3 triazolyl-4-yl |
| 32(a-d) | —$(CH_2)_2$— | —$CH_2(C_3H_5)$ | 4-imidazolyl |
| 33(a-d) | —$(CH_2)_2$— | $CH_3$ | 4-thiazolyl |
| 34(a-d) | —$(CH_2)_2$— | —$CH_2CH_2OH$ | 4-thiazolyl |
| 35(a-d) | —$(CH_2)_2$— | —$(CH_2)_2CH(OH)CH_2OH$ | 4-thiazolyl |
| 36(a-d) | $CH_3$, H | —$(CH_2)_2CH(OH)CH_2OH$ | 4-thiazolyl |
| 37(a-d) | —$(CH_2)_2$— | $CH_3$ | 2-oxazolyl |
| 38(a-d) | —$(CH_2)_2$— | —$CH_2CH_2OH$ | 2-oxazolyl |
| 39(a-d) | —$(CH_2)_2$— | —$(CH_2)_2CH(OH)CH_2OH$ | 2-oxazolyl |
| 40(a-d) | $CH_3$, H | —$(CH_2)_2CH(OH)CH_2OH$ | 2-oxazolyl |

Table 5a shows embodiments of this invention which are compounds of formula I, where G is $Ar_1$, $Ar_2$ or $R_{1d}$, and where $R^O$ is H, Z is F and G and X are defined in the table. Each line in the table corresponds to five species ($Y_a$, $Y_b$, $Y_c$, $Y_d$ and $Y_e$) which differ only at position Y, where $Y_a$=$SCH_3$; $Y_b$=Br; $Y_c$=I; $Y_d$=Cl; $Y_e$=$CH_3$.

TABLE 5a

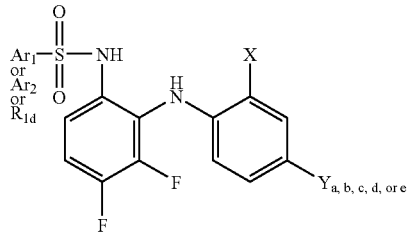

$Y_a = SCH_3$; $Y_b = Br$; $Y_c = I$; $Y_d = Cl$; $Y_e = CH_3$

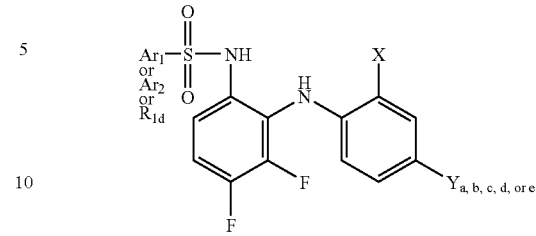

$Y_a = SCH_3$; $Y_b = Br$; $Y_c = I$; $Y_d = Cl$; $Y_e = CH_3$

| Compound # | G = $R_{1d}$, $Ar_1$, or $Ar_2$ | X |
|---|---|---|
| 1 (a-e) | phenyl | Cl |
| 2 (a-e) | phenyl | F |
| 3 (a-e) | 2-F-phenyl | Cl |
| 4 (a-e) | 2-F-phenyl | F |
| 5 (a-e) | 3-F-phenyl | Cl |
| 6 (a-e) | 3-F-phenyl | F |
| 7 (a-e) | 4-F-phenyl | Cl |
| 8 (a-e) | 4-F-phenyl | F |
| 9 (a-e) | 2,4-di-F-phenyl | Cl |
| 10 (a-e) | 2,4-di-F-phenyl | F |
| 11 (a-e) | 2,5-di-F-phenyl | Cl |
| 12 (a-e) | 2,5-di-F-phenyl | F |
| 13 (a-e) | 2,6-di-F-phenyl | Cl |
| 14 (a-e) | 2,6-di-F-phenyl | F |
| 15 (a-e) | 3,4-di-F-phenyl | Cl |
| 16 (a-e) | 3,4-di-F-phenyl | F |
| 17 (a-e) | 3,5-di-F-phenyl | Cl |
| 18 (a-e) | 3,5-di-F-phenyl | F |
| 19 (a-e) | 2,6-di-F-phenyl | Cl |
| 20 (a-e) | 2,6-di-F-phenyl | F |
| 21 (a-e) | 2,3,4-tri-F-phenyl | Cl |
| 22 (a-e) | 2,3,4-tri-F-phenyl | F |
| 23 (a-e) | 3,4,5-tri-F-phenyl | Cl |
| 24 (a-e) | 3,4,5-tri-F-phenyl | F |
| 25 (a-e) | penta-F-phenyl | Cl |
| 26 (a-e) | penta-F-phenyl | F |
| 27 (a-e) | 3-Cl-4-F-phenyl | Cl |
| 28 (a-e) | 3-Cl-4-F-phenyl | F |
| 29 (a-e) | 2-Cl-4-F-phenyl | Cl |
| 30 (a-e) | 2-Cl-4-F-phenyl | F |
| 31 (a-e) | 2-F-3-Cl-phenyl | Cl |
| 32 (a-e) | 2-F-3-Cl-phenyl | F |
| 33 (a-e) | 2-F-4-Cl-phenyl | Cl |
| 34 (a-e) | 2-F-4-Cl-phenyl | F |
| 35 (a-e) | 2-F-5-Cl-phenyl | Cl |
| 36 (a-e) | 2-F-5-Cl-phenyl | F |
| 37 (a-e) | 3-cyano-4-F-phenyl | Cl |
| 38 (a-e) | 3-cyano-4-F-phenyl | F |
| 39 (a-e) | 2-Cl-phenyl | Cl |
| 40 (a-e) | 2-Cl-phenyl | F |
| 41 (a-e) | 3-Cl-phenyl | Cl |
| 42 (a-e) | 3-Cl-phenyl | F |
| 43 (a-e) | 4-Cl-phenyl | Cl |
| 44 (a-e) | 4-Cl-phenyl | F |
| 45 (a-e) | 2,3-di-Cl-phenyl | Cl |
| 46 (a-e) | 2,3-di-Cl-phenyl | F |
| 47 (a-e) | 2,5-di-Cl-phenyl | Cl |
| 48 (a-e) | 2,5-di-Cl-phenyl | F |
| 49 (a-e) | 2,6-di-Cl-phenyl | Cl |
| 50 (a-e) | 2,6-di-Cl-phenyl | F |
| 51 (a-e) | 3,5-di-Cl-phenyl | Cl |
| 52 (a-e) | 3,5-di-Cl-phenyl | F |
| 53 (a-e) | 2,4-di-Cl-phenyl | Cl |
| 54 (a-e) | 2,4-di-Cl-phenyl | F |
| 55 (a-e) | 3,4-di-Cl-phenyl | Cl |
| 56 (a-e) | 3,4-di-Cl-phenyl | F |
| 57 (a-e) | 2,4,6-tri-Cl-phenyl | Cl |
| 58 (a-e) | 2,4,6-tri-Cl-phenyl | F |
| 59 (a-e) | 2-Cl-4-$CF_3$-phenyl | Cl |
| 60 (a-e) | 2-Cl-4-$CF_3$-phenyl | F |
| 61 (a-e) | 2-$CF_3$-phenyl | Cl |
| 62 (a-e) | 2-$CF_3$-phenyl | F |
| 63 (a-e) | 3-$CF_3$-phenyl | Cl |
| 64 (a-e) | 3-$CF_3$-phenyl | F |
| 65 (a-e) | 4-$CF_3$-phenyl | Cl |
| 66 (a-e) | 4-$CF_3$-phenyl | F |
| 67 (a-e) | 2-$CF_3O$ phenyl | Cl |
| 68 (a-e) | 2-$CF_3O$ phenyl | F |
| 69 (a-e) | 3-$CF_3O$ phenyl | Cl |
| 70 (a-e) | 3-$CF_3O$ phenyl | F |
| 71 (a-e) | 4-$CF_3O$ phenyl | Cl |
| 72 (a-e) | 4-$CF_3O$ phenyl | F |
| 73 (a-e) | 2-$CHF_2O$ phenyl | Cl |
| 74 (a-e) | 2-$CHF_2O$ phenyl | F |
| 75 (a-e) | 2-methyl-5-nitro-phenyl | Cl |
| 76 (a-e) | 2-methyl-5-nitro-phenyl | F |
| 77 (a-e) | 2-cyano-phenyl | Cl |
| 78 (a-e) | 2-cyano-phenyl | F |
| 79 (a-e) | 3-cyano-phenyl | Cl |
| 80 (a-e) | 3-cyano-phenyl | F |
| 81 (a-e) | 4-cyano-phenyl | Cl |
| 82 (a-e) | 4-cyano-phenyl | F |
| 83 (a-e) | 4-methoxy-phenyl | Cl |
| 84 (a-e) | 4-methoxy-phenyl | F |
| 85 (a-e) | 3,4-dimethoxy-phenyl | Cl |
| 86 (a-e) | 3,4-dimethoxy-phenyl | F |
| 87 (a-e) | 3-carbamyl-phenyl | Cl |
| 88 (a-e) | 3-carbamyl-phenyl | F |
| 89 (a-e) | 3-carboxyl-phenyl | Cl |
| 90 (a-e) | 3-carboxyl-phenyl | F |
| 91 (a-e) | 3-(N,N-dimethylcarbamoyl)phenyl | Cl |
| 92 (a-e) | 3-(N,N-dimethylcarbamoyl)phenyl | F |
| 93 (a-e) | 4-methylsulfonyl-phenyl | Cl |
| 94 (a-e) | 4-methylsulfonyl-phenyl | F |
| 95 (a-e) | 3-(1,3,4 oxadiazol-2-yl)phenyl | Cl |
| 96 (a-e) | 3-(1,3,4 oxadiazol-2-yl)phenyl | F |
| 97 (a-e) | 3-(1,3,4 thiadiazol-2-yl)phenyl | Cl |
| 98 (a-e) | 3-(1,3,4 thiadiazol-2-yl)phenyl | F |
| 99 (a-e) | 3-(5-methyl-1-1,3,4-oxadiazol)phenyl | Cl |
| 100 (a-e) | 3-(5-methyl-1-1,3,4-oxadiazol)phenyl | F |
| 101 (a-e) | 3-(5-methyl-1-1,3,4-thiadiazol)phenyl | Cl |
| 102 (a-e) | 3-(5-methyl-1-1,3,4-thiadiazol)phenyl | F |
| 103 (a-e) | 3-amidinyl-phenyl | Cl |
| 104 (a-e) | 3-amidinyl-phenyl | F |
| 105 (a-e) | 3-(1H-tetrazolyl)phenyl | Cl |
| 106 (a-e) | 3-(1H-tetrazolyl)phenyl | F |
| 107 (a-e) | 4-acetamido-phenyl | Cl |
| 108 (a-e) | 4-acetamido-phenyl | F |
| 109 (a-e) | 3-Cl-4-[(N-morpholinylcarbonyl)amino]phenyl | Cl |
| 110 (a-e) | 3-Cl-4-[(N-morpholinylcarbonyl)amino]phenyl | F |
| 111 (a-e) | 3-Cl-4-[(N-pyrrolidinylcarbonyl)amino]phenyl | Cl |
| 112 (a-e) | 3-Cl-4-[(N-pyrrolidinylcarbonyl)amino]phenyl | F |
| 113 (a-e) | 3,5-dimethylisoxazolyl | Cl |
| 114 (a-e) | 3,5-dimethylisoxazolyl | F |
| 115 (a-e) | 4-(N-morpholinylsulfonyl)phenyl | Cl |
| 116 (a-e) | 4-(N-morpholinylsulfonyl)phenyl | F |
| 117 (a-e) | 3-F-benzyl | Cl |
| 118 (a-e) | 3-F-benzyl | F |
| 119 (a-e) | 4-F-benzyl | Cl |
| 120 (a-e) | 4-F-benzyl | F |
| 121 (a-e) | 3-F-phenyl-ethyl | Cl |
| 122 (a-e) | 3-F-phenyl-ethyl | F |
| 123 (a-e) | 4-F-phenyl-ethyl | Cl |
| 124 (a-e) | 4-F-phenyl-ethyl | F |

TABLE 5a-continued

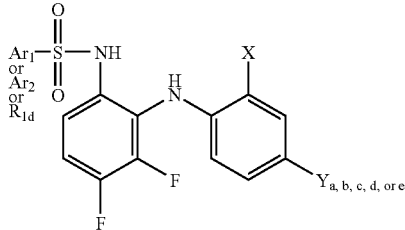

$Y_a = SCH_3$; $Y_b = Br$; $Y_c = I$; $Y_d = Cl$; $Y_e = CH_3$

| Compound # | G = $R_{1d}$, $Ar_1$, or $Ar_2$ | X |
|---|---|---|
| 125 (a-e) | 8-quinolinyl | Cl |
| 126 (a-e) | 8-quinolinyl | F |
| 127 (a-e) | 2-thienyl | Cl |
| 128 (a-e) | 2-thienyl | F |
| 129 (a-e) | 2,3-di-Cl-thien-5-yl | Cl |
| 130 (a-e) | 2,3-di-Cl-thien-5-yl | F |
| 131 (a-e) | 1,3,5 trimethyl-1H-pyrazolyl | Cl |
| 132 (a-e) | 1,3,5 trimethyl-1H-pyrazolyl | F |
| 133 (a-e) | 1,3-dimethyl-5-Cl-1H-pyrazolyl | Cl |
| 134 (a-e) | 1,3-dimethyl-5-Cl-1H-pyrazolyl | F |
| 135 (a-e) | 1-methyl-3CF$_3$-1H-pyrazol-4-yl | Cl |
| 136 (a-e) | 1-methyl-3CF$_3$-1H-pyrazol-4-yl | F |
| 137 (a-e) | 2-acetamido-4-methyl-thiazol-5-yl | Cl |
| 138 (a-e) | 2-acetamido-4-methyl-thiazol-5-yl | F |
| 139 (a-e) | 2,4-dimethyl-thiazol-5-yl | Cl |
| 140 (a-e) | 2,4-dimethyl-thiazol-5-yl | F |
| 141 (a-e) | 1,2-dimethyl-1H-imidazol-4-yl | Cl |
| 142 (a-e) | 1,2-dimethyl-1H-imidazol-4-yl | F |

Table 5b shows embodiments of this invention which are compounds of formula I, where G is $Ar_1$, $Ar_2$ or $R_{1d}$, and where $R^0$ is H, Z is F and G and X are defined in the table. Each line in the table corresponds to five species ($Y_a$, $Y_b$, $Y_c$, $Y_d$ and $Y_e$) which differ only at position Y, where $Y_a$=phenyl; $Y_b$=3-substituted phenyl; $Y_c$=3-pyridyl; $Y_d$=4-pyridyl; $Y_e$=3-pyrazolyl.

TABLE 5b

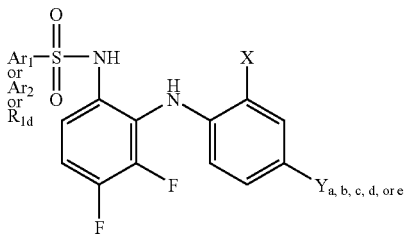

$Y_a$ = phenyl; $Y_b$ = 3-substituted phenyl;
$Y_c$ = 3-pyridyl; $Y_d$ = 4-pyridyl; $Y_e$ = 3-pyrazolyl

| Compound # | G = $R_{1d}$, $Ar_1$, or $Ar_2$ | X |
|---|---|---|
| 1 (a-e) | phenyl | Cl |
| 2 (a-e) | phenyl | F |
| 3 (a-e) | 2-F-phenyl | Cl |
| 4 (a-e) | 2-F-phenyl | F |
| 5 (a-e) | 3-F-phenyl | Cl |
| 6 (a-e) | 3-F-phenyl | F |
| 7 (a-e) | 4-F-phenyl | Cl |
| 8 (a-e) | 4-F-phenyl | F |
| 9 (a-e) | 2,4-di-F-phenyl | Cl |
| 10 (a-e) | 2,4-di-F-phenyl | F |
| 11 (a-e) | 2,5-di-F-phenyl | Cl |
| 12 (a-e) | 2,5-di-F-phenyl | F |

TABLE 5b-continued

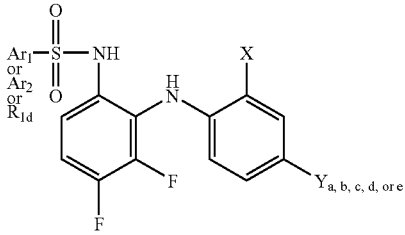

$Y_a$ = phenyl; $Y_b$ = 3-substituted phenyl;
$Y_c$ = 3-pyridyl; $Y_d$ = 4-pyridyl; $Y_e$ = 3-pyrazolyl

| Compound # | G = $R_{1d}$, $Ar_1$, or $Ar_2$ | X |
|---|---|---|
| 13 (a-e) | 2,6-di-F-phenyl | Cl |
| 14 (a-e) | 2,6-di-F-phenyl | F |
| 15 (a-e) | 3,4-di-F-phenyl | Cl |
| 16 (a-e) | 3,4-di-F-phenyl | F |
| 17 (a-e) | 3,5-di-F-phenyl | Cl |
| 18 (a-e) | 3,5-di-F-phenyl | F |
| 19 (a-e) | 2,6-di-F-phenyl | Cl |
| 20 (a-e) | 2,6-di-F-phenyl | F |
| 21 (a-e) | 2,3,4-tri-F-phenyl | Cl |
| 22 (a-e) | 2,3,4-tri-F-phenyl | F |
| 23 (a-e) | 3,4,5-tri-F-phenyl | Cl |
| 24 (a-e) | 3,4,5-tri-F-phenyl | F |
| 25 (a-e) | penta-F-phenyl | Cl |
| 26 (a-e) | penta-F-phenyl | F |
| 27 (a-e) | 3-Cl-4-F-phenyl | Cl |
| 28 (a-e) | 3-Cl-4-F-phenyl | F |
| 29 (a-e) | 2-Cl-4-F-phenyl | Cl |
| 30 (a-e) | 2-Cl-4-F-phenyl | F |
| 31 (a-e) | 2-F-3-Cl-phenyl | Cl |
| 32 (a-e) | 2-F-3-Cl-phenyl | F |
| 33 (a-e) | 2-F-4-Cl-phenyl | Cl |
| 34 (a-e) | 2-F-4-Cl-phenyl | F |
| 35 (a-e) | 2-F-5-Cl-phenyl | Cl |
| 36 (a-e) | 2-F-5-Cl-phenyl | F |
| 37 (a-e) | 3-cyano-4-F-phenyl | Cl |
| 38 (a-e) | 3-cyano-4-F-phenyl | F |
| 39 (a-e) | 2-Cl-phenyl | Cl |
| 40 (a-e) | 2-Cl-phenyl | F |
| 41 (a-e) | 3-Cl-phenyl | Cl |
| 42 (a-e) | 3-Cl-phenyl | F |
| 43 (a-e) | 4-Cl-phenyl | Cl |
| 44 (a-e) | 4-Cl-phenyl | F |
| 45 (a-e) | 2,3-di-Cl-phenyl | Cl |
| 46 (a-e) | 2,3-di-Cl-phenyl | F |
| 47 (a-e) | 2,5-di-Cl-phenyl | Cl |
| 48 (a-e) | 2,5-di-Cl-phenyl | F |
| 49 (a-e) | 2,6-di-Cl-phenyl | Cl |
| 50 (a-e) | 2,6-di-Cl-phenyl | F |
| 51 (a-e) | 3,5-di-Cl-phenyl | Cl |
| 52 (a-e) | 3,5-di-Cl-phenyl | F |
| 53 (a-e) | 2,4-di-Cl-phenyl | Cl |
| 54 (a-e) | 2,4-di-Cl-phenyl | F |
| 55 (a-e) | 3,4-di-Cl-phenyl | Cl |
| 56 (a-e) | 3,4-di-Cl-phenyl | F |
| 57 (a-e) | 2,4,6-tri-Cl-phenyl | Cl |
| 58 (a-e) | 2,4,6-tri-Cl-phenyl | F |
| 59 (a-e) | 2-Cl-4-CF$_3$-phenyl | Cl |
| 60 (a-e) | 2-Cl-4-CF$_3$-phenyl | F |
| 61 (a-e) | 2-CF$_3$-phenyl | Cl |
| 62 (a-e) | 2-CF$_3$-phenyl | F |
| 63 (a-e) | 3-CF$_3$-phenyl | Cl |
| 64 (a-e) | 3-CF$_3$-phenyl | F |
| 65 (a-e) | 4-CF$_3$-phenyl | Cl |
| 66 (a-e) | 4-CF$_3$-phenyl | F |
| 67 (a-e) | 2-CF$_3$O phenyl | Cl |
| 68 (a-e) | 2-CF$_3$O phenyl | F |
| 69 (a-e) | 3-CF$_3$O phenyl | Cl |
| 70 (a-e) | 3-CF$_3$O phenyl | F |
| 71 (a-e) | 4-CF$_3$O phenyl | Cl |
| 72 (a-e) | 4-CF$_3$O phenyl | F |
| 73 (a-e) | 4-CHF$_2$O-phenyl | Cl |

TABLE 5b-continued

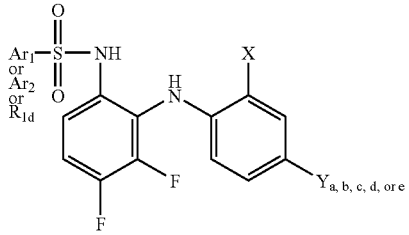

$Y_a$ = phenyl; $Y_b$ = 3-substituted phenyl;
$Y_c$ = 3-pyridyl; $Y_d$ = 4-pyridyl; $Y_e$ = 3-pyrazolyl

| Compound # | G = $R_{1d}$, $Ar_1$, or $Ar_2$ | X |
|---|---|---|
| 74 (a-e) | 4-CHF$_2$O-phenyl | F |
| 75 (a-e) | 2-methyl-5-nitro-phenyl | Cl |
| 76 (a-e) | 2-methyl-5-nitro-phenyl | F |
| 77 (a-e) | 2-cyano-phenyl | Cl |
| 78 (a-e) | 2-cyano-phenyl | F |
| 79 (a-e) | 3-cyano-phenyl | Cl |
| 80 (a-e) | 3-cyano-phenyl | F |
| 81 (a-e) | 4-cyano-phenyl | Cl |
| 82 (a-e) | 4-cyano-phenyl | F |
| 83 (a-e) | 4-methoxy-phenyl | Cl |
| 84 (a-e) | 4-methoxy-phenyl | F |
| 85 (a-e) | 3,4-dimethoxy-phenyl | Cl |
| 86 (a-e) | 3,4-dimethoxy-phenyl | F |
| 87 (a-e) | 3-carbamyl-phenyl | Cl |
| 88 (a-e) | 3-carbamyl-phenyl | F |
| 89 (a-e) | 3-carboxyl-phenyl | Cl |
| 90 (a-e) | 3-carboxyl-phenyl | F |
| 91 (a-e) | 3-(N,N-dimethylcarbamoyl)phenyl | Cl |
| 92 (a-e) | 3-(N,N-dimethylcarbamoyl)phenyl | F |
| 93 (a-e) | 4-methylsulfonyl-phenyl | Cl |
| 94 (a-e) | 4-methylsulfonyl-phenyl | F |
| 95 (a-e) | 3-(1,3,4 oxadiazol-2-yl)phenyl | Cl |
| 96 (a-e) | 3-(1,3,4 oxadiazol-2-yl)phenyl | F |
| 97 (a-e) | 3-(1,3,4 thiadiazol-2-yl)phenyl | Cl |
| 98 (a-e) | 3-(1,3,4 thiadiazol-2-yl)phenyl | F |
| 99 (a-e) | 3-(5-methyl-1,3,4-oxadiazol)phenyl | Cl |
| 100 (a-e) | 3-(5-methyl-1,3,4-oxadiazol)phenyl | F |
| 101 (a-e) | 3-(5-methyl-1,3,4-thiadiazol)phenyl | Cl |
| 102 (a-e) | 3-(5-methyl-1,3,4-thiadiazol)phenyl | F |
| 103 (a-e) | 3-amidinyl-phenyl | Cl |
| 104 (a-e) | 3-amidinyl-phenyl | F |
| 105 (a-e) | 3-(1H-tetrazolyl)phenyl | Cl |
| 106 (a-e) | 3-(1H-tetrazolyl)phenyl | F |
| 107 (a-e) | 4-acetamido-phenyl | Cl |
| 108 (a-e) | 4-acetamido-phenyl | F |
| 109 (a-e) | 3-Cl-4-[(N-morpholinylcarbonyl)amino]phenyl | Cl |
| 110 (a-e) | 3-Cl-4-[(N-morpholinylcarbonyl)amino]phenyl | F |
| 111 (a-e) | 3-Cl-4-[(N-pyrrolidinylcarbonyl)amino]phenyl | Cl |
| 112 (a-e) | 3-Cl-4-[(N-pyrrolidinylcarbonyl)amino]phenyl | F |
| 113 (a-e) | 3,5-dimethylisoxazolyl | Cl |
| 114 (a-e) | 3,5-dimethylisoxazolyl | F |
| 115 (a-e) | 4-(N-morpholinylsulfonyl)phenyl | Cl |
| 116 (a-e) | 4-(N-morpholinylsulfonyl)phenyl | F |
| 117 (a-e) | 3-F-benzyl | Cl |
| 118 (a-e) | 3-F-benzyl | F |
| 119 (a-e) | 4-F-benzyl | Cl |
| 120 (a-e) | 4-F-benzyl | F |
| 121 (a-e) | 3-F-phenyl-ethyl | Cl |
| 122 (a-e) | 3-F-phenyl-ethyl | F |
| 123 (a-e) | 4-F-phenyl-ethyl | Cl |
| 124 (a-e) | 4-F-phenyl-ethyl | F |
| 125 (a-e) | 8-quinolinyl | Cl |
| 126 (a-e) | 8-quinolinyl | F |
| 127 (a-e) | 2-thienyl | Cl |
| 128 (a-e) | 2-thienyl | F |
| 129 (a-e) | 2,3-di-Cl-thien-5-yl | Cl |
| 130 (a-e) | 2,3-di-Cl-thien-5-yl | F |

TABLE 5b-continued

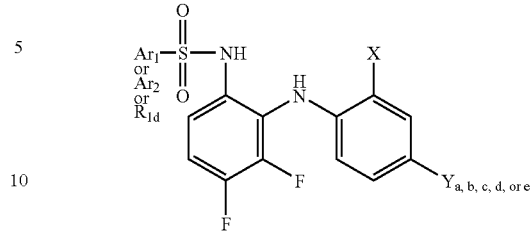

$Y_a$ = phenyl; $Y_b$ = 3-substituted phenyl;
$Y_c$ = 3-pyridyl; $Y_d$ = 4-pyridyl; $Y_e$ = 3-pyrazolyl

| Compound # | G = $R_{1d}$, $Ar_1$, or $Ar_2$ | X |
|---|---|---|
| 131 (a-e) | 1,3,5 trimethyl-1H-pyrazolyl | Cl |
| 132 (a-e) | 1,3,5 trimethyl-1H-pyrazolyl | F |
| 133 (a-e) | 1,3-dimethyl-5-Cl-1H-pyrazolyl | Cl |
| 134 (a-e) | 1,3-dimethyl-5-Cl-1H-pyrazolyl | F |
| 135 (a-e) | 1-methyl-3-CF$_3$-1H-pyrazol-4-yl | Cl |
| 136 (a-e) | 1-methyl-3-CF$_3$-1H-pyrazol-4-yl | F |
| 137 (a-e) | 2-acetamido-4-methyl-thiazol-5-yl | Cl |
| 138 (a-e) | 2-acetamido-4-methyl-thiazol-5-yl | F |
| 139 (a-e) | 2,4-dimethyl-thiazol-5-yl | Cl |
| 140 (a-e) | 2,4-dimethyl-thiazol-5-yl | F |
| 141 (a-e) | 1,2-dimethyl-1H-imidazol-4-yl | Cl |
| 142 (a-e) | 1,2-dimethyl-1H-imidazol-4-yl | F |
| 143 (a-e) | 1-(2-hydroxyethyl) cyclopropyl | F |
| 144 (a-e) | 1-(3-hydroxypropyl) cyclopropyl | F |
| 145 (a-e) | 1-(2,3-dihydroxypropyl) cyclopropyl | F |
| 146 (a-e) | 1-(3,4-dihydroxybutyl) cyclopropyl | F |
| 147 (a-e) | 1-(2,3-dihydroxypropyl) cyclobutyl | F |

Synthetic Procedures

In another aspect, methods for synthesizing the compounds described herein are provided. In some embodiments, the compounds described herein can be prepared by the methods described below. The procedures and examples below are intended to illustrate those methods. Neither the procedures nor the examples should be construed as limiting the invention in any way. Compounds described herein may also be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting materials used for the synthesis of the compounds as described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. The table below entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

Examples of Covalent Linkages and Precursors Thereof

| Covalent Linkage Product | Electrophile | Nucleophile |
|---|---|---|
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Azindines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Protecting or blocking groups may be selected from:

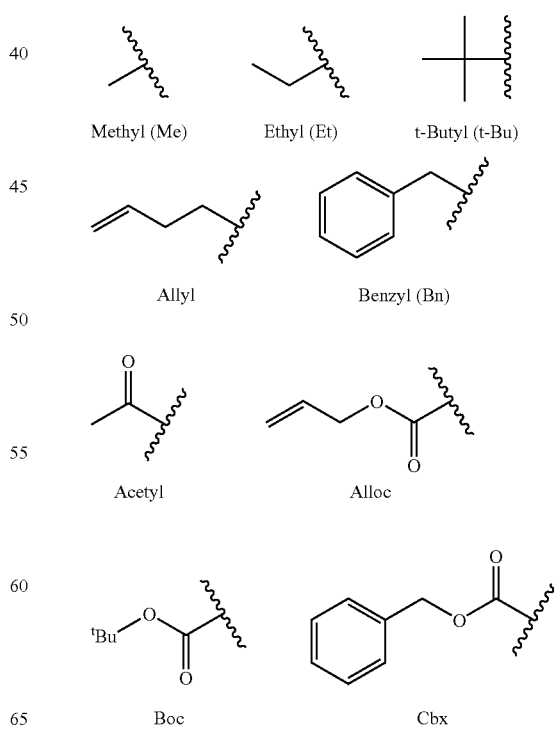

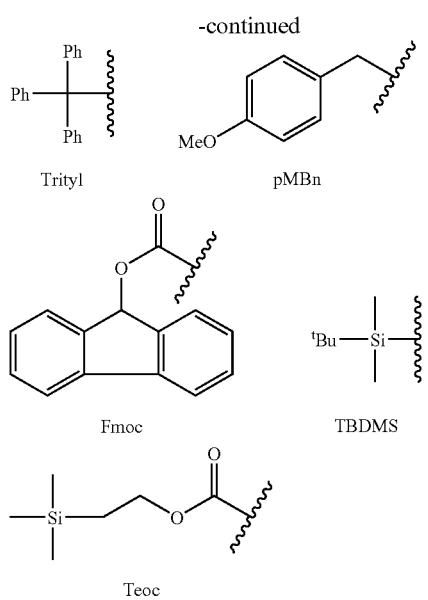

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference in their entirety.

Preparing Compounds of Formula I

Compounds of this invention can be prepared by a variety of methods. The procedures below are intended to illustrate those methods, and the examples given are intended to illustrate the scope of this invention. Neither the methods not the examples should be construed as limiting the invention in any way.

I. The Preparation of Compound of Formula VI is Outlined Below

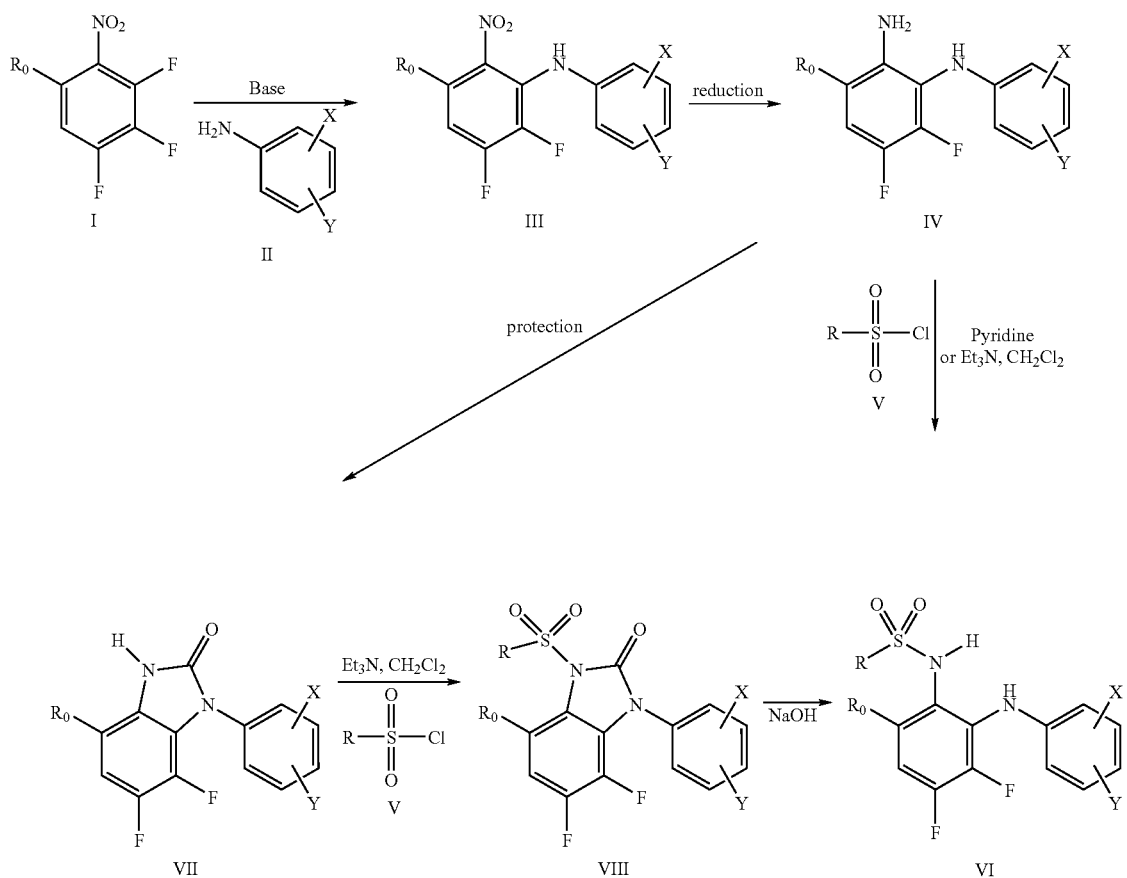

Scheme I above illustrates the preparation of sulfonamide derivatives of formula VI. 1,2 Diamine derivative (formula IV) can be easily prepared in two steps from the desired nitro derivatives (formula I). Compounds of formula IV can be reacted with the sulfonyl chloride derivatives (formula V, see next scheme) to form the desired sulfonamide. Alternatively, the 1,2 diamine derivatives IV can be protected to for an imidazolidone (formula VII), before being reacted with the corresponding sulfonyl chloride. Deprotection of the 1,2 diamine VIII under basic conditions provided the desired material VI.

II. The General Route to Synthesis Compound of General Formula V is Outlined Below

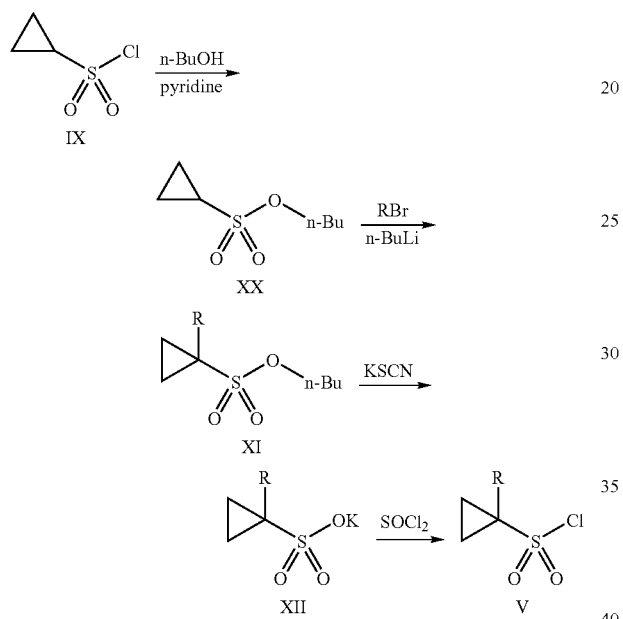

Scheme II above shows one example of the preparation of complex sulfonyl chloride. Compound XX can be synthesized from IX, alkylated, and converted to the potassium salt XII. Treatment of the salt with $SOCl_2$ or $POCl_3$ affords the desired compounds. Other more specific procedures to prepare unique sulfonyl chloride derivatives are reported in the experimental section.

III. The General Route to Synthesis Compound of General Formula XIII is Outlines Scheme 3.

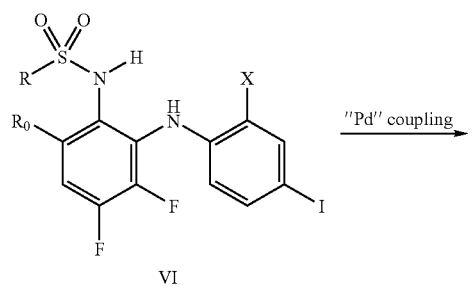

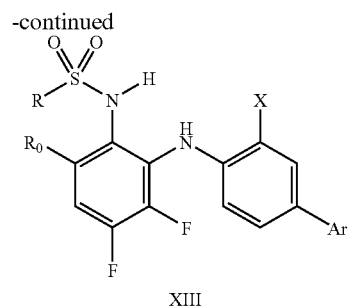

Scheme III above illustrates the preparation of sulfonamide derivatives of general formula XIII. For example, these compounds can be easily obtained by reacting the compound VI with a boronic acid using a palladium catalyst under Suzuki conditions.

IV. The General Route to Synthesis Compound of General Formula XIII is Outlines Scheme 4.

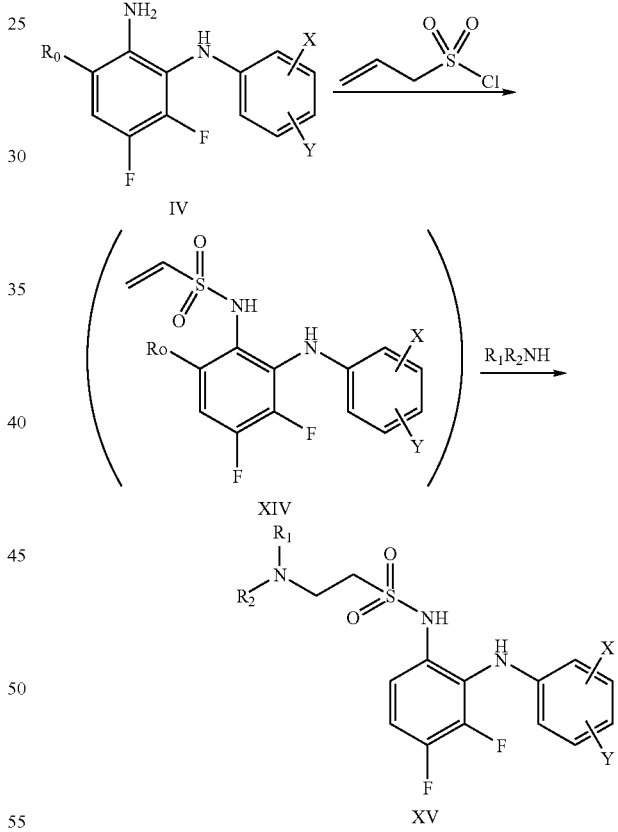

Scheme IV above illustrates the preparation of sulfonamide derivatives of general formula XV. The vinyl sulfonamide (XIV) is reacted with amines to form derivatives of general formulas XV.

Further Forms of Compounds of Formula I

Isomers of Compounds of Formula I

The compounds described herein may exist as geometric isomers. The compounds described herein may possess one or more double bonds. The compounds presented herein include all cis, trans, syn, anti, entgegen (E), and zusammen (Z) isomers as well as the corresponding mixtures thereof. In some situations, compounds may exist as tautomers. The compounds described herein include all possible tautomers within the formulas described herein. The compounds described herein may possess one or more chiral centers and each center may exist in the R or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion may also be useful for the applications described herein. The compounds described herein can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chiral chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, herein incorporated by reference in its entirety.

Labeled Compounds of Formula I

Also described herein are isotopically-labeled compounds of formula I and methods of treating disorders. For example, the invention provides for methods of treating diseases, by administering isotopically-labeled compounds of formula I. The isotopically-labeled compounds of formula I can be administered as pharmaceutical compositions. Thus, compounds of formula I also include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chloride, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, pharmaceutically acceptable salts, esters, prodrugs, solvate, hydrates or derivatives thereof which contain the aforementioned isotopes and/or other isotopes of other atoms are within the scope of this invention. Certain isotopically-labeled compounds of formula I, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds, pharmaceutically acceptable salt, ester, prodrug, solvate, hydrate or derivative thereof can generally be prepared by carrying out procedures described herein, by substituting a readily available isotopically labeled reagent for a non-isotopically labeled reagent.

The compounds described herein may be labeled by other means, including, but not limited to, the use of chromophores or fluorescent moieties, bioluminescent labels, or chemiluminescent labels.

Pharmaceutically Acceptable Salts of Compounds of Formula I

Also described herein are pharmaceutically acceptable salts of compounds of formula I and methods of treating disorders. For example, the invention provides for methods of treating diseases, by administering pharmaceutically acceptable salts of compounds of formula I. The pharmaceutically acceptable salts of compounds of formula I can be administered as pharmaceutical compositions.

Thus, the compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Solvates of Compounds of Formula I

Also described herein are solvates of compounds of formula I and methods of treating disorders. For example, the invention provides for methods of treating diseases, by administering solvates of compounds of formula I. The solvates of compounds of formula I can be administered as pharmaceutical compositions.

Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs of Compounds of Formula I

Also described herein are polymorphs of compounds of formula I and methods of treating disorders. For example, the invention provides for methods of treating diseases, by administering polymorphs of compounds of formula I. The polymorphs of compounds of formula I can be administered as pharmaceutical compositions.

Thus, the compounds described herein include all their crystalline forms, known as polymorphs. Polymorphs include the different crystal packing arrangements of the same elemental composition of a compound. Polymorphs may have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Prodrugs of Compounds of Formula I

Also described herein are prodrugs of compounds of formula I and methods of treating disorders. For example, the invention provides for methods of treating diseases, by administering prodrugs of compounds of formula I. The prodrugs of compounds of formula I can be administered as pharmaceutical compositions.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyamino acid) bonded to an acid group where the peptide is metabolized to reveal the active moiety.

Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.*, 269:$G_{210}$-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein in their entirety.

Additionally, prodrug derivatives of compounds described herein can be prepared by methods known to those of ordinary skill in the art (e.g., for further details see Saulnier et al., (1994), Bioorganic and Medicinal Chemistry Letters, Vol. 4, p. 1985). By way of example only, appropriate prodrugs can be prepared by reacting a non-derivatized compound of formula I with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds may be a prodrug for another derivative or active compound.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

Compounds of formula I having free amino, amido, hydroxy or carboxylic groups can be converted into prodrugs. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Sites on the aromatic ring portions of compounds of formula I may be susceptible to various metabolic reactions, therefore incorporation of appropriate substituents on the aromatic ring structures, can reduce, minimize or eliminate this metabolic pathway.

Pharmaceutical Compositions

Described herein are pharmaceutical compositions. In some embodiments, the pharmaceutical compositions comprise an effective amount of a compound formula I, or a pharmaceutically acceptable salt, ester, prodrug, solvate, hydrate or derivative thereof. In some embodiments, the pharmaceutical compositions comprise an effective amount of a compound formula I, or a pharmaceutically acceptable salt, ester, prodrug, solvate, hydrate or derivative thereof and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human.

MEK Modulation

Also described herein are methods of modulating MEK activity by contacting MEK with an amount of a compound of formula I sufficient to modulate the activity of MEK. Modulate can be inhibiting or activating MEK activity. In some embodiments, the invention provides methods of inhibiting MEK activity by contacting MEK with an amount of a compound of formula I sufficient to inhibit the activity of MEK. In some embodiments, the invention provides methods of inhibiting MEK activity in a solution by contacting said solution with an amount of a compound of formula I sufficient to inhibit the activity of MEK in said solution. In some embodiments, the invention provides methods of inhibiting MEK activity in a cell by contacting said cell with an amount of a compound described herein sufficient to inhibit the activity of MEK in said cell. In some embodiments, the invention provides methods of inhibiting MEK activity in a tissue by contacting said tissue with an amount of a compound described herein sufficient to inhibit the activity of MEK in said tissue. In some embodiments, the invention provides methods of inhibiting MEK activity in an organism by contacting said organism with an amount of a compound described herein sufficient to inhibit the activity of MEK in said organism. In some embodiments, the invention provides methods of inhibiting MEK activity in an animal by contacting said animal with an amount of a compound described herein sufficient to inhibit the activity of MEK in said animal. In some embodiments, the invention provides methods of inhibiting MEK activity in a mammal by contacting said mammal with an amount of a compound described herein sufficient to inhibit the activity of MEK in said mammal. In some embodiments, the invention provides methods of inhibiting MEK activity in a human by contacting said human with an amount of a compound described herein sufficient to inhibit the activity of MEK in said human.

Abnormal Cell Growth

Also described herein are compounds, pharmaceutical compositions and methods for inhibiting abnormal cell growth. In some embodiments, the abnormal cell growth occurs in a mammal. Methods for inhibiting abnormal cell growth comprise administering an effective amount of a compound of formula I, or a pharmaceutically acceptable salt, ester, prodrug, solvate, hydrate or derivative thereof, wherein abnormal cell growth is inhibited. Methods for inhibiting abnormal cell growth in a mammal comprise administering to the mammal an amount of a compound of formula I, or a pharmaceutically acceptable salt, ester, prodrug, solvate, hydrate or derivative thereof, wherein the amounts of the compound, salt, ester, prodrug, solvate, hydrate or derivative, is effective in inhibiting abnormal cell growth in the mammal.

In some embodiments, the methods comprise administering an effective amount of a compound of formula I, or a pharmaceutically acceptable salt, ester, prodrug, solvate, hydrate or derivative thereof, in combination with an amount of a chemotherapeutic, wherein the amounts of the compound, salt, ester, prodrug, solvate, hydrate or derivative, and of the chemotherapeutic are together effective in inhibiting abnormal cell growth. Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

Also described are methods for inhibiting abnormal cell growth in a mammal comprising administering to the mammal an amount of a compound of formula I, or a pharmaceutically acceptable salt, ester, prodrug, solvate, hydrate or derivative thereof, in combination with radiation therapy, wherein the amounts of the compound, salt, ester, prodrug, solvate, hydrate or derivative, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of formula I in this combination therapy can be determined as described herein.

The invention also relates to a method of and to a pharmaceutical composition of inhibiting abnormal cell growth in a mammal which comprises an amount of a compound of formula I, or a pharmaceutically acceptable salt, ester, prodrug, solvate, hydrate or derivative thereof, or an isotopically-labeled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrixmetalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

Modes of Administration

Described herein are compounds of formula I or a pharmaceutically acceptable salt, solvate, polymorph, ester, tautomer or prodrug thereof. Also described, are pharmaceutical compositions comprising a compound of formula I or a pharmaceutically acceptable salt, solvate, polymorph, ester, tautomer or prodrug thereof. The compounds and compositions described herein may be administered either alone or in combination with pharmaceutically acceptable carriers, excipients or diluents, in a pharmaceutical composition, according to standard pharmaceutical practice.

Administration of the compounds and compositions described herein can be effected by any method that enables delivery of the compounds to the site of action. These methods include oral routes, intraduodenal routes, parenteral injection (including intravenous, subcutaneous, intraperitoneal, intramuscular, intravascular or infusion), topical, and rectal administration. For example, compounds described herein can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue. Those of ordinary skill in the art are familiar with formulation and administration techniques that can be employed with the compounds and methods of the invention, e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

Pharmaceutical preparations may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical preparations may also be formulated in rectal compositions such as suppositories or retention enemas, e.g., containing conventional suppository bases such as cocoa butter, polyethylene glycol, or other glycerides.

Pharmaceutical preparations may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Formulations

The compounds or compositions described herein can be delivered in a vesicle, e.g., a liposome (see, for example, Langer, *Science* 1990, 249, 1527-1533; Treat et al., *Liposomes in the Therapy of Infectious Disease and Cancer*, Lopez-Bernstein and Fidler, Ed., Liss, N.Y., pp. 353-365, 1989). The compounds and pharmaceutical compositions described herein can also be delivered in a controlled release system. In one embodiment, a pump may be used (see, Sefton, 1987, CRC Crit. Ref. Biomed. Eng. 14:201; Buchwald et al. *Surgery*, 1980 88, 507; Saudek et al. *N. Engl. J. Med.* 1989, 321, (574). Additionally, a controlled release system can be placed in proximity of the therapeutic target. (See, Goodson, *Medical Applications of Controlled Release*, 1984, Vol. 2, pp. 115-138). The pharmaceutical compositions described herein can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate. Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

Pharmaceutical compositions may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

Pharmaceutical compositions may be in the form of a sterile injectable aqueous solution. Among the acceptable vehicles and solvents that may be employed are water, Ringer's solution and isotonic sodium chloride solution. The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion. The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump. The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Pharmaceutical compositions may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing a compound or composition of the invention can be used. As used herein, topical application can include mouth washes and gargles.

Pharmaceutical compositions may be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 7000 mg of compound, and preferably includes, e.g., from about 0.05 mg to about 2500 mg. The quantity of active compound in a unit dose of preparation may be varied or adjusted from about 0.1 mg to 1000 mg, preferably from about 1 mg to 300 mg, more preferably 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ value of the compound used. In combinational applications in which the compound is not the sole therapy, it may be possible to administer lesser amounts of compound and still have therapeutic or prophylactic effect.

Dosage Forms

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 18th Edition (1990).

Combination Therapies

The compounds described herein or a pharmaceutically acceptable salt, solvate, polymorph, ester, tautomer or prodrug thereof may be administered as a sole therapy. The compounds described herein or a pharmaceutically acceptable salt, solvate, polymorph, ester, tautomer or prodrug thereof may also be administered in combination with another therapy or therapies.

By way of example only, if one of the side effects experienced by a patient upon receiving one of the compounds described herein is hypertension, then it may be appropriate to administer an anti-hypertensive agent in combination with the compound. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, the compounds/compositions may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician. The particular choice of compound (and where appropriate, other therapeutic agent and/or radiation) will depend upon the diagnosis of the attending physicians and their judgment of the condition of the patient and the appropriate treatment protocol. Other therapeutic agents may include chemotherapeutic agents, such as anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

The compounds and compositions described herein (and where appropriate chemotherapeutic agent and/or radiation) may be administered concurrently (e.g., simultaneously, essentially simultaneously or within the same treatment protocol) or sequentially, depending upon the nature of the disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation need not be administered simultaneously or essentially simultaneously, and the initial order of administration of the compound/composition, and the chemotherapeutic agent and/or radiation, may not be important. Thus, the compounds/compositions of the invention may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the compounds/compositions of the invention followed, where determined advantageous, by the administration of the chemotherapeutic agent and/or radiation, and so on until the treatment protocol is complete. Thus, in accordance with experience and knowledge, the practicing physician can modify each protocol for the administration of a compound/composition for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Specific, non-limiting examples of possible combination therapies include use of the compounds of the invention with agents found in the following pharmacotherapeutic classifications as indicated below. These lists should not be construed to be closed, but should instead serve as illustrative examples common to the relevant therapeutic area at present. Moreover, combination regimens may include a variety of routes of administration and should include oral, intravenous, intraocular, subcutaneous, dermal, and inhaled topical.

For the treatment of oncologic diseases, proliferative disorders, and cancers, compounds according to the present invention may be administered with an agent selected from the group comprising: aromatase inhibitors, antiestrogen, anti-androgen, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, IMiDs, protein or lipid phosphatase targeting agents, anti-angiogenic agents, Akt inhibitors, IGF-I inhibitors, FGF3 modulators, mTOR inhibitors, Smac mimetics, HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, HSP90 inhibitors, multikinase inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors, and aminopeptidase inhibitors.

For the treatment of oncologic diseases, proliferative disorders, and cancers, compounds according to the present invention may be administered with an agent selected from the group comprising: dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, carminomycin, idarubicin, epirubicin, esorubicin, mitoxantrone, bleomycins A, $A_2$, and B, camptothecin, Irinotecan®, Topotecan®, 9-aminocamptothecin, 10,11-methylenedioxycamptothecin, 9-nitrocamptothecin, bortezomib, temozolomide, TAS103, NPI0052, combretastatin, combretastatin A-2, combretastatin A-4, calicheamicins, neocarcinostatins, epothilones A B, C, and semi-synthetic variants, Herceptin®, Rituxan®, CD40 antibodies, asparaginase, interleukins, interferons, leuprolide, and pegaspargase, 5-fluorouracil, fluorodeoxyuridine, ptorafur, 5'-deoxyfluorouridine, UFT, MITC, S-1 capecitabine, diethylstilbestrol, tamoxifen, toremefine, tolmudex, thyrnitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

For the treatment of inflammatory diseases and pain, compounds according to the present invention may be administered with an agent selected from the group comprising: corticosteroids, non-steroidal anti-inflammatories, muscle relaxants and combinations thereof with other agents, anaesthetics and combinations thereof with other agents, expectorants and combinations thereof with other agents, antidepressants, anticonvulsants and combinations thereof; antihypertensives, opioids, topical cannabinoids, and other agents, such as capsaicin.

For the treatment of inflammatory diseases and pain, compounds according to the present invention may be administered with an agent selected from the group comprising: betamethasone dipropionate (augmented and non-augemnted), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halocinonide, clocortalone pivalate, dexosimetasone, flurandrenalide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocaine, EMLA Cream (Eutectic Mixture of Local Anesthetics (lidocaine 2.5% and prilocaine 2.5%), guaifenesin, guaifenesin/ketoprofen/cyclobenzaprine, amitryptiline, doxepin, desipramine, imipramine, amoxapine, clomipramine, nortriptyline, protriptyline, duloxetine, mirtazepine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab; n) nitric oxide synthase inhibitors, particularly inhibitors of inducible nitric oxide synthase; and other agents, such as capsaicin.

For the treatment of ophthalmologic disorders and diseases of the eye, compounds according to the present invention may be administered with an agent selected from the group comprising: beta-blockers, carbonic anhydrase inhibitors, alpha. -and .beta.-adrenergic antagonists including a1-adrenergic antagonists, .alpha.2 agonists, miotics, prostaglandin analogs, corticosteroids, and immunosuppressant agents.

For the treatment of ophthalmologic disorders and diseases of the eye, compounds according to the present invention may be administered with an agent selected from the group comprising: timolol, betaxolol, levobetaxolol, carteolol, levobunolol, propranolol, brinzolamide, dorzolamide, nipradilol, iopidine, brimonidine, pilocarpine, epinephrine, latanoprost, travoprost, bimatoprost, unoprostone, dexamethasone, prednisone, methylprednisolone, azathioprine, cyclosporine, and immunoglobulins.

For the treatment of autoimmune disorders, compounds according to the present invention may be administered with an agent selected from the group comprising: corticosteroids, immunosuppressants, prostaglandin analogs and antimetabolites.

For the treatment of autoimmune disorders, compounds according to the present invention may be administered with an agent selected from the group comprising: dexamethasome, prednisone, methylprednisolone, azathioprine, cyclosporine, immunoglobulins, latanoprost, travoprost, bimatoprost, unoprostone, infliximab, rutuximab and methotrexate.

For the treatment of metabolic disorders, compounds according to the present invention may be administered with an agent selected from the group comprising: insulin, insulin derivatives and mimetics, insulin secretagogues, insulin sensitizers, biguanide agents, alpha-glucosidase inhibitors, insulinotropic sulfonylurea receptor ligands, protein tyrosine phosphatase-IB (PTP-1B) inhibitors, GSK3 (glycogen synthase kinase-3) inhibitors, GLP-1 (glucagon like peptide-1), GLP-1 analogs, DPPIV (dipeptidyl peptidase IV) inhibitors, RXR ligands sodium-dependent glucose co-transporter inhibitors, glycogen phosphorylase A inhibitors, an AGE breaker, PPAR modulators, and non-glitazone type PPARS agonist.

For the treatment of metabolic disorders, compounds according to the present invention may be administered with an agent selected from the group comprising: insulin, metformin, Glipizide, glyburide, Amaryl, meglitinides, nateglinide, repaglinide, PT-112, SB-517955, SB4195052, SB-216763, NN-57-05441, NN-57-05445, GW-0791, AGN- .sup.194.sup.204, T-1095, BAY R3401, acarbose Exendin-4, DPP728, LAF237, vildagliptin, MK-0431, saxagliptin, GSK23A, pioglitazone, rosiglitazone, (R)-1-{4-[5-methyl-2-(4-trifluoromethyl-phenyl)-oxazol-4-ylmethoxy]-benzenesulfonyl}2,3-dihydro-1H-indole-2-carboxylic acid described in the patent application WO 03/043985, as compound 19 of Example 4, and GI-262570.

Diseases

Described herein are methods of treating a disease in an individual suffering from said disease comprising administering to said individual an effective amount of a composition comprising a compound of formula I or a pharmaceutically acceptable salt, solvate, polymorph, ester, tautomer or prodrug thereof.

The invention also extends to the prophylaxis or treatment of any disease or disorder in which MEK kinase plays a role including, without limitation: oncologic, hematologic, inflammatory, ophthalmologic, neurological, immunologic, cardiovascular, and dermatologic diseases as well as diseases caused by excessive or unregulated pro-inflammatory cytokine production including for example excessive or unregulated TNF, IL-1, IL-6 and IL-8 production in a human, or other mammal. The invention extends to such a use and to the use of the compounds for the manufacture of a medicament for treating such cytokine-mediated diseases or disorders. Further, the invention extends to the administration to a human an effective amount of a MEK inhibitor for treating any such disease or disorder.

Diseases or disorders in which MEK kinase plays a role, either directly or via pro-inflammatory cytokines including the cytokines TNF, IL-1, IL-6 and IL-8, include, without limitation: dry eye, glaucoma, autoimmune diseases, inflammatory diseases, destructive-bone disorders, proliferative disorders, neurodegenerative disorders, viral diseases, allergies, infectious diseases, heart attacks, angiogenic disorders, reperfusion/ischemia in stroke, vascular hyperplasia, organ hypoxia, cardiac hypertrophy, thrombin-induced platelet aggregation, and conditions associated with prostaglandin endoperoxidase synthetase-2 (COX-2).

In certain aspects of the invention, the disease is a hyperproliferative condition of the human or animal body, including, but not limited to cancer, hyperplasias, restenosis, inflammation, immune disorders, cardiac hypertrophy, atherosclerosis, pain, migraine, angiogenesis-related conditions or disorders, proliferation induced after medical conditions, including but not limited to surgery, angioplasty, or other conditions.

In further embodiments, said hyperproliferative condition is selected from the group consisting of hematologic and nonhematologic cancers. In yet further embodiments, said hematologic cancer is selected from the group consisting of multiple myeloma, leukemias, and lymphomas. In yet further embodiments, said leukemia is selected from the group consisting of acute and chronic leukemias. In yet further embodiments, said acute leukemia is selected from the group consisting of acute lymphocytic leukemia (ALL) and acute nonlymphocytic leukemia (ANLL). In yet further embodiments, said chronic leukemia is selected from the group consisting of chronic lymphocytic leukemia (CLL) and chronic myelogenous leukemia (CML). In further embodiments, said lymphoma is selected from the group consisting of Hodgkin's lymphoma and non-Hodgkin's lymphoma. In further embodiments, said hematologic cancer is multiple myeloma. In other embodiments, said hematologic cancer is of low, intermediate, or high grade. In other embodiments, said nonhematologic cancer is selected from the group consisting of: brain cancer, cancers of the head and neck, lung cancer, breast cancer, cancers of the reproductive system, cancers of the digestive system, pancreatic cancer, and cancers of the urinary system. In further embodiments, said cancer of the digestive system is a cancer of the upper digestive tract or colorectal cancer. In further embodiments, said cancer of the urinary system is bladder cancer or renal cell carcinoma. In further embodiments, said cancer of the reproductive system is prostate cancer.

Additional types of cancers which may be treated using the compounds and methods described herein include: cancers of oral cavity and pharynx, cancers of the respiratory system, cancers of bones and joints, cancers of soft tissue, skin cancers, cancers of the genital system, cancers of the eye and orbit, cancers of the nervous system, cancers of the lymphatic system, and cancers of the endocrine system. In certain embodiments, these cancer s may be selected from the group consisting of: cancer of the tongue, mouth, pharynx, or other oral cavity; esophageal cancer, stomach cancer, or cancer of the small intestine; colon cancer or rectal, anal, or anorectal cancer; cancer of the liver, intrahepatic bile duct, gallbladder, pancreas, or other biliary or digestive organs; laryngeal, bronchial, and other cancers of the respiratory organs; heart cancer, melanoma, basal cell carcinoma, squamous cell carcinoma, other non-epithelial skin cancer; uterine or cervical cancer; uterine corpus cancer; ovarian, vulvar, vaginal, or other female genital cancer; prostate, testicular, penile or other male genital cancer; urinary bladder cancer; cancer of the kidney; renal, pelvic, or urethral cancer or other cancer of the genito-urinary organs; thyroid cancer or other endocrine cancer; chronic lymphocytic leukemia; and cutaneous T-cell lymphoma, both granulocytic and monocytic.

Yet other types of cancers which may be treated using the compounds and methods described herein include: adenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, hemangioblastoma, hepatocellular carcinoma, hepatoma, Kaposi's sarcoma, large cell carcinoma, leiomyosarcoma, liposarcoma, lymphangiosarcoma, lymphangioendotheliosarcoma, medullary thyroid carcinoma, medulloblastoma, meningioma mesothelioma, myelomas, mykosarcoma neuroblastoma, neurofibrosarcoma, oligodendroglioma, osteogenic sarcoma, epithelial ovarian cancer, papillary carcinoma, papillary adenocarcinomas, parathyroid tumors, pheochromocytoma, pinealoma, plasmacytomas, retinoblastoma, rhabdomyosarcoma, sebaceous gland carcinoma, seminoma, skin cancers, melanoma, small cell lung carcinoma, squamous cell carcinoma, sweat gland carcinoma, synovioma, thyroid cancer, uveal melanoma, and Wilm's tumor.

Also described are methods for the treatment of a hyperproliferative disorder in a mammal that comprise administering to said mammal a therapeutically effective amount of a compound of formula I, or a pharmaceutically acceptable salt, ester, prodrug, solvate, hydrate or derivative thereof, in combination with an anti-tumor agent. In some embodiments, the anti-tumor agent is selected from the group consisting of mitotic inhibitors, alkylating agents, anti-metabolites, intercalating antibiotics, growth factor inhibitors, cell cycle inhibitors, enzyme inhibitors, topoisomerase inhibitors, biological response modifiers, anti-hormones, angiogenesis inhibitors, and anti-androgens.

The disease to be treated using the compounds, compositions and methods described herein may be a hematologic disorder. In certain embodiments, said hematologic disorder is selected from the group consisting of sickle cell anemia, myelodysplastic disorders (MDS), and myeloproliferative disorders. In further embodiments, said myeloproliferative disorder is selected from the group consisting of polycythemia vera, myelofibrosis and essential thrombocythemia.

The compounds, compositions and methods described herein may be useful as anti-inflammatory agents with the additional benefit of having significantly less harmful side effects. The compounds, compositions and methods described herein are useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. The compounds, compositions and methods described herein are also useful in treating osteoporosis and other related bone disorders. These compounds, compositions and methods described herein can also be used to treat gastrointestinal conditions such as reflux esophagitis, diarrhea, inflammatory bowel disease, Crohn's disease, gastritis, irritable bowel syndrome and ulcerative colitis. The compounds, compositions and methods described herein may also be used in the treatment of pulmonary inflammation, such as that associated with viral infections and cystic fibrosis. In addition, the compounds, compositions and methods described herein are also useful in organ transplant patients either alone or in combination with conventional immunomodulators. Yet further, the compounds, compositions and methods described herein are useful in the treatment of pruritis and vitaligo. In particular, compounds, compositions and methods described herein are useful in treating the particular inflammatory disease rheumatoid arthritis.

Further inflammatory diseases which may be prevented or treated include, without limitation: asthma, allergies, respiratory distress syndrome or acute or chronic pancreatitis. Furthermore, respiratory system diseases may be prevented or treated including but not limited to chronic obstructive pulmonary disease, and pulmonary fibrosis. In addition, MEK kinase inhibitors described herein are also associated with prostaglandin endoperoxidase synthetase-2 (COX-2) production. Pro-1-inflammatory mediators of the cyclooxygenase pathway derived from arachidonic acid, such as prostaglandins, are produced by inducible COX-2 enzyme. Regulation of COX-2 would regulate these pro-inflammatory mediators, which affect a wide variety of cells and are important and critical inflammatory mediators of a wide variety of disease states and conditions. In particular, these inflammatory mediators have been implicated in pain, such as in the sensitization of pain receptors, and edema. Accordingly, additional MEK kinase-mediated conditions which may be prevented or treated include edema, analgesia, fever and pain such as neuromuscular pain, headache, dental pain, arthritis pain and pain caused by cancer.

Further, the disease to be treated by the compounds, compositions and methods described herein may be an ophthalmologic disorder. Ophthalmologic diseases and other diseases in which angiogenesis plays a role in pathogenesis, may be treated or prevented and include, without limitation, dry eye (including Sjogren's syndrome), macular degeneration, closed and wide angle glaucoma, retinal ganglion degeneration, ocular ischemia, retinitis, retinopathies, uveitis, ocular photophobia, and of inflammation and pain associated with acute injury to the eye tissue. The compounds, compositions and methods described herein can be used to treat glaucomatous retinopathy and/or diabetic retinopathy. The compounds, compositions and methods described herein can also be used to treat post-operative inflammation or pain as from ophthalmic surgery such as cataract surgery and refractive surgery. In further embodiments, said ophthalmologic disorder is selected from the group consisting of dry eye, closed angle glaucoma and wide angle glaucoma.

Further, the disease to be treated by the compounds, compositions and methods described herein may be an autoimmune disease. Autoimmune diseases which may be prevented or treated include, but are not limited to: rheumatoid arthritis, inflammatory bowel disease, inflammatory pain, ulcerative colitis, Crohn's disease, periodontal disease, temporomandibular joint disease, multiple sclerosis, diabetes, glomerulonephritis, systemic lupus erythematosus, scleroderma, chronic thyroiditis, Grave's disease, hemolytic anemia, autoimmune gastritis, autoimmune neutropenia, thrombocytopenia, chronic active hepatitis, myasthenia gravis, atopic dermatitis, graft vs. host disease, and psoriasis. Inflammatory diseases which may be prevented or treated include, but are not limited to: asthma, allergies, respiratory distress syndrome or acute or chronic pancreatitis. In particular, compounds, compositions and methods described herein are useful in treating the particular autoimmune diseases rheumatoid arthritis and multiple sclerosis.

Further, the disease to be treated by the compounds, compositions and methods described herein may be a dermatologic disorder. In certain embodiments, said dermatologic disorder is selected from the group including, without limitation, melanoma, basal cell carcinoma, squamous cell carcinoma, and other non-epithelial skin cancer as well as psoriasis and persistent itch, and other diseases related to skin and skin structure, may be treated or prevented with MEK kinase inhibitors of this invention.

Metabolic diseases which may be treated or prevented include, without limitation, metabolic syndrome, insulin resistance, and Type 1 and Type 2 diabetes. In addition, the compositions described herein can be used to treat insulin resistance and other metabolic disorders such as atherosclerosis that are typically associated with an exaggerated inflammatory signaling.

The compounds, compositions and methods described herein are also useful in treating tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, hypersensitivity, swelling occurring after injury, ischemias including myocardial ischemia, cardiovascular ischemia, and ischemia secondary to cardiac arrest, and the like. The compounds, compositions and methods described herein can also be used to treat allergic rhinitis, respiratory distress syndrome, endotoxin shock syndrome, and atherosclerosis.

Further, the disease to be treated by the compounds, compositions and methods described herein may be a cardiovascular condition. In certain embodiments, said cardiovascular condition is selected from the group consisting of atherosclerosis, cardiac hypertrophy, idiopathic cardiomyopathies, heart failure, angiogenesis-related conditions or disorders, and proliferation induced after medical conditions, including, but not limited to restenosis resulting from surgery and angioplasty.

Further, the disease to be treated by the compounds, compositions and methods described herein may be a neurological disorder. In certain embodiments, said neurologic disorder is selected from the group consisting of Parkinson's disease, Alzheimer's disease, Alzheimer's dementia, and central nervous system damage resulting from stroke, ischemia and trauma. In other embodiments, said neurological disorder is selected from the group consisting of epilepsy, neuropathic pain, depression and bipolar disorders.

Further, the disease to be treated by the compounds, compositions and methods described herein may cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, the compounds and compositions are for the treatment of a non-cancerous hyperproliferative disorder such as benign hyperplasia of the skin (e.g., psoriasis), restenosis, or prostate (e.g., benign prostatic hypertrophy (BPH)).

Further, the disease to be treated by the compounds, compositions and methods described herein may pancreatitis, kidney disease (including proliferative glomerulonephritis and diabetes-induced renal disease), pain, a disease related to vasculogenesis or angiogenesis, tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer in a mammal.

Further, the disease to be treated by the compounds, compositions and methods described herein may the prevention of blastocyte implantation in a mammal.

Patients that can be treated with the compounds described herein, or a pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, and myeloproliferative disorders; bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Miillerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

Kits

The compounds, compositions and methods described herein provide kits for the treatment of disorders, such as the ones described herein. These kits comprise a compound, compounds or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The compounds described herein can be utilized for diagnostics and as research reagents. For example, the compounds described herein, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds and formulations of the present invention are also useful for veterinary treatment of companion animals, exotic animals and farm animals, including mammals, rodents, and the like. More preferred animals include horses, dogs, and cats.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

EXAMPLES

General Procedures for the Synthesis of Sulfonamides

Procedure A: To a solution of the amine (1 eq) in anhydrous dichloromethane (3 mL/mmole) was added anhydrous triethylamine (5 eq). To this solution was added the sulfonyl chloride (1 eq) and the solution was stirred at room temperature for 16 h. The solvent was evaporated and the residue was purified by flash column chromatography on silica.

Procedure B: To a stirred solution of the amine (1 eq) in anhydrous pyridine (5 ml/mmole) was added the sulfonyl chloride (1-5 eq). The reaction mixture was stirred at 40° C. for 48 hours. The reaction mixture was partitioned with water and EtOAc. The organic layer was washed with brine, dried (MGSO$_4$) and concentrated under reduced pressure. The residue was purified by flash column chromatography on silica.

Procedure C: Substitution of the iodo-atom:

A suspension containing 1 eq. aryl iodide, 1.5 equiv. of the boronic acid or boronic ester, 0.25 eq. PdCl$_2$(dppf)×DCM and 10 eq. anhydrous K$_2$CO$_3$ powder in a deoxygenated mixture of dioxane and water (3:1) was heated in a microwave reactor for 60 min at 115° C. It was extracted using aq. NH$_4$Cl/THF, and the organic fraction was dried using Na$_2$SO$_4$. The crude reaction products were purified using flash-column chromatography (Si, EtOAc/Hexanes, or CHCl$_3$/MeOH). Yields: 20-40%.

Procedure D: Synthesis of N-(3,4-difluoro-2-(2-fluoro-4-iodophenylamino)phenyl)-2-(alkylamino)ethanesulfonamide: 2-Chloro-ethanesulfonyl chloride (0.1 ml, 1 mmol) was added to a solution of 5,6-difluoro-N-(2-fluoro-4-iodophenyl)benzene-1,2-diamine (0.364 g, 1 mmol) and triethylamine (0.28 ml, 2 mmol) in CH$_2$Cl$_2$ (5 ml) and the reaction mixture was stirred at room temperature for 16 h. Then it's treated with an excess amine (10 eq) either in solution or as a neat liquid. The reaction mixture stirred at room temperature for additional 6 h. The reaction mixture diluted with CH$_2$Cl$_2$ (10 ml) and water (10 ml). The organic layer was sequentially washed with dil. HCl (2×20 ml, 2N) and saturated NaHCO$_3$ (2×10 ml) solution. Then the CH$_2$Cl$_2$ layer dried (MgSO$_4$) and evaporated to obtain the crude product. The impure product was purified under preparative HPLC conditions to obtain the pure products in 50-60% yield.

Example 1

N-(3,4-difluoro-2-(2-fluoro-4-iodophenylamino)phenyl)methanesulfonamide

Step A: 2,3-Difluoro-N-(2-fluoro-4-iodophenyl)-6-nitroaniline

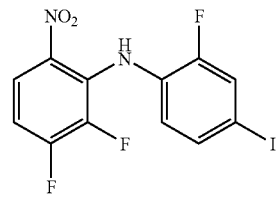

To a solution of 2-fluoro-4-iodoaniline (11.40 g, 47 mmol) in 100 ml anhydrous THF at 0° C., 47 ml of a 1M solution of LHMDS in THF (47 mmol) was added dropwise. The color of the solution turned dark purple. The solution was transferred via cannula to a dropping funnel, and the solution (containing the amine free base) was added in small portions to a solution of 2,3,4-trifluoronitrobenzene (8.321 g, 47.0 mmol) in anhydrous THF (50 ml) at 0° C. After completion of addition the mixture was stirred under argon at room temperature for 15 hours. The volume of the solvent was reduced, followed by extraction using ethyl acetate and brine. The organic layer was dried over sodium sulfate, the solvent was removed, and the obtained dark oil was purified by flash chromatography (EtOAc/hexane 1:5, $R_f$=0.58) yielding the crude product, which became a brown solid upon drying in vacuo (yield: 6.23 g, 33.6%): m/z=393 [M−1]⁻.

Step B: 5,6-Difluoro-N1-(2-fluoro-4-iodophenyl)benzene-1,2-diamine

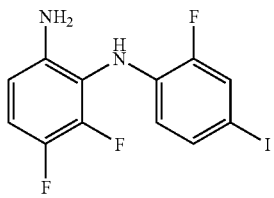

To a solution of nitro-diarylamine (6.23 g, 15.8 mmol) in 300 ml ethanol was added iron powder (13.74 g, 246 mmol) and ammonium chloride (13.59 g, 254 mmol) and the mixture was heated with stirring at 100° C. oil bath temperature for 14 hours. It was filtered and the residue washed two times with ethanol. The ethanol was removed in vacuo, and the residue was extracted using ethyl acetate/1M NaOH solution. During the extraction, more precipitate was formed which was filtered and discarded. The combined organic layers were washed with brine and dried over sodium sulfate. The solvent was removed, and the crude product was recrystallized from CHCl₃/hexane (1:50). The product was obtained as brown needles (2.094 g, 66%), $R_f$=0.44 (EtOAc/Hex 1:3), ¹H-NMR (500 MHz, CDCl₃), δ=7.40-7.38 (dd, 1H, J=11.3 Hz, J=1.5 Hz), 7.25-7.23 (d, 1H, J=8.5 Hz), 6.97-6.92 (q, 1H, J=9 Hz), 6.51-6.48 (m, 1H), 6.24-6.21 (t, 1H, J=9 Hz), 5.3 (s, 1H, NH, br), 3.80 (s, 2H, NH₂, br), LRMS (ESI): m/z=365 [M+H]⁻.

Step C: N-(3,4-difluoro-2-(2-fluoro-4-iodophenylamino)phenyl)methanesulfonamide

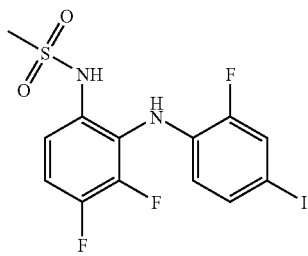

According to the general procedure A, 5,6-difluoro-N1-(2-fluoro-4-iodophenyl)benzene-1,2-diamine was reacted with methanesulfonyl chloride to obtain the desired product. ¹H NMR: (500 MHz, CDCl₃): δ=7.38-7.37 (d, 1H), 7.35-7.34 (m, 1H), 7.27-7.26 (m, 1H), 7.20-7.0 (q, 1H), 6.68 (s, 1H, br), 6.15-6.12 (q, 1H), 5.65 (s, 1H, br), 2.95 (s, 3H); m/z=441 [M−1]⁻.

Example 2

2 N-3,4-difluoro-2-(2-fluoro-4-iodophenylamino)phenyl)cyclopropanesulfonamide

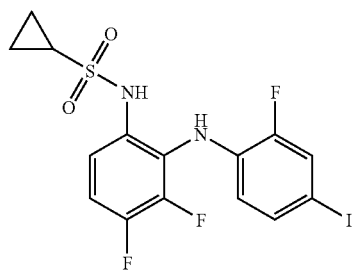

According to the general procedure A, 5,6-difluoro-N1-(2-fluoro-4-iodophenyl)benzene-1,2-diamine was reacted with cyclopropanesulfonyl chloride to obtain the desired product. ¹H NMR: (500 MHz, CDCl₃): δ=7.38-7.37 (d, 1H), 7.35-7.34 (m, 1H), 121-1 Id (m, 1H), 7.20-7.0 (q, 1H), 6.68 (s, 1H, br), 6.15-6.12 (q, 1H), 5.65 (s, 1H, br), 3.25-3.20 (m, 1H), 2.4-2.3 (m, 2H), 2.0-1.8 (m, 2H); m/z=467 [M−1]⁻.

Example 3

N-(3,4-difluoro-2-(2-fluoro-4-iodophenylamino)phenyl)propane-2-sulfonamide

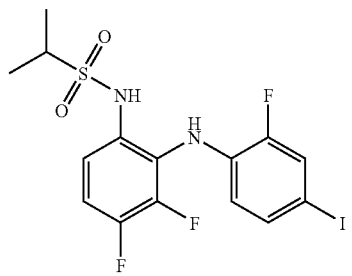

According to the general procedure A, 5,6-difluoro-N1-(2-fluoro-4-iodophenyl)benzene-1,2-diamine was reacted with isopropylsulfonyl chloride to obtain the desired product. Yield: 39%. ¹H-NMR (500 MHz, CDCl₃): δ=7.50-7.43 (m, 1H), 7.35-7.34 (m, 1H), 7.27-7.26 (m, 1H), 7.15-7.09 (q, 1H, J=1.6 Hz), 6.62 (s, 1H, br), 6.22-6.18 (q, 1H, J=1.5 Hz), 5.65 (s, 1H, br), 3.30-3.28 (m, 1H), 1.38-1.37 (d, 6H, J=1.2 Hz); m/z=469 [M−I]⁻.

Example 4

N-(3,4-difluoro-2-(2-fluoro-4-iodophenylamino)phenyl)butane-1-sulfonamide

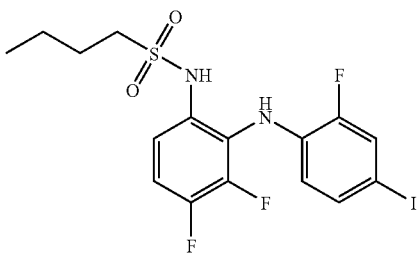

According to the general procedure A, 5,6-difluoro-N1-(2-fluoro-4-iodophenyl)benzene-1,2-diamine was reacted with n-butylsulfonyl chloride to obtain the desired product. Yield: 55%. $^1$H-NMR (500 MHz, CDCl$_3$): δ=7.50-7.43 (m, 1H), 7.35-7.34 (m, 1H), 7.27-7.26 (m, 1H), 7.15-7.09 (q, 1H, J=1.6 Hz), 6.62 (s, 1H, br), 6.22-6.18 (q, 1H, J=1.5 Hz)$_5$ 5.65 (s, 1H, br), 3.06-3.031 (t, 2H, J=1.4 Hz), 1.75-1.71 (m, 2H), 1.38-1.36 (m, 2H), 0.87-0.86 (t, 3H, J=1.3 Hz); m/z=483 [M−1]$^-$.

Example 5

N-(3,4-difluoro-2-(2-fluoro-4-iodophenylamino)phenyl)-2,2,2-trifluoro ethane sulfonamide

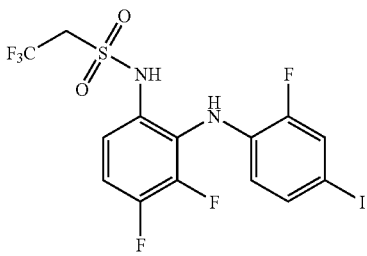

According to the general procedure A, 5,6-difluoro-N1-(2-fluoro-4-iodophenyl)benzene-1,2-diamine was reacted with 1,1,1-trifluoroethylsulfonyl chloride to obtain the desired product. Yield: 28%; m/z=509 [M−1]$^-$.

Example 6

N-(3,4-difluoro-2-(2-fluoro-4-iodophenylamino)phenyl)butane-2-sulfonamide

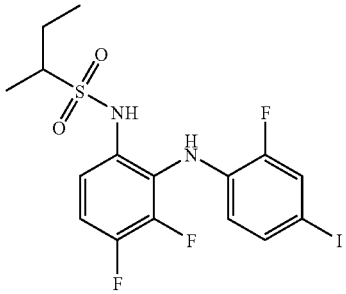

According to the general procedure A, 5,6-difluoro-N1-(2-fluoro-4-iodophenyl)benzene-1,2-diamine was reacted with sec-butylsulfonyl chloride to obtain the desired product. Yield: 22%. $^1$H-NMR (500 MHz, MeOH[d4]): δ=7.60-7.40 (m, 3H), 7.18-7.00 (q, 1H), 6.55-6.45 (m, 1H), 3.55-3.50 (m, 1H), 2.20-2.00 (m, 1H), 1.80-1.60 (m, 1H), 1.43-1.40 (d, 3H), 1.06-1.04 (t, 3H); m/z=483 [M−1]$^-$.

Example 7

N-(3,4-difluoro-2-(2-fluoro-4-iodophenylamino)phenyl)-N-methyl cyclopropane sulfonamide

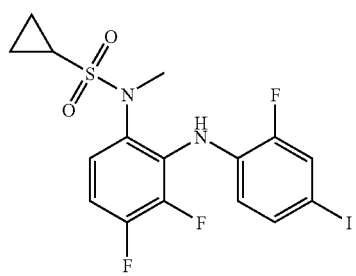

To a solution of N-(3,4-difluoro-2-(2-fluoro-4-iodophenylamino)phenyl)cyclopropane-sulfonamide (see Example 2) (283.9 mg, 0.61 mmol) in 3 ml anhydrous THF was added at −78° C. a 1M solution of LHMDS (0.6 ml, 0.6 mol) and the solution was stirred for 10 min at this temperature. Then, methyl iodide (0.8 ml, 1.824 g, 12.9 mmol) was added and the mixture was warmed to room temperature and stirred for 7 h. The solvent was removed and the residue extracted using EtOAc and brine. The organic fractions were dried using Na$_2$SO$_4$ and the solvent was removed. The obtained crude product was purified using flash-column chromatography (Si, EtOAc/Hexanes 1:2, R$_f$=0.45). Yield: 205 mg, 70%). $^1$H-NMR (500 MHz, CDCl$_3$): δ=7.41-7.39 (d, 1H, J=10 Hz), 7.30-7.29 (d, 1H, J=8.0 Hz), 7.23-7.20 (m, 1H), 6.98-6.93 (q, 1H, J=8.5 Hz), 6.60 (s, 1H, br), 6.51-6.47 (m, 1H), 3.23 (s, 3H), 2.46-2.42 (m, 1H), 1.19-1.16 (m, 2H), 1.04-1.02 (m, 2H); m/z=481 [M−1]$^-$.

Example 8

1-Chloro-N-(3,4-difluoro-2-(2-fluoro-4-iodophenylamino)phenyl)methane sulfonamide

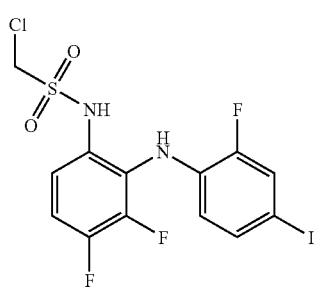

According to the general procedure A, 5,6-difluoro-N1-(2-fluoro-4-iodophenyl)benzene-1,2-diamine was reacted with chloromethanesulfonyl chloride to obtain the desired product, m/z=475 [M−1]$^-$.

Example 9

N-(3,4-difluoro-2-(2-fluoro-4-iodophenylaminophenyl)-2-methylpropane-2-sulfonamide

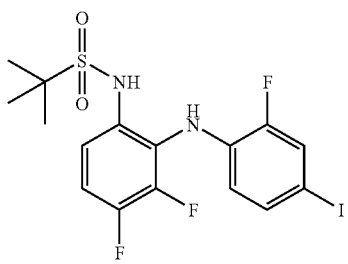

According to the general procedure B, 5,6-difluoro-N1-(2-fluoro-4-iodophenyl)benzene-1,2-diamine was reacted with 2-methylpropane-2-sulfonyl chloride (synthesized according to the literature procedure) to obtain the desired product.

$^1$H NMR (300 MHz, CDCl$_3$): δ 7.50 (m, 1H), 7.43 (dd, J=1.8 & 10.5 Hz, 1H), 7.28 (br s, 1H), 7.10 (dd, J=9.0 & 17.7 Hz, 1H), 6.48 (br s, D$_2$O exchangeable, 1H), 6.19 (t, J=7.8 & 9.6 Hz, 1H), 5.58 (br s, D$_2$O exchangeable, 1H), 1.39 (s, 9H); m/z=383 [M–1]$^-$.

Example 10

N-(3,4-difluoro-2-(2-fluoro-4-iodophenylamino)phenyl)cyclopentanesulfonamide

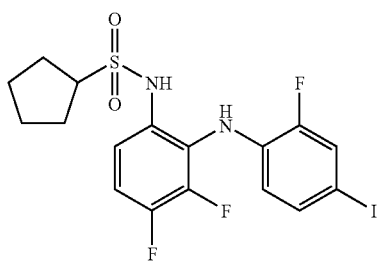

According to the general procedure B, 5,6-difluoro-N1-(2-fluoro-4-iodophenyl)benzene-1,2-diamine was reacted with cyclopentanesulfonyl chloride to obtain the desired product $^1$H NMR (300 MHz, CDCl$_3$): δ 7.42 (dd, J=2.1 & 10.5 Hz, 1H), 7.36 (ddd, J=2.4, 4.8, & 9.3 Hz, 1H), 7.25 (m, 2H), 7.10 (dd, J=9.6 & 17.7 Hz, 1H), 6.67 (br s, D$_2$O exchangeable, 1H), 6.20 (dt, J=1.5, 8.4 & 17.4 Hz, 1H), 3.53 (p, 1H), 1.80 (m, 8H); m/z=495 [M–1]$^-$.

Example 11

N-(3,4-difluoro-2-(2-fluoro-4-iodophenylamino)phenyl)cyclohexanesulfonamide

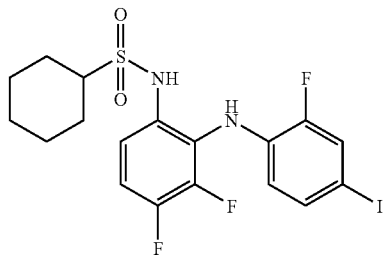

According to the general procedure B, 5,6-difluoro-N1-(2-fluoro-4-iodophenyl)benzene-1,2-diamine was reacted with cyclohexanesulfonyl chloride to obtain the desired product.

$^1$H NMR (300 MHz, CDCl$_3$): δ 7.43 (dd, J=1.5 & 10.2 Hz, 1H), 7.37 (ddd, J=2.4, 4.8 & 9.6 Hz, 1H), 7.27 (m, 1H), 7.11 (dd, J=9.3 & 18.0 Hz, 1H), 6.64 (br s, 1H), 6.18 (dt, J=1.5, 9.0 & 17.4 Hz, 1H), 5.63 (br s, 1H), 2.95 (triplet of triplet, 2.10-1.16 (m, 10H); m/z=509 [M–1]$^-$.

Example 12

N-(3,4-difluoro-2-(2-fluoro-4-iodophenylaminophenyl)-t-methylcyclopropane-1-sulfonamide Step A: n-Butyl 3-chloro-1-propanesulfonate

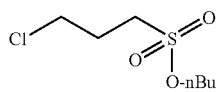

Triethylamine (28 ml, 200 mmol) in CH$_2$Cl$_2$ (50 ml) was slowly added to an ice-cooled solution of 3-chloro-1-propanesulfonyl chloride (36.6 g, 200 mmol) and 1-butanol (18.4 g, 240 m mol) in CH$_2$Cl$_2$ (250 ml) and stirring was continued for 16 h. The mixture was diluted with CH$_2$Cl$_2$ (200 ml), washed (aqueous HCl) and dried (MgSO$_4$) and the solvent was evaporated to obtain the titled product 1 (40.85 g, 95%) in crude form as slightly yellow oil which was used for the next reaction without further purification. $^1$H NMR (CDCl$_3$)) δ 0.94 (t, J=7.5 Hz, 3H), 1.44 (sextet, 2H), 1.72 (quintet, 2H), 2.31 (quintet, 2H), 3.27 (t, J=6.9 Hz, 2H), 3.68 (t, J=6.3 Hz), 4.23 (t, J=6.6 Hz, 2H).

Step B: 1-Butyl cyclopropanesulfonate

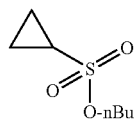

Solutions of 1-butyl 3-chloro-1-propanesulfonate (4.6 g, 21.39 mmol in 25 ml THF) and of butyllithium (14.7 ml, 23.53 mmol, 1.6M, THF) were simultaneously added to THF (150 ml) at −78° C. under nitrogen atmosphere. The solution was allowed to warm to 0° C. and then quenched with water (2 ml). The volatiles evaporated under reduced pressure and the residue extracted with $CH_2Cl_2$ (150 ml). The extract was washed with water and dried ($MgSO_4$) and evaporated to give crude desired product (3.23 g, 78.22%) in almost pure form as pale yellow oil which was used for next step without further purification. $^1$H NMR (300 MHz, $CDCl_3$) δ 0.94 (t, J=7.5 Hz, 3H), 1.07 (m, 2H), 1.25 (m, 2H), 1.45 (sextet, 2H), 1.74 (quintet, 2H), 2.45 (heptet, 1H), 4.23 (t, J=6.6 Hz, 2H).

Step C: Butyl 1-Methyl-cyclopropanesulfonate

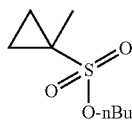

To a solution of 1-Butyl cyclopropanesulfonate (1 g, 5.58 mmol) in THF (15 ml) butyllithium solution (3.84 ml, 6.14 mmol, 1.6M, THF) was slowly added at −78° C. under nitrogen atmosphere. After 15 minutes MeI (0.72 ml, 11.16 mmol) was added and the solution was allowed to warm to 0° C. and quenched with water (1 ml). The volatiles evaporated under reduced pressure and the residue extracted with $CH_2Cl_2$ (100 ml). The extract was washed with water, dried ($MgSO_4$) and evaporated. The residue was purified over silica gel chromatography (eluants: hexane/$CH_2Cl_2$) to obtain the titled product (0.59 g, 55.0%) as a colorless oil. $^1$H NMR (300 MHz, $CDCl_3$)) δ 0.84 (m, 2H), 0.95 (t, J=7.2 Hz, 3H), 1.43 (m, 4H), 1.53 (s, 3H), 1.74 (m, 2H), 4.21 ((t, J=6.6 Hz, 2H).

Step D: 1-Potassium 1-Methyl-cyclopropanesulfonate

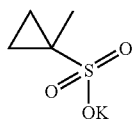

A mixture of 1-Butyl 1-Methyl-cyclopropanesulfonate (0.386 g, 2 mmol) and potassium thiocyanate (0.194 g, 2 mmol) in DME (5 ml) and water (5 ml) was refluxed for 16 h. The volatiles were evaporated to obtain the crude sulfonate (0.348 g, quantitative) which was dried under vacuum at 50° C. for 16 h. The crude product was used in the next reaction without further purification. $^1$H NMR (300 MHz, $D_2O$) δ 0.56 (t, J=6.3 Hz, 2H), 0.96 (t, J=6.3 Hz, 2H), 1.26 (s, 3H).

Step E: 1-Methyl-cyclopropanesulfonylchloride

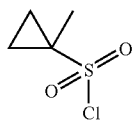

A solution of 1-potassium 1-methyl-cyclopropanesulfonate (0.348 g, 2 mmol), thionyl chloride (5 ml) and DMF (5 drops) was refluxed at 60° C. for 16 h. The volatiles evaporated under reduced pressure and the residue extracted with $CH_2Cl_2$ (50 ml). The extract was washed with water, dried ($MgSO_4$) and evaporated to obtain the crude product as yellow gummy oil which was used in the next reaction without further purification.

Step F: N-(3,4-difluoro-2-(2-fluoro-4-iodophenylamino)phenyl)-1-methylcyclopropane-1-sulfonamide

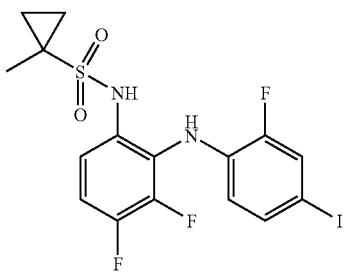

According to the general procedure B, 5,6-difluoro-N1-(2-fluoro-4-iodophenyl)benzene-1,2-diamine was reacted with 1-methyl-cyclopropanesulfonylchloride to obtain the desired product. $^1$H NMR (300 MHz, $CDCl_3$): δ 7.42 (dd, J=1.8 & 10.5 Hz, 1H), 7.36 (ddd, J=2.4, 4.5 & 9.0 Hz, 1H), 7.27 (d, J=6.0 Hz, 1H), 7.07 (dd, J=9.3 & 17.7 Hz, 1H), 6.24 (dt, J=2.1, 8.7 & 17.4 Hz, 1H), 5.86 (br s, 1H), 1.43 (s, 3H), 1.33 (t, J=5.4 Hz, 2H), 0.75 (dd, J=5.1 & 6.3 Hz, 2H); m/z=481 [M−1]$^-$.

Example 13

N-(3,4-difluoro-2-(2-fluoro-4-iodophenylamino)phenyl)-1-(2,3-dihydroxypropyl)cyclopropane-1-sulfonamide Step A: Butyl cyclopropanesulfonate

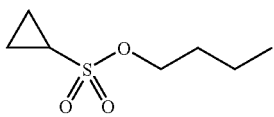

Cyclopropanesulfonyl chloride (5 g, 35 mmol, 1 eq) was dissolved in an excess BuOH (20 ml), the reaction mixture was cooled at −10° C. and pyridine (5.8 mL, 70 mmol, 2 eq) was slowly added dropwise. The mixture was slowly warmed at room temperature and stirred overnight. The solvent was removed under reduced pressure and the resulting white solid was dissolved in $CHCl_3$. The organic phase was washed with water, brine and dried ($MgSO_4$) and concentrated to give an oil (4.8 g, 24.9 mmol, 71%). $^1$H NMR (300 MHz, $CDCl_3$): δ

4.25 (t, 2H), 2.46 (m, 1H), 1.74 (m, 2H), 1.45 (m, 2H), 1.25 (dd, 2H), 1.09 (dd, 2H), 0.93 (t, 3H).

Step B: Butyl 1-allylcyclopropane-1-sulfonate

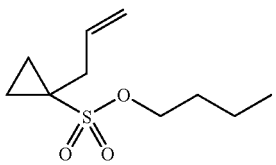

To a solution of 1-butyl cyclopropanesulfonate (4.8 g, 24.9 mmol) in THF at −78° C. was added simultaneously butyllithium solution (15.6 ml, 24.9 mmol, 1.6M, THF) and allyl iodide (24.9 mmol) under nitrogen atmosphere. The reaction mixture was stirred 2 hours at −78° C. and 3 hours at room temperature. The volatiles were evaporated under reduced pressure and the residue extracted with $CH_2Cl_2$ (100 ml). The extract was washed with water, dried ($MgSO_4$) and evaporated. The residue was purified over silica gel chromatography (eluants: hexane/$CH_2Cl_2$) to obtain the titled product (3.75 g, 69.0%) as a colorless oil. $^1H$ NMR (300 MHz, $CDCl_3$): δ 5.6 (m, 1H), 5.13-5.08 (t, 2H), 4.21 (t, 2H), 2.65 (d, 2H), 1.7 (m, 2H), 1.4 (m, 4H), 0.93 (m, 5H).

Step C: Potassium 1-allylcyclopropane-1-sulfonate

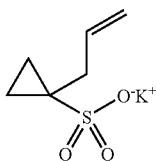

A mixture of 1-butyl 1-methyl-cyclopropanesulfonate (3.75 g, 17.2 mmol) and potassium thiocyanate (1.7 g, 17.2 mmol) in DME (20 ml) and water (20 ml) was refluxed for 16 h. The volatiles were evaporated to obtain the crude sulfonate (3.44 g, quantitative) which was dried under vacuum at 50° C. for 16 h. The crude product was used in the next reaction without further purification. $^1H$ NMR ($CDCl_3$): δ 5.6 (m, 1H), 4.91-4.85 (dd, 2H), 2.471-2.397 (d, 2H), 0.756 (m, 2H), 0.322 (m, 2H).

Step D: 1-allylcyclopropane-1-sulfonyl chloride

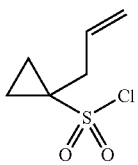

A solution of potassium 1-allylcyclopropane-1-sulfonate (3.44 g, 17.2 mmol), thionyl chloride (10 ml) and DMF (5 drops) was refluxed at 60° C. for 16 h. The volatiles evaporated under reduced pressure and the residue extracted with $CH_2Cl_2$ (50 ml). The extract was washed with water, dried ($MgSO_4$) and evaporated to obtain the crude product as yellow gummy oil which was washed with hexane and used in the next reaction without further purification (2.7 g, 15 mmol, 87%).

$^1HNMR$ (300 MHz, $CDCl_3$): δ 5.728 (m, 1H), 5.191 (t, 2H), 2.9 (d, 2H), 0.756 (m, 2H), 0.322 (m, 2H).

Step E: 1-allyl-N-(3,4-difluoro-2-(2-fluoro-4-iodophenylamino)phenyl)cyclopropane-1-sulfonamide

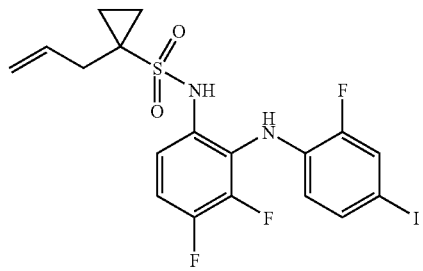

According to the general procedure B, 5,6-difluoro-N1-(2-fluoro-4-iodophenyl)benzene-1,2-diamine was reacted with 1-allylcyclopropane-1-sulfonyl chloride to obtain the desired product. m/z=507 [M−1]$^-$.

Step F: N-(3,4-difluoro-2-(2-fluoro-4-iodophenylamino)phenyl)-1-(2,3-dihydroxypropylcyclopropane-1-sulfonamide

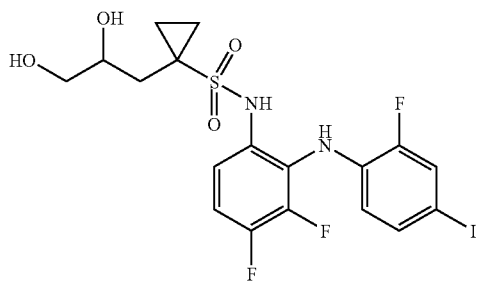

1-Allyl-N-(3,4-difluoro-2-(2-fluoro-4-iodophenylamino)phenyl)cyclopropane-1-sulfonamide (0.77 g, 1.52 mmol) and 4-methylmorpholine N-oxide (0.18 g, 1.52 mmol) were dissolved in THF (50 mL). Osmium tetroxide was added at room temperature (0.152 mmol, 0.965 mL, 4% in $H_2O$) and the reaction mixture was stirred at room temperature for 16 hours. EtOAc was added, the organic phase was washed with water, dried ($MgSO_4$) and concentrated under reduced pressure. The residue was purified over silica gel chromatography (eluants: EtOAc/MeOH) to obtain the titled product (0.65 g, 79%). $^1H$ NMR (300 MHz, $CDCl_3+D_2O$): δ 7.38 (dd, J=1.8 & 10.5 Hz, 1H), 7.36 (ddd, J=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]$^-$.

Example 14

(S)-N-(3,4-difluoro-2-(2-fluoro-4-iodophenylamino)phenyl)-1-(2,3-dihydroxypropyl)cyclopropane-1-sulfonamide

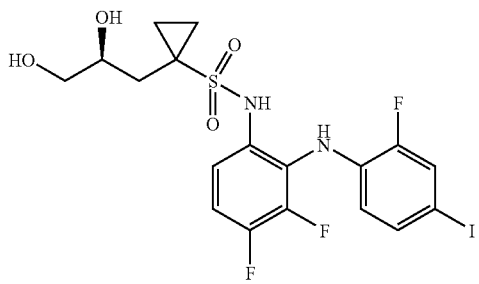

The pure S isomer was obtained by chiral HPLC separation of the racemic mixture (example 13). $^1$H NMR (300 MHz, CDCl$_3$+D$_2$O): δ 7.38 (dd, J=1.8 & 10.5 Hz, 1H), 7.36 (ddd, J=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]$^−$.

Example 15

(R)-N-(3,4-difluoro-2-(2-fluoro-4-iodophenylamino)phenyl)-1-(2,3-dihydroxypropyl)cyclopropane-1-sulfonamide

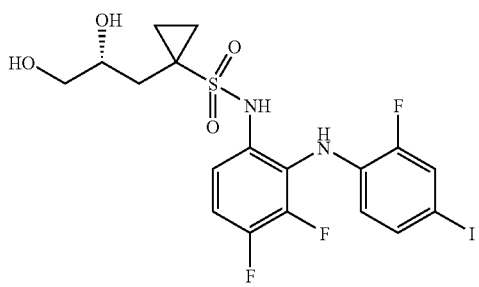

The pure R isomer was obtained by chiral HPLC separation of the racemic mixture (example 13). $^1$H NMR (300 MHz, CDCl$_3$+D$_2$O): δ 7.38 (dd, J=1.8 & 10.5 Hz, 1H), 7.36 (ddd, J=2.4, 5.1 & 9.3 Hz, 1H), 7.25 (d, J=8.7 Hz, 1H), 7.02 (dd, J=9.0 & 17.7 Hz, 1H), 6.27 (dt, J=3.0, 8.7 & 17.4 Hz, 1H), 3.92 (m, 1H), 3.54 (dd, J=3.9 & 11.1 Hz, 1H), 3.39 (dd, J=6.6 & 11.1 Hz, 1H), 2.16 (dd, J=9.6 & 15.9 Hz, 1H), 1.59 (d, J=14.1 Hz, 1H), 1.41 (m, 1H), 1.26 (m, 1H), 0.83 (m, 2H); m/z=542 [M−1]$^−$.

Example 16

N-(3,4-difluoro-2-(2-fluoro-4-iodophenylamino)phenyl)-1-(2-hydroxyethyl)cyclopropane-1-sulfonamide

Step A: 2-d-bromocyclopropyl)ethanol

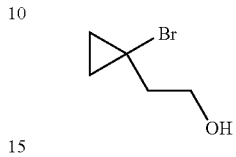

To a solution of neat diethyl zinc (3.3 ml, 3.977 g, 30 mmol) in 100 ml anhydrous DCM was added very slowly trifluoroacetic acid (2.31 ml, 3.4188 g, 30 mmol) dropwise at 0° C. (Caution: Violent gas evolution, exothermic!). After completed addition of the TFA, the suspension was stirred for 20 min at the same temperature, followed by the addition of diiodo methane (2.45 ml, 8.134 g, 30.4 mmol). It was further stirred at 0° C. for 20 min, and then a solution of 3-bromobut-3-en-1-ol (1 ml, 1.523 g, 10.1 mmol) in 10 ml DCM was added at the same temperature. After complete addition, the mixture was warmed to room temperature and stirred for 4 hours. The mixture was quenched with 100 ml MeOH and 40 ml brine, and it was further stirred for 30 min. The solvents were reduced, and the residue extracted using CHCl$_3$/aq. NH$_4$Cl. The organic layers were collected, washed with brine and water, and the solvent was removed to give 2-(1-bromocyclopropyl)-ethanol in sufficient purity (1.6564 g, 100%). $^1$H-NMR (500 MHz, CDCl$_3$): δ=3.90-3.83 (t, 2H), 1.91-1.87 (t, 2H), 1.71 (s, 1H, br), 1.14-1.09 (m, 2H), 0.83-0.79 (m, 2H).

Step B: TBS protected 2-(1-bromocyclopropyl)ethanol

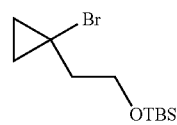

To a solution of the cyclopropyl alcohol (Step A) (1.303 g, 7.95 mmol) in 30 ml anhydrous DCM was added anhydrous pyridine (1.2 ml, 1.1736 g, 14.8 mmol) and TBSOTf (2.7 ml, 3.1077 g, 11.76 mol) and the solution was stirred at room temperature for 16 h. It was extracted with CHCl$_3$/brine and the organic fraction was dried with MgSO$_4$. The solvent was reduced and the crude product purified using flash-column chromatography (Si, CHCl$_3$/hexanes 1:10, R$_f$=0.4). Yield: 0.796 g, 36%. $^1$H-NMR (500 MHz, CDCl$_3$): δ=3.95-3.75 (t, 2H), 1.95-1.85 (t, 2H), 1.15-1.05 (m, 2H), 0.95-0.80 (m, HH), 0.15-0.05 (s, 6H).

Step C: TBS protected 2-(1-chlorosulfonylcyclopropyl)ethanol

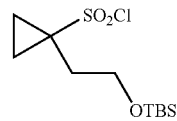

To a solution of the cyclopropyl bromide prepared in step B (1.1227 g, 4.04 mmol) in 15 ml anhydrous diethyl ether was added a 1.7 M solution of t-BuLi in pentane (4.8 ml, 8.16 mmol) at −78° C. The solution was stirred for 30 min at this temperature, and was then transferred via a transfer canola into a solution of freshly distilled sulfuryl chloride (0.65 ml, 1.029 g, 8.1 mmol) in 8 ml diethyl ether at −78° C. The yellow suspension was warmed to room temperature. The solvent was removed, and the residue was dried in vacuo to remove excessive sulfuryl chloride. Then, the residue was extracted two times with hexane, and after filtration the solvent was evaporated in vacuo to give the sulfonyl chloride in sufficient purity as a colorless oil. Yield: 870 mg (72%). $^1$H-NMR (300 MHz, CDCl$_3$): δ=3.95-3.85 (t, 2H), 2.35-2.25 (t, 2H), 1.80-1.70 (m, 2H), 1.45-1.38 (m, 2H), 0.90 (s, 9H), 0.10 (s, 6H).

Step D: TBS-protected N-(3,4-difluoro-2-(2-fluoro-4-iodophenylamino)phenyl)-1-(2-hydroxyethyl)cyclopropane 1-sulfonamide

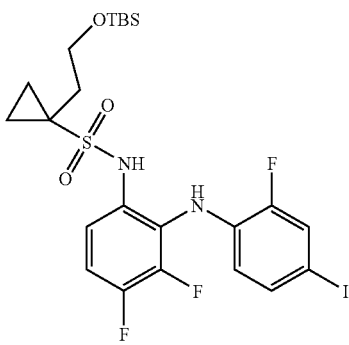

According to the general procedure B, 5,6-difluoro-N1-(2-fluoro-4-iodophenyl)benzene-1,2-diamine was reacted with the cyclopropylsulfonyl chloride prepared in step C to obtain the desired product. $^1$H-NMR (300 MHz, CDCl$_3$): δ=7.44-7.39 (dd, 1H), 7.32-7.24 (m, 2H), 7.1-6.98 (q, 1H), 6.34-6.24 (m, 1H), 6.16 (s, 1H, br), 3.85-3.75 (t, 2H), 2.15-2.00 (t, 2H), 1.35-1.20 (m, 2H), 0.95-0.75 (m, 11H), 0.10 (s, 6H); m/z=625 [M−1]$^-$.

Step E: N-(3,4-difluoro-2-(2-fluoro-4-iodophenylamino)phenyl)-1-(2-hydroxyethyl)cyclopropane-1-sulfonamide

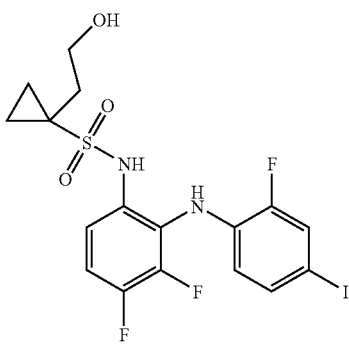

To a solution of the TBS-protected sulfonamide prepared in step D (21 mg, 0.033 mmol) in 1 ml THF was added 0.1 ml aq. 1.2N HCl solution at 0° C. and the solution was stirred for 2 h. The solvents were reduced and the residue was extracted using aq. NaHCO$_3$ solution and EtOAc. The organic fractions were dried with MgSO$_4$ and the volatiles were removed. The crude product was purified using flash-column chromatography (Si, CHCl$_3$/MeOH 10:1, R$_f$=0.45) to give the pure product. Yield: 16.9 mg (100%). $^1$H-NMR (300 MHz, CDCl$_3$): δ=7.44-7.39 (dd, 1H), 7.32-7.24 (m, 2H), 7.1-6.98 (q, 1H), 6.34-6.24 (m, 1H), 6.16 (s, 1H, br), 3.85-3.75 (t, 2H), 2.15-2.00 (t, 2H), 1.35-1.20 (m, 2H), 0.95-0.85 (m, 2H); m/z=511 [M−1]$^-$.

Example 17

N-(3,4-difluoro-2-(2-fluoro-4-iodophenylamino)phenyl)-3-hydroxypropane-1-sulfonamide

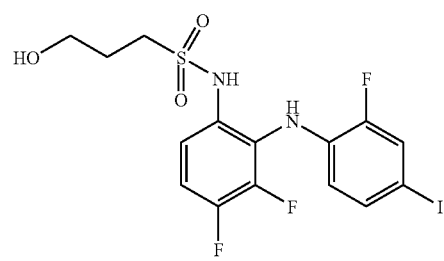

To a solution of 3-chloro-N-(3,4-difluoro-2-(2-fluoro-4-iodophenylamino)phenyl)-propane-1-sulfonamide (69.4 mg, 0.138 mmol) in a mixture of 8 ml 1,4-dioxane and 2 ml H$_2$O was added KOH powder (0.674 g, 12.0 mmol) and the mixture was heated to the reflux temperature for 3 days. It was extracted using EtOAc/brine, the organic fraction was dried with Na$_2$SO$_4$ and the volatiles were removed. The residue was purified using flash-column chromatography (Si, DCM/MeOH 5:1, R$_f$=0.3). Yield: 41 mg (62%). $^1$H-NMR (500 MHz, MeOH [d4]): δ=7.38-7.21 (d, 1H), 7.23-7.21 (d, 1H), 7.06-7.00 (q, 1H), 6.52-6.50 (m, 1H), 6.17-6.13 (t, 1H), 3.30-3.27 (t, 2H), 2.86-2.83 (t, 2H), 2.05-2.00 (m, 2H); m/z=485 [M−1]$^-$.

Example 18

N-(3,4-difluoro-2-(2-fluoro-4-iodophenylamino)phenyl)-2-methyl-5-(trifluoromethyl)furan-3-sulfonamide

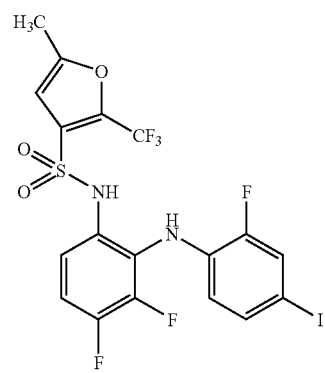

According to the general procedure B, 5,6-difluoro-N1-(2-fluoro-4-iodophenyl)benzene-1,2-diamine (0.182 mmol) was reacted with 2-methyl-5-(trifluoromethyl)furan-3-sulfonyl chloride (0.5 mmol) to form N-(3,4-difluoro-2-(2-fluoro-4-iodophenylamino)phenyl)-2-methyl-5-(trifluoromethyl)furan-3-sulfonamide. $^1$H NMR (CDCl$_3$) δ 2.2 (s, 3H), 5.3 (s, 1H), 6.0 (dt, 1H), 6.8 (s, 1H), 6.95 (s, 1H), 7.0-7.3 (m, 3H), 7.4 (dd, 1H).

Example 19

N-(5-(N-(3,4-difluoro-2-(2-fluoro-4-iodophenylamino)phenyl)sulfamoyl)-methylthiazol-2-yl)acetamide

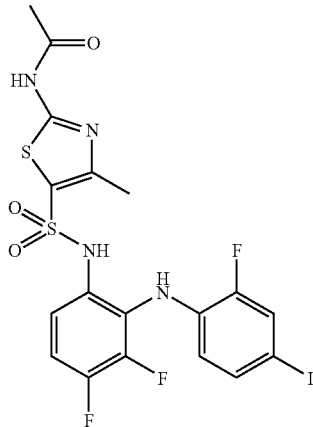

According to the general procedure B, 5,6-difluoro-N1-(2-fluoro-4-iodophenyl)benzene-1,2-diamine (0.182 mmol) was reacted with 2-acetamido-4-methylthiazole-5-sulfonyl chloride (0.5 mmol) to obtain N-(5-(N-(3,4-difluoro-2-(2-fluoro-4-iodophenylamino)phenyl)sulfamoyl)-4-methylthiazol-2-yl)acetamide. $^1$H NMR (CDCl$_3$)) δ 2.1 (s, 3H), 2.2 (s, 3H), 5.9 (dt, 1H), 6.05 (s, 1H), 7.0-7.6 (m, 3H), 7.4 (dd, 1H), 8.0 (s, 1H).

Example 20

5-(5-Chloro-1,2,4-thiadiazol-3-yl)-N-(3,4-difluoro-2-(2-fluoro-4-iodophenylamino)phenyl)thiophene-2-sulfonamide

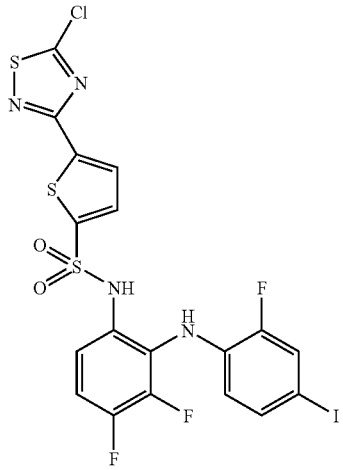

According to the general procedure B, 5,6-difluoro-N1-(2-fluoro-4-iodophenyl)benzene-1,2-diamine (0.182 mmol) was reacted with 5-(5-chloro-1,2,4-thiadiazol-3-yl)thiophene-2-sulfonyl chloride (0.5 mmol) to obtain 5-(5-chloro-1,2,4-thiadiazol-3-yl)-N-(3,4-difluoro-2-(2-fluoro-4-iodophenylamino)phenyl)thiophene-2-sulfonamide. $^1$H NMR (300 MHz, CDCl$_3$) δ 5.8 (dt, 1H), 5.95 (s, 1H), 6.95 (d, 1H), 7.4 (m, 2H), 7.6 (d, 1H), 7.8 (s, 1H).

Example 21

N-(3,4-difluoro-2-(2-fluoro-4-iodophenylamino)phenyl)-3,5-dimethylisoxazole-4-sulfonamide

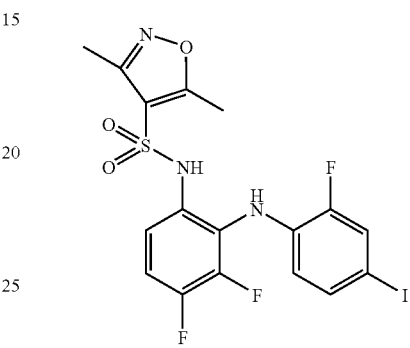

According to the general procedure B, 5,6-difluoro-N1-(2-fluoro-4-iodophenyl)benzene-1,2-diamine (0.182 mmol) was reacted with 3,5-dimethylisoxazole-4-sulfonyl chloride (0.5 mmol) to obtain N-(3,4-difluoro-2-(2-fluoro-4-iodophenylamino)phenyl) 3,5-dimethylisoxazole-4-sulfonamide. $^1$H NMR (300 MHz, CDCl$_3$)) δ 2.2 (s, 3H), 2.4 (s, 3H), 5.8 (s, 1H), 6.0 (dt, 1H), 5.95 (s, 1H), 6.9 (s, 1H), 7.0 (q, 1H), 7.2 (m, 3H), 7.4 (dd, 1H).

Example 22

5-Chloro-N-(3,4-difluoro-2-(2-fluoro-4-iodophenylamino)phenyl)-1,3-dimethyl-1H-pyrazole-4-sulfonamide

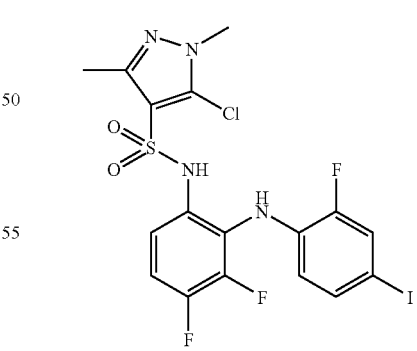

According to the general procedure B, 5,6-difluoro-N1-(2-fluoro-4-iodophenyl)benzene-1,2-diamine (0.182 mmol) was reacted with 5-chloro-1,3-dimethyl-1H-pyrazole-4-sulfonyl chloride (0.5 mmol) to obtain 5-chloro-N-(3,4-difluoro-2-(2-fluoro-4-iodophenylamino)phenyl)-1,3-dimethyl-1H-pyrazole-4-sulfonamide. $^1$H NMR (300 MHz, CDCl₃)) δ 2.1 (s, 3H), 3.6 (s, 3H), 5.8 (s, 1H), 5.95 (dt, 1H), 7.0 (q, 1H), 7.2 (d, 1H), 7.3 (m, 2H), 7.4 (dd, 1H).

Example 23

N-(3,4-difluoro-2-(2-fluoro-4-iodophenylamino)phenyl)-2,5-dimethylfuran-3-sulfonamide

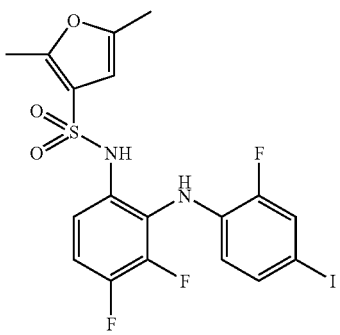

According to the general procedure B, 5,6-difluoro-N1-(2-fluoro-4-iodophenyl)benzene-1,2-diamine (0.182 mmol) was reacted with 2,5-dimethylfuran-3-sulfonyl chloride (0.5 mmol) to obtain N-(3,4-difluoro-2-(2-fluoro-4-iodophenylamino)phenyl)-2,5-dimethylfuran-3-sulfonamide. ¹H NMR (300 MHz, CDCl₃)) δ 2.2 (s, 3H), 2.3 (s, 3H), 5.8 (s, 1H), 6.0 (dt, 1H), 6.8 (s, 1H), 7.0 (q, 1H), 7.2 (d, 1H), 7.3 (m, 2H), 7.4 (dd, 1H).

Example 24

N-(3,4-difluoro-2-(2-fluoro-4-iodophenylamino)phenyl)-1-methyl-3-(trifluoromethyl)-1H-pyrazole-4-sulfonamide

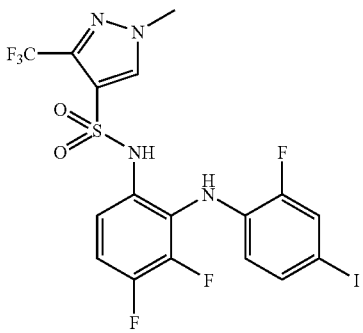

According to the general procedure B, 5,6-difluoro-N1-(2-fluoro-4-iodophenyl)benzene-1,2-diamine (0.182 mmol) was reacted with 1-methyl-3-(trifluoromethyl)-1H-pyrazole-4-sulfonyl chloride (0.5 mmol) to obtain N-(3,4-difluoro-2-(2-fluoro-4-iodophenylamino)phenyl)-1-methyl-3-(trifluoromethyl)-1H-pyrazole-4-sulfonamide. ¹H NMR (300 MHz, CDCl₃)) δ 3.8 (s, 3H), 5.7 (s, 1H), 6.0 (dt, 1H), 7.0 (q, 1H), 7.2 (m, 2H), 7.4 (dd, 1H), 7.8 (s, 1H).

Example 25

N-(3,4-difluoro-2-(2-fluoro-4-iodophenylaminophenyl)-2,4-dimethylthiazole-5-sulfonamide

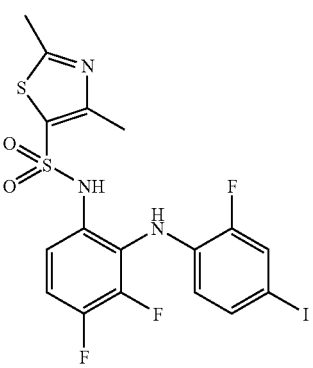

According to the general procedure B, 5,6-difluoro-N1-(2-fluoro-4-iodophenyl)benzene-1,2-diamine (0.182 mmol) was reacted with 2,4-dimethylthiazole-5-sulfonyl chloride (0.5 mmol) to obtain N-(3,4-difluoro-2-(2-fluoro-4-iodophenylamino)phenyl)-2,4-dimethylthiazole-5-sulfonamide. ¹H NMR (300 MHz, CDCl₃)) δ 2.3 (s, 3H), 2.6 (s, 3H), 5.7 (s, 1H), 5.9 (dt, 1H), 7.1 (q, 1H), 7.2 (d, 1H), 7.3 (m, 1H), 7.4 (d, 1H), 7.4 (s, 1H).

Example 26

N-(3,4-difluoro-2-(2-fluoro-4-iodophenylamino)phenyl)-1,2-dimethyl-1H-imidazole-4-sulfonamide

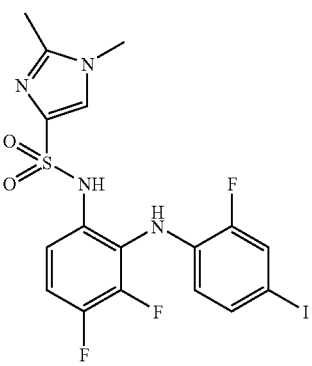

According to the general procedure B, 5,6-difluoro-N1-(2-fluoro-4-iodophenyl)benzene-1,2-diamine was reacted with 1,2-dimethyl-1H-imidazole-4-sulfonyl chloride to obtain the title compound. ¹H NMR (300 MHz, CDCl₃): δ 7.95 (br s, 1H), 7.37 (dd, J=1.8 & 10.8 Hz, 1H), 7.32-7.14 (m, 3H), 6.98 (dd, J=9.6 & 17.7 Hz, 1H), 5.87 (dt, J=4.2, 9.0 & 17.4 Hz, 1H), 5.55 (br s, 1H), 3.49 (s, 3H), 2.31 (s, 3H).

Example 27

N-(3,4-difluoro-2-(2-fluoro-4-iodophenylamino)phenyl)thiophene-3-sulfonamide

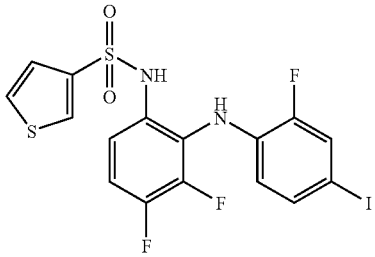

According to the general procedure B, 5,6-difluoro-N1-(2-fluoro-4-iodophenyl)benzene-1,2-diamine was reacted with thiophene-3-sulfonyl chloride to obtain the title compound. $^1$H NMR (300 MHz, CDCl$_3$): δ 8.00 (dd, J=1.2 & 3.3 Hz, 1H), 7.45 (dd, J=0.9 & 5.1 Hz, 1H), 7.35 (m, 2H), 7.27 (m, 2H), 6.91 (dd, J=9.3 & 17.1 Hz, 1H), 6.64 (ddd, J=2.1, 4.8 & 8.7 Hz, 1H), 6.34 (dt, J=5.4, 8.7 & 14.1 Hz, 1H), 5.98 (br d, J=2.1 Hz, D$_2$O exchangeable, 1H).

Example 28

N-(3,4-difluoro-2-(2-fluoro-4-iodophenylaminophenyl)furan-2-sulfonamide

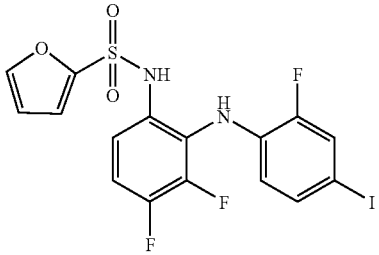

According to the general procedure B, 5,6-difluoro-N1-(2-fluoro-4-iodophenyl)benzene-1,2-diamine was reacted with furan-2-sulfonyl chloride to obtain the title compound. $^1$H NMR (300 MHz, CDCl$_3$): δ 7.53 (br s, D$_2$O exchangeable, 1H), 7.38 (dd, J=1.8 & 10.5 Hz, 1H), 7.30 (d, J=8.4 Hz, 1H), 7.21 (d, J=3.0 Hz, 1H), 6.96 (dd, J=8.7 & 16.5 Hz, 1H), 6.87 (ddd, J=1.8, 5.1 & 9.0 Hz, 1H), 6.53 (dd, J=1.8 & 3.6 Hz, 1H), 6.44 (dt, J=5.1, 8.7 & 13.8 Hz, 1H), 6.22 (br s, D$_2$O exchangeable, 1H).

Example 29

N-(3,4-difluoro-2-(2-fluoro-4-iodophenylamino)phenyl)-5-methylthiophene-2-sulfonamide

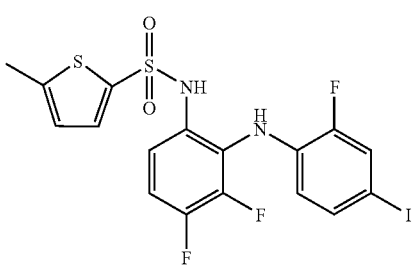

According to the general procedure B, 5,6-difluoro-N1-(2-fluoro-4-iodophenyl)benzene-1,2-diamine was reacted with 5-methylthiophene-2-sulfonyl chloride to obtain the title compound. $^1$H NMR (300 MHz, CDCl$_3$): δ 7.34 (dd, J=0.9 & 10.2 Hz, 1H), 7.30 (ddd, J=2.1, 4.8 & 9.0 Hz, 1H), 7.25 (d, J=3.9 Hz, 1H), 7.07 (m, 2H), 6.65 (dd, J=1.2 & 3.9 Hz, 1H), 5.89 (dt, J=2.4, 8.7 & 17.4 Hz, 1H), 5.54 (br s, D$_2$O exchangeable, 1H), 2.46 (s, 3H).

Example 30

5-Chloro-N-(3,4-difluoro-2-(2-fluoro-4-iodophenylamino)phenyl)thiophene-2-sulfonamide

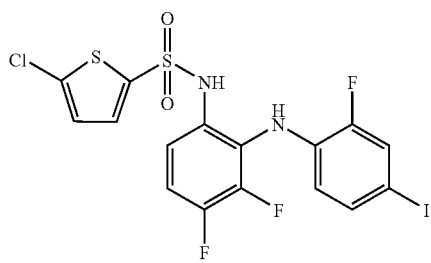

According to the general procedure B, 5,6-difluoro-N1-(2-fluoro-4-iodophenyl)benzene 1,2-diamine was reacted with 5-chlorothiophene-2-sulfonyl chloride to obtain the title compound. $^1$H NMR (300 MHz, CDCl$_3$): δ 7.38 (dd, J=1.5 & 10.2 Hz, 1H), 7.32 (ddd, J=2.1, 5.1 & 9.3 Hz, 1H), 7.25 (d, J=3.9 Hz, 1H), 7.10 (dd, J=9.0 & 18.6 Hz, 3H), 6.84 (d, J=4.2 Hz, 1H), 5.86 (dt, J=1.8, 8.7 & 17.4 Hz, 1H), 5.49 (br s, D$_2$O exchangeable, 1H).

Example 31

5-Bromo-N-(3,4-difluoro-2-(2-fluoro-4-iodophenylamino)phenyl)thiophene-2-sulfonamide

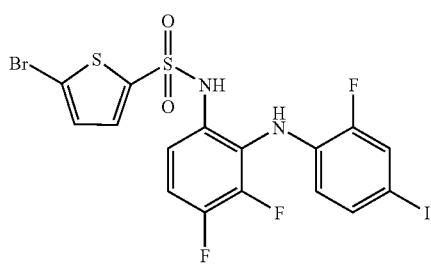

According to the general procedure B, 5,6-difluoro-N1-(2-fluoro-4-iodophenyl)benzene 1,2-diamine was reacted with 5-bromothiophene-2-sulfonyl chloride to obtain the title compound. $^1$H NMR (300 MHz, CDCl$_3$): δ 7.39-7.29 (m, 2H), 7.20-7.05 (m, 3H), 6.96 (d, J=3.6 Hz, 1H), 5.85 (dt, J=2.1, 9.0 & 17.4 Hz, 1H), 5.54 (br s, 1H).

Example 32

4-Bromo-N-(3,4-difluoro-2-(2-fluoro-4-iodophenylamino)phenyl)thiophene-3-sulfonamide

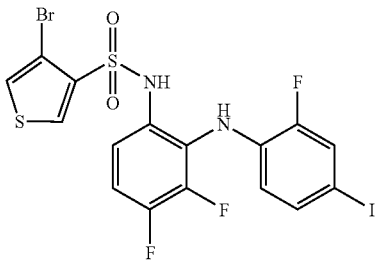

According to the general procedure B, 5,6-difluoro-N1-(2-fluoro-4-iodophenyl)benzene 1,2-diamine was reacted with 4-bromothiophene-3-sulfonyl chloride to obtain the title compound. $^1$H NMR (300 MHz, CDCl$_3$): δ 7.48 (br m, 2H), 7.39 (dd, J=1.8 & 10.5 Hz, 1H), 7.28 (ddd, J=2.4, 4.8 & 9.0 Hz, 1H), 7.17 (d, J=8.4 Hz, 1H), 7.02 (m, 1H), 6.02 (dt, J=2.4, 8.7 & 17.4 Hz, 1H), 5.68 (br s, 1H).

Example 33

4-Bromo-5-chloro-N-(3,4-difluoro-2-(2-fluoro-4-iodophenylamino)phenyl)thiophene-2-sulfonamide

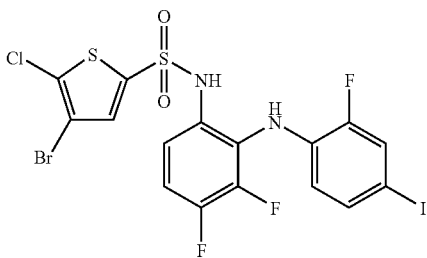

According to the general procedure B, 5,6-difluoro-N1-(2-fluoro-4-iodophenyl)benzene 1,2-diamine was reacted with 4-bromo-5-chlorothiophene-2-sulfonyl chloride to obtain the title compound. $^1$H NMR (300 MHz, CDCl$_3$): δ 7.42-7.34 (m, 2H), 7.25 (br m, 3H), 7.13 (dd, J=9.0 & 17.1 Hz, 1H), 6.02 (dt, J=2.4, 6.6 & 17.4 Hz, 1H), 5.52 (br s, 1H).

Example 34

3-Bromo-5-chloro-N-(3,4-difluoro-2-(2-fluoro-4-iodophenylamino) phenyl)thiophene-2-sulfonamide

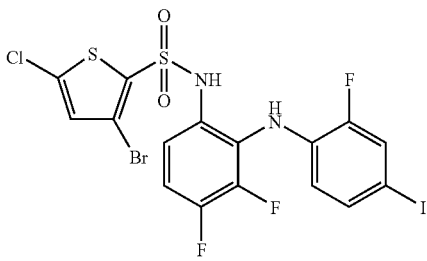

According to the general procedure B, 5,6-difluoro-N1-(2-fluoro-4-iodophenyl)benzene 1,2-diamine was reacted with 3-bromo-5-chlorothiophene-2-sulfonyl chloride to obtain the title compound. $^1$H NMR (300 MHz, CDCl$_3$): δ 7.41 (dd, J=2.1 & 10.5 Hz, 1H), 7.35 (br m, 2H), 7.31 (dd, J=2.1 & 4.2 Hz, 1H), 7.19 (d, J=8.7 Hz, 1H), 7.08 (dd, J=9.0 & 17.4 Hz, 1H), 6.02 (dt, J=2.1, 8.4 & 17.1 Hz, 1H), 5.59 (br s, 1H).

Example 35

N-(3,4-difluoro-2-(2-fluoro-4-iodophenylamino)phenyl)-2,5-dimethylthiophene-3-sulfonamide

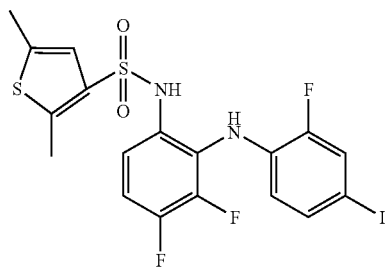

According to the general procedure B, 5,6-difluoro-N1-(2-fluoro-4-iodophenyl)benzene 1,2-diamine was reacted with 2,5-dimethylthiophene-3-sulfonyl chloride to obtain the title compound. $^1$H NMR (300 MHz, CDCl$_3$): δ 7.39 (dd, J=1.8 & 10.2 Hz, 1H), 7.24-7.16 (br m, 2H), 7.13 (dd, J=9.0 & 17.4 Hz, 1H), 6.77 (d, J=9.6 Hz, 1H), 5.98 (dt, J=2.4, 8.7 & 17.4 Hz, 1H), 5.55 (br s, 1H), 2.33 (s, 6H).

Example 36

2,5-Dichloro-N-(3,4-difluoro-2-(2-fluoro-4-iodophenylamino)phenyl)thiophene-3-sulfonamide

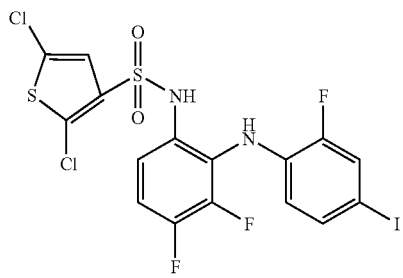

According to the general procedure B, 5,6-difluoro-N1-(2-fluoro-4-iodophenyl)benzene 1,2-diamine was reacted with 2,5-dichlorothiophene-3-sulfonyl chloride to obtain the title compound. $^1$H NMR (300 MHz, CDCl$_3$): δ 7.41 (dd, J=1.5 & 10.5 Hz, 1H), 7.28-7.20 (m, 2H), 7.08 (dd, J=9.0 & 17.4 Hz, 2H), 6.99 (s, 1H), 6.03 (dt, J=2.1, 8.7 & 17.4 Hz, 1H), 5.56 (br s, 1H).

Example 37

Methyl 3-(N-(3,4-difluoro-2-(2-fluoro-4-iodophenylamino)phenyl)sulfamoyl)thiophene-2-carboxylate

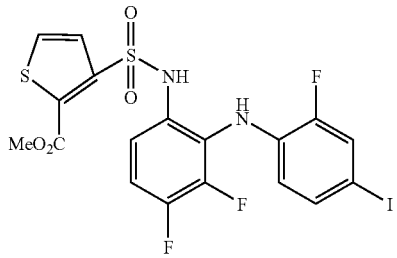

According to the general procedure B, 5,6-difluoro-N1-(2-fluoro-4-iodophenyl)benzene 1,2-diamine was reacted with methyl 3-(chlorosulfonyl)thiophene-2-carboxylate to obtain the title compound. $^1$H NMR (300 MHz, CDCl$_3$): δ 8.58 (s, 1H), 7.43 (dd, J=5.1 & 10.8 Hz, 2H), 7.35 (dd, J=1.8 & 10.2 Hz, 1H), 7.31 (ddd, J=2.1, 4.2 & 9.3 Hz, 1H), 7.04 (m, 2H), 5.88 (dt, J=2.7, 8.7 & 17.4 Hz, 1H), 5.65 (br s, 1H), 3.85 (s, 3H).

Example 38

Methyl 5-(N-(3,4-difluoro-2-(2-fluoro-4-iodophenylamino)phenyl)sulfamoyl)-1-methyl-1H-pyrrole-2-carboxylate

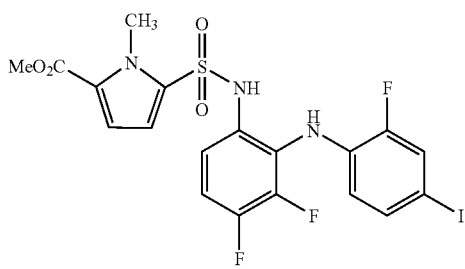

According to the general procedure B, 5,6-difluoro-N1-(2-fluoro-4-iodophenyl)benzene 1,2-diamine was reacted with methyl 5-(chlorosulfonyl)-1-methyl-1H-pyrrole-2-carboxylate to obtain the title compound. $^1$H NMR (300 MHz, CDCl$_3$): δ 7.37 (dd, J=1.8 & 10.5 Hz, 1H), 7.29 (m, 2H), 7.12-6.94 (m, 4H), 5.87 (dt, J=1.8, 8.4 & 17.4 Hz, 1H), 5.56 (br s, 1H), 3.65 (s, 3H), 3.75 (s, 3H).

Example 39

N-(3,4-difluoro-2-(2-fluoro-4-iodophenylamino)phenyl)-5-methylisoxazole-4-sulfonamide

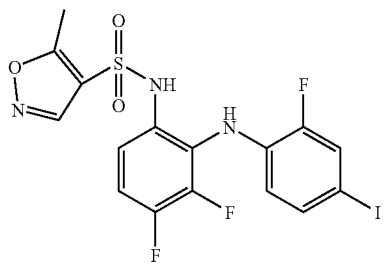

According to the general procedure A, 5,6-difluoro-N1-(2-fluoro-4-iodophenyl)benzene 1,2-diamine was reacted with the corresponding sulfonyl chloride to obtain the title compound. Yield: 22%; m/z=508 [M−1]$^-$.

Example 40

3-Chloro-N-(3,4-difluoro-2-(2-fluoro-4-iodophenylamino)phenyl)propane-1-sulfonamide

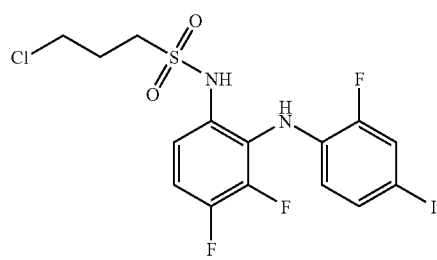

According to the general procedure A, 5,6-difluoro-N1-(2-fluoro-4-iodophenyl)benzene-1,2-diamine was reacted with 3-chloropropane-1-sulfonyl chloride to obtain the desired product. $^1$H NMR (500 MHz, CDCl$_3$): δ=7.39-7.38 (d, 1H), 7.35-7.34 (m, 1H), 7.27-7.26 (m, 1H), 7.10-7.0 (q, 1H), 6.63 (s, 1H, br), 6.15-6.11 (q, 1H), 5.60 (s, 1H, br), 3.60-3.56 (t, 2H), 3.22-3.20 (m, 2H), 2.22-2.16 (m, 2H).

Example 41

N-(2-(4-chloro-2-fluorophenylamino)-3,4-difluorophenyl)cyclopropanesulfonamide

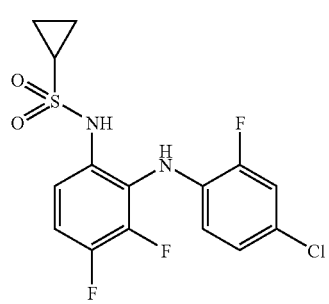

See example 1. $^1$H NMR (300 MHz, CDCl$_3$) δ 0.85-0.95 (m, 2H), 1.05-1.15 (ra, 2H), 2.2-2.4 (m, 1H), 5.8 (s, 1H), 6.3 (t, 1H), 6.6-7.4 (m, 5H); m/z=375 [M−1]$^-$.

Example 42

N-(3,4-difluoro-2-(4-iodo-2-methylphenylamino)phenyl)cyclopropanesulfonamide

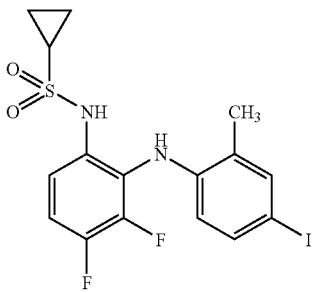

See example 1. $^1$H NMR (CDCl$_3$) δ 0.80-1.0 (m, 2H), 1.05-1.20 (m, 2H), 1.55 (s, 3H), 2.4-2.5 (m, 1H), 5.6 (s, 1H), 6.2 (dd, 1H), 6.4 (s, 1H), 7.1 (q, 1H), 7.3-7.4 (m, 2H), 7.5 (s, 1H); m/z=463 [M−1]$^-$.

Example 43

N-(2-(4-tert-butyl-2-chlorophenylamino)-3,4-difluorophenyl)cyclopropanesulfonamide

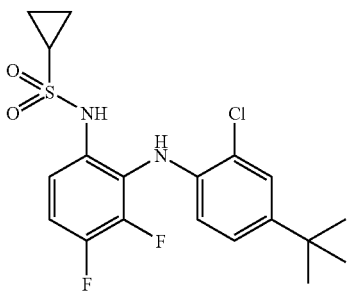

See example 1. $^1$H NMR (300 MHz, CDCl$_3$) δ 0.9-1.0 (m, 2H), 1.05-1.20 (m, 2H), 1.3 (s, 9H), 2.4-2.5 (m, 1H), 5.8 (s, 1H), 6.3 (dd, 1H), 6.6 (s, 1H), 7.0-7.2 (m, 2H), 7.3-7.4 (m, 2H); m/z=413 [M−1]$^-$.

Example 44

N-(2-(2,4-dichlorophenylamino)-3,4-difluorophenyl)cyclopropanesulfonamide

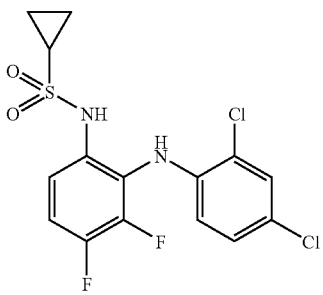

See example 1. $^1$H NMR (300 MHz, CDCl$_3$) δ 0.9-1.0 (m, 2H), 1.05-1.20 (m, 2H), 2.4-2.5 (m, 1H), 6.0 (s, 1H), 6.3 (dd, 1H), 6.6 (s, 1H), 7.0-7.2 (m, 2H), 7.3-7.4 (m, 2H); m/z=392 [M−1]$^-$.

Example 45

3-Chloro-N-(3,4-difluoro-2-(2-fluoro-4-trifluoromethyl)phenylamino)phenyl)propane-1-sulfonamide

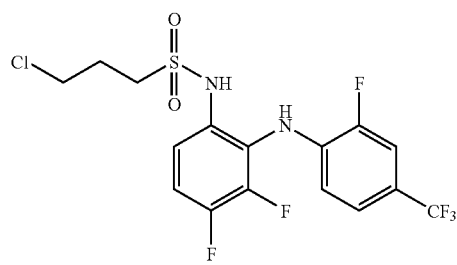

See example 1. $^1$H NMR (300 MHz, CDCl$_3$): δ 7.39-7.26 (m, 2H), 7.25 (m, 1H), 7.18 (dd, J=9.0 & 17.7 Hz, 1H), 6.78 (br s, D$_2$O exchangeable, 1H), 6.50 (t, J=8.1 Hz, 1H), 6.00 (br d, D$_2$O exchangeable, J=1.5 Hz, 1H), 3.63 (t, J=6.0 & 6.3 Hz, 2H), 3.29 (t, J=7.2 & 7.8 Hz, 2H), 2.26 (quintet, 2H); m/z=445 [M−1]$^-$.

Example 46

N-(3,4-difluoro-2-(2-chloro-4-trifluoromethyl)phenylamino)methanesulfonamide

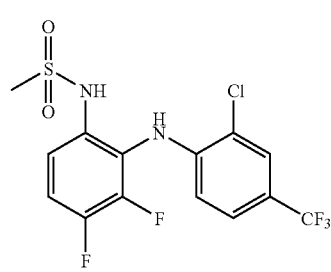

See example 1. $^1$H NMR (300 MHz, CDCl$_3$): δ 7.65 (d, J=7.8 Hz, 1H), 7.33 (m, 2H), 7.19 (dd, J=9.3 & 17.4 Hz, 1H), 6.90 (br s, D$_2$O exchangeable, 1H), 6.45 (dd, J=1.5 & 8.4 Hz, 1H), 6.39 (br s, D$_2$O exchangeable, 1H), 3.02 (s, 3H); m/z=399 [M−1]$^-$.

Example 47

3-Chloro-N-(3,4-difluoro-2-(2-chloro-4-trifluoromethyl)phenylamino)phenyl)propane-1-sulfonamide

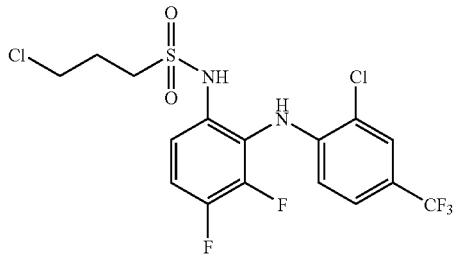

See example 1. $^1$H NMR (300 MHz, CDCl$_3$): δ 7.66 (d, J=1.5 Hz, 1H), 7.36 (m, 2H), 7.19 (dd, J=9.0 & 17.4 Hz, 1H), 6.91 (br s, D$_2$O exchangeable, 1H), 6.50 (dd, J=8.4 & 1.5 Hz, 1H), 6.37 (s, D$_2$O exchangeable, 1H), 3.62 (t, J=6.0 Hz, 2H), 3.29 (t, J=7.5 & 7.8 Hz, 2H), 2.27 (quintet, 2H); m/z=462 [M−1]$^-$.

Example 48

3-Chloro-N-(3,4-difluoro-2-(2-bromo-4-trifluoromethyl)phenylamino)phenyl)propane-1-sulfonamide

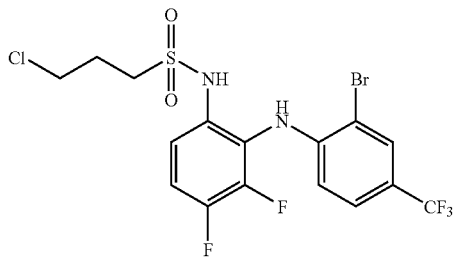

See example 1. $^1$H NMR (300 MHz, CDCl$_3$): δ 7.82 (s, 1H), 7.38 (m, 2H), 7.20 (dd, J=9.0 & 17.7 Hz, 1H), 6.62 (br s, D$_2$O exchangeable, 1H), 6.43 (d, J=8.4 Hz, 1H), 6.23 (s, D$_2$O exchangeable, 1H), 3.65 (t, J=6.0 Hz, 2H), 3.30 (t, J=7.5 Hz, 2H), 2.28 (quintet, 2H); m/z=506 [M−1]$^-$.

Example 49

Cyclopropanesulfonic acid (3,4,6-trifluoro-2-(2-fluoro-4-iodo-phenylamino)-phenyl)-amide Step A: (2-Fluoro-4-iodo-phenyl)-(2,3,5-trifluoro-6-nitro-phenyl)-amine

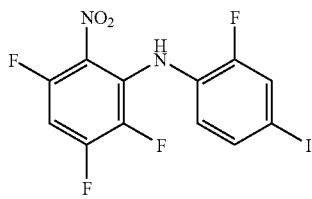

A stirred solution of 2-fluoro-4-iodoaniline (3.64 gm, 15.37 mmol) in dry THF (100 ml) under nitrogen was cooled to −78° C. and a solution of 1.0 M lithium hexa methyl disilazide (LiN(SiMe$_3$)$_2$) "LHMDS" (15.37 ml, 15.37 mmol) was added slowly. This reaction mixture was kept stirring at −78° C. for another hour and then 2,3,4,6-tetrafluoronitrobenzene was added. The reaction mixture was allowed to warm to room temperature and stirring continued for another 16 hours. Ethyl acetate (200 ml) was added to the reaction mixture and was washed with water. Organic layer was dried over sodium sulfate and further purified by column chromatography to provide yellow solid (3.75 gm, yield: 59.24%). M−H$^+$: 410.9. $^1$H NMR (DMSO, 300 MHz): 6.85 (t, 1H); 7.38 (d, 1H); 7.62 (m, 2H); 8.78 (s, 1H).

Step B: 3,4,6-Trifluoro-N$^2$-(2-Fluoro-4-iodo-phenyl)-benzene-1,2-diamine

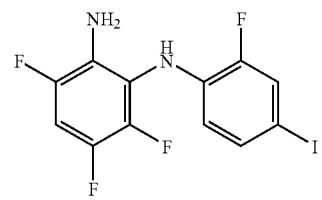

To the stirred solution of (2-fluoro-4-iodo-phenyl)-(2,3,5-trifluoro-6-nitro-phenyl)-amine 3 (5.2 gm, 12.62 mmol) in EtOH (200 ml), ammonium chloride (10.12 gm, 189.3 mmol) and iron powder (10.57 gm, 189.3 mmol) was added. This reaction mixture was kept stirring at reflux for 16 hours. Reaction mixture was allowed to cool and was filtered over celite and concentrated to dryness. The residue obtained was taken into EtOAc and was washed with water. The EtOAc layer was dried over sodium sulfate and further purified by crystallization from EtOH to provide off-white solid (3.2 gm, yield: 66.39%). M−H$^+$: 381.1. $^1$H NMR (DMSO, 300 MHz): 5.0 (s, 2H); 6.2 (t, 1H); 7.2-7.3 (m, 2H); 7.45 (s, 1H); 7.5 (d, 1H).

Step C: 4.6.7-Trifluoro-1-(2-Fluoro-4-iodo-phenyl)-1,3-dihydrobenzoimidazole-2-one

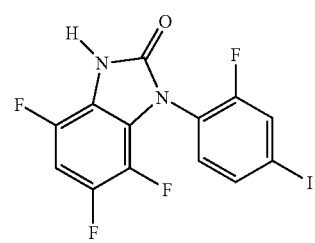

To the stirred solution of 3,4,6-trifluoro-N2-(2-Fluoro-4-iodo-phenyl)-benzene-1,2-diamine 3 (0.285 gm, 0.74 mmol) in CH$_2$Cl$_2$ (2 ml), 1,1'-carbonyldiimidazole (0.125 gm, 0.75 mmol) was added. This reaction mixture was kept stirring at room temperature for 16 hours when product precipitated out. The white solid was filtered and used further without any purification. (0.2 gm, yield: 65.85%): m/z=407 [M−1]$^-$.

Step D/E: Cyclopropanesulfonic acid (3,4,6-trifluoro-2-(2-fluoro-4-iodo-phenylamino)-phenyl)-amide

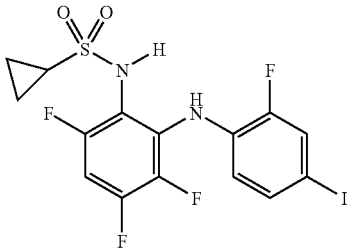

A stirred solution of 4,6,7-trifluoro-1-(2-fluoro-4-iodo-phenyl)-1,3,-dihydrobenzimidazol-2-one (0.2 gm, 0.41 mmol) in dry THF (4 ml) under nitrogen was cooled to −78° C. and a solution of 1.0 M LiHMDS (0.41 ml, 0.41 mmol) was added slowly. (2 ml) followed by addition of cyclopropanesulfonyl chloride (0.050 ml, 0.49 mmol). This reaction mixture was kept stirring at room temperature for 16 hours, concentrated to dryness and was taken into EtOAc. The EtOAc was washed with water, dried over sodium sulfate and concentrated to dryness. The residue obtained 1-cyclopropanesulfonyl-4,5,7-trifluoro-3-(2-fluoro-4-iodo-phenyl)-1,3-dihydro-benzimidazol-2-one 5 was taken into dioxane (2 ml) and to this 1.0 N NaOH (0.5 ml) was added and kept stirring at room 50° C. for 16 hours. TLC indicated incomplete reaction, the product was purified by HPLC to provide off-white solid (4.4 mg) M+H$^+$: 484.7, M−H$^+$: 486.7. $^1$H NMR (CDCl$_3$, 300 MHZ): 0.9-1.1-(m, 2H); 1.1-1.2 (m, 2H); 2.45-2.55 (m, 1H); 6.05 (s, 1H); 6.44-6.54 (m, 1H); 7.1 (s, 1H); 7.4-7.7 (d, 1H); 7.38-7.44 (dd, 1H); m/z=485 [M−1]$^−$.

Example 50

N-(3,4-difluoro-2-(4-fluoro-2-iodophenylamino)-6-ethoxyphenyl)cyclopropane sulfonamide

Step A: (2J-Difluoro-5-methoxy-6-nitro-phenyl)-(2-fluoro-4-iodo-phenyl)-amine

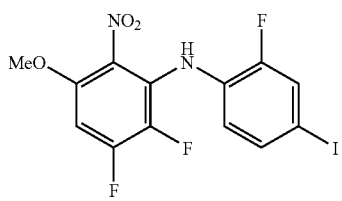

A stirred solution of (2-fluoro-4-iodo-phenyl)-(2,3,5-trifluoro-6-nitro-phenyl)-amine (1.23 gm, 3 mmol) in dry THF (25 ml) under nitrogen was cooled to −78° C. and a solution of 25% NaOMe (0.68 ml, 0.3 mmol) was added slowly. Reaction mixture was allowed to warm to room temperature and stirring continued for another 16 hours. TLC indicated incomplete reaction. Ethyl acetate (100 ml) was added to the reaction mixture and was washed with water. Organic layer was dried over sodium sulfate and further purified by column chromatography to provide yellow solid (0.6 gm, yield: 47.6%); m/z=424 [M=H]$^+$.

Step B: 5,6-Difluoro-N1-(4-fluoro-2-iodophenyl)-3-methoxybenzene-1,2-diamine

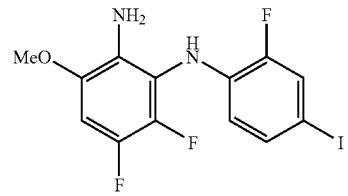

To the stirred solution of (2,3-difluoro-5-methoxy-6-nitro-phenyl)-(2-fluoro-4-iodo-phenyl)-amine (0.57 gm, 1.34 mmol) in EtOH (20 ml), ammonium chloride (1.18 gm, 20.16 mmol) and iron powder (1.15 gm, 21.44 mmol) was added. This reaction mixture was kept stirring at reflux for 16 hours. Reaction mixture was allowed to cool and was filtered over celite and concentrated to dryness. The residue obtained was taken into EtOAc and was washed with water. The EtOAc layer was dried over sodium sulfate and further purified by crystallization from EtOH to provide off-white solid (0.47 gm, yield: 90.3%). M−H$^+$: 393.2. $^1$H NMR (DMSO, 300 MHz): 3.76 (s, 3H); 6.1 (t, 1H); 6.8-7.0 (m, 1H); 7.2 (d, 1H); 7.35 (s, 1H); 7.42 (d, 1H).

Step C: 6,7-Difluoro-1-(4-fluoro-2-iodophenyl)-4-methoxy-1H-benzo[d]imidazol-2(3H)-one

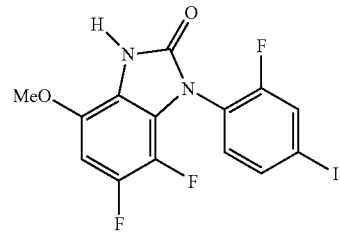

To the stirred solution of 5,6-difluoro-N1-(4-fluoro-2-iodophenyl)-3-methoxybenzene-1,2-diamine (0.17 gm, 0.43 mmol) in CH$_2$Cl$_2$ (2 ml), 1,1'-Carbonyldiimidazole (0.085 gm, 0.53 mmol) was added. This reaction mixture was kept stirring at room temperature for 16 hours when product precipitated out. The white solid was filtered and used further without any purification. (0.089 gm); m/z=419 [M−1]$^−$.

Step D/F: N-(3,4-difluoro-2-(4-fluoro-2-iodophenylamino)-6-methoxyphenyl)cyclopropanesulfonamide

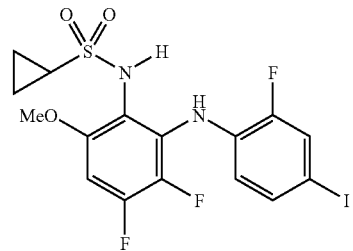

A stirred solution of 1-(cyclopropylsulfonyl)-4,5-difluoro-3-(2-fluoro-4-iodophenyl)-7-methoxy-1H-benzo[d]imidazol-2(3H)-one (0.89 gm, 0.17 mmol) in dry THF (4 ml) under nitrogen was cooled to −78° C. and a solution of 1.0 M LiHMDS (0.17 ml, 0.17 mmol) was added slowly. (2 ml) followed by addition of cyclopropanesulfonyl chloride (0.021 ml, 0.21 mmol). This reaction mixture was kept stirring at room temperature for 16 hours, concentrated to dryness and was taken into EtOAc. The EtOAc was washed with water, dried over sodium sulfate and concentrated to dryness. The resulting 1-(cyclopropylsulfonyl)-4,5-difluoro-3-(2-fluoro-4-iodophenyl)-7-methoxy-1H-benzo[d]imidazol-2(3H)-one was taken into dioxane (2 ml) and to this 1.0 N NaOH (0.5 ml) was added and kept stirring at room 50° C. for 16 hours. TLC indicated incomplete reaction, the product was purified by HPLC to provide off-white solid (2.5 mg) M+H$^+$: 484.7, M−H$^+$: 497.3. $^1$H NMR (CDCl$_3$, 300 MHz): 0.85-0.95 (m, 2H); 1.05-1.15 (m, 2H); 2.4-2.5 (m, 1H); 3.9 (s, 3H); 6.1 (s, 1H); 6.4-6.6 (m, 2H); 7.3 (m, 1H); 7.35-7.4 (dd, 1H); m/z=497 [M−1]$^−$.

Example 51

Methylsulfonic acid (3,4-difluoro-2-(2-fluoro-4-iodo-phenylamino)-6-methoxy-phenyl)-amide

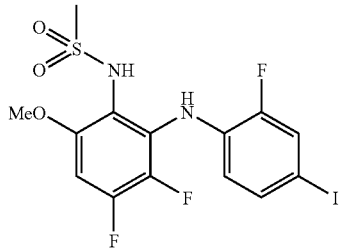

A stirred solution of 5,6-difluoro-N1-(4-fluoro-2-iodophenyl)-3-methoxybenzene-1,2-diamine (0.150 gm, 0.38 mmol) in dry CH$_2$Cl$_2$ (4 ml), TEA (0.264 ml, 1.9 mmol) and methanesulfonyl chloride was added slowly. This reaction mixture was kept stirring at room temperature for 16 hours, TLC indicated incomplete reaction along with starting material two products were observed. The reaction mixture was washed with water, organic layer was dried over sodium sulfate and concentrated to dryness, the product was purified by column chromatography. The minor product was found to be the expected compound (6.4 mg). M−H$^+$: 471.5. $^1$H NMR (CDCl$_3$, 300 MHz): 3.9 (s, 3H); 6.05 (s, 1H); 6.4-6.5 (m, 1H); 6.5-6.6 (m, 1H); 7.2 (s, 1H); 7.28 (d, 1H); 7.35-7.4 (d, 1H); m/z=471 [M−1]$^−$.

Example 52

1-(2,3-Dihydroxy-propyl)-cyclopropanesulfonic acid [3,4,6-trifluoro-2-(4-fluoro-2-iodo-phenylamino)-phenyl]-amide Step A: 1-Allyl-cyclopropanesulfonic acid[3,4,6-trifluoro-2-(2-fluoro-4-iodo-phenylamino)phenyl]-amide

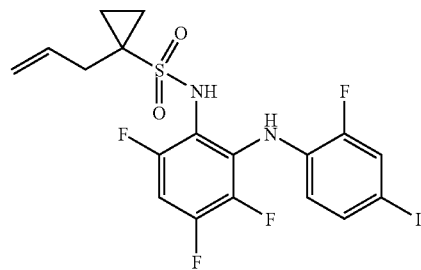

According to the general procedure B, 1-allyl-cyclopropanesulfonyl chloride was reacted with 3,5,6-trifluoro-N'-(2-fluoro-4-iodophenyl)benzene-1,2-diamine to obtain the title product. $^1$H NMR (CDCl$_3$, 300 MHz): δ 7.41 (dd, 1H), 7.38 (dd, 1H), 7.09 (s, 1H), 6.78 (m, 1H), 6.49 (m, 1H), 5.96 (s, 1H), 5.86 (m, 1H), 5.18 (d, 2H), 2.76 (d, 2H), 1.23 (m, 2H), 0.872 (m, 2H).

Step B: 1-(2,3-D hydroxypropyl)-N-(3,4,6-trifluoro-2-(2-fluoro-4-iodophenylamino)phenyl)cyclopropane-1-sulfonamide

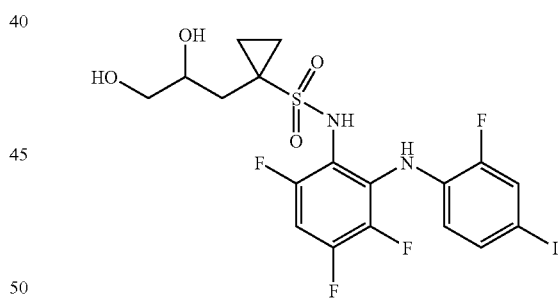

1-Allyl-cyclopropanesulfonic acid [3,4,6-trifluoro-2-(2-fluoro-4-iodo-phenylamino)-phenyl]-amide (110 mg, 0.21 mmol) and 4-methylmorpholine N-oxide (24.6 mg, 0.21 mmol) was dissolved in THF (8 mL). Osmium tetroxide was added at room temperature (0.021 mmol, 0.153 mL, 4% in H$_2$O) and the reaction mixture was stirred at room temperature for 16 hours. EtOAc was added, the organic phase was washed with water, dried (MgSO$_4$) and concentrated under reduced pressure. The residue was purified over silica gel chromatography (eluants: EtOAc/MeOH) to obtain the titled product (0.89 g, 75%). $^1$H NMR (CDCl$_3$, 300 MHz): δ 7.39 (dd, J=1.5 & 10.6 Hz, 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz, 1H), 3.53 (dd. J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]−.

Example 53

(S)-1-(2,3-dihydroxypropyl)-N-(3,4,6-trifluoro-2-(2-fluoro-4-iodophenylamino)phenyl)cyclopropane-1-sulfonamide

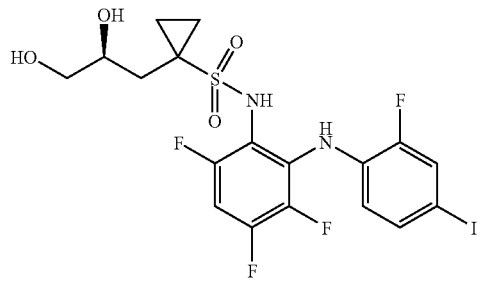

The pure S isomer was obtained by chiral HPLC separation of the racemic mixture (example 52). $^1$H NMR (CDCl$_3$, 300 MHz): δ 7.39 (dd, J=1.5 & 10.6 Hz, 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz$_5$ 1H), 3.53 (dd, J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]−.

Example 54

(R)-1-(2,3-dihydroxypropyl)-N-(3,4,6-trifluoro-2-(2-fluoro-4-iodophenylamino)phenyl)cyclopropane-1-sulfonamide

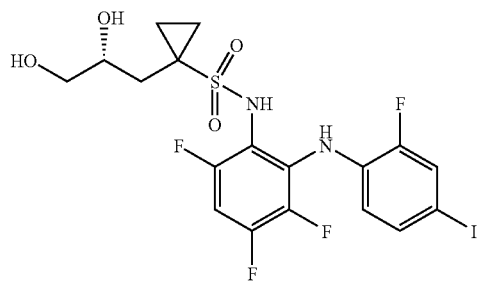

The pure R isomer was obtained by chiral HPLC separation of the racemic mixture (example 52). $^1$H NMR (CDCl$_3$, 300 MHz): δ 7.39 (dd, J=1.5 & 10.6 Hz, 1H), 7.29 (d, J=8.8 Hz, 1H), 7.28 (s, 1H), 6.97 (s, 1H), 6.76 (m, 1H), 6.49 (m, 1H), 4.13 (m, 1H), 3.66 (dd, J=3.7 & 11.4 Hz, 1H), 3.53 (dd, J=6.7 & 11.2 Hz, 1H), 2.50 (dd, J=10.0 & 16.1 Hz, 1H), 1.6 (m, 1H), 1.46 (m, 1H), 1.28 (m, 1H), 1.20 (m, 2H), 0.92 (m, 2H); m/z=559 [M−1]−.

Example 55

N-(3,4-difluoro-2-(2-fluoro-4-iodophenylamino)phenyl)-1-(2,3-dihydroxypropyl)cyclopropane-1-sulfonamide Step A: 1-Allyl-N-3,4-difluoro-2-(2-fluoro-4-iodophenylamino)-6-methoxyphenyl)cyclopropane-1-sulfonamide

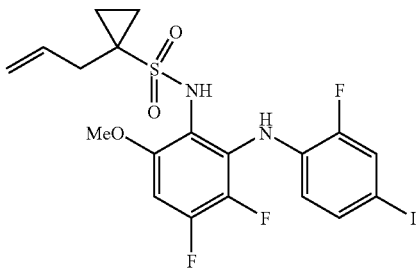

According to the general procedure B, 1-allyl-cyclopropanesulfonyl chloride was reacted with 5,6-difluoro-N1-(2-fluoro-4-iodophenyl)-3-methoxybenzene-1,2-diamine to obtain the title product. $^1$H NMR (CDCl$_3$, 300 MHz): δ 7.417 (dd, 1H), 7.309 (s, 1H), 7.25 (m, 1H), 6.89 (m, 1H), 6.52 (m, 1H), 6.427 (m, 1H), 6.03 (s, 1H), 5.668 (m, 1H), 5.11 (t, 1H), 3.9 (s, 3H), 2.75 (d, 2H), 1.21 (m, 2H), 0.767 (m, 2H).

Step B: N-(3,4-difluoro-2-(2-fluoro-4-iodophenylamino)phenyl)-1-(2,3-dihydroxypropyl)cyclopropane-1-sulfonamide

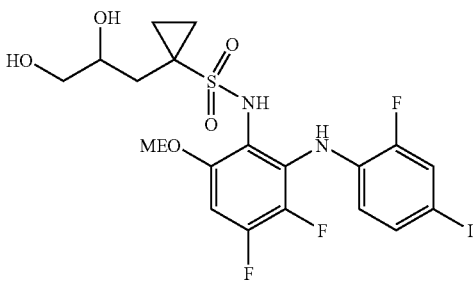

1-Allyl-N-(3,4-difluoro-2-(2-fluoro-4-iodophenylamino)-6-methoxyphenyl)cyclopropane-1-sulfonamide (97 mg, 0.18 mmol) and 4-methylmorpholine N-oxide (21 mg, 0.18 mmol) were dissolved in THF (8 mL). Osmium tetroxide was added at room temperature (0.018 mmol, 0.13 mL, 4% in H$_2$O) and the reaction mixture was stirred at room temperature for 16 hours. EtOAc was added, the organic phase was washed with water, dried (MgSO$_4$) and concentrated under reduced pressure. The residue was purified over silica gel chromatography (eluants: EtOAc/MeOH) to obtain the titled product (0.80 g, 78%). $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 1.11 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]−.

Example 56

(S)-N-(3,4-difluoro-2-(2-fluoro-4-iodophenyl-amino)-6-methoxyphenyl)-1-(2,3-dihydroxypropyl)cyclopropane-1-sulfonamide

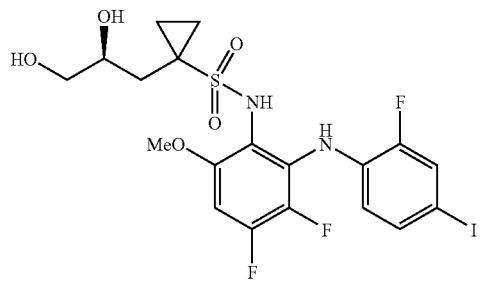

The pure S isomer was obtained by chiral HPLC separation of the racemic mixture (example 55). $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (r, 2H), 0.86 (m, 2H); m/z=571 [M−1]$^−$.

Example 57

(R)-N-(3,4-difluoro-2-(2-fluoro-4-iodophenyl-amino)-6-methoxyphenyl)-1-(2,3-dihydroxypropyl)cyclopropane-1-sulfonamide

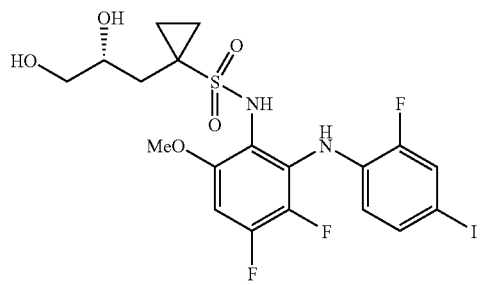

The pure R isomer was obtained by chiral HPLC separation of the racemic mixture (example 55). $^1$H NMR (CDCl$_3$, 300 MHz): δ 7.38 (dd, J=1.7 & 10.3 Hz, 1H), 7.26 (m, 1H), 7.14 (s, 1H), 6.87 (s, 1H), 6.53 (dd, J=6.8 & 11.4 Hz, 1H), 6.43 (m, 1H), 4.06 (m, 1H), 3.89 (s, 3H), 3.63 (dd, J=3.7 & 11.1 Hz, 1H), 3.49 (dd, J=6.4 & 11.1 Hz, 1H), 2.3 (dd, J=9.7 & 16.1 Hz, 1H), 1.77 (dd, J=1.9 & 16.0 Hz, 1H), 1.37 (m, 1H), 1.25 (m, 1H), 1.21 (m, 2H), 0.86 (m, 2H); m/z=571 [M−1]$^−$.

Example 58

1-(2-hydroxyethyl)-N-(3,4,6-trifluoro-2-(2-fluoro-4-iodophenylamino)phenyl)cyclopropane-1-sulfonamide Step A: TBS-protected 1-(2-hydroxyethyl)-N-(3,4,6-trifluoro-2-(2-fluoro-4-iodophenylamino)phenyl)cyclopropane-1-sulfonamide

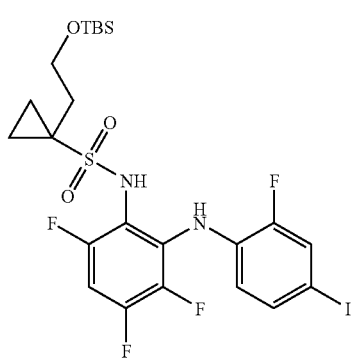

According to the general procedure B, the sulfonyl chloride prepared in step C of example 16 was reacted with 5,6-difluoro-N1-(2-fluoro-4-iodophenyl)-3-fluorobenzene-1,2-diamine to obtain the title product. Yield: 13%. $^1$H-NMR (300 MHz, CDCl$_3$): δ=7.51 (s, 1H, br), 7.37-7.35 (d, 1H), 7.27-7.25 (d, 1H), 6.94 (s, 1H, br), 6.78-6.68 (m, 1H), 6.46-6.44 (m, 1H), 3.90-3.88 (t, 2H), 2.12-2.10 (t, 2H), 1.31-1.28 (m, 2H), 0.91-0.89 (m, 2H), 0.86 (s, 9H), 0.05 (s, 6H); m/z=643 [M−1]$^−$.

Step B: 1-(2-hydroxyethyl)-N-(3,4,6-trifluoro-2-(2-fluoro-4-iodophenylamino)-phenyl)cyclopropane-1-sulfonamide

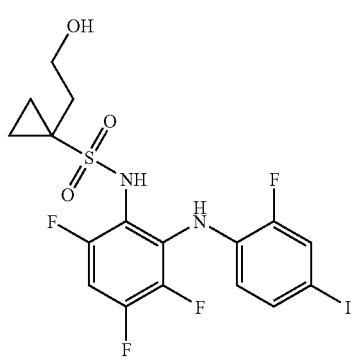

Same procedure as in step E, example 16. Yield: 100%. $^1$H-NMR (300 MHz, CDCl$_3$): δ=7.51 (s, 1H, br), 7.37-7.35 (d, 1H), 7.27-7.25 (d, 1H), 6.94 (s, 1H, br), 6.78-6.68 (m, 1H), 6.46-6.44 (m, 1H), 3.90-3.88 (t, 2H), 2.12-2.10 (t, 2H), 1.31-1.28 (m, 2H), 0.91-0.89 (m, 2H); m/z=529 [M−1]$^−$.

Example 59

N-(3,4-difluoro-2-(2-fluoro-4-iodophenylamino)-6-methoxyphenyl)-1-(2-hydroxyethyl)cyclopropane-1-sulfonamide Step A: TBS-protected N-(3,4-difluoro-2-(2-fluoro-4-iodophenylamino)-6-methoxyphenyl)-1-(2-hydroxyethyl)cyclopropane-1-sulfonamide

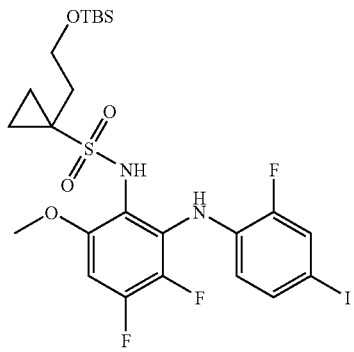

According to the general procedure B, the sulfonyl chloride prepared in step C of example 16 was reacted with 5,6-difluoro-N1-(2-fluoro-4-iodophenyl)-3-methoxy-benzene-1,2-diamine to obtain the title product. Yield: 37%. $^1$H-NMR (300 MHz, CDCl$_3$): δ=7.40-7.34 (dd, 1H), 7.23-7.21 (m, 1H), 6.61 (s, 1H, br), 6.57-6.49 (dd, 1H), 6.48-6.39 (m, 1H), 3.9-3.7 (m, 5H), 2.15-2.05 (t, 2H), 1.30-1.20 (m, 2H), 0.95-0.80 (m, 1H), 0.05 (s, 6H); m/z=655 [M−1]$^-$.

Step B: N-(3,4-difluoro-2-(2-fluoro-4-iodophenylamino)-6-methoxyphenyl)-1-(2-hydroxyethyl)cyclopropane-1-sulfonamide

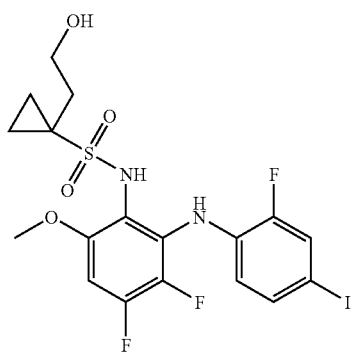

Same procedure as in step E, example 16. Yield: 100%. $^1$H-NMR (300 MHz, CDCl$_3$): δ=7.40-7.34 (dd, 1H), 7.23-7.21 (m, 1H), 6.61 (s, 1H, br), 6.57-6.49 (dd, 1H), 6.48-6.39 (m, 1H), 3.9-3.7 (m, 5H), 2.15-2.05 (t, 2H), 1.30-1.20 (r, 2H), 0.95-0.80 (m, 2H); m/z=541 [M−1]$^-$.

Example 60

N-(3,4-difluoro-2-(2-fluoro-4-iodophenylamino)-6-methoxyphenyl)-1-(3-hydroxy-2-(hydroxymethyl)propyl)cyclopropane-1-sulfonamide Step A: Dimethyl 2-(2-bromoallyl)malonate

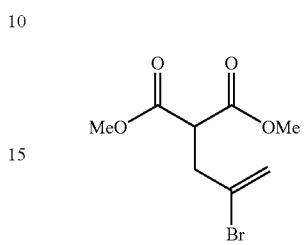

To a suspension of sodium hydride (5.0 g, 125 mmol) in HMPA (50 ml, distilled from calcium hydride) was added a solution of dimethyl malonate (11.7 ml, 100 mmol) in HMPA (5 ml) at 0° C. under argon. The mixture was heated to 50° C. and stirred 1 hour. Following this the solution was again cooled to 0° C., and a solution of 2,3-dibromopropene (12.2 ml, 100 mmol) in HMPA (5 ml) was added to the reaction mixture. Next, the solution was warmed to 40° C. and stirred for 1 hour. The reaction mixture was quenched with aq. HCl (10%, 88 ml) and extracted with ether (3×45 ml). The organic fractions were collected, dried over MgSO$_4$, and the solvent was removed in vacuo. The crude oil was purified via silica gel chromatography (eluants: chloroform/hexane) to obtain the titled product as a colorless oil (16.3 g, 65%). $^1$H-NMR (300 MHz, CDCl$_3$) δ 5.70 (d, J=1.8 Hz, 1H), 5.48 (d, J=1.8 Hz, 1H), 3.63 (t, J=7.5 Hz, 1H), 3.76 (s, 6H), 3.04 (d, J=7.5 Hz, 2H).

Step B: 2-(2-Bromoallyl)propane-1,3-diol

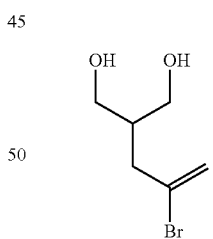

Lithium aluminum hydride (1.9 g, 7.65 mmol) was slurried in anhydrous diethyl ether (50 ml) and cooled to −78° C. in a dry ice/acetone bath. A solution of the product from step A (0.639 g, 16.84 mmol) in dry ether (26 ml) was then added dropwise. After the malonate was added, the solution was allowed warm to room temperature and stirring was continued for 3 hours. The reaction was quenched with brine (50 ml), extracted with ethyl acetate (3×25 ml) and dried over MgSO$_4$. The solvent was removed in vacuo to give the desired product (1.3 g, 86%) which was used for the next step without further purification. $^1$H-NMR (300 MHz, CDCl$_3$) δ 5.66 (d, J=1.2 Hz, 1H), 5.48 (d, J=1.5 Hz, 1H), 3.86 (m, 2H), 3.73 (m, 2H), 2.51 (d, J=7.5 Hz, 2H), 2.40 (br s, 2H), 2.15 (m, 1H).

Step C: Di-tert-butyldimethylsilyl protected 2-(2-bromoallyl)propane-1,3-diol

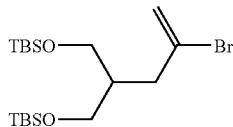

The product from step B (2.8 g, 14.20 mmol) was dissolved in anhydrous THF (140 ml). Anhydrous pyridine (2.5 ml, 31.24 mmol) was added, and the solution was cooled to 0° C. tert-Butyldimethylsilyltriflate (7.2 ml, 31.24 mmol) was added dropwise, and upon completion, the reaction solution was heated to 35° C. After stirring for 6 days, the reaction was quenched with 100 ml brine, extracted with ethyl acetate (3×50 ml) and dried over MgSO$_4$. The combined organic phases were evaporated to obtain the crude product (5.5 g, 91%) as a yellow oil which was used in the next step without further purification. $^1$H-NMR (300 MHz, CDCl$_3$) δ 5.54 (d, J=0.9 Hz, 1H), 5.40 (d, J=1.2 Hz, 1H), 3.55 (d, J=5.4, 4H), 2.40 (d, J=6.9 Hz, 2H), 1.97 (m, 1H), 0.85 (s, 18H), 0.02 (s, 9H).

Step D: Di-tert-butyldimethylsilyl protected 2-((1-bromocyclopropyl)methyl)propane-1,3-diol

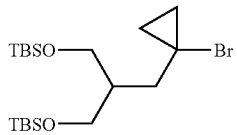

A reaction flask was charged with anhydrous CH$_2$Cl$_2$ (10 ml) and diethyl zinc (1.0 M in hexanes, 4.65 ml, 4.65 mmol) at 0° C. Trifluoroacetic acid (0.358 ml, 4.65 mmol) was added dropwise and the solution was allowed to stir for 20 minutes. Diiodomethane (0.375 ml, 4.65 mmol) was then added and the solution was stirred for another 20 minutes. Finally, the product from step C (0.492 g, 1.16 mmol) was added and the solution was allowed to warm to ambient temperature, stirring for 16 hours. The reaction was quenched with saturated aqueous NH$_4$Cl. The layers were partitioned and the aqueous phase was extracted with chloroform (3×5 ml). The combined organic phases were washed with brine (10 ml), dried over MgSO$_4$, and the volatiles were removed in vacuo. The resulting crude was purified via silica gel chromatography (eluants: chloroform/hexanes) to provide the product as a clear oil (0.280 g, 64%). $^1$H-NMR (300 MHz, CDCl$_3$) δ 3.66 (d, J=5.4, 4H), 2.08 (m, 1H), 1.64 (d, J=6.9 Hz, 2H), 1.13 (m, 2H), 0.88 (s, 18H), 0.81 (m, 2H), 0.04 (s, 9H).

Step E: Di-tert-butyldimethylsilyl protected 1-(3-hydroxy-2-(hydroxymethyl)propyl)cyclopropane-1-sulfonyl chloride

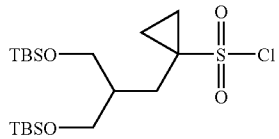

The product from step D (0.507 g, 1.16 mmol) was dissolved in anhydrous ether (6 ml) and the reaction solution was cooled to -78° C. Following this, tert-butyllithium (1.7 M in pentane, 1.50 ml, 2.55 mmol) was added dropwise over 5 minutes. After stirring for 0.5 hours, the lithiated product was transferred via cannula to a stirred solution of sulfuryl chloride (0.206 ml, 2.55 mmol) in dry ether (6 ml) at -78° C. Once the transfer is complete, the solution was allowed to warm to room temperature, the solvent was evaporated and the resulting white solid was slurried in dry hexanes. This slurry was immediately filtered through celite, and all volatiles were removed in vacuo. The resulting crude product (0.376 g, 71%) was isolated as a yellow oil and was used in the following step without further purification. $^1$H-NMR (300 MHz, CDCl$_3$) δ 3.60 (m, 4H), 2.16 (m, 1H), 2.03 (d, 2H), 0.88 (s, 18H), 0.04 (s, 9H).

Step F: Di-tert-butyldimethylsilyl protected N-(3,4-difluoro-2-(2-fluoro-4-iodophenylamino)-6-methoxyphenyl) 1-(3-hydroxy-2-(hydroxymethyl)propyl)cyclopropane-1-sulfonamide

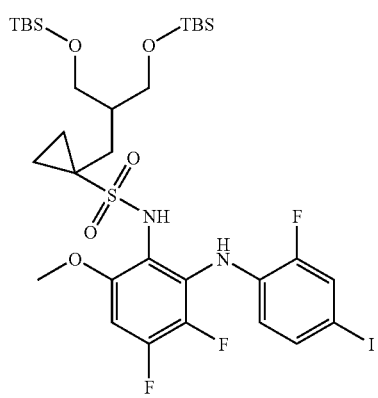

5,6-difluoro-N1-(2-fluoro-4-iodophenyl)-3-methoxybenzene-1,2-diamine (8.8 mg, 0.022 mmol) was dissolved in anhydrous pyridine (0.5 ml) under an argon atmosphere. The product from step E (20.5 mg, 0.045 mmol), dissolved in dry pyridine (0.5 ml), was added to the reaction flask and the mixture was heated at 80° C. for 21 hours. The solvent was removed in vacuo and the resulting crude was purified via silica gel chromatography (eluents: ethyl acetate/hexanes) to provide the title compound (2.75 mg, 15%). m/z 813.5 (M-1).

Step G: N-(3,4-difluoro-2-(2-fluoro-4-iodophenylamino)-6-methoxyphenyl)-1-(3-hydroxy-2-(hydroxymethyl)propyl)cyclopropane-1-sulfonamide

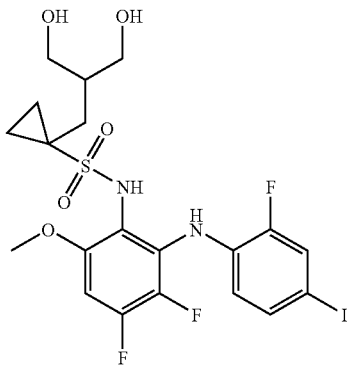

The product from step F (27.9 mg, 0.0342 mmol) was dissolved in THF (1 ml) and treated with aqueous HCl (1.2 N, 0.2 ml) at 0° C. The resulting solution was stirred for 4 hours. Following this, the reaction was quenched with saturated aqueous NaHCO$_3$, extracted with ethyl acetate, dried over MgSO$_4$ and the volatiles were removed in vacuo. The resulting crude was purified via silica gel chromatography (eluents: methanol/chloroform) followed by LC-MS purification to provide the title compound (11.8 mg, 59%). $^1$H-NMR (300 MHz, CD$_3$OD) δ 7.32 (dd, 1H), 7.21 (d, 1H), 6.76 (dd, 1H), 6.33 (m, 1H), 3.82 (s, 3H), 3.52 (d, 4H), 2.01 (m, 1H), 1.88 (d, 2H), 1.07 (m, 2H), 0.75 (m, 2H), m/z 585.3 (M−1)⁻.

Example 61

N-(3,4-difluoro-2-(2-fluoro-4-iodophenylamino)-6-methoxyphenyl)cyclobutane sulfonamide Step A: Cyclobutanesulfonyl chloride

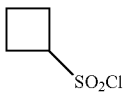

To a suspension of Mg turnings (0.790 g, 32.5 mmol) in 20 ml anhydrous diethyl ether was added a solution of cyclobutylbromide (1.8 ml, 2.5722 g, 19.1 mmol) in 20 ml diethyl ether in small portions with strong stirring. After the initial exothermic reaction had ceased, the mixture was further heated to the reflux temperature for 30 min. The suspension was cooled down to room temperature and the supernatant was added in small portions to an ice-cold solution of sulfuryl chloride (4.6 ml, 7.728 g, 57.2 mmol) in 30 ml anhydrous DCM. After complete addition, the suspension was warmed to room temperature and the volatiles were removed in vacuo. The residue was dried in oil-pump vacuo for 15 min, then it was extracted with hexane (150 ml). The hexane suspension was filtered and the hexane was removed in vacuo to give the crude product as dark purple oil which was used for the next step without further purification. There is still some unreacted cyclopropylbromide present. Crude yield: 1.1 g (38%).

Step B: N-(3,4-difluoro-2-(2-fluoro-4-iodophenylamino)-6-methoxyphenyl)cyclobutanesulfonamide

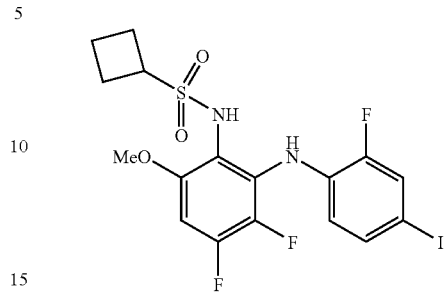

According to the general procedure B, the cyclobutylsulfonyl chloride prepared in the step above was reacted with 5,6-difluoro-N1-(2-fluoro-4-iodophenyl)-3-methoxy-benzene-1,2-diamine to obtain the title product. Yield: 75%. $^1$H-NMR (300 MHz, CDCl$_3$): δ=7.44 (s, 1H, br), 7.41-7.36 (dd, 1H), 7.24-7.23 (m, 1H), 6.54-6.38 (m, 2H), 5.90 (s, 1H, br), 3.85-3.75 (m, 5H), 2.60-2.40 (m, 2H), 2.25-2.15 (m, 1H), 2.15-1.95 (m, 2H); m/z=511 [M−1]⁻.

Example 62

N-(3,4-difluoro-2-(2-fluoro-4-iodophenylamino)-6-methylphenyl)-1-(2,3-dihydroxypropyl)cyclopropane-1-sulfonamide Step A: (3,4,5-Trifluorophenyl)methanol

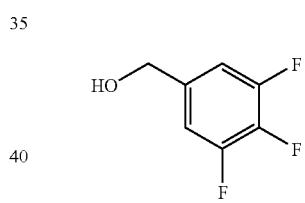

To a cooled (−5° C.) solution of 3,4,5-trifluorobenzaldehyde (7.0 g, 43.75 mmol) in a mixture (50 ml, 9:1) of THF and water NaBH$_4$ (1.662 g, 43.75 mmol) was slowly added in portions over a period of 30 min. The reaction mixture was allowed to attain room temperature over a period of 2 h and carefully poured into ice-cold dil HCl (200 ml, 1N). The oily layer was extracted into CH$_2$Cl$_2$ (250 ml) and the organic layer washed with water (200 ml), dried (MgSO$_4$) and evaporated. The crude product (7.08 g, quantitative) obtained was taken forward without further purification.

Step B: 5-(Bromomethyl)-1,2,3-trifluorobenzene

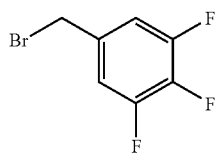

To a solution of the (3,4,5-Trifluorophenyl)methanol (40 mmol) in CH$_2$Cl$_2$ (150 ml), a solution of thionyl bromide (6.16 ml, 80 mmol) in CH$_2$Cl$_2$ (50 ml) was added slowly. The reaction mixture stirred at room temperature for 16 h and poured into ice-water (200 ml). The organic layer was separated and washed with saturated NaHCO$_3$ (2×200 ml), water (200 ml), dried (MgSO$_4$) and evaporated to obtain the corresponding bromo compound as a pale yellow oil in quantitative yield. The crude product was carried forward for the next reaction without further purification.

Step C: 1,2,3-Trifluoro-5-methylbenzene

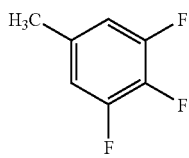

The above bromo compound (40 mmol) was mixed with triethylsilane (48 mmol) and the reaction mixture was treated with solid PdCl$_2$ (4 mmol) in small portions. After a few minutes a vigorous exothermic reaction was ensued and care was taken to reflux the contents of the flask by placing a reflux condenser. The reaction mixture was stirred at room temperature for additional 6 h and the contents were allowed to settle over 16 h. Then the crude liquid product was decanted carefully and carried forward for the next reaction without further purification. It was assumed that the reaction proceeds in quantitative yield.

Step D: 1,2,3-Trifluoro-5-methyl-4-nitrobenzene

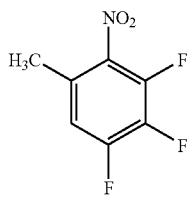

1,2,3-Trifluoro-5-methylbenzene (40 mmol) was added to conc. H$_2$SO$_4$ (50 ml) at 0-5° C. Then the reaction mixture was slowly treated with conc. HNO$_3$ (3.39 ml, 48.44 mmol, 90%) while maintaining the internal temperature below 20° C. The reaction mixture was stirred at room temperature for 16 h and poured onto ice (300 g) and the oily layer was extracted with CH$_2$Cl$_2$ (2×125 ml). The organic layer was washed with water (2×200 ml), brine (200 ml) and dried (MgSO$_4$) and evaporated to obtain the crude product which was purified over flash silica gel chromatography to obtain the title product (6.5 g, 85%). $^1$H-NMR (300 MHz, CDCl$_3$): δ 6.96 (septet, 1H), 2.39 (s, 3H). $^{19}$FNMR (CDCl$_3$): δ −128.18, −141.50, −159.05.

Step E: 2,3-Difluoro-N-(2-fluoro-4-iodophenyl)-5-methyl-6-nitroaniline

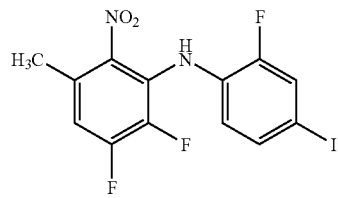

2-Fluoro-4-iodoaniline and 1,2,3-trifluoro-5-methyl-4-nitrobenzene were reacted using the condition described in Example 1 (Step A) to form the title compound. M−H$^+$: 407.9

Step F: 5,6-Difluoro-N1-(2-fluoro-4-iodophenyl)-3-methylbenzene-1,2-diamine

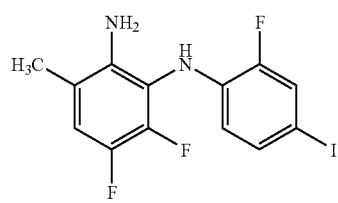

1,2,3-Difluoro-N-(2-fluoro-4-iodophenyl)-5-methyl-6-nitroaniline was reduced using the condition described in Example 1 (step B) to form the title compound. M−H$^+$: 377.4

Step G: 1-Allyl-N-(3,4-difluoro-2-(2-fluoro-4-iodophenylamino)-6-methylphenyl)cyclopropane-1-sulfonamide

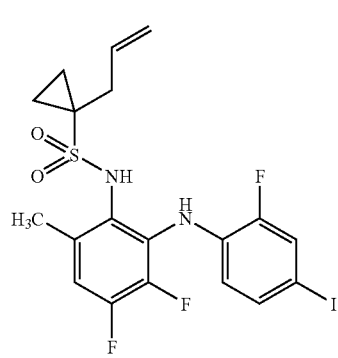

According to the general procedure B, 1-allyl-cyclopropanesulfonyl chloride (142 mg, 142 mg) was reacted with 5,6-difluoro-N-1-(2-fluoro-4-iodophenyl)-3-methylbenzene-1,2-diamine (150 mg, 0.4 mmol) to obtain the title product (100 mg, 47%); m/z=521 [M−1]$^−$.

Step H: N-(3,4-difluoro-2-(2-fluoro-4-iodophenylamino)-6-methylphenyl)-1-(2,3-dihydroxypropyl)cyclopropane-1-sulfonamide

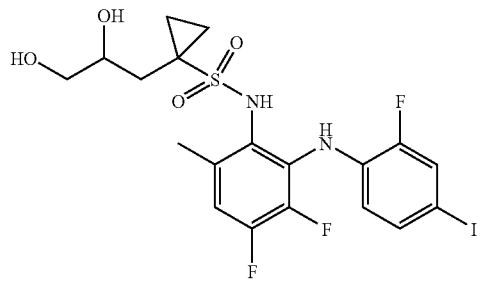

1-Allyl-N-(3,4-difluoro-2-(2-fluoro-4-iodophenylamino)-6-methylphenyl)cyclopropane-1-sulfonamide (150 mg, 0.29 mmol) and 4-methylmorpholine N-oxide (33 mg, 0.29 mmol) was dissolved in THF (5 mL). Osmium tetroxide was added at room temperature (0.029 mmol, 0.18 mL, 4% in $H_2O$) and the reaction mixture was stirred at room temperature for 16 hours. EtOAc was added, the organic phase was washed with water, dried ($MgSO_4$) and concentrated under reduced pressure. The residue was purified over silica gel chromatography (eluants: EtOAc/MeOH) to obtain the titled product (0.110 g, 68%). $^1$H-NMR (300 MHz, $CDCl_3$): δ 7.07 (m, 1H), 6.97 (br m, 2H), 6.84 (m, 2H), 6.60 (br m, 2H), 3.98 (br r, 1H), 3.58 (m, 1H), 3.43 (m, 1H), 3.20 (d, J=3.9 Hz, 1H), 2.42 (s, 3H), 2.31 (dd, J=9.9 & 15.6 Hz, 1H), 2.01 (br t, 1H), 2.31 (dd, J=9.9& 15.6 Hz, 1H), 1.66 (dd, J=2.1 & 15.9 Hz, 1H), 1.52 ((m, 1H), 1.40 (m, 1H), 0.91 (m, 2H).

Example 63

1-(2,3-Dihydroxypropyl)-N-(6-ethyl-3,4-difluoro-2-(2-fluoro-4-iodophenylamino)phenyl)cyclopropane-1-sulfonamide Step A: 1-(3,4,5-Trifluorophenyl)ethanol

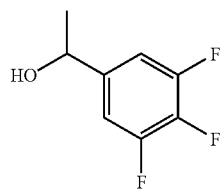

An ethereal solution (17.41 ml, 52.24 mmol, 3M) of MeMgBr was slowly added at −78° C. to a solution of 3,4,5-trifluorobenzaldehyde (6.96 g, 43.53 mmol) in THF (125 ml). The reaction mixture was stirred at room temperature for 16 h and was cooled (0° C.) and was quenched, sequentially, with excess ethyl acetate (10 ml) and water (5 ml). Excess anhydrous $MgSO_4$ (5 g) was added and stirred for 30 minutes at room temperature. The suspension was filtered over celite and the solids were washed with ethyl acetate (2×25 ml). The combined filtrate was evaporated to obtain the product in quantitative yield (7.65 g).

Step B: 5-(1-Bromoethyl)-1,2,3-trifluorobenzene

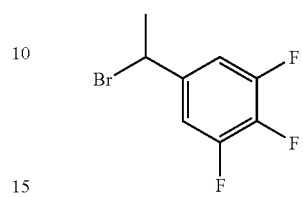

To a solution of the 1-(3,4,5-Trifluorophenyl)ethanol: (7.65 g, 43.5 mmol) in $CH_2Cl_2$ (250 ml), a solution of thionyl bromide (18.1 g, 87 mmol) in $CH_2Cl_2$ (50 ml) was added slowly. The reaction mixture stirred at room temperature for 16 h and poured into ice-water (200 ml). The organic layer was separated and washed with saturated $NaHCO_3$ (2×200 ml), water (200 ml), dried ($MgSO_4$) and evaporated to obtain the corresponding bromo compound as a pale yellow oil in quantitative yield (10.4 g). The crude product was carried forward for the next reaction without further purification.

Step C: 5-Ethyl-1,2,3-trifluorobenzene

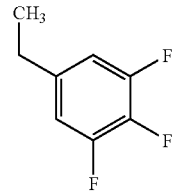

The above bromo compound (9.65 g, 40.4 mmol) was mixed with triethylsilane (41 mmol) and the reaction mixture was treated with solid $PdCl_2$ (177 mg, 4 mmol) in small portions. After a few minutes a vigorous exothermic reaction was ensued and care was taken to reflux the contents of the flask by placing a reflux condenser. The reaction mixture was stirred at room temperature for additional 6 h and the contents were allowed to settle over 16 h. Then the crude liquid product was decanted carefully and carried forward for the next reaction without further purification. It was assumed that the reaction proceeds in quantitative yield.

Step D: 1-Ethyl-3,4,5-trifluoro-2-nitrobenzene

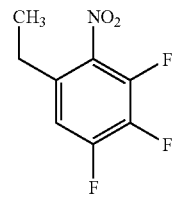

1,2,3-Trifluoro-5-methylbenzene (6.46 g, 40.4 mmol) was added to conc. $H_2SO_4$ (50 ml) at 0-5° C. Then the reaction mixture was slowly treated with conc. HNO₃ (3.39 ml, 48.44 mmol, 90%) while maintaining the internal temperature below 20° C. The reaction mixture was stirred at room temperature for 16 h and poured onto ice (300 g) and the oily layer was extracted with CH₂Cl₂ (2×125 ml). The organic layer was washed with water (2×200 ml), brine (200 ml) and dried (MgSO₄) and evaporated to obtain the crude product which was purified over flash silica gel chromatography to obtain the title product (6.6 g, 79%). ¹H NMR (CDCl₃): δ 6.98 (septet, 1H), 2.68 (q, 2H), 1.26 (t, J=7.8 & 7.2 Hz, 3H).

Step E: 3-Ethyl-5,6-difluoro-N-(2-fluoro-4-iodophenyl)-2 nitroaniline

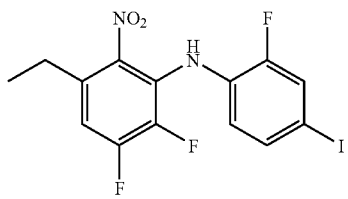

2-Fluoro-4-iodoaniline (2.05 g, 10 mmol) and 1-ethyl-3,4,5-trifluoro-2-nitrobenzene (2.37 g, 10 mmol) were reacted using the condition described in example 1 (Step A) to form the title compound (2.47 g, 60%); m/z=407 [M−1]⁻.

Step F: 3-Ethyl-5,6-difluoro-N1-(2-fluoro-4-iodophenyl)benzene-1,2-diamine

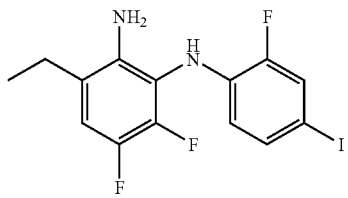

1,2,3-Trifluoro-5-methyl-4-nitrobenzene (2.47 g, 5.85 mmol) was reduced using the condition described in example 1 (Step B) to form the title compound. M−H⁺: 393

Step G: 1-Allyl-N-(6-ethyl-3,4-difluoro-2-(2-fluoro-4-iodophenylamino)phenyl)cyclopropane-1-sulfonamide

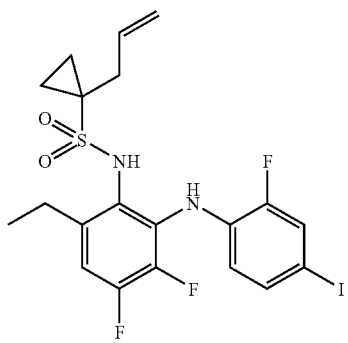

According to the general procedure B, 1-allyl-cyclopropanesulfonyl chloride (230 mg, 1.27 mmol) was reacted with 5,6-difluoro-N1-(2-fluoro-4-iodophenyl)-3-methylbenzene-1,2-diamine (100 mg, 0.255 mmol) to obtain the title product (72 mg, 53%); m/z=535 [M−1]⁻.

Step H: 1-(2,3-Dihydroxypropyl)-N-(6-ethyl-3,4-difluoro-2-(2-fluoro-4-iodophenylamino)phenyl)cyclopropane-1-sulfonamide

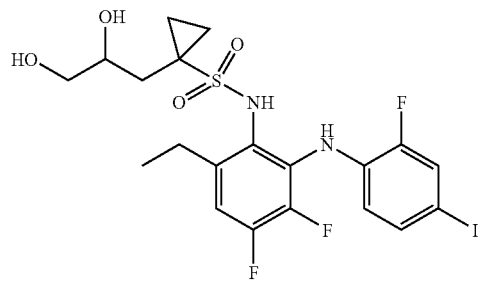

1-Allyl-N-(3,4-difluoro-2-(2-fluoro-4-iodophenylamino)-6-methylphenyl)cyclopropane-1-sulfonamide (70 mg, 0.13 mmol) and 4-methylmorpholine N-oxide (15 mg, 0.13 mmol) was dissolved in THF (2 mL). Osmium tetroxide was added at room temperature (0.013 mmol) 0.075 mL, 4% in H₂O) and the reaction mixture was stirred at room temperature for 16 hours. EtOAc was added, the organic phase was washed with water, dried (MgSO₄) and concentrated under reduced pressure. The residue was purified over silica gel chromatography (eluants: EtOAc/MeOH) to obtain the titled product. ¹H NMR (300 MHz, CDCl₃): δ 7.38 (dd, J=2.1 & 10.8 Hz, 1H), 7.27 (m, 2H), 7.12 (br s, 1H), 6.91 (dd, J=8.1 & 10.8 Hz, 1H), 6.69 (br s, 1H), 6.36 (dt, J=4.8, 8.7 & 13.5 Hz, 1H), 4.00 (m, 1H), 3.62 (dd, J=3.6 & 10.5 Hz, 1H), 3.47 (br m, 2H), 2.81 (q, 2H), 2.40 (dd, J=10.2 & 15.9 Hz, 1H), 1.73 (br m, 2H), 1.58 (m, 1H), 1.43 (m, 1H), 0.94 (m, 2H).

Example 64

N-(3,4-difluoro-2-(2-fluoro-4-iodophenylamino)-6-(2-methoxyethoxy)phenyl)-1-(2,3-dihydroxypropyl)cyclopropane-1-sulfonamide Step A:
1,2,3-Trifluoro-5-(2-methoxyethoxy)-4-nitrobenzene

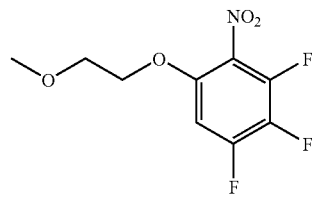

To a mixture of 3,4,5-trifluoro-2-nitrophenol (1.93, 10 mmol), Ph₃P (3.93 g, 15 mmol), and 2-methoxy-ethanol (1.18 ml, 15 mmol) in anhydrous THF (25 ml) a solution of diisopropyl azodicarboxylate (2.91 ml, 15 mmol) in THF (5 ml) was added at 0° C. and the reaction mixture was stirred at room temperature for 16 h. The volatiles were evaporated and the residue was dissolved in CH₂Cl₂ (100 ml) and the organic layer was washed with water (100 ml), brine (100 ml) dried (MgSO₄) and evaporated. The residue obtained was purified over flash silica gel chromatography to obtain the titled product in 68% (1.70 g) yield. ¹H NMR (300 MHz, CDCl₃): δ 6.78 (ddd, J=2.4, 6.0, 11.7 Hz, 1H), 4.19 (t, J=4.5 Hz, 2H), 3.72 (t, J=4.5 Hz, 2H), 3.39 (s, 3H).

Step B: 2,3-Difluoro-N-(2-fluoro-4-iodophenyl)-5-(2-methoxyethoxy)-6-nitroaniline

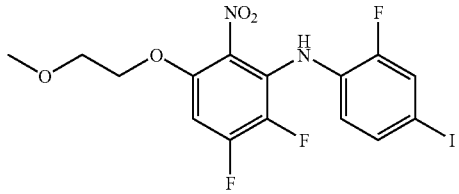

2-Fluoro-4-iodoaniline (1.6 g, 6.8 mmol) and 1,2,3-trifluoro-5-(2-methoxyethoxy)-4-nitrobenzene (1.7 g, 6.8 mmol) were reacted using the condition described in Example 1 (Step A) to form the title compound (1.02 g, 32%); m/z=467 [M−1].

Step C: 5,6-Difluoro-N-(2-fluoro-4-iodophenyl)-3-(2-methoxyethoxy)benzene-1,2-diamine

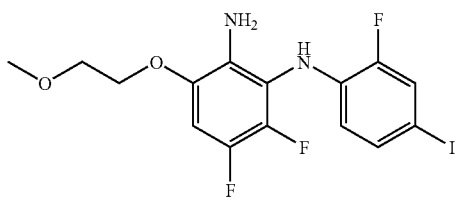

2,3-Difluoro-N-(2-fluoro-4-iodophenyl)-5-(2-methoxyethoxy)-6-nitroaniline (1.017 g, 2.17 mmol) was reduced using the condition described in Example 1 (Step B) to form the title compound; m/z=337 [M−1].

Step D: 1-Allyl-N-(3,4-difluoro-2-(2-fluoro-4-iodophenylamino)-6-(2-methoxyethoxy)phenyl)cyclopropane-1-sulfonamide

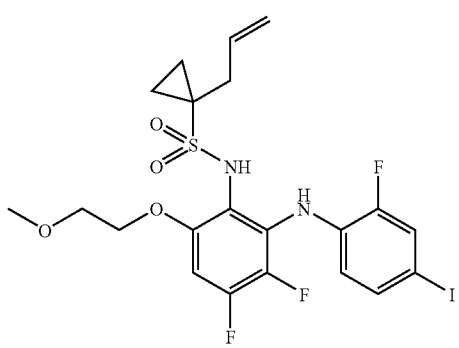

According to the general procedure B, 1-allyl-cyclopropanesulfonyl chloride (450 mg, 2.5 mmol) was reacted with 5,6-difluoro-N1-(2-fluoro-4-iodophenyl)-3-(2-methoxyethoxy)benzene-1,2-diamine (219 mg, 2.5 mmol) to obtain the title product (230 mg, 78%); m/z=581 [M−1]⁻.

Step E: N-(3,4-difluoro-2-(2-fluoro-4-iodophenylamino)-6-(2-methoxyethoxy)phenyl)-1-(2,3-dihydroxypropyl)cyclopropane-1-sulfonamide

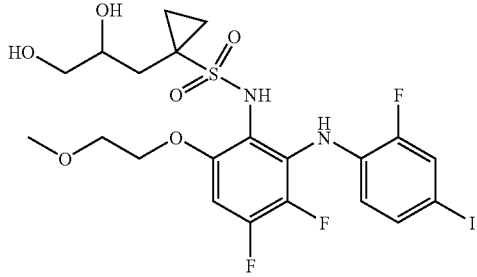

1-allyl-N-(3,4-difluoro-2-(2-fluoro-4-iodophenylamino)-6-(2-methoxyethoxy)phenyl)cyclopropane-1-sulfonamide (230 mg, 0.395 mmol) and 4-methylmorpholine N-oxide (46 mg, 0.395 mmol) was dissolved in THF (2 mL). Osmium tetroxide was added at room temperature (0.039 mmol, 0.25 mL, 4% in H$_2$O) and the reaction mixture was stirred at room temperature for 16 hours. EtOAc was added, the organic phase was washed with water, dried (MgSO$_4$) and concentrated under reduced pressure. The residue was purified over silica gel chromatography (eluants: EtOAc/MeOH) to obtain the titled product. $^1$H NMR (300 MHz, CDCl$_3$): δ7.36 (dd, J=1.8 & 10.5 Hz, 1H), 7.27 ((m, 2H), 6.56 (dd, J=6.9 & 11.4 Hz, 1H), 6.40 (dt, J=5.7, 7.5 & 12.9 Hz, 1H), 4.17 (m, 2H), 4.01 (m, 1H), 3.78 (m, 2H), 3.60 (dd, J=3.6 & 11.1 Hz, 1H), 3.47 (m, 1H), 3.45 (s, 3H), 2.36 (dd, J=9.6 & 15.9 Hz, 1H), 1.78 (dd, J=2.4 & 15.6 Hz, 1H), 1.45-1.25 (m, 2H), 0.89 (m, 2H).

Example 65

2,4-dichloro-N-(3,4-difluoro-2-(2-fluoro-4-iodophenylamino)phenyl)benzene sulfonamide

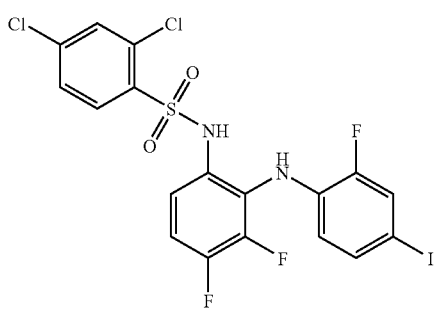

Synthesized by method A using the appropriate sulfonyl chloride, m/z=571 [M−1].

Example 66

2-chloro-N-(3,4-difluoro-2-(2-fluoro-4-iodophenylamino)phenyl)-4-(trifluoromethyl)benzenesulfonamide

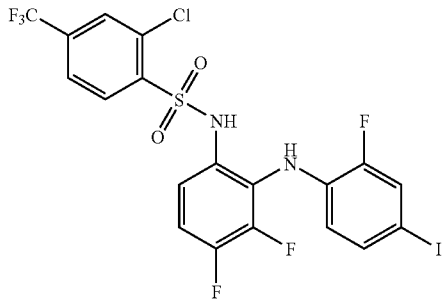

Synthesized by method A using the appropriate sulfonyl chloride, m/z=605 [M−1].

Example 67

N-(3,4-difluoro-2-(2-fluoro-4-iodophenylamino)phenyl)-2-(trifluoromethoxy)benzene sulfonamide

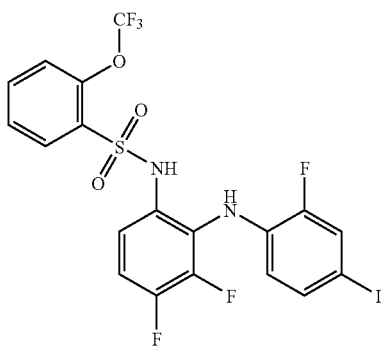

Synthesized by method A using the appropriate sulfonyl chloride, m/z=587 [M−1].

Example 68

4-(N-(3,4-difluoro-2-(2-fluoro-4-iodophenylamino)phenyl)sulfamoyl)benzoic acid

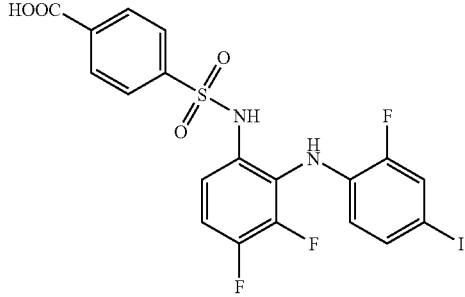

Synthesized by method A using the appropriate sulfonyl chloride, m/z=584 [M−1].

Example 69

N-(3,4-difluoro-2-(2-fluoro-4-iodophenylamino)phenyl)benzenesulfonamide

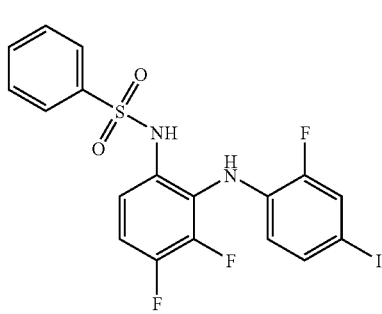

Synthesized by method A using the appropriate sulfonyl chloride, m/z=503 [M−1].

Example 70

N-(3,4-difluoro-2-(2-fluoro-4-iodophenylamino)phenyl)-2-fluorobenzene sulfonamide

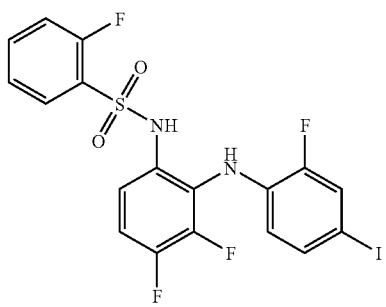

Synthesized by method A using the appropriate sulfonyl chloride, m/z=521 [M−1].

General Procedure D: Substitution of the Iodine Atom:

A suspension containing 1 eq. aryl iodide, 1.5 equiv. of the boronic acid or boronic ester, 0.25 eq. PdCl$_2$(dppf)×DCM and 10 eq. anhydrous K$_2$CO$_3$ powder in a deoxygenated mixture of dioxane and water (3:1) was heated in a microwave reactor for 60 min at 115° C. It was extracted using aq. NH$_4$Cl/THF, and the organic fraction was dried using Na$_2$SO$_4$. The crude reaction products were purified using flash-column chromatography (Si, EtOAc/Hexanes, or CHCl$_3$/MeOH). Yields: 20-40%.

Example 71

N-(3,4-difluoro-2-(2-fluoro-4-methylphenylamino)phenyl)cyclopropanesulfonamide

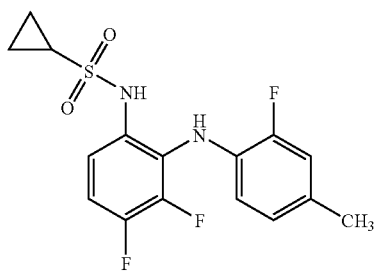

General procedure D: $^1$H-NMR (500 MHz, CDCl$_3$): δ=7.38-7.36 (m, 1H), 7.06-7.03 (q, 1H), 6.92-6.90 (1H), 6.73-6.72 (d, 1H), 6.63 (s, 1H, br), 6.37-6.33 (t, 1H), 5.54 (s, 1H, br), 2.42-2.39 (m, 1H), 2.25 (s, 3H), 1.14-1.11 (m, 2H), 0.94-0.90 (m, 2H); m/z=355 [M−1].

Where racemic mixtures of chiral compounds have been resolved into separate enantiomers, the phrase "substantially free" of the epimer, as used herein, means an enantiomeric excess of at least 90%.

Example 72

N-(3,4-difluoro-2-(2-fluoro-4-(1H-pyrazol-4-yl)phenylamino)phenyl)cyclopropane sulfonamide

Step A: 2,3-Difluoro-N-(2-fluoro-4-iodophenyl)-6-nitroaniline

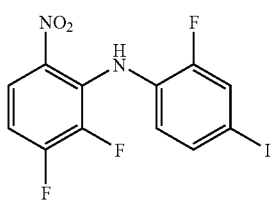

To a solution of 2-fluoro-4-iodoaniline (11.40 g, 47 mmol) in 100 ml anhydrous THF at 0° C., 47 ml of a 1M solution of LHMDS in THF (47 mmol) was added dropwise. The color of the solution turned dark purple. The solution was transferred via cannula to a dropping funnel, and the solution (containing the amine free base) was added in small portions to a solution of 2,3,4-trifluoronitrobenzene (8.321 g, 47.0 mmol) in anhydrous THF (50 ml) at 0° C. After completion of addition the mixture was stirred under argon at room temperature for 15 hours. The volume of the solvent was reduced, followed by extraction using ethyl acetate and brine. The organic layer was dried over sodium sulfate, the solvent was removed, and the obtained dark oil was purified by flash chromatography (EtOAc/hexane 1:5, R$_f$=0.58) yielding the crude product, which became a brown solid upon drying in vacuo (yield: 6.23 g, 33.6%); m/z=393 [M−1]$^-$.

Step B: 5,6-Difluoro-N1-(2-fluoro-4-iodophenyl)benzene-1,2-diamine

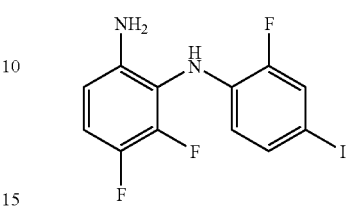

To a solution of nitro-diarylamine (6.23 g, 15.8 mmol) in 300 ml ethanol was added iron powder (13.74 g, 246 mmol) and ammonium chloride (13.59 g, 254 mmol) and the mixture was heated with stirring at 100° C. oil bath temperature for 14 hours. It was filtered and the residue washed two times with ethanol. The ethanol was removed in vacuo, and the residue was extracted using ethyl acetate/1M NaOH solution. During the extraction, more precipitate was formed which was filtered and discarded. The combined organic layers were washed with brine and dried over sodium sulfate. The solvent was removed, and the crude product was recrystallized from CHCl$_3$/hexane (1:50). The product was obtained as brown needles (2.094 g, 66%). R$_f$=0.44 (EtOAc/Hex 1:3). $^1$H-NMR (500 MHz, CDCl$_3$): δ=7.40-7.38 (dd, 1H, J=11.3 Hz, J=1.5 Hz), 7.25-7.23 (d, 1H, J=8.5 Hz), 6.97-6.92 (q, 1H, J=9 Hz), 6.51-6.48 (m, 1H), 6.24-6.21 (t, 1H, J=9 Hz), 5.3 (s, 1H, NH, br), 3.80 (s, 2H, NH$_2$, br); LRMS (ESI): m/z=365 [M+H]$^+$.

Step C: N-(3,4-difluoro-2-(2-fluoro-4-iodophenylamino)phenyl)cyclopropane sulfonamide

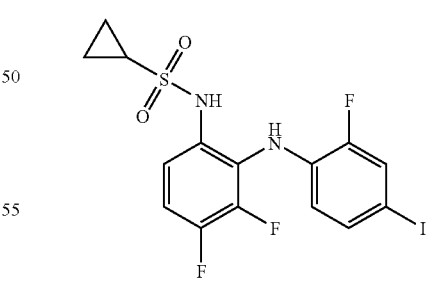

According to the general procedure A, 5,6-difluoro-N1-(2-fluoro-4-iodophenyl)benzene-1,2-diamine was reacted with cyclopropanesulfonyl chloride to obtain the desired product. (500 MHz, CDCl$_3$): δ=7.38-7.37 (d, 1H), 7.35-7.34 (m, 1H), 7.27-7.26 (m, 1H), 7.20-7.0 (q, 1H), 6.68 (s, 1H, br), 6.15-6.12 (q, 1H), 5.65 (s, 1H, br), 3.25-3.20 (m, 1H), 2.4-2.3 (m, 2H), 2.0-1.8 (m, 2H); m/z=467 [M−1]$^-$.

Step D: N-(3,4-difluoro-2-(2-fluoro-4-(1H-pyrazol-4-yl)phenylamino)phenyl)cyclopropanesulfonamide

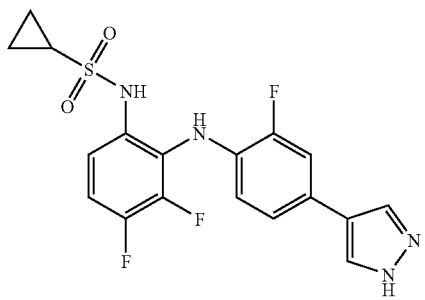

General procedure C: $^1$H-NMR (500 MHz, CDCl$_3$): δ=8.00-7.90 (m, 2H), 7.30-7.20 (m, 2H), 7.15-7.10 (m, 1H), 7.05-7.00 (m, 1H), 6.70-6.60 (m, 1H), 2.40-2.35 (m, 1H), 1.05-1.0 (m, 2H), 0.95-0.85 (m, 2H); m/z=407 [M−1]$^−$.

Example 73

N-(3,4-difluoro-2-(2-fluoro-4-(1-methyl-1H-pyrazol-4-yl)phenylamino)phenyl)cyclopropanesulfonamide

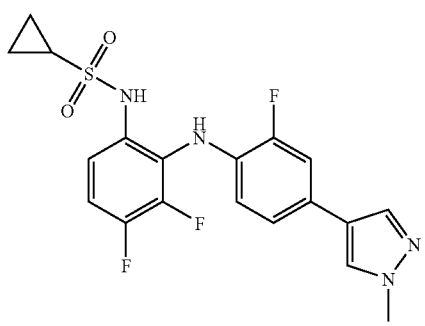

General procedure C: $^1$H-NMR (500 MHz, CDCl$_3$): δ=7.95 (s, 1H), 7.75 (s, 1H), 7.30-7.20 (m, 2H), 7.15-7.10 (m, 1H), 7.05-7.00 (m, 1H), 6.70-6.60 (m, 1H), 3.95 (s, 3H), 2.40-2.35 (m, 1H), 1.05-1.0 (m, 2H), 0.95-0.85 (m, 2H); m/z=421 [M−1]$^−$.

Example 74

N-(3,4-difluoro-2-(2-fluoro-4-(1H-pyrazol-3-yl)phenylamino)phenyl)cyclopropanesulfonamide

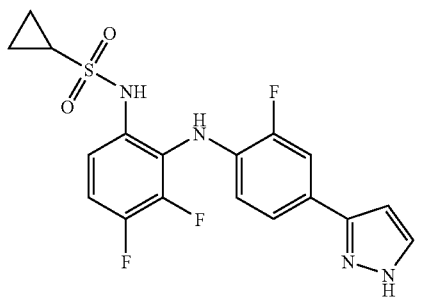

General procedure C: $^1$H-NMR (500 MHz, CDCl$_3$): δ=7.90 (s, 1H), 7.80 (s, 1H), 7.30-7.20 (m, 2H), 7.15-7.10 (m, 1H), 7.05-7.00 (m, 1H), 6.70-6.60 (m, 1H), 3.95 (s, 3H), 2.40-2.35 (m, 1H), 1.05-1.0 (m, 2H), 0.95-0.85 (m, 2H); m/z=407 [M−1]$^−$.

Example 75

N-(3,4-difluoro-2-(2-fluoro-4-(pyridin-4-yl)phenylamino)phenyl)cyclopropanesulfonamide

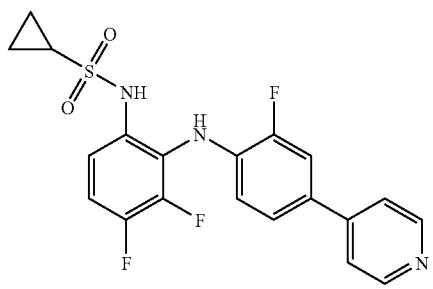

General procedure C: $^1$H-NMR (500 MHz, CDCl$_3$): δ=8.62-8.61 (d, 2H), 7.43-7.41 (m, 4H), 7.23-7.22 (m, 1H), 7.16-7.11 (q, 1H), 6.61-6.58 (t, 1H), 6.11 (s, 1H, br), 2.53-2.50 (m, 1H), 1.21-1.10 (m, 2H), 1.02-0.99 (m, 2H); m/z=418 [M−1]$^−$.

Example 76

N-(3,4-difluoro-2-(2-fluoro-4-(pyridin-3-yl)phenylamino)phenyl)cyclopropanesulfonamide

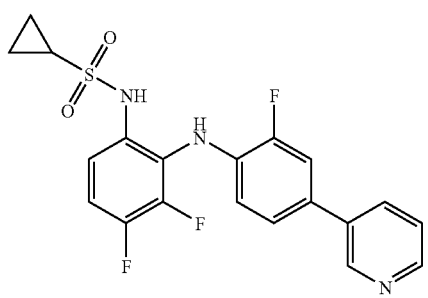

General procedure C: $^1$H-NMR (500 MHz, [D6]-DMSO): δ=9.45 (s, 1H), 8.91 (s, 1H), 8.54 (s, 1H), 8.07-8.06 (d, 1H), 7.76-7.70 (m, 2H), 7.46-7.34 (m, 2H), 7.34-7.33 (d, 2H), 6.80-6.78 (m, 1H), 0.86-0.79 (m, 4H); m/z=418 [M−1]$^−$.

Example 77

N-(2-(4-cyano-2-fluorophenylamino)-3,4-difluorophenyl)cyclopropanesulfonamide

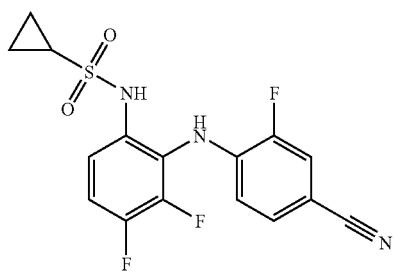

A suspension containing the aryl iodide (75.5 mg, 0.161 mmol), CuCN (46.6 mg, 0.520 mmol and Pd(OAc)$_2$ (0.47 mg) in 1 ml anhydrous DMF was heated to 130° C. for 60 min. in a microwave reactor. The mixture was extracted using brine/THF, and the organic fractions were dried using Na$_2$SO$_4$. Subsequent flash-column chromatography gave the product as a dark red semi-solid (R$_f$=0.42 (EtOAc/Hexanes 1:1). Yield: 15%. m/z=366 [M−1]$^-$.

Example 78

N-(3,4-difluoro-2-(3-fluorobiphenyl-4-ylamino)phenyl)cyclopropanesulfonamide

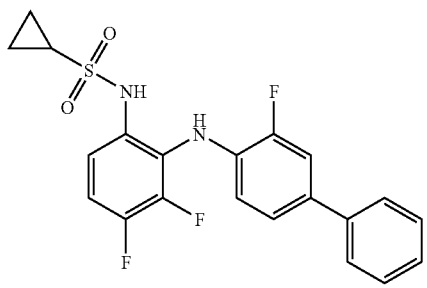

General procedure C: $^1$H-NMR (500 MHz, CDCl$_3$): δ=7.55-7.53 (m, 2H), 7.45-7.3 (m, 5H), 7.20-7.15 (d, 1H), 7.13-7.10 (q, 1H), 6.70 (s, 1H, br), 6.60-6.55 (t, 1H), 5.75 (s, 1H, br), 2.53-2.50 (m, 1H), 1.21-1.10 (m, 2H), 1.02-0.99 (m, 2H); m/z=417 [M−1]$^-$.

Example 79

N-(2-(3'-acetyl-3-fluorobiphenyl-4-ylamino)-3,4-difluorophenyl)cyclopropanesulfonamide

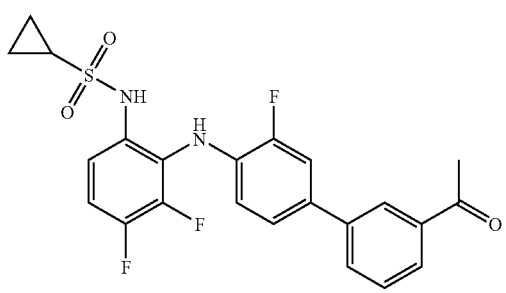

General procedure C: $^1$H-NMR (500 MHz, CDCl$_3$): δ=8.6 (s, 1H), 7.86-7.85 (d, 1H), 7.68-7.66 (d, 1H), 7.49-7.46 (t, 1H), 7.38-7.33 (m, 2H), 7.20-7.18 (d, 1H), 7.09-7.03 (q, 1H), 6.90 (s, 1H, br), 6.57-6.54 (t, 1H), 5.90 (s, 1H), br), 2.61 (s, 3H), 2.46-2.43 (m, 1H), 1.15-1.13 (m, 2H), 0.94-0.91 (m, 2H); m/z=459 [M−1]$^-$.

Example 80

N-(2-(4'-cyano-3-fluorobiphenyl-4-ylamino)-3,4-difluorophenyl)cyclopropanesulfonamide

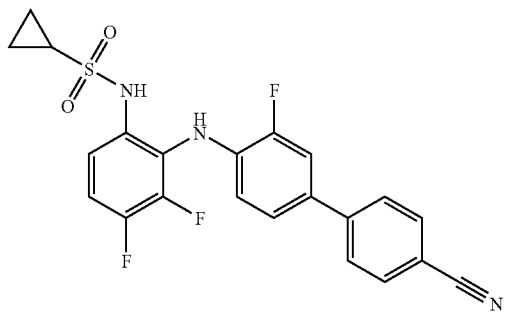

General procedure C: $^1$H-NMR (500 MHz, CDCl$_3$): δ=7.68-7.66 (m, 2H), 7.58-7.57 (m, 2H), 7.38-7.35 (m, 2H), 7.20-7.18 (d, 1H), 7.18-7.02 (q, 1H), 6.67 (s, 1H, br), 6.58-6.54 (t, 1H), 5.99 (s, 1H, br), 2.47-2.44 (m, 1H), 1.15-1.13 (m, 2H), 0.94-0.91 (m, 2H); m/z=442 [M−1]$^-$.

Example 81

N-(2-(3,4'-difluorobiphenyl-4-ylamino)-3,4-difluorophenyl)cyclopropanesulfonamide

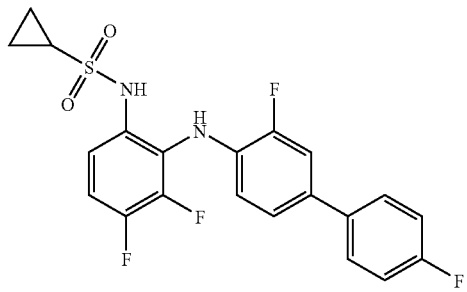

General procedure C: $^1$H-NMR (500 MHz, CDCl$_3$): δ=7.44-7.37 (m, 3H), 7.29-7.27 (d, 1H), 7.11-7.05 (m, 4H), 6.70 (s, 1H, br), 6.53-6.50 (t, 1H), 5.81 (s, 1H, br), 2.47-2.44 (m, 1H), 1.15-1.13 (m, 2H), 0.94-0.91 (m, 2H); m/z=435 [M−1]$^-$.

Example 82

N-(3,4-difluoro-2-(3-fluoro-4'-(methylsulfonamido)biphenyl-4-ylamino)phenyl)cyclopropanesulfonamide

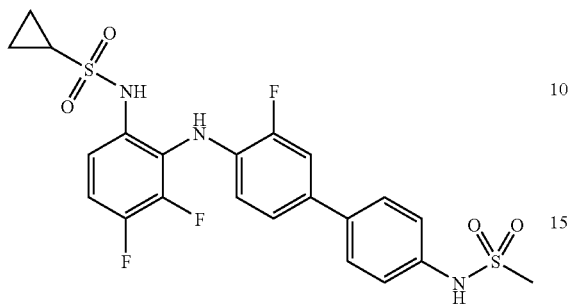

General procedure C: ¹H-NMR (500 MHz, [D6]-DMSO): δ=9.39 (s, 1H, br), 7.63-7.60 (m, 3H), 7.53-7.50 (d, 1H), 7.30-7.23 (m, 4H), 7.74-7.65 (m, 1H), 2.99 (s, 3H), 0.80-0.73 (m, 4H); m/z=510 [M−1]⁻.

Example 83

N-(3,4-difluoro-2-(2-fluoro-4-methylphenylamino)phenyl)cyclopropanesulfonamide

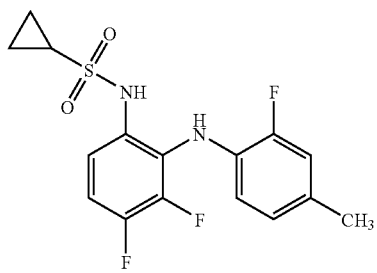

General procedure C: ¹H-NMR (500 MHz, CDCl₃): δ=7.38-7.36 (m, 1H), 7.06-7.03 (q, 1H), 6.92-6.90 (1H), 6.73-6.72 (d, 1H), 6.63 (s, 1H, br), 6.37-6.33 (t, 1H), 5.54 (s, 1H, br), 2.42-2.39 (m, 1H), 2.25 (s, 3H), 1.14-1.11 (m, 2H), 0.94-0.90 (m, 2H); m/z=355 [M−1]⁻.

Example 84

4'-(6-(cyclopropanesulfonamido)-2,3-difluorophenylamino)-3'-fluorobiphenyl-3-carboxylic acid

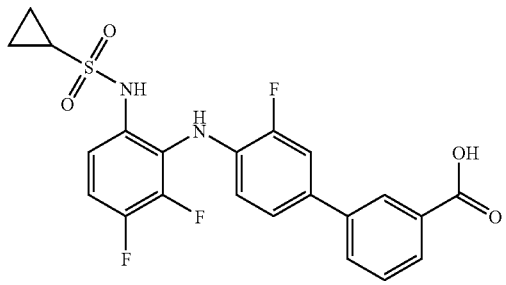

General procedure C: ¹H-NMR (500 MHz, [D4]-MeOH): δ=8.21 (s, 1H), 7.93-7.91 (d, 1H), 7.73-7.72 (d, 1H), 7.47-7.43 (m, 2H), 7.33-7.31 (d, 2H), 7.15-7.12 (q, 1H), 6.71-6.68 (m, 1H), 2.51-2.46 (m, 1H), 0.94-0.93 (m, 2H), 0.88-0.87 (m, 2H); m/z=499 [M−1]⁻.

Example 85

N-(3,4-difluoro-2-(3-fluoro-3'-(methylsulfonamido)biphenyl-4-ylamino)phenyl)cyclopropanesulfonamide

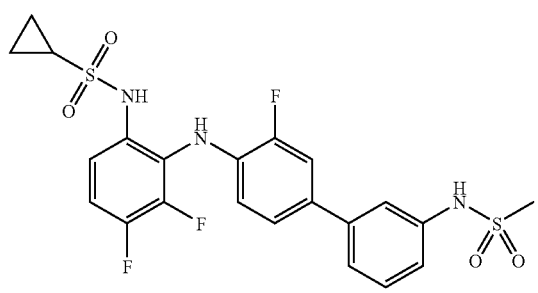

General procedure C: ¹H-NMR (500 MHz, [D4]-MeOH): δ=7.92 (s, 1H), 7.46-7.34 (m, 5H), 7.34-7.31 (d, 1H), 7.29-7.22 (m, 1H), 7.16-7.15 (q, 1H), 6.74-6.71 (m, 1H), 2.80 (s, 3H), 2.54-2.51 (m, 1H), 0.94-0.92 (m, 2H), 0.91-0.90 (m, 2H); m/z=510 [M−1]⁻.

Example 86

N-(3,4-difluoro-2-(3-fluoro-2'-(methylsulfonamido)biphenyl-4-ylamino)phenyl)cyclopropanesulfonamide

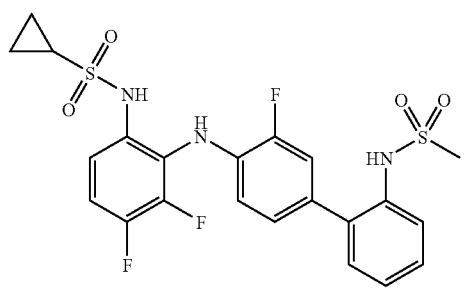

General procedure C: ¹H-NMR (500 MHz, [D4]-MeOH): δ=7.50-7.49 (d, 1H), 7.40-7.32 (m, 4H), 7.29-7.28 (d, 1H), 7.26-7.10 (m, 2H), 6.73-6.71 (m, 1H), 2.80 (s, 3H), 2.51-2.49 (m, 1H), 0.94-0.92 (m, 2H), 0.91-0.90 (m, 2H); m/z=510 [M−1]⁻.

Example 87

N-(3,4-difluoro-2-(3-fluoro-4'-(trifluoromethoxy)biphenyl-4-ylamino)phenyl)cyclopropanesulfonamide

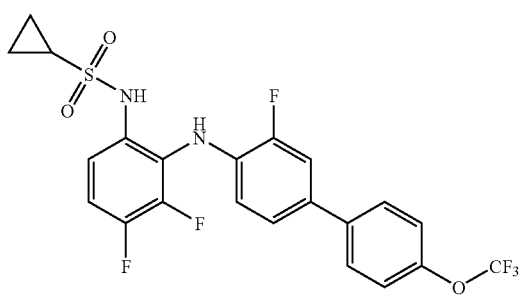

General procedure C: ¹H-NMR (500 MHz, [D4]-MeOH): δ=7.69-7.67 (d, 2H), 7.46-7.43 (d, 1H), 7.36-7.33 (m, 4H), 7.30-7.29 (q, 1H), 6.73-6.72 (m, 1H), 2.51-2.49 (m, 1H), 0.94-0.92 (m, 2H), 0.91-0.90 (m, 2H); m/z=501 [M−1]⁻.

Example 88

N-(3,4-Difluoro-2-(2-fluoro-4-iodophenylamino)phenyl)-2-(methylamino)ethanesulfonamide

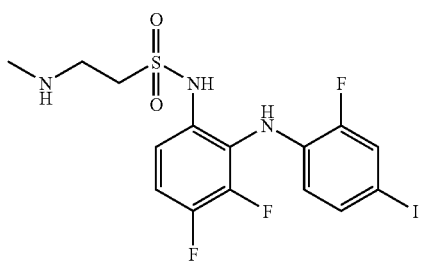

General procedure D. ¹H NMR (300 MHz, CDCl₃): δ 9.01 (br s, D₂O exchangeable, 1H), 7.36 (dd, J=2.1 & 10.5 Hz, 1H), 7.27 (m, 1H), 7.17 (m, 1H), 7.03 (dd, J=9.0 & 16.8 Hz, 1H), 6.48 (s, D₂O exchangeable, 1H), 6.31 (dt, J=3.0, 8.7 & 17.4 Hz, 1H), 3.45 (br t, 2H), 3.31 (br s, 2H), 2.65 (s, 3H), 1.80 (br s, D₂O exchangeable, 1H).

Example 89

N-(3,4-difluoro-2-(2-fluoro-4-iodophenylamino)phenyl)-2-(2-(dimethylamino)ethylamino)ethanesulfonamide

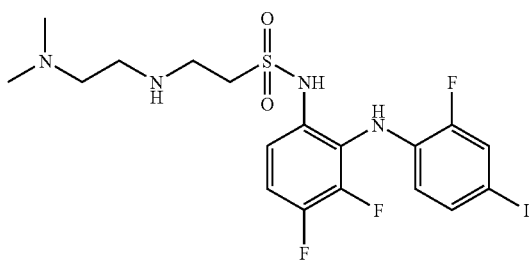

General procedure D. ¹H NMR (300 MHz, CDCl₃): δ 7.35 (m, 1H), 7.25 (m, 1H), 7.18 (d, J=8.7 Hz, 1H), 7.02 (dd, J=8.7 & 18.0 Hz, 1H), 6.38 (m, 1H), 6.18 (dd, J=8.7 & 17.1 Hz, 1H), 3.62 (t, J=5.7 & 6.3 Hz, 2H), 3.35 (m, 2H), 3.26 (m, 2H), 3.26 (t, J=5.7 & 6.6 Hz, 2H), 3.11 (t, J=5.1 & 6.0 Hz, 2H), 2.85 (s, 6H).

Example 90

N-(3,4-difluoro-2-(2-fluoro-4-iodophenylamino)phenyl)-2-(ethyl(methyl)amino)ethanesulfonamide

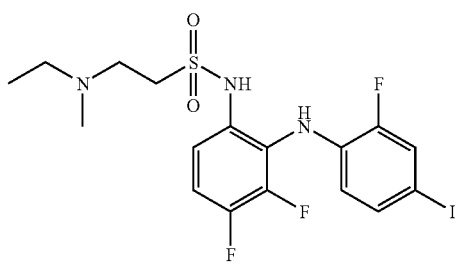

General procedure D. ¹H NMR (300 MHz, (CDCl₃+D₂O)): δ 7.39 (dd, J=1.5 & 10.5 Hz, 1H), 7.31 (m, 2H), 7.07 (dd, J=9.0 & 17.4 Hz, 1H), 6.30 (dt, J=2.4, 9.0 & 17.4 Hz, 1H), 3.55 (t, J=6.9 & 7.8 Hz, 2H), 3.38 (br t, J=6.0 & 8.7 Hz, 2H), 3.05 (q, 2H), 2.69 (s, 3H), 1.31 (t, J=7.2 Hz, 3H).

Example 91

N-(3,4-difluoro-2-(2-fluoro-4-iodophenylamino)phenyl)-2-(4-methylpiperazin-1-yl)ethanesulfonamide

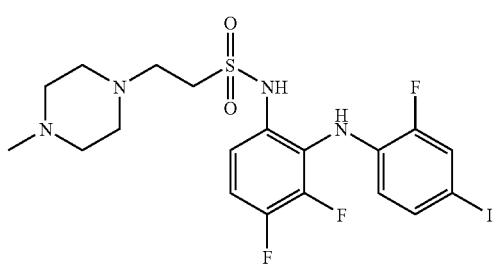

General procedure D. ¹H NMR (300 MHz, CD₃OD): δ 7.45 (dd, J=2.1 & 10.8 Hz, 1H), 7.30 (m, 2H), 7.16 (dd, J=9.6 & 17.7 Hz, 1H), 6.39 (dt, J=3.3, 9.3 & 17.7 Hz, 1H), 3.26 (m, J=7.5 Hz, 2H), 3.10 (br m, 6H), 2.87 (s, 3H), 2.82 (t, J=7.5 Hz, 2H), 2.48 (br m, 4H).

Biological Activity

Generation of IC50 Data

Materials and preparation of reagents: Human GST-MEK1 and the constitutively active allele GST-MEK1 CA (harboring the mutations Ser218Asp and Ser222Asp) were subcloned into the yeast expression vector pGEM4Z (Promega, Madison, Wis.) from the wild type human MEK1 cDNA. GST-MEK1$^{CA}$ was expressed in *Escherichia coli* and partially purified using Glutathione Sepharose 4B affinity resin (Amersham Pharmacia Biotech, Piscataway, N.J.). The ERK2 allele was subcloned from MAPK2/Erk2 cDNA (wild type) in pUSEamp (Upstate Biotechnology, Inc., Waltham, Mass.) into the vector pET21a (Novagen, Madison, Wis.) resulting in an N-terminal histidine-tagged mouse ERK2 allele. ERK2 was expressed and purified to homogeneity [Zhang, 1993 #33]. Myelin basic protein (MBP) was purchased from Gibco BRL (Rockville, Md.). EasyTides adenosine 5'-triphosphate (ATP) ([γ-$^{33}$P]) (NEN Perkin Elmer, Wellesley, Mass.) was the source of radiolabel for all kinase reactions. Activated Raf-1 (truncated) and activated MAPKinase 2/ERK2 were purchased from Upstate, Inc. (Lake Placid, N.Y.). 4-20% Criterion Precast gels were purchased from Bio-Rad (Hercules, Calif.).

Determination of enzymatic activity: Compounds were diluted from dimethylsulfoxide (DMSO) stocks into 1×HMNDE (20 mM HEPES pH 7.2, 1 mM $MgCl_2$, 100 mM NaCl, 1.25 mM DTT, 0.2 mM EDTA). A typical 25-microliter assay contained 0.002 nanomoles MEK1$^{CA}$, 0.02 nanomoles ERK2, 0.25 nanomoles MBP, 0.25 nanomoles unlabeled ATP, and 0.1 μCi [γ$^{33}$P] ATP. The screening assay essentially comprised four additions. Five μl of diluted compound were dispensed to 96-well assay plates. Ten 1 of 2.5× enzyme cocktail (MEK1$^{CA}$ and ERK2 only) were then added to each well followed by a pre-incubation for 30 minutes at ambient temperature. Ten μl of 2.5× substrate cocktail (labeled and unlabeled ATP plus MBP) were then added, followed by incubation for 60 minutes at ambient temperature. Finally, 100 μl of 10% trichloroacetic acid (TCA) were added and incubated for 30 minutes at room temperature to halt the reaction and precipitate radiolabeled protein products. Reaction products were harvested on glass fiber 96 well filter plates prewetted with water and 1% pyrophosphate. The filter plate was then washed 5 times with water. Water was displaced by absolute ethanol and the plate was allowed to air dry for 30 minutes at room temperature. A back seal was applied manually and 40 μl of scintillation cocktail were dispensed to each well. A top seal was applied and the plate was counted in the TopCount for two seconds per well.

For certain experiments a truncated version of MEK that requires activation by Raf kinase were used.

Generation of EC50 Data

Effects of compounds in the cell were determined by Western blotting for phosphorylated ERK. MDA-MB-231 breast cancer cells were plated in a 48 well plate at 20,000 cells per well and grown in a 37° humidified $CO_2$ incubator. The following day, the growth media (DMEM+10% fetal bovine serum) was removed and replaced with starve media (DMEM+0.1% fetal bovine serum). Cells were incubated in the starve media for sixteen hours and then treated with a range of compound concentrations for thirty minutes. After incubation with compound, cells were stimulated with 100 ng/ml EGF for five minutes. The cells were then lysed and analyzed by Western blot using a monoclonal antibody raised to phosphorylated ERK. The signal was amplified using a secondary antibody conjugated to a near-IR dye and detected on a Licor Odyssey scanner. The intensity of signal was quantitated and this data was used to generate dose response curves and EC50 calculations.

| Compound Number | Structure | Activity μM |
|---|---|---|
| 1000 | 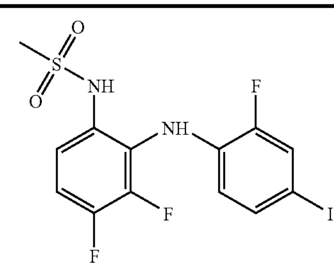 | A |
| 1001 | 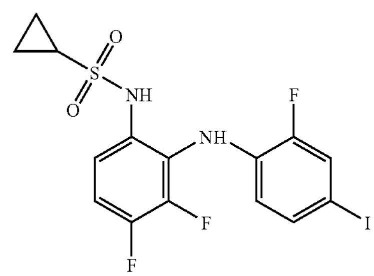 | A |
| 1002 | 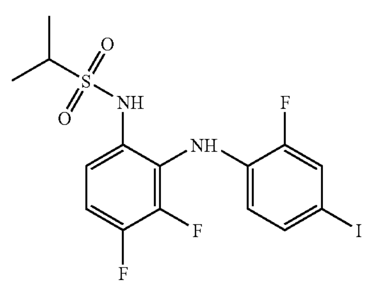 | B |

-continued

| Compound Number | Structure | Activity μM |
|---|---|---|
| 1003 | 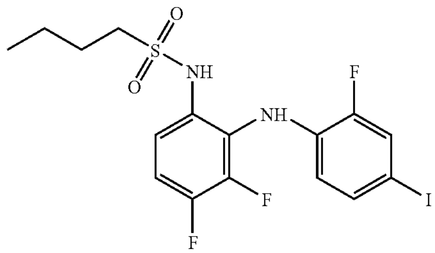 | C |
| 1004 | 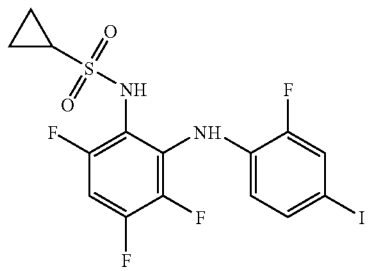 | C |
| 1005 | 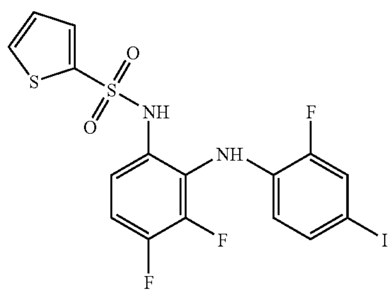 | C |
| 1006 | 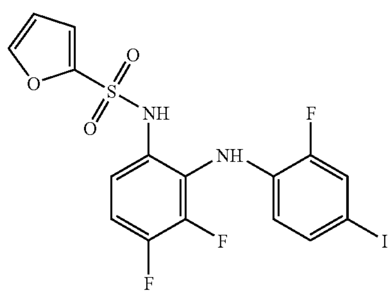 | C |
| 1007 | 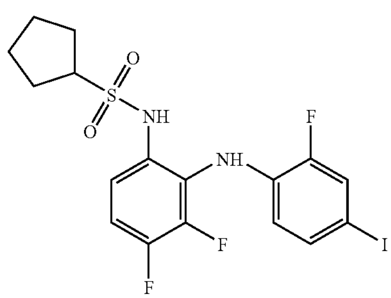 | C |

-continued

| Compound Number | Structure | Activity μM |
|---|---|---|
| 1008 | 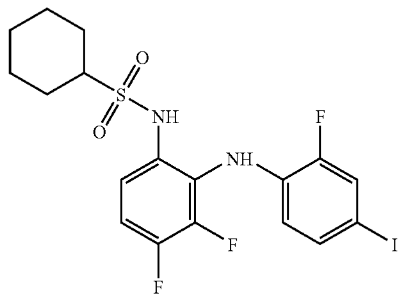 | C |
| 1009 | 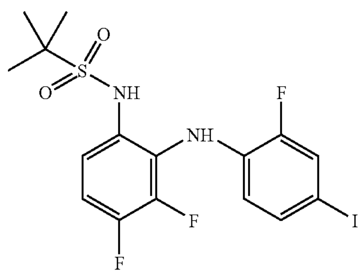 | C |
| 1010 | 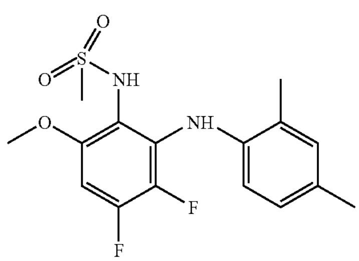 | A |
| 1011 | 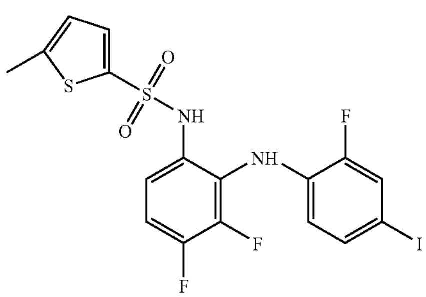 | C |
| 1012 | 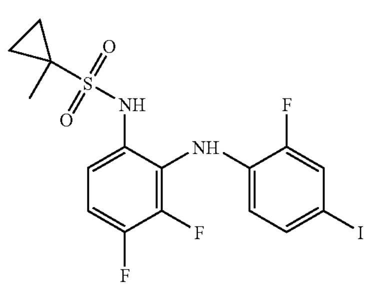 | B |

-continued

| Compound Number | Structure | Activity μM |
|---|---|---|
| 1013 | 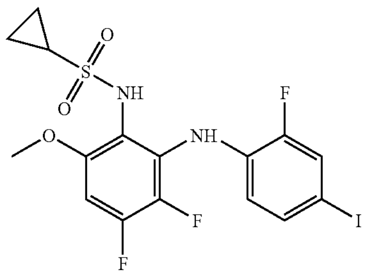 | B |
| 1014 | 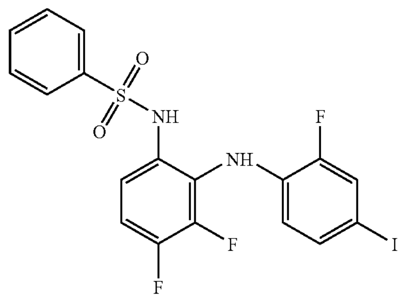 | C |
| 1015 | 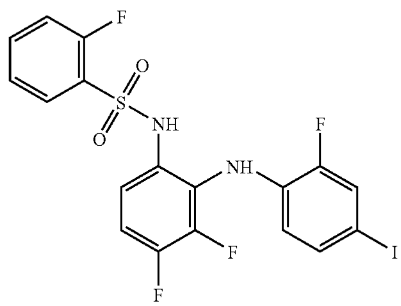 | D |
| 1016 | 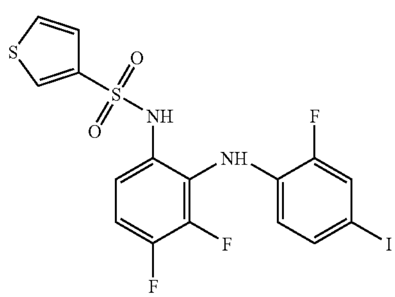 | C |
| 1017 | 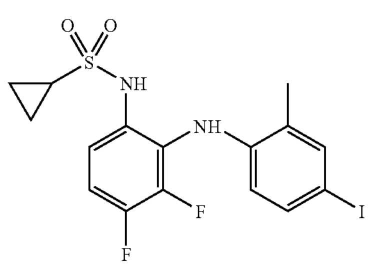 | B |

-continued

| Compound Number | Structure | Activity μM |
|---|---|---|
| 1018 (Racemic) | 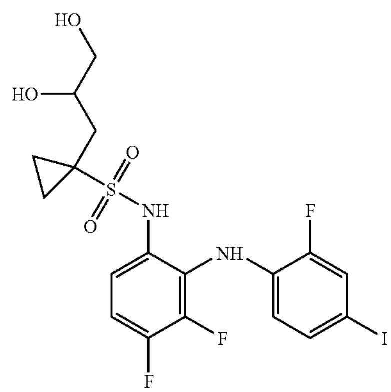 | A |
| 1019 (Racemic) | 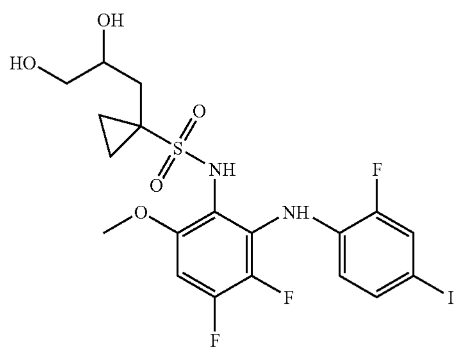 | A |
| 1020 (Racemic) | 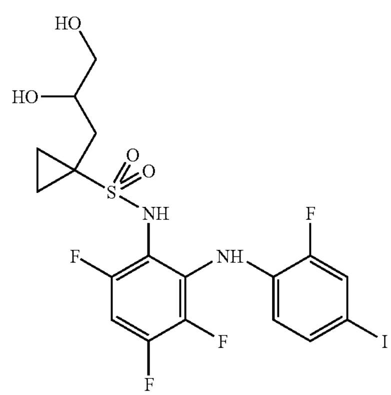 | A |
| 1021 (S isomer) | 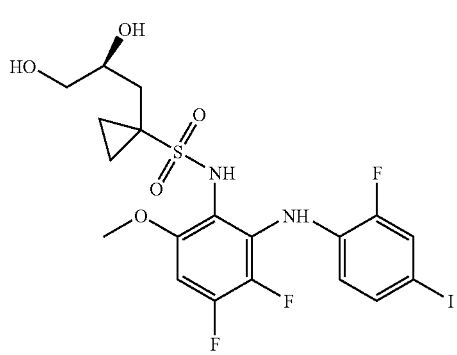 | A |

-continued

| Compound Number | Structure | Activity μM |
|---|---|---|
| 1022 (R isomer) | 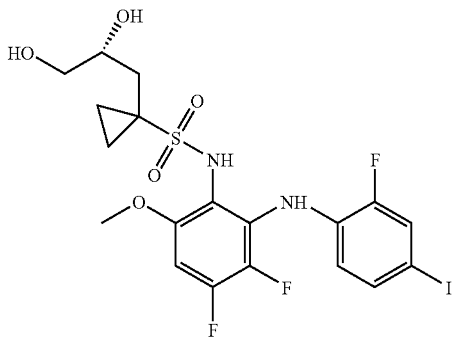 | B |
| 1023 (R isomer) | 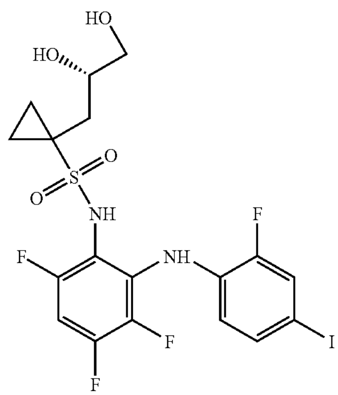 | B |
| 1024 (S isomer) | 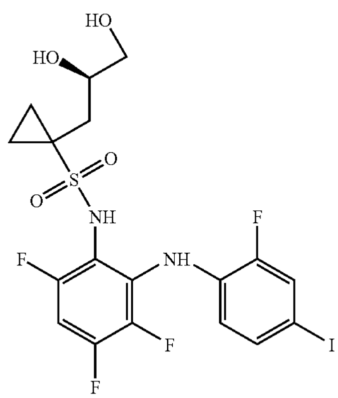 | B |
| 1025 | 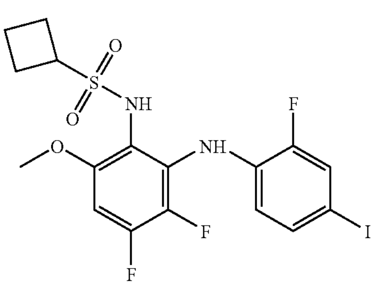 | B |

-continued
| Compound Number | Structure | Activity μM |
|---|---|---|
| 1026 | 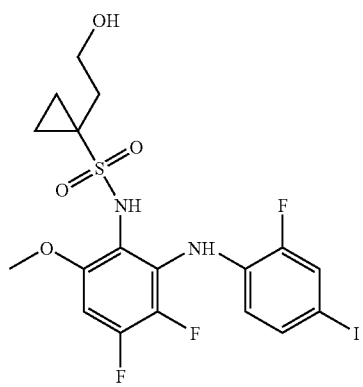 | A |
| 1027 | 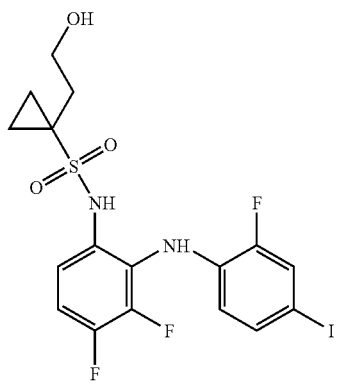 | A |
| 1028 | 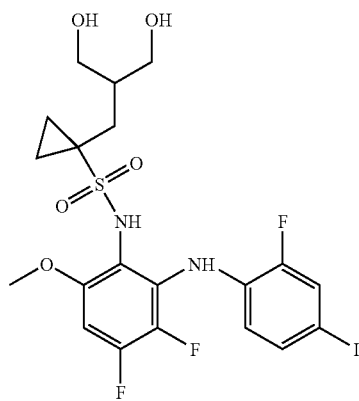 | A |
| 1029 | 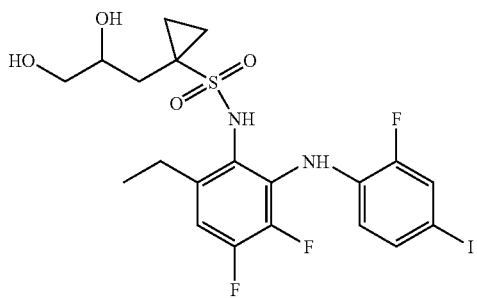 | C |

-continued

| Compound Number | Structure | Activity μM |
|---|---|---|
| 1030 | 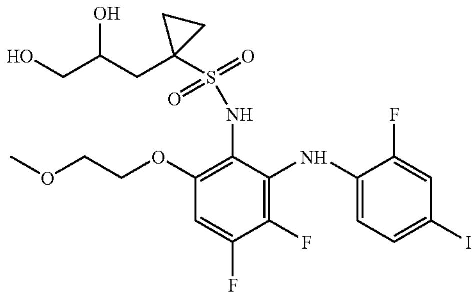 | C |
| 1031 | 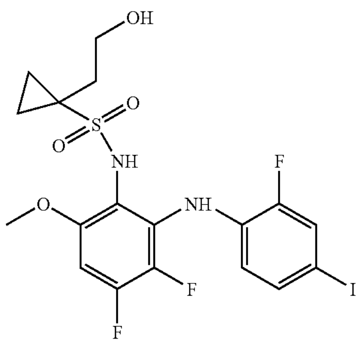 | A |

Legend:
A, $EC_{50}$ = <2.0 nM;
B, $EC_{50}$ = 2.0-15 nM;
C, $EC_{50}$ = 15 nM-100 nM;
D, $EC_{50}$ > 100 nM, $IC_{50}$ < 20 μM;
F, $EC_{50}$ > 100 nM, $IC_{50}$ > 20 μM

| CPD # | Structure | MDA pERK ELISA $EC_{50}$ |
|---|---|---|
| 0497618 | 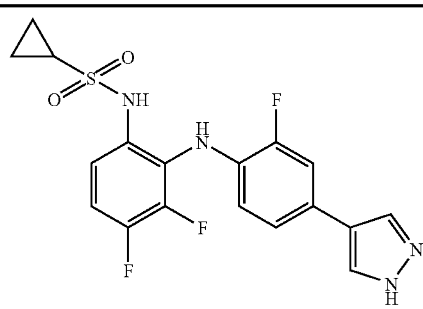 | E |
| 0497620 | 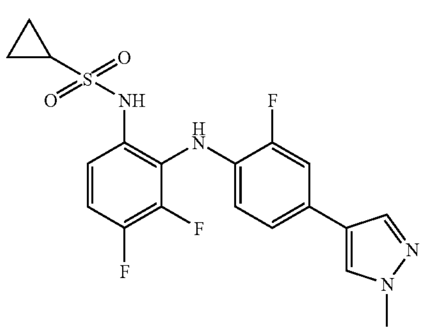 | E |

| CPD # | Structure | MDA pERK ELISA EC$_{50}$ |
|---|---|---|
| 0497654 | 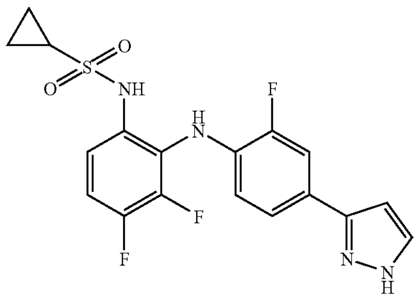 | D |
| 0497688 | 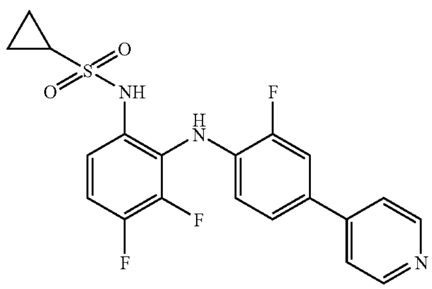 | E |
| 0497689 | 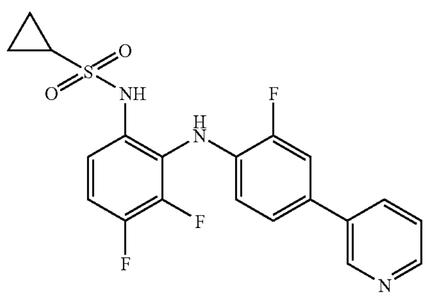 | E |
| 0497692 | 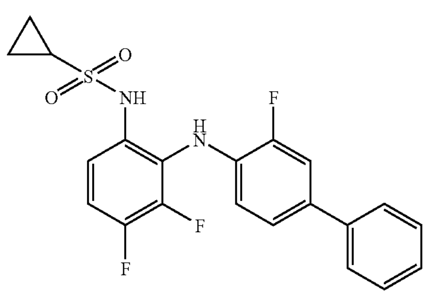 | E |
| 0499266 | 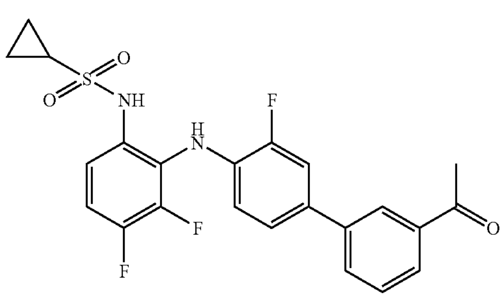 | E |

-continued

| CPD # | Structure | MDA pERK ELISA EC$_{50}$ |
|---|---|---|
| 0499267 | 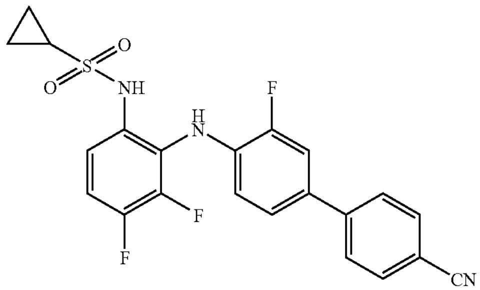 | ND |
| 0499268 | 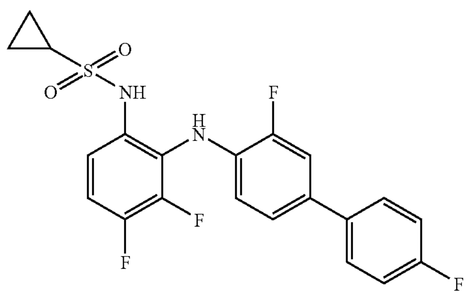 | ND |
| 0499271 | 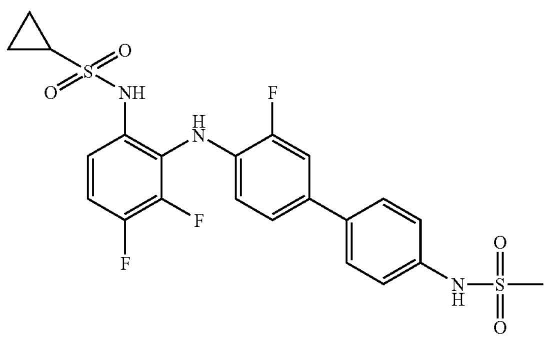 | E |
| 0530701 | 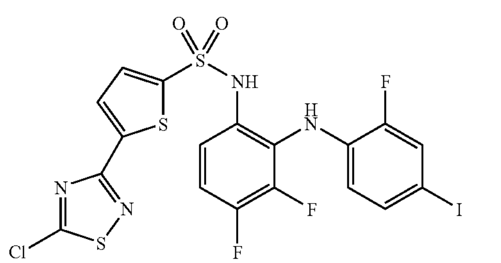 | D |
| 0530716 | 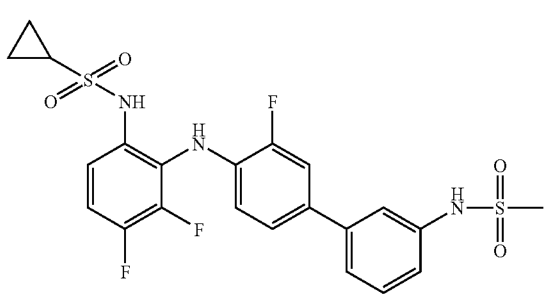 | ND |

-continued

| CPD # | Structure | MDA pERK ELISA EC$_{50}$ |
|---|---|---|
| 0530717 | 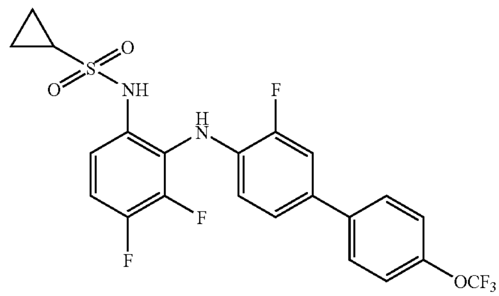 | ND |
| 0561599 | 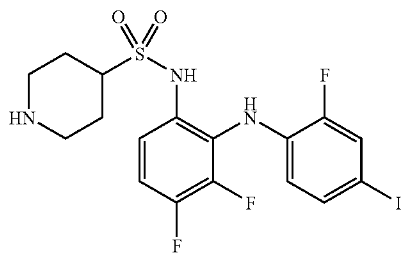 | C |
| 0561608 | 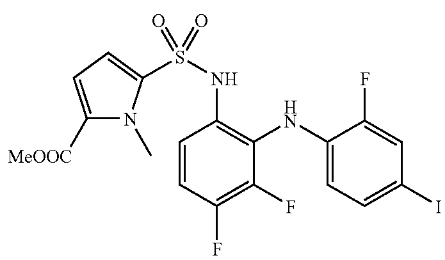 | C |
| 0620926 | 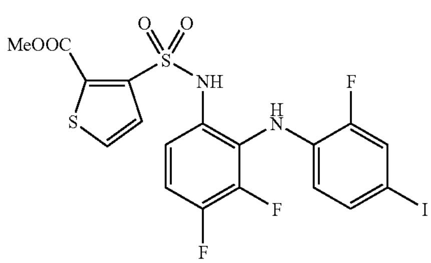 | E |
| 0620927 | 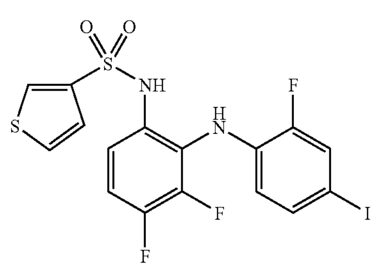 | C |

-continued

| CPD # | Structure | MDA pERK ELISA EC$_{50}$ |
|---|---|---|
| 0621002 | 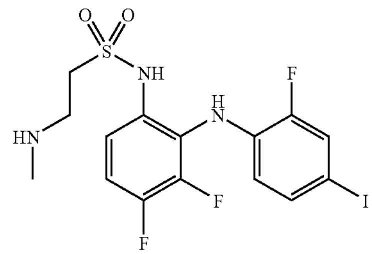 | C |
| 0621016 | 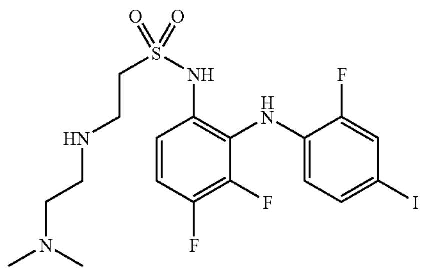 | C |
| 0621026 | 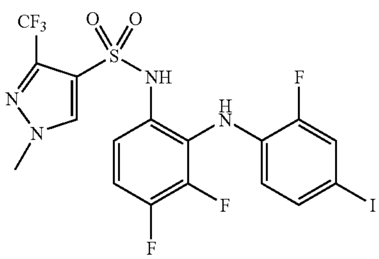 | D |
| 0621029 | 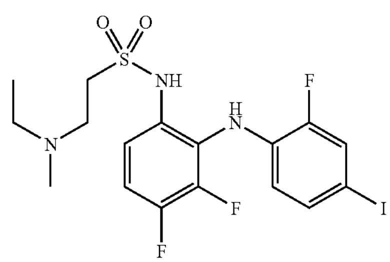 | D |
| 0621030 | 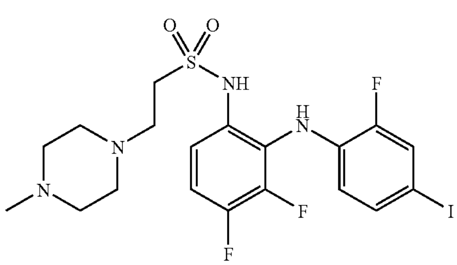 | ND |

Legend:
A, EC$_{50}$ = <2.0 nM;
B, EC$_{50}$ = 2.0-15 nM;
C, EC$_{50}$ = 15 nM-100 nM;
D, EC$_{50}$ = 100 nM-200 nM;
E, EC$_{50}$ > 200 nM;
ND = not yet determined

What is claimed is:

1. The compound (S)-N-(3,4-difluoro-2-(2-fluoro-4-iodophenylamino)-6-methoxyphenyl)-1-(2,3-dihydroxypropyl)cyclopropane-1-sulfonamide:

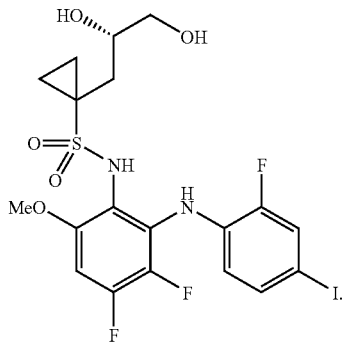

2. A pharmaceutical composition comprising a therapeutically effective amount of (S)-N-(3,4-difluoro-2-(2-fluoro-4-iodophenylamino)-6-methoxyphenyl)-1-(2,3-dihydroxypropyl)cyclopropane-1-sulfonamide:

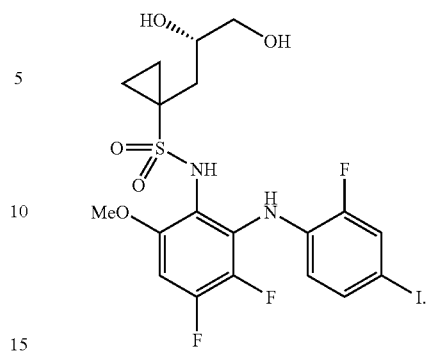

3. The composition of claim 2, further comprising a pharmaceutically acceptable carrier.

4. The composition of claim 3, substantially free of (R)-N-(3,4-difluoro-2-(2-fluoro-4-iodophenylamino)-6-methoxyphenyl)-1-(2,3-dihydroxypropyl)cyclopropane-1-sulfonamide.

* * * * *